United States Patent
Ishikawa et al.

(10) Patent No.: US 6,420,558 B1
(45) Date of Patent: Jul. 16, 2002

(54) AMINOPIPERIDINE DERIVATES AS INTEGRIN $\alpha_V\beta_3$ ANTAGONISTS

(75) Inventors: Minoru Ishikawa; Shoichi Murakami; Mikio Yamamoto; Dai Kubota; Mitsugu Hachisu; Kiyoaki Katano; Keiichi Ajito, all of Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/673,017

(22) PCT Filed: Apr. 9, 1999

(86) PCT No.: PCT/JP99/01903

§ 371 (c)(1),
(2), (4) Date: Oct. 10, 2000

(87) PCT Pub. No.: WO99/52872

PCT Pub. Date: Oct. 21, 1999

(30) Foreign Application Priority Data

Apr. 9, 1998 (JP) .......................................... 10-097066

(51) Int. Cl.[7] .................. C07D 239/02; C07D 213/08; C07D 211/98; C07D 233/00; A61K 31/505

(52) U.S. Cl. ........................... 544/330; 544/333; 546/1; 546/304; 546/329; 546/339; 546/244; 546/246; 546/248; 548/304.4; 548/311.1; 514/275; 514/259; 514/331; 514/394; 514/398

(58) Field of Search ........................... 548/304.4, 311.1; 544/330, 333; 546/1, 304, 329, 339, 244, 246, 248; 514/275, 259, 331, 394, 398

(56) References Cited

FOREIGN PATENT DOCUMENTS

| WO | 97/8145 | | 3/1997 |
|----|---------|---|--------|
| WO | 9708145 | * | 3/1997 |
| WO | 97/23451 | | 7/1997 |
| WO | 9723451 | * | 7/1997 |
| WO | 97/36858 | | 10/1997 |
| WO | 97/36860 | | 10/1997 |
| WO | 97/36861 | | 10/1997 |
| WO | 97/36862 | | 10/1997 |

OTHER PUBLICATIONS

K.C.Nicolaou et al.;"Design,Synthesis & Biol Evaln . . . "; Tetrahedron 53/26,8751–78(1997).*

J. Takagi et al., "Structural Change and Activity Regulation of β1 Integrin", The 50th Annual Meeting of the Japan Society for Cell Biology, S5–1, 1997.

T.A.Springer, "Folding of the N-terminal, ligand-binding region on integrin α-subunits into a β-propeller domain", Proc. Natl. Acad. Sci. USA, 94, 65–72, 1997.

A. Irie et al., "Ligand Recognition Mechanism of Integrin: Region on Integrin α4 Subunit, Critical to Ligand Binding", The 50th Annual Meeting of the Japan Society for Cell Biology, S5–2, 1997.

Y. Okada et al., "Integrin $\alpha_v\beta_3$ is Expressed in Selected Microvessels after Focal Cerebral Ischemia," Am. J. Pathol., 149(1), 37–44, 1996.

S.S. Srivatsa et al, "Selective Alpha v Beta Integrin Blockade Limits Neointimal Hyperplasia and Lumen Stenosis in the Stented Porcine Coronary Artery Injury Model", The 69th Annual Meeting of American Heart Association, 0231, 1996.

J.F. Gourvest et al., "Antiresorptive Activity of a Non Peptidic Ligand of the $\alpha_v\beta_3$ Vitronectin Receptor", The 18th Annual Meeting of The American Society for Bone and Mineral Research, P228, 1996.

S.B. Rodan et al., "A High Affinity Non–Peptide $\alpha_v\beta_3$ Ligand Inhibits Osteoclast Activity In Vitro and In Vivo", The 18th Annual Meeting of The American Society for Bone and Mineral Research, M430, 1996.

T.L. Yue et al., "Sk&F107260, A Cyclic RGD Peptide, Inhibits Integrin $\alpha_v\beta_3$–Medicated Vascular Smooth Muscle Cell Migration and Reduces Neointima Formation Following Balloon Injury to the Rat Carotid Artery", The 70th Annual Meeting of American Heart Association, 3733, 1997.

A.L. Racanelli, "Inhibition of Neointimal Formation by a Nonpeptide $\alpha_v B_3$ Antagonist in a Rabbit Model", The 70th Annual Meeting of American Heart Association, 3734, 1997.

(List continued on next page.)

Primary Examiner—Richard L. Raymond
Assistant Examiner—Sudhaker B. Patel
(74) Attorney, Agent, or Firm—Wenderoth, Lind & Ponack, L.L.P.

(57) ABSTRACT

An objective of the present invention is to provide compounds having integrin $\alpha_v\beta_3$ antagonistic activity, cell adhesion inhibitory activity, GP IIb/IIIa antagonistic activity, and/or human platelet aggregation inhibitory activity, and, therapeutic agents for treating cardiovascular diseases, angiogenesis-related diseases, cerebrovascular diseases and the like and for inhibiting platelet aggregation. The derivatives according to the present invention are compounds represented by formula (I) or pharmaceutically acceptable salts or solvates thereof:

(I)

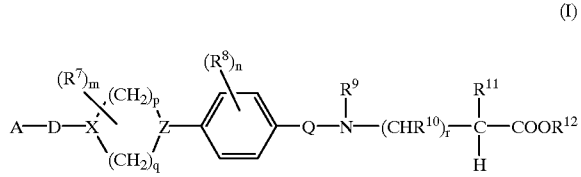

wherein A represents a five- to seven-membered heterocyclic group containing two nitrogen atoms or the like; D represents >$NH_2$, >$CH_2$ or the like; X and Z represent CH or a nitrogen atom; $R^7$ and $R^8$ represent alkyl, halogen or the like; Q represents >C=O, >$CH_2$ or the like; $R^9$ represents H, alkyl, aralkyl or the like; $R^{10}$ represents H, alkynyl or the like; $R^{11}$ represents H, substituted amino or the like; $R^{12}$ represents H or alkyl; m is 0 to 5; n is 0 to 4; p and q are each 1 to 3; and r is 0 or 1.

10 Claims, No Drawings

OTHER PUBLICATIONS

W.S. Westlin et al., "Peptidomimetic Antagonists of $\alpha_v\beta_3$ in Angiogenesis and Solid Tumor Growth", Conference of American IBC, Feb. 23, 1998.

E.T. Choi et al., "Inhibition of neointimal by hyperplasia by blocking $\alpha_v\beta_3$ integrin with a small peptide antagonist GpenGRGDSPCA", J. Vasc. Surg., 19, 125–134, 1994.

M. Goodman et al., "A Novel RGD Containing Dodecapeptidomimetic which Exhibits Selective Binding to the $\alpha_v\beta_3$ Receptor", Bioorg.Med.Chem.Lett., 7(8), 997–1002, 1997.

R. Hirschman et al., "De Novo Design and Synthesis of Somatostatin Non–Peptide Peptidomimetics Utilizing $\beta$–D–Glucose as a Novel Scaffolding", J. Am. Chem. Soc., 115, 12550–12568, 1993.

K.C. Nicolau et al., "Design, Synthesis and Biological Evaluation of Carbohydrate–Based Mimetics of cRGDFV", Tetrahedron, 53(26), 8751–8778, 1997.

D.M. Perreault, "The Advantages of Using Rigid Polyaza–Clefts for Hydrogen–Bonding Molecular Recognition", Tetrahedron, 51(2), 353–362, 1995.

K. Kikugawa et al., "Platelet Aggregration Inhibitors. X. [1] S–Substituted 2–Thioadenosines and Their Derivatives", Japan Chem. Pharm. Bull., 25(10), 2624–2637, 1977.

P.C. Brooks, "Integrin $\alpha_v\beta_3$: A Therapeutic Target", DN&P, 10(8), 456–461, 1997.

M. Okada et al., "Restenosis prevention by the anti–GP IIb/IIIa chimeric antibody", Gendai Iryo, 29(11), 2753 (1997).

W.C. Kouns et al., "Reversible Conformational Changes Induced by Glycoprotein IIb–IIIa by a Potent and Selective Peptidomimetric Inhibitor", Blood, 80, 2539–2547, 1992.

R. Pytela et al., "Arginine–Glycine–Aspartic Acid Adhesion Receptors", Method in Enzymology, 144, 475–489, 1987.

L. Liaw et al., "Osteopontin Promotes Vascular Cell Adhesion and Spreading and Is Chemotactic for Smooth Miuscle Cells In Vitro", Circulation Research, 74(2), 214–224, 1994.

E. Engvall et al., "Affinity of Fibronectin to Collagens of Different Genetic Types and to Fibrinogen", J. Exp. Med. 147, 1584–1595, 1978.

* cited by examiner

AMINOPIPERIDINE DERIVATES AS INTEGRIN $\alpha_v\beta_3$ ANTAGONISTS

This application is a 371 application of PCT/JP99/01903 filed Apr. 9, 1999.

BACKGROUND OF THE INVENTION

1. Field of the Invention

The present invention relates to aminopiperidine derivatives having integrin $\alpha_v\beta_3$ antagonistic activity and pharmaceuticals comprising the same.

2. Background Art

A signal transduction system is very important to organisms from the viewpoint of maintaining life and inheriting the life over to the next generation, specifically from the viewpoints of physiological significance, mechanisms for the regulation of gene expression and the like. It has recently been clarified that integrins, glycoprotein receptors which are involved in cell adhesion and penetrate cell membranes, are related, for example, to wound healing and hemostasis, phagocytosis, biophylaxis, and the construction of cytoskeletons and, in addition, as such are molecules for signal transduction. For this reason, in recent years, organic chemistry associated with integrins has suddenly become drawn attention from the viewpoint of pharmacology, as well as from the viewpoints of molecular biology and cell biology.

It is being elucidated that, while the conformation of integrins undergoes a dynamic and complicate change, integrins binds to various ligands to transmit signal in both intracellular and extracellular directions (Junichi Takagi et al., The 50th Annual Meeting of the Japan Society for Cell Biology, S5-1, 1997). T. A. Springer of Harvard Medical School has recently predicted that a certain activated integrin has a β-propeller structure and binds to a ligand on the upper face of the β-propeller (Proc. Natl. Acad. Sci. USA, 94, 65, 1997). This hypothesis was also supported by researchers in our country (Atsushi Irie et al., The 50th Annual Meeting of the Japan Society for Cell Biology, S5-2, 1997), and three-dimensional analysis on a molecular level associated with the activation of integrins, binding between integrins and ligands and the like has been initiated on a full scale.

Among them, integrin $\alpha_v\beta_{3\ binds}$ binds to various extracellular matrixes, that is, ligands deeply involved, for example, in biodynamics or the crisis of diseases, such as vitronectin, fibrinogen, fibronectin, osteopontin, thrombospondin, von Willebrand factors, and collagen, to form complexes. Accordingly, integrin $\alpha_v\beta_3$ is of special interest as a potential drug target. In fact, $\alpha_v\beta_3$ is expressed in a large amount in B cells, macrophages, monocytes, smooth muscle cells, activated endothelial cells and the like. Further, $\alpha_v\beta_3$ is known not to be strongly expressed in endothelial cells in a resting stage, but to be highly activated in the course of growth and infiltration, that is, in vascularization, wound healing, and inflamed sites. Further, the correlation between the frequency of expression of $\alpha_v\beta_3$ and the increase in infiltration of cancer has been observed in various cancer cells. On the other hand, a group of researchers at Scripps Research Institute in U.S.A. have clarified by advanced computer-assisted video imaging microscopy that microvascular expression of $\alpha_v\beta_3$ is observed during experimental middle cerebral artery occlusion and reperfusion in a baboon as a model (Y. Okada et al., Am. J. Pathol., 149, 37, 1996).

As described above, relationship of cell species, which express integrin $\alpha_v\beta_3$ in vivo, with $\alpha_v\beta_3$ activation stage, biophylaxis mechanism and the like has led to an expectation of clinical application of molecules having integrin $\alpha_v\beta_3$ antagonistic activity in various fields. In fact, compounds having integrin $\alpha_v\beta_3$ antagonistic activity are intended to be used clinically, and the results of animal tests on compounds having $\alpha_v\beta_3$ antagonistic activity in a wide range of diseases have been reported (S. S. Srivatsa et al., The 69th Annual Meeting of American Heart Association, 0231, 1996 (DuPont-Merck); J. F. Gourvest et al., The 18th Annual Meeting of The American Society for Bone and Mineral Research, p228, 1996 (Roussel-Hoechst); S. B. Rodan et al., The 18th Annual Meeting of The American Society for Bone and Mineral Research, M430, 1996 (Merck); T. L. Yue et al., The 70th Annual Meeting of American Heart Association, 3733, 1997 (SmithKline Beecham); A. L. Racanelli et al., The 70th Annual Meeting of American Heart Association, 3734, 1997 (DuPont-Merck); and W. S. Westlin, Conference of American IBC, Feb. 23, 1998 (Searle & Co.)).

From the viewpoint of chemical structure, compounds having integrin $\alpha_v\beta_3$ antagonistic activity can be classified into antibodies, low-molecular peptide and compounds analogous thereto, and small molecules. All the antagonists are structurally related to the sequence of tripeptide RGD (arginine-glycine-aspartic acid) that are considered indispensable for recognition in the attachment of a ligand. Low-molecular peptides having antagonistic activity include disintegrins derived from venom of snakes and, in addition, cyclic peptides. One of them, GpenGRGDSPCA, has been reported to inhibit migration of smooth muscle cells and to block integrin $\alpha_v\beta_3$, thereby actually inhibiting neointima formation in rabbits (E. T. Choi et al., J. Vasc. Surg.,19, 125, 1994). On the other hand, the cyclic peptide containing BTD designed by a β-turn mimic has been proved to strongly binds to $\alpha_v\beta_3$ receptors (M. Goodman et al., Bioorg. Med. Chem. Lett., 7, 997, 1997).

Several methods are known for designing small molecules through the utilization of the amino acid sequence of interest (RGD being used herein) as a key. For example, a peptide mimetic for constructing a new molecule based on the backbone of a peptide chain is generally known in the art. The concept of a new de novo design focused on the chemical structure and spatial configuration of amino acid side chains has been introduced for the first time early in the 1990s (R. Hirschman et al., J. Am. Chem. Soc., 115, 12550, 1993). An attempt to apply this approach to the design and synthesis of $\alpha_v\beta_3$ antagonists has already been initiated (K. C. Nicolaou et al., Tetrahedron, 53, 8751, 1997).

Up to now, small molecules having $\alpha_v\beta_3$ antagonistic activity are disclosedipn WO 9532710, WO 9637492, WO 9701540, WO 9708145, WO 9723451, WO 9723480, WO 9724119, WO 9726250, WO 9733887, WO 9736858, WO 9736859, WO 9736860, WO 9736861, WO 9736862, and EP 0796855. Low-molecular organic compounds having $\alpha_v\beta_3$ antagonistic activity are also disclosed in U.S. Pat. Nos. 5,843,906 and 5,852,210, WO 9737655, WO 9808840, WO 9818460, WO 981359, WO 9835949, WO 9846220, British Patent Nos. 2326609 and 2327672, WO 9843962, WO 9724336, WO 9830542, WO 9905107, EP 820988, EP 820991, EP 853084, and Bioorganic & Medicinal Chemistry, 6, 1185–1208 (1998), which were published after the priority date of the present application.

SUMMARY OF THE INVENTION

The present inventors have found that a certain group of derivatives have potent integrin $\alpha_v\beta_3$ antagonistic activity.

The present inventors have also found that a certain group of derivatives have potent cell adhesion inhibitory activity. The present inventors have further found that a certain group of derivatives have potent GP IIb/IIIa antagonistic activity and human platelet aggregation inhibitory activity.

Accordingly, an object of the present invention is to provide a compound having integrin $\alpha_v\beta_3$ antagonistic activity, cell adhesion inhibitory activity, GP IIb/IIIa antagonistic activity, and/or human platelet aggregation inhibitory activity.

Another object of the present invention is to provide a therapeutic agent for treating a disease selected from the group consisting of integrin $\alpha_v\beta_3$-mediated diseases, diseases such that the inhibition of cell adhesion is effective for the treatment of said diseases, and diseases such that GP IIb/IIIa antagonistic action and/or platelet aggregation inhibitory action are effective for the treatment of said diseases, and an agent for inhibiting platelet aggregation.

The compounds according to the present invention are those represented by formula (I) or a pharmaceutically acceptable salt or solvate thereof:

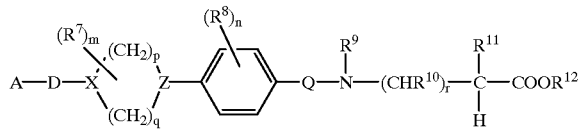

(I)

wherein

A represents a saturated or unsaturated five- to seven-membered heterocyclic group containing two nitrogen atoms, which heterocyclic group is optionally condensed with other saturated or unsaturated five- to seven-membered carbocyclic ring or heterocyclic ring to form a bicyclic group, which heterocyclic group and bicyclic group are optionally substituted by $C_{1-6}$ alkyl, amino, $C_{1-6}$ alkoxy, $C_{1-6}$ alkoxycarbonyl, or aralkyl and the $C_{1-6}$ alkyl, amino, $C_{1-6}$ alkoxy, $C_{1-6}$ alkoxycarbonyl, and aralkyl groups are optionally substituted by $C_{1-6}$ alkyl or $C_{1-6}$ alkoxy, or a group represented by formula

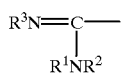

wherein $R^1$, $R^2$, and $R^3$, which may be the same or different, represent a hydrogen atom, $C_{1-6}$ alkyl, $C_{2-6}$ alkenyl, $C_{2-6}$ alkynyl, aralkyl, or nitrile, or $R^1$ and $R^2$ may together form group —$(CH_2)_i$—, wherein i is 4 or 5, or group —$(CH_2)_2$—O—$(CH_2)_2$—, which $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl;

D represents >$NR^4$ wherein $R^4$ represents a hydrogen atom or $C_{1-6}$ alkyl which is optionally substituted by phenyl optionally substituted by $C_{1-6}$ alkoxy; >$CR^5R^6$ wherein $R^5$ and $R^6$ each represent a hydrogen atom or $C_{1-6}$ alkyl which is optionally substituted by phenyl optionally substituted by $C_{1-6}$ alkoxy; —O—; or —S—;

X and Z, which may be the same or different, represent CH or N;

$R^7$ represents $C_{1-6}$ alkyl, $C_{1-6}$ alkoxy, a halogen atom, amino, nitro, hydroxyl, or an oxygen atom, which $C_{1-6}$ alkyl and $C_{1-6}$ alkoxy are optionally substituted by a halogen atom, $C_{1-6}$ alkoxy, amino, or hydroxyl;

$R^8$ represents $C_{1-6}$ alkyl, $C_{1-6}$ alkoxy, a halogen atom, amino, nitro, or hydroxyl, which $C_{1-6}$ alkyl and $C_{1-6}$ alkoxy are optionally substituted by a halogen atom, $C_{1-6}$ alkoxy, amino, or hydroxyl;

Q represents >C=O, >$CHR^{13}$, or >$CHOR^{13}$ wherein $R^{13}$ represents a hydrogen atom or $C_{1-6}$ alkyl;

$R^9$ represents a hydrogen atom, $C_{1-6}$ alkyl, $C_{2-6}$ alkenyl, $C_{2-6}$ alkynyl, or aralkyl, which $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl;

$R^{10}$ represents a hydrogen atom, $C_{1-6}$ alkyl, $C_{2-6}$ alkenyl, $C_{2-6}$ alkynyl, aralkyl, or amino, which $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl and which amino is optionally substituted by $C_{1-6}$ alkyl, $C_{1-6}$ alkoxycarbonyl, benzenesulfonyl in which the phenyl portion is optionally substituted by $C_{1-6}$ alkyl, or benzyloxycarbonyl in which the phenyl portion is optionally substituted by $C_{1-6}$ alkyl;

$R^{11}$ represents a hydrogen atom, $C_{1-6}$ alkyl, $C_{2-6}$ alkenyl, $C_{2-6}$ alkynyl, aralkyl, or amino, which $C_{1-6}$ alkyl, $C_{2-6}$ alkenyl, $C_{2-6}$ alkynyl, and aralkyl are optionally substituted by a halogen atom, $C_{1-6}$ alkoxy, amino, or hydroxyl and which amino is optionally substituted by carboxyl, sulfonyl, $C_{1-6}$ alkyl, $C_{1-6}$ alkylcarbonyl, $C_{1-6}$ alkoxycarbonyl, $C_{1-6}$ alkylsulfonyl, —C(=O)—O—$(CH_2)_u$—$R^{14}$ wherein u is an integer of 0 to 4 and $R^{14}$ represents a saturated or unsaturated five- to seven-membered carbocyclic or heterocyclic group, which carbocyclic group and heterocyclic group are optionally substituted by $C_{1-6}$ alkyl, $C_{1-6}$ alkoxy, phenyl optionally condensed with the carbocyclic or heterocyclic group, carboxyl, hydroxyl, nitro, amino, $C_{1-6}$ alkylamino, or a halogen atom, or —S(=O)$_2$—$(CH_2)_v$—$R^{14}$ wherein v is an integer of 0 to 4 and $R^{14}$ is as defined above;

$R^{12}$ represents a hydrogen atom or $C_{1-6}$ alkyl;

m is an integer of 0 to 5;

n is an integer of 0 to 4;

p is an integer of 1 to 3;

q is an integer of 1 to 3; and r is 0 or 1.

The compounds according to the present invention are useful in the treatment of integrin $\alpha_v\beta_3$-mediated diseases, diseases where the inhibition of cell adhesion is of therapeutic benefit, and diseases where GP IIb/IIIa antagonistic action and/or platelet aggregation inhibitory action are of therapeutic benefit. The compounds according to the present invention are also useful as an agent for inhibiting platelet aggregation.

DETAILED DESCRIPTION OF THE INVENTION

Compound

The terms "$C_{1-6}$ alkyl" and "$C_{1-6}$ alkoxy" as used herein as a group or a part of a group mean straight chain, branched chain, or cyclic alkyl and alkoxy having 1 to 6, preferably 1 to 4 carbon atoms.

The terms "$C_{2-6}$ alkenyl" and "$C_{2-6}$ alkynyl" as used herein as a group or a part of a group mean straight chain, branched chain, or cyclic alkenyl and alkynyl having 2 to 6, preferably 2 to 4 carbon atoms.

Examples of $C_{1-6}$ alkyl include methyl, ethyl, n-propyl, isopropyl, cyclopropyl, cyclopropylmethyl, n-butyl, i-butyl, s-butyl, t-butyl, n-pentyl, cyclopentyl, n-hexyl, and cyclohexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl.

Examples of $C_{2-6}$ alkynyl include 2-propynyl and ethinyl.

Examples of "saturated or unsaturated five- to seven-membered carbocyclic groups" include phenyl.

The term "saturated or unsaturated five- to seven-membered heterocyclic ring" as used herein means a five- to seven-membered heterocyclic ring containing at least one hetero-atom selected from oxygen, nitrogen, and sulfur atoms, preferably a five- to seven-membered heterocyclic ring containing one nitrogen atom, more preferably a five- or six-membered heterocyclic ring containing one nitrogen atom. The term "hetero-atom" as used herein means an oxygen, nitrogen, or sulfur atom. Examples of saturated or unsaturated five- to seven-membered heterocyclic groups include pyrimidyl, 1,4,5,6-tetrahydropyrimidyl, imidazolyl, tetrahydro-[1,3]diazepinyl, and imidazolidinyl.

The saturated or unsaturated heterocyclic group may be condensed with other saturated or unsaturated heterocyclic ring to form a bicyclic ring. Such condensed cyclic groups include benzimidazolyl, naphthyl, and azabenzimidazolyl, for example, imidazo[4,5-b]pyridyl.

The term "aralkyl" as used herein as a group or a part of a group means a $C_{1-6}$ alkyl, preferably $C_{1-4}$ alkyl, substituted by a saturated or unsaturated five- to seven-membered carbocyclic group or heterocyclic group. Examples of aralkyls include benzyl and phenethyl.

The term "halogen atom" means a fluorine, chlorine, bromine, or iodine atom.

In preferred combinations of X with Z, X represents CH while Z represents N, or both X and Z represent N.

When D represents $>NR^4$, X preferably represents CH.

When D represents $>CR^5R^6$, X preferably represents N.

When D represents —O—, X preferably represents CH.

When D represents —S—, X preferably represents CH.

D preferably represents $>NH$ or $>CH_2$.

The bicyclic heterocyclic group represented by A is preferably a nine- or ten-membered heterocyclic group, more preferably, a nine- or ten-membered heterocyclic group containing two or three nitrogen atoms.

Preferably, A represents a group represented by formula

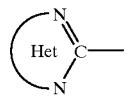

wherein
Het represents a saturated or unsaturated five- to seven-membered heterocyclic group containing two nitrogen atoms, which heterocyclic group is optionally condensed with other saturated or unsaturated five- to seven-membered carbocyclic ring or heterocyclic ring to form a bicyclic group, which heterocyclic group and bicyclic group are optionally substituted by $C_{1-6}$ alkyl, amino, $C_{1-6}$ alkoxy, $C_{1-6}$ alkoxycarbonyl, or aralkyl, which $C_{1-6}$ alkyl, amino, $C_{1-6}$ alkoxy, $C_{1-6}$ alkoxycarbonyl, and aralkyl are optionally substituted by $C_{1-6}$ alkyl or $C_{1-6}$ alkoxy.

More preferably, A represents a group of formula

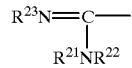

wherein
$R^{21}$, $R^{22}$, and $R^{23}$, which may be the same or different, represent a hydrogen atom, $C_{1-6}$ alkyl, $C_{1-6}$ alkoxy, $C_{1-6}$ alkoxycarbonyl, $C_{2-6}$ alkenyl, or aralkyl, which $C_{1-6}$ alkyl, $C_{1-6}$ alkoxy, $C_{1-6}$ alkoxycarbonyl, $C_{2-6}$ alkenyl, and aralkyl are optionally substituted by a halogen atom, $C_{1-6}$ alkoxy, amino, or hydroxyl, or $R^{21}$ and $R^{23}$ may together form group —(CH$_2$)$_4$—, group —(CH$_2$)$_3$—, group —CHR$^{24}$CH$_2$CH$_2$— wherein $R^{24}$ represents $C_{1-6}$ alkyl or amino, which amino is optionally substituted by $C_{1-6}$ alkyl, $C_{1-6}$ alkoxycarbonyl, aralkyl, or aralkyloxycarbonyl, group —CH$_2$CHR$^{24}$CH$_2$— wherein $R^{24}$ is as defined above, group —CH$_2$CH$_2$—, group —CHR$^{24}$CH$_2$— wherein $R^{24}$ is as defined above, group —CR$^{25}$=CR$^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, —CR$^{24}$=CH—CH=CH— wherein $R^{24}$ is as defined above, —CH=CR$^{24}$—CH=CH— wherein $R^{24}$ is as defined above, —N=CH—CH=CH—, or —CH=N—CH=CH—, or $R^{21}$ and $R^{23}$ may together form

=CH—CH=CH—,

=CH—CH=N—, or

=CH—N=CH—, and $R^{22}$ may represent a single bond between $R^{21}$ and the nitrogen atom attached to $R^{21}$.

In the compound represented by formula (I), one or more hydrogen atoms in the following portion may be substituted by $R^7$.

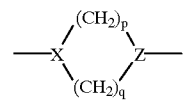

When m is zero (0), $R^7$ is absent. When m is 1, one hydrogen atom in the above portion is substituted by $R^7$. When m is 2 or more, two or more hydrogen atoms in the above portion are substituted by $R^7$. In this case, the substituents may be the same or different. When $R^7$ represents an oxygen atom, the bond between the $R^7$ and the above portion is a double bond. m is preferably an integer of 0 to 2.

In the compound represented by formula (I), one or more hydrogen atoms in the phenylene portion may be substituted by $R^8$.

When n is zero (0), $R^8$ is absent. When n is 1, one hydrogen atom in the phenylene portion is substituted by $R^8$.

When n is 2 or more, two or more hydrogen atoms in the phenylene portion are substituted by $R^8$. In this case, the substituents may be the same or different. n is preferably an integer of 0 to 2.

Q preferably represents >C=O or >CH$_2$.

$R^9$ preferably represents a hydrogen atom, $C_{1-6}$ alkyl, preferably methyl, propyl, or cyclopropylmethyl, or aralkyl, preferably benzyl or phenethyl.

$R^{10}$ preferably represents a hydrogen atom, $C_{2-6}$ alkynyl, or optionally substituted amino, more preferably a hydrogen atom or $C_{2-6}$ alkynyl.

When r is zero (0), —(CHR$^{10}$)$_r$— represents a single bond. r is preferably 1.

$R^{11}$ preferably represents a hydrogen atom, $C_{2-6}$ alkynyl, or optionally substituted amino, more preferably a hydrogen atom or optionally substituted amino.

A hydrogen atom(s) in amino represented by $R^{11}$ may be substituted by two substituents which may be the same or different.

A preferred example of —C(=O)—O—(CH$_2$)$_u$—R$^{14}$ as a substituent for amino represented by $R^{11}$ is a group wherein u is an integer of 0 to 3, more preferbly 0 or 1, and $R^{14}$ represents a five- to seven-membered carbocyclic group, more preferably phenyl.

A preferred example of —S(=O)$_2$—(CH$_2$)$_v$—R$^{14}$ as a substituent for amino represented by $R^{11}$ is a group wherein v is an integer of 0 to 3, more preferably 0 or 1, and $R^{14}$ represents a five- to seven-membered carbocyclic group, more preferably phenyl.

Preferably, one or more hydrogen atoms in the carbocyclic group and the heterocyclic group represented by $R^{14}$ are substituted by $C_{1-6}$ alkyl, more preferably methyl, $C_{1-6}$ alkoxy, more preferably methoxy, carboxyl, hydroxyl, nitro, amino, or a halogen atom.

The substituent for amino represented by $R^{11}$ is preferably $C_{1-6}$ alkyl, $C_{1-6}$ alkylcarbonyl, $C_{1-6}$ alkoxycarbonyl, $C_{1-6}$ alkylsulfonyl, benzyloxycarbonyl in which the phenyl portion is optionally substituted by $C_{1-6}$ alkyl, $C_{1-6}$ alkoxy, carboxyl, hydroxyl, nitro, amino, or a halogen atom, or benzenesulfonyl in which the phenyl portion is optionally substituted by $C_{1-6}$ alkyl, $C_{1-6}$ alkoxy, carboxyl, hydroxyl, nitro, amino, or a halogen atom.

A group of preferred compounds represented by formula (I) are those wherein

A represents a group of formula

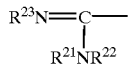

wherein
$R^{21}$, $R^{22}$, and $R^{23}$ are as defined above;
D represents >NH;
X represents CH;
Z represents N;
Q represents >C=O or >CH$_2$;
$R^9$ represents a hydrogen atom, $C_{1-6}$ alkyl, or aralkyl, which $C_{1-6}$ alkyl and aralkyl are optionally substituted by a halogen atom, $C_{1-6}$ alkoxy, amino, or hydroxyl;
$R^{10}$ represents a hydrogen atom or $C_{2-6}$ alkynyl;
$R^{11}$ represents a hydrogen atom or amino, which amino is optionally substituted by $C_{1-6}$ alkyl; acetyl; $C_{1-6}$ alkoxycarbonyl; $C_{1-6}$ alkylsulfonyl; benzyloxycarbonyl in which the phenyl portion is optionally substituted; or benzenesulfonyl in which the phenyl portion is optionally substituted;
m and n each represent an integer of 0 to 2;
p is 2;
q is 1 or 2; and
r is 1; and
those wherein
A represents a group of formula

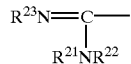

wherein
$R^{21}$, $R^{22}$, and $R^{23}$ are as defined above;
D represents >CH$_2$;
X and Z both represent N;
Q represents >C=O or >CH$_2$;
$R^9$ represents a hydrogen atom, $C_{1-6}$ alkyl, or aralkyl, which $C_{1-6}$ alkyl and aralkyl are optionally substituted by a halogen atom, $C_{1-6}$ alkoxy, amino, or hydroxyl;
$R^{10}$ represents a hydrogen atom or $C_{2-6}$ alkynyl;
$R^{11}$ represents a hydrogen atom or amino, which amino is optionally substituted by $C_{1-6}$ alkyl; acetyl; $C_{1-6}$ alkoxycarbonyl; $C_{1-6}$ alkylsulfonyl; benzyloxycarbonyl in which the phenyl portion is optionally substituted; or benzenesulfonyl in which the phenyl portion is optionally substituted;
m and n are each an integer of 0 to 2;
p is 2;
q is 1 or 2; and
r is 1.

Particularly preferred compounds represented by formula (I) are as follows:

1. t-butyl (2S)-benzenesulfonylamino-3-[4-{4-(pyrimidin-2-ylamino)piperidin-1-yl}benzoylamino]-propionate;
2. (2S)-benzenesulfonylamino-3-[4-{4-(pyrimidin-2-ylamino)piperidin-1-yl}benzoylamino]propionic acid;
3. (2S)-benzenesulfonylamino-3-[4-{4-(1,4,5,6-tetrahydropyrimidin-2-ylamino)piperidin-1-yl}benzoylamino]propionic acid;
4. t-butyl (2S)-benzenesulfonylamino-3-[4-{(3S)-(pyrimidin-2-ylamino)pyrrolidin-1-yl}benzoylamino]-propionate;
5. (2S)-benzenesulfonylamino-3-[4-{(3S)-(pyrimidin-2-ylamino)pyrrolidin-1-yl}benzoylamino]-propionic acid;
6. (2S)-benzenesulfonylamino-3-[4-{(3S)-(1,4,5,6-tetrahydropyrimidin-2-ylamino)pyrrolidin-1-yl}benzoylamino]propionic acid;
7. t-butyl (2S)-benzenesulfonylamino-3-[4-{(3R)-(pyrimidin-2-ylamino)pyrrolidin-1-yl}benzoylamino]-propionate;
8. (2S)-benzenesulfonylamino-3-[4-{(3R)-(pyrimidin-2-ylamino)pyrrolidin-1-yl}benzoylamino]-propionic acid;
9. t-butyl (2S)-benzenesulfonylamino-3-[4-{4-(1H-benzimidazol-2-ylamino)piperidin-1-yl}benzoylamino]-propionate;
10. (2S)-benzenesulfonylamino-3-[4-{4-(1H-benzimidazol-2-ylamino)piperidin-1-yl}benzoylamino]-propionic acid;
11. ethyl (3S)-[4-{4-(pyrimidin-2-ylamino)-piperidin-1-yl}benzoylamino]pent-4-ynate;
12. (3S)-[4-{4-(pyrimidin-2-ylamino)piperidin-1-yl}benzoylamino]pent-4-ynic acid;
13. t-butyl (2S)-(benzyloxycarbonyl)amino-3-[4-{4-(pyrimidin-2-ylamino)piperidin-1-yl}benzoylamino]-propionate;
14. (2S)-(benzyloxycarbonyl)amino-3-[4-{4-(pyrimidin-2-ylamino)piperidin-1-yl}benzoylamino]-propionic acid;

15. (2S)-amino-3-[4-{4-(1,4,5,6-tetrahydropyrimidin-2-ylamino)piperidin-1-yl}benzoylamino]-propionic acid;
16. (2S)-(benzyloxycarbonyl)amino-3-[4-{4-(1,4,5,6-tetrahydropyrimidin-2-ylamino)piperidin-1-yl}-benzoylamino]propionic acid;
17. (2S)-butane-1-sulfonylamino-3-[4-{4-(1,4,5,6-tetrahydropyrimidin-2-ylamino)piperidin-1-yl}benzoyl-amino]propionic acid;
18. t-butyl (2S)-benzenesulfonylamino-3-[N-(cyclopropylmethyl)-N-[4-{4-(pyrimidin-2-ylamino)-piperidin-1-yl}benzoyl]amino]propionate;
19. (2S)-benzenesulfonylamino-3-[N-(cyclopropylmethyl)-N-[4-{4-(pyrimidin-2-ylamino)piperidin-1-yl}-benzoyl]amino]propionic acid;
20. (2S)-benzenesulfonylamino-3-[N-(cyclopropylmethyl)-N-[4-{4-(1,4,5,6-tetrahydropyrimidin-2-ylamino)-piperidin-1-yl}benzoyl]amino]propionic acid;
21. t-butyl (2S)-benzenesulfonylamino-3-{4-(4-guanidinopiperidin-1-yl)benzoylamino}propionate;
22. (2S)-benzenesulfonylamino-3-{4-(4-guanidinopiperidin-1-yl)benzoylamino}propionic acid;
23. t-butyl 3-[4-{4-(1H-benzimidazol-2-ylamino)-piperidin-1-yl}benzoylamino]-(2S)-{(benzyloxycarbonyl)-amino}propionate;
24. 3-[4-{4-(1H-benzimidazol-2-ylamino)-piperidin-1-yl}benzoylamino]-(2S)-{(benzyloxycarbonyl)-amino}propionic acid;
25. t-butyl (2S)-(benzyloxycarbonyl)amino-3-[4-[4-{(1-t-butoxycarbonyl-1H-benzimidazol-2-yl)amino}piperidin-1-yl]benzoylamino]propionate;
26. t-butyl (2S)-amino-3-[4-[4-{(1-t-butoxy-carbonyl-1H-benzimidazol-2-yl)amino}piperidin-1-yl]-benzoylamino]propionate;
27. t-butyl (2S)-(butane-1-sulfonylamino)-3-[4-[4-{(1-t-butoxycarbonyl-1H-benzimidazol-2-yl)amino}-piperidin-1-yl]benzoylamino]propionate;
28. (2S)-butane-1-sulfonylamino-3-[4-{4-(1H-benzimidazol-2-ylamino)piperidin-1-yl}benzoylamino]-propionic acid;
29. (2S)-amino-3-[4-{4-(1H-benzimidazol-2-ylamino) piperidin-1-yl}benzoylamino]propionic acid;
30. t-butyl 3-[4-[4-{(1-t-butoxycarbonyl-1H-benz-imidazol-2-yl)amino}piperidin-1-yl]benzoylamino]-(2S)-{(2,4,6-trimethylbenzenesulfonyl)amino}propionate;
31. 3-[4-{4-(1H-benzimidazol-2-ylamino)piperidin-1-yl}benzoylamino]-(2S)-{(2,4,6-trimethylbenzene-sulfonyl)amino}propionic acid;
32. t-butyl 3-[4-[4-{(1-t-butoxycarbonyl-1H-benz-imidazol-2-yl)amino}piperidin-1-yl]benzoylamino]-(2S)-{(4-fluorobenzenesulfonyl)amino}propionate;
33. 3-[4-{4-(1H-benzimidazol-2-ylamino)piperidin-1-yl}benzoylamino]-(2S)-{(4-fluorobenzenesulfonyl)-amino}propionic acid;
34. t-butyl 3-[4-[4-{(1-t-butoxycarbonyl-1H-benzimidazol-2-yl)amino}piperidin-1-yl]benzoylamino]-(2S)-{(4-nitrobenzenesulfonyl)amino}propionate;
35. 3-[4-{4-(1H-benzimidazol-2-ylamino)piperidin-1-yl}benzoylamino]-(2S)-{(4-nitrobenzenesulfonyl) amino}-propionic acid;
36. (2S)-(4-aminobenzenesulfonyl)amino-3-[4-{4-(1H-benzimidazol-2-ylamino)piperidin-1-yl}benzoylamino]-propionic acid;
37. t-butyl (2S)-benzenesulfonylamino-3-[4-[4-{(1H-imidazo[4,5-b]pyridin-2-yl)amino}piperidin-1-yl] benzoylamino]propionate;
38. (2S)-benzenesulfonylamino-3-[4-[4-{(1H-imidazo[4,5-b]pyridin-2-yl)amino}piperidin-1-yl]benzoyl-amino] propionic acid;
39. t-butyl (2S)-benzenesulfonylamino-3-[4-[4-[{4,5-dihydro-1-(4-methoxybenzyl)-1H-imidazol-2-yl}-amino] piperidin-1-yl]benzoylamino]propionate;
40. (2S)-benzenesulfonylamino-3-[4-{4-(4,5-dihydro-1H-imidazol-2-ylamino)piperidin-1-yl}benzoyl-amino] propionic acid;
41. t-butyl (2S)-benzenesulfonylamino-3-[4-{4(4,5,6,7-tetrahydro-1H-[1,3]diazepin-2-ylamino)-piperidin-1-yl}benzoylamino]propionate;
42. (2S)-benzenesulfonylamino-3-[4-{4-(4,5,6,7-tetrahydro-1H-[1,3]diazepin-2-ylamino)piperidin-1-yl}-benzoylamino]propionic acid;
43. t-butyl (2S)-benzenesulfonylamino-3-[4-[4-[{N-methyl-N-(pyrimidin-2-yl)}amino]piperidin-1-yl]-benzoylamino]propionate;
44. (2S)-benzenesulfonylamino-3-[4-[4-[{N-methyl-N-(pyrimidin-2-yl)}amino]piperidin-1-yl]benzoylamino]-propionic acid;
45. (2S)-benzenesulfonylamino-3-[4-[4-[{N-methyl-N-(1,4,5,6-tetrahydropyrimidin-2-yl)}amino]piperidin-1-yl] benzoylamino]propionic acid;
46. t-butyl (2S)-benzenesulfonylamino-3-[4-{4-(pyrimidin-2-ylamino)piperidin-1-yl}benzylamino]-propionate;
47. (2S)-benzenesulfonylamino-3-[4-{4-(pyrimidin-2-ylamino )piperidin-1-yl}benzylamino]propionic acid;
48. (2S)-benzenesulfonylamino-3-[4-{4-(1,4,5,6-tetrahydropyrimidin-2-ylamino)piperidin-1-yl}benzyl-amino]propionic acid;
49. (2S)-benzenesulfonylamino-3-[N-benzyl-N-[4-{4-(1,4,5,6-tetrahydropyrimidin-2-ylamino)piperidin-1-yl}benzyl]amino]propionic acid;
50. t-butyl (2S)-benzenesulfonylamino-3-[3-fluoro-4-{4-(pyrimidin-2-ylamino)piperidin-1-yl}benzoyl-amino] propionate;
51. (2S)-benzenesulfonylamino-3-[3-fluoro-4-{4-(pyrimidin-2-ylamino)piperidin-1-yl}benzoylamino]-propionic acid;
52. (2S)-benzenesulfonylamino-3-[3-fluoro-4-{4-(1,4,5,6-tetrahydropyrimidin-2-ylamino)piperidin-1-yl}-benzoylamino]propionic acid;
53. t-butyl (2S)-benzenesulfonylamino-3-[3-fluoro-4-{4-(4,5-dihydro-1H-imidazol-2-ylamino)-piperidin-1-yl}benzoylamino]propionate;
54. (2S)-benzenesulfonylamino-3-[3-fluoro-4-{4-(4,5-dihydro-1H-imidazol-2-ylamino)piperidin-1-yl}-benzoylamino]propionic acid;
55. t-butyl (2S)-benzenesulfonylamino-3-[2,3-difluoro-4-{4-(pyrimidin-2-ylamino)piperidin-1-yl}-benzoylamino] propionate;
56. (2S)-benzenesulfonylamino-3-[2,3-difluoro-4-{4-(pyrimidin-2-ylamino)piperidin-1-yl}benzoylamino]-propionic acid;
57. (2S)-benzenesulfonylamino-3-[2,3-difluoro-4-{4-(1,4,5,6-tetrahydropyrimidin-2-ylamino)piperidin-1-yl}benzoylamino]propionic acid;
58. t-butyl (2S)-benzenesulfonylamino-3-[3-chloro-4-{4-(pyrimidin-2-ylamino)piperidin-1-yl}benzoyl-amino] propionate;
59. (2S)-benzenesulfonylamino-3-[3-chloro-4-{4-(pyrimidin-2-ylamino)piperidin-1-yl}benzoylamino]-propionic acid;
60. (2S)-benzenesulfonylamino-3-[3-chloro-4-{4-(1,4,5,6-tetrahydropyrimidin-2-ylamino)piperidin-1-yl}-benzoylamino]propionic acid;
61. t-butyl 2-(N-benzenesulfonyl-N-methyl)-amino-3-[4-{4-(pyrimidin-2-ylamino)piperidin-1-yl}-benzoylamino] propionate;

62. 2-(N-benzenesulfonyl-N-methyl)amino-3-[4-{4-(pyrimidin-2-ylamino)piperidin-1-yl}benzoylamino]-propionic acid;
63. 2-(N-benzenesulfonyl-N-methyl)amino-3-[4-{4-(1,4,5,6-tetrahydropyrimidin-2-ylamino)piperidin-1-yl}-benzoylamino]propionic acid;
64. t-butyl (2S)-(benzyloxycarbonyl)amino-3-[3-fluoro-4-[4-[{N-(1,4,5,6-tetrahydropyrimidin-2-yl)-N-(4-methoxybenzyl)}amino]piperidin-1-yl]benzoylamino]-propionate;
65. t-butyl (2S)-amino-3-[3-fluoro-4-[4-[{N-(1,4,5,6-tetrahydropyrimidin-2-yl)-N-(4-methoxybenzyl)}-amino]piperidin-1-yl]benzoylamino]propionate;
66. t-butyl 3-[3-fluoro-4-[4-[[N-{1,4,5,6-tetrahydropyrimidin-2-yl)-N-(4-methoxybenzyl)}amino]-piperidin-1-yl]benzoylamino]-(2S)-{(4-nitrobenzenesulfonyl)amino}propionate;
67. 3-[3-fluoro-4-{4-(1,4,5,6-tetrahydro-pyrimidin-2-ylamino)piperidin-1-yl}benzoylamino]-(2S)-{(4-nitrobenzenesulfonyl)amino}propionic acid;
68. (2S)-(4-aminobenzenesulfonyl)amino-3-[3-fluoro-4-{4-(1,4,5,6-tetrahydropyrimidin-2-ylamino)-piperidin-1-yl}benzoylamino]propionic acid;
69. t-butyl (2S)-(benzyloxycarbonyl)amino-3-[3-fluoro-4-{4-(pyrimidin-2-ylamino)piperidin-1-yl}benzoyl-amino]propionate;
70. t-butyl (2S)-amino-3-[3-fluoro-4-{4-(pyrimidin-2-ylamino)piperidin-1-yl}benzoylamino]-propionate;
71. t-butyl 3-[3-fluoro-4-{4-(pyrimidin-2-ylamino)piperidin-1-yl}benzoylamino]-(2S)-{(4-methoxy-benzenesulfonyl)amino}propionate;
72. 3-[3-fluoro-4-{4-(pyrimidin-2-ylamino)-piperidin-1-yl}benzoylamino]-(2S)-{(4-methoxybenzene-sulfonyl)amino}propionic acid;
73. 3-[3-fluoro-4-{4-(1,4,5,6-tetrahydro-pyrimidin-2-ylamino)piperidin-1-yl}benzoylamino]-(2S)-{(4-methoxybenzenesulfonyl)amino}propionic acid;
74. 3-[3-fluoro-4-{4-(pyrimidin-2-ylamino)-piperidin-1-yl}benzoylamino]-(2S)-{(4-hydroxybenzene-sulfonyl)amino}propionic acid;
75. 3-[3-fluoro-4-{4-(1,4,5,6-tetrahydro-pyrimidin-2-ylamino)piperidin-1-yl}benzoylamino]-(2S)-{(4-hydroxybenzenesulfonyl)amino}propionic acid;
76. t-butyl (2S)-(4-carboxybenzenesulfonyl)-amino-3-[3-fluoro-4-{4-(pyrimidin-2-ylamino)piperidin-1-yl}benzoylamino]propionate;
77. (2S)-(4-carboxybenzenesulfonyl)amino-3-[3-fluoro-4-{4-(pyrimidin-2-ylamino)piperidin-1-yl}benzoyl-amino]propionic acid;
78. (2S)-(4-carboxybenzenesulfonyl)amino-3-[3-fluoro-4-{4-(1,4,5,6-tetrahydropyrimidin-2-ylamino)-piperidin-1-yl}benzoylamino]propionic acid;
79. t-butyl (2S)-acetamido-3-[3-fluoro-4-[4-[{N-(1,4,5,6-tetrahydropyrimidin-2-yl)-N-(4-methoxy-benzyl)}amino]piperidin-1-yl]benzoylamino]propionate;
80. (2S)-acetamido-3-[3-fluoro-4-{4-(1,4,5,6-tetrahydropyrimidin-2-ylamino)piperidin-1-yl}benzoyl-amino]propionic acid;
81. t-butyl (2S)-(benzyloxycarbonyl)amino-3-[2,3-difluoro-4-{4-(pyrimidin-2-ylamino)piperidin-1-yl}-benzoylamino]propionate;
82. t-butyl (2S)-amino-3-[2,3-difluoro-4-{4-(pyrimidin-2-ylamino)piperidin-1-yl}benzoylamino]-propionate;
83. t-butyl 3-[2,3-difluoro-4-{4-(pyrimidin-2-ylamino)piperidin-1-yl}benzoylamino]-(2S)-{(4-methoxy-benzenesulfonyl)amino}propionate;
84. 3-[2,3-difluoro-4-{4-(pyrimidin-2-ylamino)-piperidin-1-yl}benzoylamino]-(2S)-{(4-hydroxybenzene-sulfonyl)amino}propionic acid;
85. 3-[2,3-difluoro-4-{4-(1,4,5,6-tetrahydro-pyrimidin-2-ylamino)piperidin-1-yl}benzoylamino]-(2S)-{(4-hydroxybenzenesulfonyl)amino}propionic acid;
86. t-butyl (2S)-(4-carboxybenzenesulfonyl)-amino-3-[2,3-difluoro-4-{4-(pyrimidin-2-ylamino)-piperidin-1-yl}benzoylamino]propionate;
87. (2S)-(4-carboxybenzenesulfonyl)amino-3-[2,3-difluoro-4-{4-(pyrimidin-2-ylamino)piperidin-1-yl}-benzoylamino]propionic acid;
88. (2S)-(4-carboxybenzenesulfonyl)amino-3-[2,3-difluoro-4-{4-(1,4,5,6-tetrahydropyrimidin-2-ylamino)-piperidin-1-yl}benzoylamino]propionic acid;
89. t-butyl (2S)-benzenesulfonylamino-3-[4-{4-(1H-benzimidazol-2-ylmethyl)piperazin-1-yl}benzoyl-amino]propionate;
90. (2S)-benzenesulfonylamino-3-[4-{4-(1H-benzimidazol-2-ylmethyl)piperazin-1-yl}benzoylamino]-propionic acid;
91. t-butyl (2S)-benzenesulfonylamino-3-[3-methoxy-4-{4-(pyrimidin-2-ylamino)piperidin-1-yl}-benzoylamino]propionate;
92. (2S)-benzenesulfonylamino-3-[3-methoxy-4-{4-(pyrimidin-2-ylamino)piperidin-1-yl}benzoylamino]-propionic acid;
93. (2S)-benzenesulfonylamino-3-[3-methoxy-4-{4-(1,4,5,6-tetrahydropyrimidin-2-ylamino)piperidin-1-yl}benzoylamino]propionic acid;
94. (2S)-benzenesulfonylamino-3-[3-hydroxy-4-{4-(pyrimidin-2-ylamino)piperidin-1-yl}benzoylamino]-propionic acid;
95. (2S)-benzenesulfonylamino-3-[3-hydroxy-4-{4-(1,4,5,6-tetrahydropyrimidin-2-ylamino)piperidin-1-yl}-benzoylamino]propionic acid;
96. t-butyl (2S)-(benzyloxycarbonyl)amino-3-[3-methoxy-4-{4-(pyrimidin-2-ylamino)piperidin-1-yl}-benzoylamino]propionate;
97. t-butyl (2S)-amino-3-[3-methoxy-4-{4-(pyrimidin-2-ylamino)piperidin-1-yl}benzoylamino]-propionate;
98. t-butyl (2S)-(4-methoxybenzenesulfonyl)-amino-3-[3-methoxy-4-{4-(pyrimidin-2-ylamino)piperidin-1-yl}benzoylamino]propionate;
99. (2S)-(4-hydroxybenzenesulfonyl)amino-3-[3-hydroxy-4-{4-(pyrimidin-2-ylamino)piperidin-1-yl}-benzoylamino]propionic acid;
100. (2S)-(4-hydroxybenzenesulfonyl)amino-3-[3-hydroxy-4-{4-(1,4,5,6-tetrahydropyrimidin-2-ylamino)-piperidin-1-yl}benzoylamino]propionic acid;
101. t-butyl (2S)-(4-carboxybenzenesulfonyl)-amino-3-[3-methoxy-4-{4-(pyrimidin-2-ylamino)piperidin-1-yl}benzoylamino]propionate;
102. (2S)-(4-carboxybenzenesulfonyl)amino-3-[3-methoxy-4-{4-(pyrimidin-2-ylamino)piperidin-1-yl}-benzoylamino]propionic acid;
103. (2S)-(4-carboxybenzenesulfonyl)amino-3-[3-methoxy-4-{4-(1,4,5,6-tetrahydropyrimidin-2-ylamino)-piperidin-1-yl}benzoylamino]propionic acid;
104. t-butyl (2S)-amino-3-[4-{4-(pyrimidin-2-ylamino)piperidin-1-yl}benzoylamino]propionate; and
105. methyl (2S)-benzenesulfonylamino-3-[4-{4-(pyrimidin-2-ylamino)piperidin-1-yl}benzoylamino]-propionate.

The compounds according to the present invention may form pharmacologically acceptable salts thereof. Such salts include non-toxic salts. Preferred salts include: hydrohalogenic acid salts such as hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, or maleic acid salts; amino acid salts such as glutamic acid salts or aspartic acid salts; alkali metal or alkaline earth metal salts such as sodium salts, potassium salts, and calcium salts; and organic alkali salts such as pyridine salts or triethylamine salts.

The compounds according to the present invention may form solvates (for example, hydrates or ethanolate).

Production of compounds

Compounds represented by formula (I), wherein X represents CH and Z represents N. may be produced according to the following scheme:

Further, in addition to ethyl 4-fluorobenzoate, other 4-halogenobenzoates which have been substituted at the 4-position, for example, ethyl 4-iodobenzoate and ethyl 4-bromobenzoate, may be used. Among them, the use of ethyl 4-fluorobenzoate is preferred from the viewpoint of yield.

Furthermore, in addition to ethyl 4-fluorobenzoate, optionally substituted 4-fluorobenzonitrile may be used as a starting compound. In this case, in a proper later step, for example, acid hydrolysis or the like may be performed for conversion to a free carboxyl group, thereby producing a compound represented by formula (VI).

An aminopiperidine of which the primary amine is optionally protected, for example, 4-aminopiperidine, may also be used as the piperidine derivative. The use of the aminopiperidine derivative is advantageous in that the step of introducing the amino group (step 2) may be omitted.

Alternatively, the compound represented by formula (II) may be produced by reacting ethyl 4-bromobenzoate with a

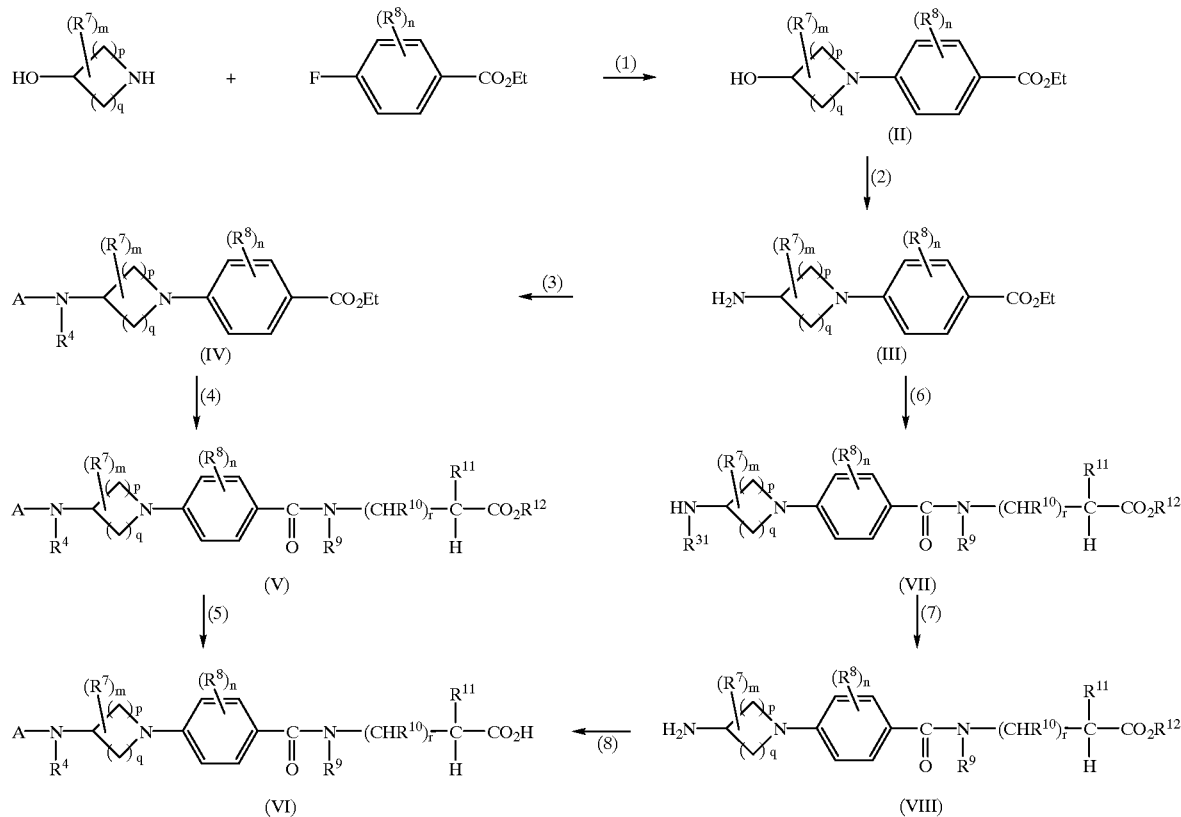

<Step 1>

An optionally substituted ethyl 4-fluorobenzoate may be reacted with 4-hydroxypiperidine or 3-pyrrolidinol which is optionally substituted at the carbon atom(s) (a piperidine derivative) in the presence of a reaction solvent, such as dimethyl sulfoxide, sulfolane, or butanol, preferably dimethyl sulfoxide, at 50° C. to 180° C., preferably 80° C. to 140° C., to prepare a compound represented by formula (II). In this reaction, an organic base such as diisopropylethylamine or an inorganic salt such as ammonium chloride may be added as an acid scavenger.

In addition to ethyl 4-fluorobenzoate, other ester compounds, for example, methyl, propyl, butyl, or benzyl ester compounds, may be used as the starting compound.

piperidine derivative in the presence of palladium, a phosphine ligand, and a base. Phosphine ligands usable herein include 2,2'-bis(diphenylphosphino)-1,1'-binaphthyl, bis (diphenylphosphino)propane, bis(diphenylphosphino) ferrocene, tri-t-butylphosphine, tri-o-tolylphosphine, and triphenylphosphine. Among them, 2,2'-bis (diphenylphosphino)-1,1'-binaphthyl is preferred. Bases include sodium t-butoxide, cesium carbonate, potassium carbonate, and triethylamine. Among them, sodium t-butoxide is preferred. Piperidines include hydroxypiperidine, pyrrolidinol, azetidinol, azepanol, and azocanol.

<Step 2>

The compound represented by formula (II) may be reacted with phthalimide and an azo compound in a reaction solvent such as tetrahydrofuran, benzene, toluene, dioxane, or dimethylformamide, preferably tetrahydrofuran, in the presence of a trialkylphosphine, preferably tributylphosphine, at −40° C. to 100° C., preferably −10° C. to 40° C., followed by the removal of the phthaloyl group to produce a compound represented by formula (III). Azo compounds include 1,1'-(azodicarbonyl)dipiperidine, diethyl azodicarboxylate, and 1,1'-azobis(N,N-dimethylformamide). Among them, 1,1'-(azodicarbonyl) dipiperidine is preferred.

Alternatively, the compound represented by formula (III) may be produced by converting the hydroxyl group in the compound represented by formula (II) to a leaving group, for example, a sulfonyloxy group such as a methanesulfonyloxy group, or a halogen atom such as a bromine atom, allowing sodium azide or a combination of hydrazoic acid with an azo compound to act on the leaving group to convert the leaving group to an azide group, and then reducing the azide group. See intermediates 35, 36, 41, 42, 43, 47, 48, 49, and 58.

<Step 3>

Group A may be introduced into the free primary amine in the compound represented by formula (III) to produce a compound represented by formula (IV). The N—C bond between the compound represented by formula (III) and group A may be formed by reacting the compound represented by formula (III) with a reagent, such as optionally modified or substituted 2-bromopyrimidine, modified or substituted 2-chlorobenzimidazole, or 2-methylthio-2-imidazoline, in the presence of a reaction solvent, such as dimethylformamide, dimethyl sulfoxide, sulfolane, pyridine, or methanol, preferably dimethylformamide, at 50° C. to 170° C., preferably 60° C. to 140° C.

Reagents usable in this step is not limited to those recited herein, and any reagent may be used so far as a carbon atom attached to two nitrogen atoms finally combines with the nitrogen atom in the primary amine attached to a carbon atom in the piperidine derivative to form a single bond. Further, optimization of the kind of substrates used and reaction conditions permits the N—C bond to be formed by reacting palladium having a valency of 0 (zero), a phosphine ligand, and a base. Furthermore, the N—C bond may be formed in accordance with the method of Tetrahedron, 51(2), 353, 1995. See intermediates 26, 27, 29, and 39.

An organic base, such as diisopropylethylamine, N-methylmorpholine, dimethylaminopyridine, or triethylamine, is preferably added as an acid scavenger from the viewpoint of improving the yield. The addition of 2 to 10 equivalents of diisopropylethylamine is preferred.

A compound represented by formula (IV) wherein $R^4$ is substituted may be prepared by conventional or reductive N-alkylation followed by the introduction of group A into the primary amino group in the compound represented by formula (III), or alternatively the introduction of group A into the primary amino group in the compound represented by formula (III) followed by N-alkylation of the secondary amino group. See intermediate 30.

Alternatively, the compound represented by formula (IV) may be produced by suitably oxidizing a hydroxyl group in the piperidine derivative portion of the compound represented by formula (II) to give a ketone which is then reductively aminated with an amino-containing compound (a compound corresponding to group A), for example, 2-aminopyrimidine.

The compound represented by formula (IV) may also be produced by reacting a compound that is previously prepared by attaching a basic functional group corresponding to group A, for example, pyrimidine or benzimidazole, to a primary amino group in an aminopiperidine, with ethyl 4-fluorobenzoate. See intermediates 16, 17, 18, 23, 24, and 25.

<Step 4>

The carboxylic ester represented by formula (IV) may be hydrolyzed, followed by the formation of an amide bond to produce a compound represented by formula (V). More specifically, a free carboxyl group prepared by hydrolysis with an alkali according to a conventional method is reacted with an amine represented by formula

$R^9HNCHR^{10}CHR^{11}COOR^{12}$ wherein $R^9$, $R^{10}$, $R^{11}$, and $R^{12}$ are as defined in formula (I), to perform condensation reaction, thereby producing the amide compound represented by formula (V).

Among the compounds represented by formula (V), compounds having an optionally substituted pyrimidine ring may be, if necessary, reduced to a corresponding tetrahydropyrimidine.

In the condensation reaction, a condensing agent, such as dicyclohexylcarbodiimide, diisopropylcarbodiimide, or 1-ethyl-3-(3-dimethylaminopropyl)carbodiimide hydrochloride, may be used either solely or in combination with a peptide synthesis reagent, such as N-hydroxysuccinimide, 1-hydroxybenzotriazole, or benzotriazol-1-yloxytri(dimethylamino)phosphonium hexafluorophosphate. The combination of these reagents permits the desired condensation reaction to proceed with high efficiency. The use of a combination of 1 to 3 equivalents of 1-ethyl-3-(3-dimethylaminopropyl)carbodiimide hydrochloride with 1 to 2 equivalents of 1-hydroxybenzotriazole is preferred from the viewpoint of optimizing the yield.

Reaction solvents usable in the condensation reaction include dimethylformamide, dioxane, and tetrahydrofuran. Among them, dimethylformamide is preferred. The reaction may be carried out at 0° C. to 80° C., preferably 20° C. to 60° C.

In the condensation reaction, a tertiary amine, such as diisopropylethylamine, N-methylmorpholine, dimethylaminopyridine, or triethylamine, may be added as an organic base from the viewpoint of improving the yield. Among these tertiary amines, N-methylmorpholine is preferably added in an amount of 2 to 10 equivalents.

The compound represented by formula (V), wherein >C=O attached to the phenylene portion is >CH$_2$, may be produced by reducing a carboxylic ester in the compound represented by formula (IV) to convert the carboxylic ester to an aldehyde group and then reductively reacting the resulting compound with an amine represented by formula

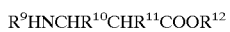
$R^9HNCHR^{10}CHR^{11}COOR^{12}$ wherein $R^9$, $R^{10}$, $R^{11}$, and $R^{12}$ are as defined above in connection with formula (I). See Example 46.

The compounds represented by formula (V) prepared by the reductive amination wherein $R^9$ represents a group other than the hydrogen atom may be produced by the step of reaction other than described above. Specifically, the free aldehyde group may be reductively reacted with an amine represented by formula

$H_2NCHR^{10}CHR^{11}COOR^{12}$ wherein $R^{10}$, $R^{11}$, and $R^{12}$ are as defined in formula (I), to produce a compound of formula (V) wherein $R^9$ represents a hydrogen atom. Thereafter, the product may be further reacted by reductive amination to introduce an alkyl, alkenyl, or aralkyl group into $R^9$. The introduction of the alkyl, alkenyl, or aralkyl group into $R^9$ is not always carried out only for the compound represented by formula (V) in the scheme. Specifically, the introduction of the alkyl, alkenyl, or aralkyl group into $R^9$ may be carried out for the compound represented by formula (VI) in the scheme. See Example 49.

In this reaction, $R^{12}$ in —$COOR^{12}$ corresponding to the carboxylic ester portion of the amine may be a hydrogen atom.

The carboxylic ester portion in the compound represented by formula (V) in the scheme may be optionally converted to a free carboxyl group to produce the compound represented by formula (VI).

The carboxylic ester portion in the compound represented by formula (V) may be converted to the intended free carboxyl group by a conventional method, for example, by hydrolysis with an alkali, hydrolysis with an acid, or reaction with an acid. The deesterification reaction may be achieved by a novel method without any restriction or limitation.

The compound represented by formula (V) as such is integrin $\alpha_v\beta_3$ antagonist and/or GP IIb/IIIa antagonist that can be orally administered. Therefore, the step of converting the carboxylic ester to the free carboxyl group is not always necessary.

Among the compounds represented by formula (VI), compounds having an optionally substituted pyrimidine ring may be optionally reduced to a corresponding tetrahydropyrimidine. The reduction may be carried out by a conventional method. Examples of reduction methods usable herein include catalytic reduction in the presence of a catalyst, such as palladium-carbon, ruthenium-carbon, rhodium-carbon, palladium oxide, platinum oxide, ruthenium oxide, rhodium platinum oxide complex, rhodium aluminum oxide complex, Raney nickel, or palladium black, and a reaction, for example, with metallic sodium or metallic lithium in liquid ammonia. Preferably, the reduction is carried out in an acidic solvent, for example, in acetic acid acidified with hydrochloric acid, in the presence of palladium-carbon with hydrogen under normal or applied pressure.

<Steps 6, 7, and 8>

The compound represented by formula (VII) may be produced by previously protecting the primary amine in the piperidine derivative portion of the compound represented by formula (III), converting the benzoic ester portion to a free carboxyl group, and reacting the carboxyl group with an amine represented by formula $R^9HNCHR^{10}CHR^{11}COOR^{12}$ wherein $R^9$, $R^{10}$, $R^{11}$, and $R^{12}$ are as defined above in connection with formula (I), to form an amide bond. In the compound represented by formula (VII), $R^{31}$ represents a protective group of the amino group. Protective groups usable for the amino group include t-butyloxycarbonyl, benzyloxycarbonyl, and p-methoxybenzyloxycarbonyl. Among them, t-butyloxycarbonyl is preferred.

Next, the protective group in the piperidine derivative portion may be removed, if necessary, followed by conversion of the carboxylic ester portion to a free carboxyl group, thereby producing a compound represented by formula (VIII).

The compound represented by formula (VI) may be produced by introducing a basic functional group corresponding to group A, for example, a pyrimidine, benzimidazole, or amidino group, into the deprotected primary amine according to step 3, and then optionally converting the carboxylic ester portion to a free carboxyl group. See intermediates 20, 21, and 22 and Examples 21 and 22.

In the scheme, for example, the compound represented by formula (IV) is first converted to the compound represented by formula (V) to form an amide bond, followed by reduction of an optionally substituted pyrimidine ring in the compound represented by formula (VI). However, for example, a basic functional group, for example, an optionally substituted pyrimidine ring, bonded to the primary amino group of the piperidine derivative among the compounds represented by formula (IV) may be reduced followed by amide bond formation.

In the compounds represented by formulae (V) and (VI) in the scheme, atomic groups, which have been constructed in the molecule, for example, $R^7$, $R^8$, $R^9$, $R^{10}$, and $R^{11}$, may be optionally converted. Regarding the conversion of $R^{11}$ in the compound represented by formula (VI), for example, reference may be made to Examples 15, 16, 17, 26, 27, 30, 32, 34, 36, 61, 65, 66, 68, 70, 71, 74, 76, 79, 82, 83, 84, 86, 97, 98, 99, 101, and 104.

The compound represented by formula (I), wherein both X and Z represent N, may be produced according to steps 3 to 5, using the corresponding phenyl piperazine derivative represented by formula (III) as a starting compound. The corresponding phenylpiperazine derivative represented by formula (III) may be produced, for example, by reacting piperazine with ethyl 4-fluorobenzoate in dimethyl sulfoxide at 120° C. according to step 1.

The compound represented by formula (I), wherein X represents N and Z represents CH, may be produced from 4-bromobenzyl alcohol with a protected hydroxyl group according to the method described in WO 94/12181. More specifically, the phenylpiperidine derivative corresponding to formula (II) may be produced by reacting 4-bromobenzyl alcohol with lithium introduced thereinto (with a protected hydroxyl group) with N-Boc-4-piperidone to prepare a phenylpiperidine derivative, reductively removing the resultant hydroxyl group, deprotecting the protected hydroxyl group, esterifying the deprotected hydroxyl group, and removing the Boc group. The compound represented by formula (I), wherein X represents N and Z represents CH, may be produced from this phenylpiperidine derivative through steps 2 to 5.

The compound represented by formula (I), wherein D represents >$CR^5R^6$, may be produced according to steps 4 and 5, using as a starting compound a compound represented by formula (IV) wherein the group corresponding to D in formula (I) represents >$CR^5R^6$. The compound represented by formula (IV), wherein the group corresponding to D in formula (I) represents >$CR^5R^6$, may be produced, for example, by reacting 2-(chloromethyl)benzimidazole with ethyl 4-(piperazin-1-yl)benzoate in dimethyl sulfoxide in the presence of potassium carbonate at room temperature. See Examples 89 and 90.

The compound represented by formula (I), wherein D represents —O—, may be produced according to steps 4 and 5, using as a starting compound a compound represented by formula (IV) wherein the group corresponding to D in formula (I) represents —O—. The compound represented by formula (IV), wherein the group corresponding to D in formula (I) represents —O—, may be produced by reacting the hydroxyl group in the compound represented by formula (II) with a basic functional group having an alkylsulfonyl group, that is, a compound corresponding to group A. This reaction may be carried out in accordance with the method described, for example, in Japanese Patent Laid-Open No. 97818/1993 and EP 468766A1.

The compound represented by formula (I), wherein D represents —S—, may be produced according to steps 4 and 5, using as a starting compound a compound represented by formula (IV) wherein the group corresponding to D in formula (I) represents —S—. The compound represented by formula (IV), wherein the group corresponding to D in formula (I) represents —S—, may be produced by halogenating the hydroxyl group in the compound represented by formula (II) and reacting the halogen atom with a basic functional group having group —SH, that is, a compound corresponding to group A. The reaction of the halogen atom with group —SH may be carried out in accordance with the method described, for example, in Res. Lab., Kohjin Co., Ltd., Japan Chem. Pharm. Bull. (1977), 25(10), 2624–37.

Use of compounds/pharmaceutical composition

The compounds according to the present invention have potent integrin $\alpha_v\beta_3$ antagonistic activity, as demonstrated in Pharmacological Test Example 1. Accordingly, the compounds according to the present invention may be used in the treatment of integrin $\alpha_v\beta_3$-mediated diseases. The integrin $\alpha_v\beta_3$ mediates cardiovascular diseases such as acute myocardial infarction, neointima formation hypertrophy, restenosis after PTCA/stent operation, unstable angina, acute coronary syndrome, angina pectoris after PTCA/stent operation, arterial sclerosis, particularly atherosclerosis; angiogenesis-related diseases such as diabetic retinopathy, diabetic vascular complication, or vascular grafting; cerebrovascular diseases such as cerebral infarction; cancers such as solid tumors or metastasis thereof, immunological diseases such as arthritis, particularly rheumatic arthritis; and osteopathy such as osteoporosis, hypercalcemia, periodontitis, hyperparathyroidism, periarticular sore, or Paget's diseases (DN & P, 10 (8), 456 (1997)). The term "therapy" or "treatment" as used herein includes "prevention" or "prophylaxis."

The compounds according to the present invention have cell adhesion inhibitory activity, as demonstrated in Pharmacological Test Example 3. Accordingly, the compounds according to the present invention may be used in the treatment of diseases where the inhibition of cell adhesion is of therapeutic benefit. More specifically, such diseases as cardiovascular diseases, angiogenesis-related diseases, cerebrovascular diseases, cancers, and immunological diseases can be treated by inhibiting adhesion between smooth muscule cells and cell adherent proteins, particularly vitronectin (DN & P, 10 (8), 456 (1997)). Further, cancers or metastasis thereof can be treated by inhibiting adhesion between vascular endothelial cells and cell adherent proteins, particularly vitronectin. Furthermore, osteopathy can be treated by inhibiting adhesion between osteoclasts and cell adherent proteins, particularly osteopontin.

The term "cell adhesion" as used herein means adhesion between vascular cells, specifically smooth muscle cells and endothelial cells, and cell adherent proteins, specifically vitronectin, osteopontin, and von Willebrand factors, adhesion between vascular cells and hemocyte cells, specifically leukocyte, and adhesion between hemocyte cells themselves, particularly adhesion between human vascular smooth muscle cells and human vitronectin.

As described in Pharmacological Test Example 2, the compounds according to the present invention have GP IIb/IIIa antagonistic activity and human platelet aggregation inhibitory activity. Therefore, the compounds according to the present invention can be used in the treatment of diseases where GP IIb/IIIa antagonism and the inhibition of human platelet aggregation are of therapeutic benefit. More specifically, the compounds according to the present invention can be used in the treatment of platelet thrombosis and thromboembolism during and after the treatment of thrombolysis and after angioplasty of coronary artery and other arteries and after bypassing of coronary artery, the improvement of peripheral circulating blood stream, and the inhibition of blood clotting during extracorporeal circulation. Furthermore, the compounds according to the present invention can be used in the treatment of thrombotic thrombocytopenic purpura and hemolytic uremic syndrome (Gendai Iryo, 29, (11), 2753 (1997)).

Not only compounds represented by formula (I) wherein $R^{12}$ represents an alkyl group, but also compounds represented by formula (I) wherein $R^{12}$ represents a hydrogen atom, for example, a compound prepared in Example 59, had oral absorption in rats (data not shown). Therefore, any of the compounds, wherein $R^{12}$ represents an alkyl group or a hydrogen atom, can be used in the treatment of the above diseases.

The compounds according to the present invention and pharmacologically acceptable salts and solvates thereof can be administered orally or parenterally by administration routes, for example, inhalation administration, rhinenchysis, instillation, subcutaneous administration, intravenous injection, intravenous drip infusion, intramuscular injection, rectal administration, or percutaneous administration, and thus may be formed into appropriate various dosage forms depending on oral or parenteral administration routes and administered to human and non-human animals.

The compounds according to the present invention may be formulated into, for example, oral preparation, such as tablets, capsules, granules, powders, pills, particulates, troches, syrups, or emulsions; liquids for external use such as inhalants, nasal drops, or eye drops; injections such as intravenous injections or intramuscular injections; intravenous drip infusions; preparations for rectal administrations; oleaginous suppositories; water-soluble suppositories; and liniments such as ointments depending upon applications thereof.

These various preparations may be prepared by conventional methods with commonly used components, for example, excipients, extenders, binders, humidifiers, disintegrants, surface active agents, lubricants, dispersants, buffers, preservatives, dissolution aids, antiseptics, flavoring agents, analgesic agents, stabilizers and the like. Non-toxic additives usable herein include, for example, lactose, fructose, glucose, starch, gelatin, magnesium carbonate, synthetic magnesium silicate, talc, magnesium stearate, methylcellulose, carboxymethylcellulose or a salt thereof, gum arabic, olive oil, propylene glycol, polyethylene glycol, syrup, petrolatum, glycerin, ethanol, citric acid, sodium chloride, sodium sulfite, sodium phosphate, ascorbic acid, and cyclodextrins.

The content of the compound according to the present invention in the medicament may vary according to the dosage form. In general, however, the content is generally 1 to 70% by weight, preferably 5 to 50% by weight, based on the whole composition. The dose for the treatment and prevention of coronary diseases and the like may be appropriately determined in consideration of, for example, the dosage route and the age, sex and severity of condition of patients, and the preparation may be administered usually in an amount of about 0.1 to 2,000 mg, preferably about 5 to 400 mg per day per adult. This dose is administered at a time daily, divided doses of several times daily, or at a time every several days.

EXAMPLES

The present invention is further illustrated by the following Examples that are not intended as a limitation of the invention.

Intermediate 1: Ethyl 4-(4-hydroxypiperidin-1-yl)benzoate

Dimethyl sulfoxide (10 ml) was added to 5.0 g of 4-hydroxypiperidine to prepare a solution, and 7.2 ml of ethyl 4-fluorobenzoate was added to the solution. The mixture was stirred at 120° C. for 3 days and was then cooled to room temperature. The reaction solution was cooled to room temperature. The reaction solution was then poured into 200 ml of water with vigorous stirring. The insolubles were collected by filtration through a glass filter, and washed twice with 50 ml of water and then once with 50 ml of hexane. The solid was dried to prepare 9.6 g of the title compound.

Physicochemical Properties of Intermediate 1
(1) Color and form: Pale yellow solid
(2) Molecular formula: $C_{14}H_{19}NO_3$
(3) Mass spectrum (EIMS): m/z 249
(4) $^1$H NMR spectrum (400 MHz, $CDCl_3$) δ (ppm): 1.37 (3H, t, $CH_2C\underline{H}_3$), 1.65 (2H, m, piperidine), 1.99 (2H, br d, piperidine), 3.09 (2H, ddd, piperidine), 3.72 (2H, dt, piperidine), 3.92 (1H, tt, piperidine), 4.32 (2H, q, $C\underline{H}_2CH_3$), 6.87 (2H, d, $C_6H_4$), 7.91 (2H, d, $C_6H_4$)

Intermediate 2: Ethyl 4-(4-phthalimidopiperidin-1-yl)benzoate

Benzene (80 ml) was added to 2.0 g of intermediate 1 to prepare a solution. Phthalimide (2.4 g) and 4.0 ml of tributylphosphine were added to the solution. The mixture was cooled to 0° C. 1,1'-(Azodicarbonyl)-dipiperidine (4.0 g) was added thereto at that temperature, and the mixture was then stirred at room temperature for 23 hr. Water (300 ml) was added to stop the reaction. The mixture was extracted three times with 300 ml of methylene chloride. The combined organic layer was then dried over anhydrous sodium sulfate, and concentrated under the reduced pressure. The residue was purified by column chromatography on silica gel (development system: chloroform-acetone=50:1) to prepare 1.6 g of the title compound.

Physicochemical Properties of Intermediate 2
(1) Color and form: Colorless solid
(2) Molecular formula: $C_{22}H_{22}N_2O_4$
(3) Mass spectrum (TSP (thermospray) MS): m/z 379 $(M+H)^+$
(4) $^1$H NMR spectrum (400 MHz, $CDCl_3$) δ (ppm): 1.38 (3H, t, $CH_2C\underline{H}_3$), 1.82 (2H, br d, piperidine), 2.62 (2H, dq, piperidine), 2.96 (2H, dt, piperidine), 4.01 (2H, br d, piperidine), 4.34 (2H, q, $C\underline{H}_2CH_3$), 4.35 (1H, m, piperidine), 6.90 (2H, d, $C_6H_4$), 7.72 (2H, dd, phthalimide), 7.83 (2H, dd, phthalimide), 7.93 (2H, d, $C_6H_4$).

Intermediate 3: Ethyl 4-(4-aminopiperidin-1-yl)benzoate

Methanol (56 ml) was added to 850 mg of intermediate 2 to prepare a suspension. Hydrazine monohydrate (4.5 ml) was added to the suspension, and the mixture was stirred at room temperature for 16 hr. The reaction solution was filtered through a glass filter, and the filtrate was concentrated under the reduced pressure. The residue was purified by column chromatography on silica gel (development system: chloroform-methanol-concentrated aqueous ammonia=30:10:1) to prepare 551 mg of the title compound.

Physicochemical Properties of Intermediate 3
(1) Color and form: Colorless solid
(2) Molecular formula: $C_{14}H_{20}N_2O_2$
(3) Mass spectrum (TSPMS): m/z 249 $(M+H)^+$
(4) $^1$H NMR spectrum (400 MHz, $CD_3OD$) δ (ppm): 1.35 (3H, t, $CH_2C\underline{H}_3$), 1.43 (2H, dq, piperidine), 1.90 (2H, br d, piperidine), 2.84 (1H, m, piperidine), 2.89 (2H, br t, piperidine), 3.92 (2H, br d, piperidine), 4.28 (2H, q, $C\underline{H}_2CH_3$), 6.94 (2H, d, $C_6H_4$), 7.84 (2H, d, $C_6H_4$)

Intermediate 4: Ethyl 4-{4-(pyrimidin-2-ylamino)piperidin-1-yl}benzoate

Dimethylformamide (10 ml) was added to 250 mg of intermediate 3 to prepare a solution, and 240 mg of 2-bromopyrimidine was added to the solution. Further, 0.1 ml of diisopropylethylamine was added thereto. The mixture was heated to 125° C., stirred for 10 hr, and then cooled to room temperature. Saturated saline (150 ml) was then added thereto, followed by extraction three times with 150 ml of methylene chloride. The combined organic layer was dried over anhydrous sodium sulfate, and concentrated under the reduced pressure. The residue was purified by column chromatography on silica gel (development system: hexane-ethyl acetate=1:1) to prepare 212 mg of the title compound.

Physicochemical Properties of Intermediate 4
(1) Color and form: Colorless solid
(2) Molecular formula: $C_{18}H_{22}N_4O_2$
(3) Mass spectrum (EIMS): m/z 326
(4) $^1$H NMR spectrum (400 MHz, $CDCl_3$) δ (ppm): 1.37 (3H, t, $CH_2C\underline{H}_3$), 1.61 (2H, br q, piperidine), 2.17 (2H, br d, piperidine), 3.08 (2H, br t, piperidine), 3.84 (2H, br d, piperidine), 4.06 (1H, m, piperidine), 4.33 (2H, q, $C\underline{H}_2CH_3$), 6.55 (1H, t, pyrimidine), 6.89 (2H, d, $C_6H_4$), 7.92 (2H, d, $C_6H_4$), 8.28 (2H, d, pyrimidine)

Intermediate 5: 4-{4-(Pyrimidin-2-ylamino)piperidin-1-yl}benzoic acid

Tetrahydrofuran (9.0 ml) and 3.0 ml of methanol were added to 100 mg of intermediate 4 to prepare a solution, and 3.0 ml of a 1 N aqueous sodium hydroxide solution was added to the solution. The mixture was stirred at 40° C. for 8 hr, and then concentrated under the reduced pressure. The residue was purified by column chromatography on silica gel (development system: chloroform-methanol-concentrated aqueous ammonia=30:10:1) to prepare 75 mg of the title compound.

Physicochemical Properties of Intermediate 5
(1) Color and form: Colorless solid
(2) Molecular formula: $C_{16}H_{18}N_4O_2$
(3) Mass spectrum (EIMS): m/z 298
(4) $^1$H NMR spectrum (400 MHz, DMSO-$d_6$) δ (ppm): 1.53 (2H, br q, piperidine), 1.91 (2H, br d, piperidine), 2.88 (2H, br t, piperidine), 3.82 (2H, br d, piperidine), 3.90 (1H, m, piperidine), 6.54 (1H, t, pyrimidine), 6.89 (2H, br d, $C_6H_4$), 7.73 (2H, br d, $C_6H_4$), 8.25 (2H, d, pyrimidine)

Example 1 t-Butyl (2S)-benzenesulfonylamino-3-[4-{4-(pyrimidin-2-ylamino)piperidin-1-yl}benzoylamino]-propionate Methylene chloride (1.0 ml) and 1.0 ml of dimethylformamide were added to 6.0 mg of intermediate 5 to prepare a solution. Diisopropylethylamine (6 μl) and 13 mg of benzotriazol-1-yloxytri(dimethylamino)phosphonium hexafluorophosphate were added to the solution. The mixture was stirred at room temperature for 3 hr. The reaction solution was added to a solution of 8.1 mg of t-butyl (2S)-N-benzenesulfonyl-2,3-diaminopropionate hydrochloride in 1.0 ml of methylene chloride cooled to −10° C. Further, 6 μl of diisopropylethylamine was added thereto, followed by stirring at that temperature for 2 hr. The reaction solution was concentrated under the reduced pressure. The residue was purified by preparative thin-layer chromatography on silica gel (development system: chloroform-methanol=10:1) to prepare 7.0 mg of the title compound.

Physicochemical Properties of Compound Prepared in Example 1
   (1) Color and form: Colorless solid
   (2) Molecular formula: $C_{29}H_{36}N_6O_5S$
   (3) Mass spectrum (TSPMS): m/z 581 (M+H)$^+$
   (4) Specific rotation: $[\alpha]_D^{25}$ +24° (c 0.35, MeOH)
   (5) $^1$H NMR spectrum (400 MHz, CDCl$_3$) δ (ppm): 1.28 (9H, s, t-Bu), 1.60 (2H, m, piperidine), 2.18 (2H, br d, piperidine), 3.06 (2H, br t, piperidine), 3.57 (1H, ddd, CONHC$\underline{H}_2$CH), 3.81 (2H, br d, piperidine), 3.90 (2H, m, CONHC$\underline{H}_2$C$\underline{H}$), 4.05 (1H, m, piperidine), 6.55 (1H, t, pyrimidine), 6.91 (2H, d, C$_6$H$_4$), 7.49 (2H, m, C$_6$H$_5$), 7.57 (1H, m, C$_6$H$_5$), 7.70 (2H, d, C$_6$H$_4$), 7.86 (2H, m, C$_6$H$_5$), 8.29 (2H, d, pyrimidine)

Example 2

(2S)-Benzenesulfonylamino-3-[4-{4-(pyrimidin-2-ylamino)piperidin-1-yl}benzoylamino]propionic acid Methylene chloride (0.3 ml) was added to 7.0 mg of the compound prepared in Example 1 to prepare a solution. Trifluoroacetic acid (0.3 ml) was added at 0° C. to the solution. The mixture was stirred at room temperature for 2 hr. The reaction solution was concentrated under the reduced pressure. The residue was purified by preparative thin-layer chromatography on silica gel (development system: chloroform-methanol-acetic acid=10:2:1), and then purified by Sephadex LH-20 (development system: methanol) to prepare 6.3 mg of the title compound.

Physicochemical Properties of Compound Prepared in Example 2
   (1) Color and form: Colorless solid
   (2) Molecular formula: $C_{25}H_{28}N_6O_5S$
   (3) Mass spectrum (FABMS): m/z 525 (M+H)$^+$
   (4) Specific rotation: $[\alpha]_D^{23}$ +65° (c 0.36, MeOH)
   (5) $^1$H NMR spectrum (400 MHz, CD$_3$OD) δ (ppm): 1.56 (2H, dq, piperidine), 1.99 (2H, br d, piperidine), 2.90 (2H, br t, piperidine), 3.46 (1H, dd, CONHC$\underline{H}_2$CH), 3.56 (1H, dd, CONHC$\underline{H}_2$CH), 3.63 (1H, dd, CONHCH$_2$C$\underline{H}$), 3.80 (2H, br d, piperidine), 3.89 (1H, m, piperidine), 6.49 (1H, t, pyrimidine), 6.89 (2H, d, C$_6$H$_4$), 7.36 (2H, m, C$_6$H$_5$), 7.43 (1H, m, C$_6$H$_5$), 7.60 (2H, d, C$_6$H$_4$), 7.75 (2H, m, C$_6$H$_5$), 8.16 (2H, d, pyrimidine)

Example 3

(2S)-Benzenesulfonylamino-3-[4-{4-(1,4,5,6-tetrahydropyrimidin-2-ylamino)piperidin-1-yl}benzoyl-amino]propionic acid Acetic acid (5.0 ml) and 0.5 ml of concentrated hydrochloric acid were added to 3.6 mg of the compound prepared in Example 2 to prepare a solution. 10% palladium-carbon (1.8 mg) was added to the solution, and the mixture was vigorously shaken under a hydrogen pressure of 3 atm at room temperature for 2.5 hr. The insolubles were collected by filtration, and washed twice with water and twice with methanol. The filtrate was combined with the washings, followed by concentration under the reduced pressure. The residue was subjected to azeotropic distillation twice each with toluene, followed by purification by preparative thin-layer chromatography on silica gel (development system: methylene chloride-ethanol-water-concentrated aqueous ammonia=8:8:1:1) and then by Sephadex LH-20 (development system: methanol) to prepare 3.2 mg of the title compound.

Physicochemical Properties of Compound Prepared in Example 3
   (1) Color and form: Colorless solid
   (2) Molecular formula: $C_{25}H_{32}N_6O_5S$
   (3) Mass spectrum (FABMS): m/z 529 (M+H)$^+$
   (4) Specific rotation: $[\alpha]_D^{20}$ +69° (c 0.16, MeOH)
   (5) $^1$H NMR spectrum (400 MHz, CD$_3$OD) δ (ppm): 1.49 (2H, br q, piperidine), 1.85 (4H, m, piperidine and tetrahydropyrimidine), 2.84 (2H, br t, piperidine), 3.26 (4H, t, tetrahydropyrimidine), 3.45 (2H, m, CONHC$\underline{H}_2$CH and piperidine), 3.53 (1H, dd, CONHC$\underline{H}_2$CH), 3.63 (1H, dd, CONHCH$_2$C$\underline{H}$), 3.73 (2H, br d, piperidine), 6.85 (2H, d, C$_6$H$_4$), 7.37 (2H, m, C$_6$H$_5$), 7.44 (1H, m, C$_6$H$_5$), 7.59 (2H, d, C$_6$H$_4$), 7.75 (2H, m, C$_6$H$_5$)

Intermediate 6: Ethyl 4-{(3R)-hydroxypyrrolidin-1-yl}benzoate

Dimethyl sulfoxide (20 ml) was added to 3.5 g of (R)-(+)-3-pyrrolidinol to prepare a solution, and 8.8 ml of ethyl 4-fluorobenzoate was added to the solution. The mixture was stirred at 110° C. for two days, and then cooled to room temperature. A saturated aqueous ammonium chloride solution (300 ml) was added thereto, followed by extraction three times with 300 ml of methylene chloride. The combined organic layer was washed twice with 200 ml of water, dried over anhydrous sodium sulfate, and concentrated under the reduced pressure. The residue was purified by column chromatography on silica gel (development system: chloroform-methanol=20:1) to prepare 7.0 g of the title compound.

Physicochemical Properties of Intermediate 6
   (1) Color and form: Colorless solid
   (2) Molecular formula: $C_{13}H_{17}NO_3$
   (3) Mass spectrum (TSPMS): m/z 236 (M+H)$^+$
   (4) $^1$H NMR spectrum (400 MHz, CDCl$_3$) δ (ppm): 1.37 (3H, t, CH$_2$C$\underline{H}_3$), 2.15 (2H, m, pyrrolidine), 3.34 (1H, br d, pyrrolidine), 3.45 (1H, dt, pyrrolidine), 3.56 (2H, m, pyrrolidine), 4.32 (2H, q, C$\underline{H}_2$CH$_3$), 4.65 (1H, m, pyrrolidine), 6.51 (2H, d, C$_6$H$_4$), 7.91 (2H, d, C$_6$H$_4$)

Intermediate 7: Ethyl 4-{(3S)-phthalimidopyrrolidin-1-yl}benzoate

Benzene (8.5 ml) was added to 200 mg of intermediate 6 to prepare a solution. Phthalimide (250 mg) and 0.4 ml of tributylphosphine were added to the solution. The mixture was cooled to 0° C., and 430 mg of 1,1'-(azodicarbonyl)-dipiperidine was added thereto at that temperature. The mixture was then stirred at room temperature for 14 hr. Water (150 ml) was added to stop the reaction, followed by extraction three times with 100 ml of ethyl acetate. The combined organic layer was dried over anhydrous sodium sulfate, and concentrated under the reduced pressure. The residue was purified by column chromatography on silica gel (development system: chloroform-acetone=50:1) to prepare 133 mg of the title compound.

Physicochemical Properties of Intermediate 7
(1) Color and form: Colorless solid
(2) Molecular formula: $C_{21}H_{20}N_2O_4$
(3) Mass spectrum (ESI (electrospray ionization) MS): m/z 365 (M+H)$^+$
(4) $^1$H NMR spectrum (400 MHz, CDCl$_3$) δ (ppm): 1.37 (3H, t, CH$_2$C$\underline{H}_3$), 2.35 (1H, ddt, pyrrolidine), 2.81 (1H, dq, pyrrolidine), 3.50 (1H, q, pyrrolidine), 3.70 (2H, m, pyrrolidine), 3.83 (1H, t, pyrrolidine), 4.32 (2H, q, C$\underline{H}_2$CH$_3$), 5.06 (1H, quintet, pyrrolidine), 6.53 (2H, d, C$_6$H$_4$), 7.75 (2H, m, phthalimide), 7.86 (2H, m, phthalimide), 7.93 (2H, d, C$_6$H$_4$)

Intermediate 8: Ethyl 4-{(3S)-aminopyrrolidin-1-yl}benzoate

Methanol (80 ml) was added to 1.5 g of intermediate 7 to prepare a suspension. Hydrazine monohydrate (8.2 ml) was added to the suspension, and the mixture was then stirred at room temperature for 15 hr. The reaction solution was concentrated under the reduced pressure. The residue was purified by column chromatography on silica gel (development system: chloroform-methanol-concentrated aqueous ammonia=30:10:1) to prepare 1.0 g of the title compound as a crude compound.

Intermediate 9: Ethyl 4-{(3S)-(pyrimidin-2-ylamino)pyrrolidin-1-yl}benzoate

Dimethylformamide (40 ml) was added to 1.0 g of intermediate 8 as the crude compound to prepare a solution. 2-Bromopyrimidine (980 mg) was added to the solution. Further, diisopropylethylamine (3.7 ml) was added thereto. The mixture was heated to 120° C., stirred for 11 hr, and then cooled to room temperature. Water (300 ml) was added thereto, followed by extraction three times with 300 ml of methylene chloride. The combined organic layer was washed with 300 ml of water, dried over anhydrous sodium sulfate, and concentrated under the reduced pressure. The residue was subjected to azeotropic distillation twice each with toluene, and then purified by column chromatography on silica gel (development system: hexane-ethyl acetate=1:1) to prepare 921 mg of the title compound.

Physicochemical Properties of Intermediate 9
(1) Color and form: Colorless solid
(2) Molecular formula: $C_{17}H_{20}N_4O_2$
(3) Mass spectrum (TSPMS): m/z 313 (M+H)$^+$
(4) $^1$H NMR spectrum (400 MHz, CDCl$_3$) δ (ppm): 1.37 (3H, t, CH$_2$C$\underline{H}_3$), 2.09 (1H, dq, pyrrolidine), 2.42 (1H, m, pyrrolidine), 3.32 (1H, dd, pyrrolidine), 3.48 (1H, ddd, pyrrolidine), 3.57 (1H, dt, pyrrolidine), 3.79 (1H, dd, pyrrolidine), 4.32 (2H, q, C$\underline{H}_2$CH$_3$), 4.70 (1H, dq, pyrrolidine), 6.52 (2H, br d, C$_6$H$_4$), 6.59 (1H, t, pyrimidine), 7.92 (2H, br d, C$_6$H$_4$), 8.30 (2H, d, pyrimidine)

Intermediate 10: 4-{(3S)-(Pyrimidin-2-ylamino) pyrrolidin-1-yl}benzoic acid

Tetrahydrofuran (24 ml) and 8.0 ml of methanol were added to 250 mg of intermediate 9 to prepare a solution. A 1 N aqueous sodium hydroxide solution (8.0 ml) was added to the solution. The mixture was stirred at 40° C. for 14 hr, and then concentrated under the reduced pressure. The residue was purified by column chromatography on silica gel (development system: chloroform-methanol-concentrated aqueous ammonia=30:10:1) to prepare 184 mg of the title compound.

Physicochemical Properties of Intermediate 10
(1) Color and form: Colorless solid
(2) Molecular formula: $C_{15}H_{16}N_4O_2$
(3) Mass spectrum (TSPMS): m/z 285 (M+H)$^+$
(4) $^1$H NMR spectrum (400 MHz, CD$_3$OD) δ (ppm): 2.04 (1H, m, pyrrolidine), 2.26 (1H, m, pyrrolidine), 3.23 (1H, dd, pyrrolidine), 3.35 (1H, m, pyrrolidine), 3.51 (1H, m, pyrrolidine), 3.63 (1H, dd, pyrrolidine), 4.51 (1H, dq, pyrrolidine), 6.52 (2H, br d, C$_6$H$_4$), 6.60 (1H, t, pyrimidine), 7.72 (2H, br d, C$_6$H$_4$), 8.30 (2H, d, pyrimidine)

Example 4 t-Butyl (2S)-benzenesulfonylamino-3-[4-{(3S)-(pyrimidin-2-ylamino)pyrrolidin-1-yl}benzoylamino]-propionate Dimethylformamide (3.5 ml) was added to 100 mg of intermediate 10 to prepare a suspension. t-Butyl (2S)-N-benzenesulfonyl-2,3-diaminopropionate hydrochloride (125 mg) was added to the suspension. Further, 57 mg of 1-hydroxybenzotriazole, 77 μl of N-methylmorpholine, and 81 mg of 1-ethyl-3-(3-dimethylaminopropyl)carbodiimide hydrochloride were added to the suspension. The mixture was stirred at room temperature for 14 hr. The reaction solution was concentrated under the reduced pressure. The residue was subjected to azeotropic distillation five times with toluene, and then purified by column chromatography on silica gel (development system: methylene chloride-methanol=50:1) to prepare 199 mg of the title compound.

Physicochemical Properties of Compound Prepared in Example 4
(1) Color and form: Colorless solid
(2) Molecular formula: $C_{28}H_{34}N_6O_5S$
(3) Mass spectrum (TSPMS): m/z 567 (M+H)$^+$
(4) Specific rotation: $[\alpha]_D^{25}$ +13° (c 1.04, MeOH)
(5) $^1$H NMR spectrum (400 MHz, CDCl$_3$) δ (ppm): 1.27 (9H, s, t-Bu), 2.07 (1H, m, pyrrolidine), 2.40 (1H, dq, pyrrolidine), 3.26 (1H, dd, pyrrolidine), 3.44 (1H, m, U pyrrolidine), 3.52 (1H, m, pyrrolidine), 3.66 (1H, ddd, CONHC$\underline{H}_2$CH), 3.74 (1H, dd, pyrrolidine), 3.84 (1H, ddd, CONHC$\underline{H}_2$CH), 3.96 (1H, dt, CONHCH$_2$C$\underline{H}$), 4.67 (1H, sextet, pyrrolidine), 6.49 (2H, d, C$_6$H$_4$), 6.60 (1H, t, pyrimidine), 7.47 (2H, t, C$_6$H$_5$), 7.55 (1H, tt, C$_6$H$_5$), 7.65 (2H, d, C$_6$H$_4$), 7.85 (2H, m, C$_6$H$_5$), 8.32 (2H, d, pyrimidine)

Example 5

(2S-Benzenesulfonylamino-3-[4-{(3S)-(pyrimidin-2-ylamino)pyrrolidin-1-yl}benzoylamino]-propionic acid Methylene chloride (1.0 ml) was added to 102 mg of the compound prepared in Example 4 to prepare a solution. Trifluoroacetic acid (1.0 ml) was added at 0° C. to the solution, and the mixture was stirred at room temperature for 3 hr. The reaction solution was concentrated under the reduced pressure. The residue was purified by column chromatography on silica gel (development system: methylene chloride-methanol=15:1) to prepare 76 mg of the title compound.

Physicochemical Properties of Compound Prepared in Example 5
(1) Color and form: Colorless solid
(2) Molecular formula: $C_{24}H_{26}N_6O_5S$
(3) Mass spectrum (TSPMS): m/z 511 (M+H)$^+$
(4) Specific rotation: $[\alpha]_D^{23}$ +22° (c 0.94, MeOH)
(5) $^1$H NMR spectrum (400 MHz, CD$_3$OD) δ (ppm): 2.12 (1H, m, pyrrolidine), 2.40 (1H, dq, pyrrolidine), 3.30 (1H, m, pyrrolidine), 3.51 (3H, m, pyrrolidine and CONHCH$_2$CH), 3.67 (1H, dd, CONHCH$_2$CH), 3.75 (1H, dd, pyrrolidine), 4.14 (1H, dd, CONHCH$_2$CH), 4.63 (1H, dq, pyrrolidine), 6.57 (2H, d, C$_6$H$_4$), 6.65 (1H, t, pyrimidine), 7.41 (2H, br t, C$_6$H$_5$), 7.48 (1H, br t, C$_6$H$_5$), 7.62 (2H, d, C$_6$H$_4$), 7.81 (2H, m, C$_6$H$_5$), 8.30 (2H, d, pyrimidine)

Example 6

(2S)-Benzenesulfonylamino-3-[4-{(3S)-(1,4,5,6-tetrahydropyrimidin-2-ylamino)pyrrolidin-1-yl}benzoylamino]propionic acid Acetic acid (5.0 ml) and 0.5 ml of concentrated hydrochloric acid were added to 54 mg of the compound prepared in Example 5 to prepare a solution. 10% palladium-carbon (25 mg) was added to the solution, and the mixture was vigorously shaken under a hydrogen pressure of 3 atm at room temperature for 3 hr. The insolubles were collected by filtration, and then washed twice with water and twice with methanol. The filtrate was combined with the washings, followed by concentration under the reduced pressure. The residue was subjected to azeotropic distillation twice each with toluene, and then purified by column chromatography on silica gel (development system: methylene chloride-ethanol-water-concentrated aqueous ammonia=8:8:1:1) and then by Sephadex LH-20 (development system: methanol-0.05 N hydrochloric acid=1:1) to prepare 29 mg of trihydrochloride of the title compound.
Physicochemical Properties of Compound Prepared in Example 6
(1) Color and form: Colorless solid
(2) Molecular formula: $C_{24}H_{30}N_6O_5S$
(3) Mass spectrum (FABMS): m/z 514 (M+H)$^+$
(4) $^1$H NMR spectrum (400 MHz, CD$_3$OD) (as trihydrochloride) δ (ppm): 1.97 (2H, quintet, tetrahydropyrimidine), 2.08 (1H, m, pyrrolidine), 2.36 (1H, dt, pyrrolidine), 3.29 (1H, m, pyrrolidine), 3.38 (4H, t, tetrahydropyrimidine), 3.43 (1H, m, pyrrolidine), 3.51 (2H, m, pyrrolidine and CONHCH$_2$CH), 3.64 (2H, m, pyrrolidine and CONHCH$_2$CH), 4.19 (1H, dd, CONHCH$_2$CH), 4.23 (1H, q, pyrrolidine), 6.59 (2H, d, C$_6$H$_4$), 7.48 (3H, m, C$_6$H$_5$), 7.65 (2H, m, C$_6$H$_4$), 7.81 (2H, m, C$_6$H$_5$)

Intermediate 11: Ethyl 4-{(3S)-hydroxypyrrolidin-1-yl}benzoate

Tetrahydrofuran (60 ml) was added to 3.0 g of intermediate 6 to prepare a solution. Triphenylphosphine (4.0 g) and 920 mg of acetic acid were added to the solution. The mixture was cooled to 0° C. Diethyl azodicarboxylate (2.4 ml) was added thereto at that temperature, and the mixture was then stirred at room temperature for 15 hr. Water (200 ml) was added to stop the reaction, followed by extraction three times with 200 ml of ethyl acetate. The combined organic layer was then dried over anhydrous sodium sulfate, and concentrated under the reduced pressure. The residue was purified by column chromatography on silica gel (development system: hexane-ethyl acetate=3:1) to prepare 2.75 g of ethyl 4-{(3S)-acetoxypyrrolidin-1-yl}benzoate ($^1$H NMR spectrum (400 MHz, CDCl$_3$) δ (ppm): 1.37 ( 3H, t, CH$_2$CH$_3$) , 2.06 (3H, S, CH$_3$CO$_2$), 2.26 (2H, m, pyrrolidine), 3.42 (1H, d, pyrrolidine), 3.50 (2H, m, pyrrolidine), 3.67 (1H, dd, pyrrolidine), 4.32 (2H, q, CH$_2$CH$_3$), 5.44 (1H, m, pyrrolidine), 6.52 (2H, br d, C$_6$H$_4$), 7.93 (2H, br d, C$_6$H$_4$)).

Subsequently, 50 ml of ethanol was added to 2.7 g of this compound to prepare a solution. Sodium ethoxide (800 mg) was added at room temperature to the solution. 3.5 hr after the addition of sodium ethoxide, the reaction solution was poured into a mixed solution composed of 800 ml of a saturated aqueous ammonium chloride solution and 800 ml of methylene chloride with stirring. The organic layer was separated, and the aqueous layer was washed twice with 500 ml of methylene chloride. The combined organic layer was dried over anhydrous sodium sulfate, and concentrated under the reduced pressure. The residue was purified by column chromatography on silica gel (development system: chloroform-acetone=20:1) to prepare 2.2 g of the title compound.
Physicochemical Properties of Intermediate 11
(1) Color and form: Colorless solid
(2) Molecular formula: $C_{13}H_{17}NO_3$
(3) Mass spectrum (APCI (atmospheric chemical ionization) MS): m/z 236 (M+H)$^+$
(4) $^1$H NMR spectrum (400 MHz, CDCl$_3$) δ (ppm): 1.37 (3H, t, CH$_2$CH$_3$), 2.15 (2H, m, pyrrolidine), 3.34 (1H, br d, pyrrolidine), 3.45 (1H, dt, pyrrolidine), 3.56 (2H, m, pyrrolidine), 4.32 (2H, q, CH$_2$CH$_3$), 4.65 (1H, m, pyrrolidine), 6.51 (2H, d, C$_6$H$_4$), 7.91 (2H, d, C$_6$H$_4$)

Intermediate 12: Ethyl 4-{(3R)-phthalimidopyrrolidin-1-yl}benzoate

Tetrahydrofuran (36 ml) was added to 1.8 g of intermediate 11 to prepare a solution. Phthalimide (1.4 g) and 2.3 ml of tributylphosphine were added to the solution, and the mixture was cooled to 0° C. 1,1'-(Azodicarbonyl)-dipiperidine (2.4 g) was added thereto at that temperature, followed by stirring at room temperature for 11 hr. After the completion of the reaction, the reaction solution was concentrated under the reduced pressure, and 100 ml of methylene chloride was added to the residue. The precipitated solid was removed by filtration through a glass filter. The filtrate was concentrated under the reduced pressure. Methanol (100 ml) was added to the residue to prepare a suspension. The precipitated solid was collected on a glass filter to prepare 2.2 g of the title compound.
Physicochemical Properties of Intermediate 12
(1) Color and form: Colorless solid
(2) Molecular formula: $C_{21}H_{20}N_2O_4$
(3) Mass spectrum (FABMS): m/z 365 (M+H)$^+$
(4) $^1$H NMR spectrum (400 MHz, CDCl$_3$) δ (ppm): 1.37 (3H, t, CH$_2$CH$_3$), 2.35 (1H, ddt, pyrrolidine), 2.81 (1H, dq, pyrrolidine), 3.50 (1H, q, pyrrolidine), 3.70 (2H, m, pyrrolidine), 3.83 (1H, t, pyrrolidine), 4.32 (2H, q, CH$_2$CH$_3$), 5.06 (1H, quintet, pyrrolidine), 6.53 (2H, d, C$_6$H$_4$), 7.75 (2H, m, phthalimide), 7.86 (2H, m, phthalimide), 7.93 (2H, d, C$_6$H$_4$)

Intermediate 13: Ethyl 4-{(3R)-aminopyrrolidin-1-yl}benzoate

Methanol (80 ml) was added to 1.5 g of intermediate 12 to prepare a suspension. Hydrazine monohydrate (8.2 ml)

was added to the suspension, and the mixture was stirred at room temperature for 13 hr. The reaction solution was concentrated under the reduced pressure. The residue was purified by column chromatography on silica gel (development system: chloroform-methanol-concentrated aqueous ammonia=30:10:1) to prepare 800 mg of the title compound.

Physicochemical Properties of Intermediate 13
(1) Color and form: Colorless solid
(2) Molecular formula: $C_{13}H_{18}N_2O_2$
(3) Mass spectrum (FABMS): m/z 235 (M+H)$^+$
(4) $^1$H NMR spectrum (400 MHz, CD$_3$OD) δ (ppm): 1.35 (3H, t, CH$_2$CH$_3$), 1.87 (1H, m, pyrrolidine), 2.24 (1H, dq, pyrrolidine), 3.10 (1H, dd, pyrrolidine), 3.34 (1H, m, pyrrolidine), 3.55 (2H, m, pyrrolidine), 3.66 (1H, dq, pyrrolidine), 4.28 (2H, q, CH$_2$CH$_3$), 6.56 (2H, br d, C$_6$H$_4$), 7.83 (2H, br d, C$_6$H$_4$)

Intermediate 14: Ethyl 4-{(3R)-(pyrimidin-2-ylamino)pyrrolidin-1-yl}benzoate

Dimethylformamide (30 ml) was added to 735 mg of intermediate 13 to prepare a solution. 2-Bromopyrimidine (750 mg) was added to the solution. Further, 2.8 ml of diisopropylethylamine was added to the solution. The mixture was heated to 120° C., stirred for 11 hr, and then cooled to room temperature. Water (300 ml) was then added thereto, followed by extraction three times with 300 ml of methylene chloride. The combined organic layer was washed with 300 ml of water, dried over anhydrous sodium sulfate, and then concentrated under the reduced pressure. The residue was subjected to azeotropic distillation twice with toluene, and then purified by column chromatography on silica gel (development system: hexane-ethyl acetate=1:1) to prepare 590 mg of the title compound.

Physicochemical Properties of Intermediate 14
(1) Color and form: Colorless solid
(2) Molecular formula: $C_{17}H_{20}N_4O_2$
(3) Mass spectrum (FABMS): m/z 313 (M+H)$^+$
(4) $^1$H NMR spectrum (400 MHz, CDCl$_3$) δ (ppm): 1.37 (3H, t, CH$_2$CH$_3$), 2.09 (1H, dq, pyrrolidine), 2.42 (1H, m, pyrrolidine), 3.32 (1H, dd, pyrrolidine), 3.48 (1H, ddd, pyrrolidine), 3.57 (1H, dt, pyrrolidine), 3.79 (1H, dd, pyrrolidine), 4.32 (2H, q, CH$_2$CH$_3$), 4.70 (1H, dq, pyrrolidine), 6.52 (2H, br d, C$_6$H$_4$), 6.59 (1H, t, pyrimidine), 7.92 (2H, br d, C$_6$H$_4$), 8.30 (2H, d, pyrimidine)

Intermediate 15: 4-{(3R)-(Pyrimidin-2-ylamino)-pyrrolidin-1-yl}benzoic acid

Tetrahydrofuran (20 ml) and 6.4 ml of methanol were added to 200 mg of intermediate 14 to prepare a solution, and 6.4 ml of a 1 N aqueous sodium hydroxide solution was added to the solution. The mixture was stirred at 40° C. for 5 hr, and then concentrated under the reduced pressure. The residue was purified by column chromatography on silica gel (development system: chloroform-methanol-concentrated aqueous ammonia=30:10:1) to prepare 156 mg of the title compound.

Physicochemical Properties of Intermediate 15
(1) Color and form: Colorless solid
(2) Molecular formula: $C_{15}H_{16}N_4O_2$
(3) Mass spectrum (TSPMS): m/z 285 (M+H)$^+$
(4) $^1$H NMR spectrum (400 MHz, CD$_3$OD) δ (ppm): 2.04 (1H, m, pyrrolidine), 2.26 (1H, m, pyrrolidine), 3.23 (1H, dd, pyrrolidine), 3.35 (1H, m, pyrrolidine), 3.51 (1H, m, pyrrolidine), 3.63 (1H, dd, pyrrolidine), 4.51 (1H, dq, pyrrolidine), 6.52 (2H, br d, C$_6$H$_4$), 6.60 (1H, t, pyrimidine), 7.72 (2H, br d, C$_6$H$_4$), 8.30 (2H, d, pyrimidine)

Example 7 t-Butyl (2S)-benzenesulfonylamino-3-[4-{(3R)-(pyrimidin-2-ylamino)pyrrolidin-1-yl}benzoylamino]-propionate Dimethylformamide (3.5 ml) was added to 100 mg of intermediate 15 to prepare a suspension, and 137 mg of t-butyl (2S)-N-benzenesulfonyl-2,3-diaminopropionate hydrochloride was added to the solution. Further, 71 mg of 1-hydroxybenzotriazole, 77 μl of N-methylmorpholine, and 101 mg of 1-ethyl-3-(3-dimethylaminopropyl)carbodiimide hydrochloride were added thereto. The mixture was stirred at room temperature for 14 hr. The reaction solution was concentrated under the reduced pressure. The residue was subjected to azeotropic distillation five times with toluene, and then purified by column chromatography on silica gel (development system: methylene chloride-methanol=40:1) to prepare 224 mg of the title compound.

Physicochemical Properties of Compound Prepared in Example 7
(1) Color and form: Colorless solid
(2) Molecular formula: $C_{28}H_{34}N_6O_5S$
(3) Mass spectrum (TSPMS): m/z 567 (M+H)$^+$
(4) Specific rotation: $[\alpha]_D^{25}$ +52° (c 0.89, MeOH)
(5) $^1$H NMR spectrum (400 MHz, CDCl$_3$) δ (ppm): 1.28 (9H, s, t-Bu), 2.09 (1H, m, pyrrolidine), 2.42 (1H, m, pyrrolidine), 3.31 (1H, dd, pyrrolidine), 3.46 (1H, m, pyrrolidine), 3.57 (2H, m, pyrrolidine and CONHCH$_2$CH), 3.77 (1H, dd, pyrrolidine), 3.90 (2H, m, CONHCH$_2$CH and CONHCH$_2$CH), 4.70 (1H, dtt, pyrrolidine), 6.54 (2H, d, C$_6$H$_4$), 6.59 (1H, t, pyrimidine), 7.48 (2H, m, C$_6$H$_5$), 7.56 (1H, br t, C$_6$H$_5$), 7.69 (2H, d, C$_6$H$_4$), 7.86 (2H, m, C$_6$H$_5$), 8.31 (2H, d, pyrimidine)

Example 8

(2S)-Benzenesulfonylamino-3-[4-{(3R)-(pyrimidin-2-ylamino)pyrrolidin-1-yl}benzoylamino]-propionic acid Methylene chloride (1.0 ml) was added to 110 mg of the compound prepared in Example 7 to prepare a solution. Trifluoroacetic acid (1.0 ml) was added at 0° C. to the solution. The mixture was stirred at room temperature for 5 hr. The reaction solution was concentrated under the reduced pressure, and then purified by column chromatography on silica gel (development system: methylene chloride-methanol=15:1) to prepare 99 mg of the title compound.

Physicochemical Properties of Compound Prepared in Example 8
(1) Color and form: Colorless solid
(2) Molecular formula: $C_{24}H_{26}N_6O_5S$
(3) Mass spectrum (FABMS): m/z 511 (M+H)$^+$
(4) Specific rotation: $[\alpha]_D^{23}$ +98° (c 0.17, CH$_2$Cl$_2$-MeOH (1:1))
(5) $^1$H NMR spectrum (400 MHz, CD$_3$OD) δ (ppm): 2.16 (1H, ddt, pyrrolidine), 2.41 (1H, dddd, pyrrolidine), 3.31 (1H, m, pyrrolidine), 3.44 (1H, m, pyrrolidine), 3.50 (1H, dd, CONHCH$_2$CH), 3.55 (1H, m, pyrrolidine), 3.69 (1H, dd, CONHC$\underline{H}_2$CH), 3.72 (1H, dd, pyrrolidine), 4.16 (1H, dd, CONHCH$_2$C$\underline{H}$), 4.68 (1H, tt, pyrrolidine), 6.55 (2H, d, C$_6$H$_4$), 6.83 (1H, t, pyrimidine), 7.40 (2H, m, C$_6$H$_5$), 7.48 (1H, tt, C$_6$H$_5$), 7.62 (2H, br d, C$_6$H$_4$), 7.81 (2H, m, C$_6$H$_5$), 8.46 (2H, br d, pyrimidine)

Intermediate 16: 4-(1H-Benzimidazol-2-ylamino)-1-(ethoxycarbonyl)piperidine

Ethyl 4-amino-1-piperidine-carboxylate (11 ml) was added to 5.0 g of 2-chlorobenzimidazole. The mixture was stirred at 170° C. for 5 hr, and then cooled to room temperature. Hot chloroform (200 ml) was then added thereto to prepare a solution. Saturated aqueous sodium carbonate solution (500 ml) was added to the solution. The organic layer was separated, and the aqueous layer was extracted twice with 200 ml of chloroform. The combined organic layer was dried over anhydrous magnesium sulfate, and then concentrated under the reduced pressure. Ethyl acetate (100 ml) was added to the residue. The insolubles were collected by filtration through a glass filter, and washed with 100 ml of ethyl acetate to prepare 6.8 g of the title compound.
Physicochemical Properties of Intermediate 16
 (1) Color and form: Light brown solid
 (2) Molecular formula: C$_{15}$H$_{20}$N$_4$O$_2$
 (3) Mass spectrum (TSPMS): m/z 289 (M+H)$^+$
 (4) $^1$H NMR spectrum (400 MHz, CD$_3$OD) δ (ppm): 1.27 (3H, t, CH$_2$C$\underline{H}_3$), 1.47 (2H, ddd, piperidine), 2.07 (2H, br d, piperidine), 3.03 (2H, m, piperidine), 3.79 (1H, tt, piperidine), 4.13 (4H, m, piperidine and C$\underline{H}_2$CH$_3$), 7.03 (2H, dd, benzimidazole), 7.23 (2H, dd, benzimidazole)

Intermediate 17: 4-(1H-Benzimidazol-2-ylamino)piperidine

47% hydrobromic acid (2.5 ml) was added to 150 mg of intermediate 16 to prepare a solution which was then heated under reflux for 7.5 hr. The reaction solution was concentrated under the reduced pressure. The residue was purified by column chromatography on silica gel (development system: chloroform-methanol-concentrated aqueous ammonia=30:10:1) to prepare 91 mg of the title compound.
Physicochemical Properties of Intermediate 17
 (1) Color and form: Colorless solid
 (2) Molecular formula: C$_{12}$H$_{16}$N$_4$
 (3) Mass spectrum (EIMS): m/z 216
 (4) $^1$H NMR spectrum (400 MHz, CD$_3$OD) δ (ppm): 1.47 (2H, dq, piperidine), 2.07 (2H, m, piperidine), 2.74 (2H, dt, piperidine), 3.10 (2H, dt, piperidine), 3.72 (1H, tt, piperidine), 6.95 (2H, dd, benzimidazole), 7.17 (2H, dd, benzimidazole)

Intermediate 18: Ethyl 4-{4-(1H-benzimidazol-2-ylamino)piperidin-1-yl}benzoate

Dimethyl sulfoxide (5.2 ml) was added to 1.1 g of intermediate 17 to prepare a solution. Ethyl 4-fluorobenzoate (0.77 ml) was added to the solution. The mixture was stirred at 140° C. for 6.5 hr, and then cooled to room temperature. Saturated saline (300 ml) was added thereto, followed by extraction three times with 300 ml of methylene chloride. The combined organic layer was washed twice with 200 ml of saturated saline, dried over anhydrous sodium sulfate, and then concentrated under the reduced pressure. The residue was purified by column chromatography on silica gel (development system: methylene chloride-methanol=25:1) to prepare 940 mg of the title compound.
Physicochemical Properties of Intermediate 18
 (1) Color and form: Colorless solid
 (2) Molecular formula: C$_{2}$H$_{24}$N$_4$O$_2$
 (3) Mass spectrum (TSPMS): m/z 365 (M+H)$^+$
 (4) $^1$H NMR spectrum (400 MHz, CD$_3$OD) δ (ppm): 1.36 (3H, t, CH$_2$C$\underline{H}_3$), 1.63 (2H, m, piperidine), 2.13 (2H, br d, piperidine), 3.07 (2H, br t, piperidine), 3.84 (1H, tt, piperidine), 3.92 (2H, br d, piperidine), 4.30 (2H, q, C$\underline{H}_2$CH$_3$), 6.97 (2H, br d, C$_6$H$_4$), 7.00 (2H, dd, benzimidazole), 7.21 (2H, dd, benzimidazole), 7.87 (2H, br d, C$_6$H$_4$)

Intermediate 19: 4-{4-(1H-Benzimidazol-2-ylamino)-piperidin-1-yl}benzoic acid

Tetrahydrofuran (9.0 ml) and 3.0 ml of methanol were added to 103 mg of intermediate 18 to prepare a solution. A 1 N aqueous sodium hydroxide solution (3.0 ml) was added to the solution. The mixture was stirred at 40° C. for 3.5 hr, and then concentrated under the reduced pressure. The residue was purified by column chromatography on silica gel (development system: chloroform-methanol-concentrated aqueous ammonia=30:10:1) to prepare 92 mg of the title compound.
Physicochemical Properties of Intermediate 19
 (1) Color and form: Pale yellow solid
 (2) Molecular formula: C$_{19}$H$_{20}$N$_4$O$_2$
 (3) Mass spectrum (TSPMS): m/z 337 (M+H)$^+$
 (4) $^1$H NMR spectrum (400 MHz, DMSO-$_6$) δ (ppm): 1.53 (2H, br q, piperidine), 2.02 (2H, br d, piperidine), 3.00 (2H, br t, piperidine), 3.83 (1H, m, piperidine), 3.89 (2H, br d, piperidine), 6.84 (2H, m, benzimidazole), 6.97 (2H, d, C$_6$H$_4$), 7.11 (2H, m, benzimidazole), 7.75 (2H, d, C$_6$H$_4$)

Example 9 t-Butyl (2S)-benzenesulfonylamino-3-[4-{4-(1H-benzimidazol-2-ylamino)piperidin-1-yl}benzoylamino]-propionate Dimethylformamide (1.5 ml) was added to 50 mg of intermediate 19 to prepare a solution. t-Butyl (2S)-N-benzenesulfonyl-2,3-diaminopropionate hydrochloride (59 mg) was added to the solution. Further, 1-hydroxybenzotriazole (30 mg), 50 ml of N-methylmorpholine, and 43 mg of 1-ethyl-3-(3-dimethylaminopropyl)carbodiimide hydrochloride were added thereto. The mixture was stirred at room temperature for 14 hr. The reaction solution was concentrated under the reduced pressure. The residue was subjected to azeotropic distillation five times with toluene. The residue was purified by preparative thin-layer chromatography on silica gel (development system: methylene chloride-methanol-concentrated aqueous ammonia=100:10:1) to prepare 62 mg of the title compound.
Physicochemical Properties of Compound Prepared in Example 9
 (1) Color and form: Colorless solid
 (2) Molecular formula: C$_{32}$H$_{38}$N$_6$O$_5$S
 (3) Mass spectrum (TSPMS): m/z 619 (M+H)$^+$
 (4) Specific rotation: $[\alpha]_D^{24}$ +27° (c 0.97, MeOH)

(5) $^1$H NMR spectrum (400 MHz, CDCl$_3$) δ (ppm): 1.23 (9H, s, t-Bu), 1.26 (2H, m, piperidine), 1.93 (2H, br d, piperidine), 2.72 (2H, t, piperidine), 3.46 (2H, br d, piperidine), 3.64 (1H, m, piperidine), 3.81 (2H, m, CONHC$\underline{H}_2$CH), 4.07 (1H, dd, CONHCH$_2$C$\underline{H}$), 6.59 (2H, d, C$_6$H$_4$), 7.00 (2H, dd, benzimidazole), 7.17 (1H, m, benzimidazole), 7.28 (1H, m, benzimidazole), 7.37 (2H, t, C$_6$H$_5$), 7.48 (1H, t, C$_6$H$_5$), 7.58 (2H, d, C$_6$H$_4$), 7.77 (2H, br d, C$_6$H$_5$)

Example 10

(2S)-Benzenesulfonylamino-3-[4-{4-(1H-benzimidazol-2-ylamino)piperidin-1-yl}benzoylamino]-propionic acid Methylene chloride (0.5 ml) was added to 60 mg of the compound prepared in Example 9 to prepare a solution. Trifluoroacetic acid (0.5 ml) was added at room temperature to the solution. The mixture was stirred at that temperature for 3.5 hr before the reaction solution was concentrated under the reduced pressure. The residue was purified by preparative thin-layer chromatography on silica gel (development system: methylene chloride-ethanol-water-concentrated aqueous ammonia=8:8:11), and then by Sephadex LH-20 (development system: methanol-concentrated aqueous ammonia=9:1) to prepare 36 mg of the title compound.

Physicochemical Properties of Compound Prepared in Example 10

(1) Color and form: Colorless solid
(2) Molecular formula: C$_{28}$H$_{30}$N$_6$O$_5$S
(3) Mass spectrum (TSPMS): m/z 563 (M+H)$^+$
(4) Specific rotation: $[\alpha]_D^{26}$ +80° (c 1.11, MeOH-conc. NH$_4$OH (9:1))
(5) $^1$H NMR spectrum (400 MHz, CD$_3$OD) δ (ppm): 1.54 (2H, br q, piperidine), 2.01 (2H, br d, piperidine), 2.95 (2H, br t, piperidine), 3.34 (2H, m, CONHC$\underline{H}_2$CH), 3.85 (2H, m, piperidine and CONHCH$_2$C$\underline{H}$), 3.86 (2H, br d, piperidine), 6.89 (2H, m, benzimidazole), 6.96 (2H, d, C$_6$H$_4$), 7.14 (2H, dd, benzimidazole), 7.47 (2H, m, C$_6$H$_5$), 7.54 (1H, br t, C$_6$H$_5$), 7.62 (2H, d, C$_6$H$_4$), 7.76 (2H, br d, C$_6$H$_5$)

Example 11

Ethyl (3S)-[4-{4-(pyrimidin-2-ylamino)piperidin-1-yl}benzoylamino]pent-4-ynate

Dimethylformamide (1.0 ml) was added to 15 mg of intermediate 5 to prepare a solution. Ethyl (3S)-ethynyl-3-aminopropionate hydrochloride (11 mg) was added to the solution. Further, 10 mg of 1-hydroxybenzotriazole, 17 µl of N-methylmorpholine, and 15 mg of 1-ethyl-3-(3-dimethylaminopropyl)carbodiimide hydrochloride were added to thereto. The mixture was stirred at room temperature for 14 hr. The reaction solution was concentrated under the reduced pressure. The residue was subjected to azeotropic distillation five times with toluene, and then purified by preparative thin-layer chromatography on silica gel (development system: methylene chloride-methanol=7:1) to prepare 15 mg of the title compound.

Physicochemical Properties of Compound Prepared in Example 11

(1) Color and form: Colorless oil
(2) Molecular formula: C$_{23}$H$_{27}$N$_5$O$_3$
(3) Mass spectrum (TSPMS): m/z 422 (M+H)$^+$
(4) Specific rotation: $[\alpha]_D^{23}$ −7.9° (c 0.74, MeOH)
(5) $^1$H NMR spectrum (400 MHz, CDCl$_3$) δ (ppm): 1.29 (3H, t, CH$_2$C$\underline{H}_3$), 1.61 (2H, ddt, piperidine), 2.17 (2H, br dd, piperidine), 2.31 (1H, d, C≡CH), 2.82 (2H, dq, CONHCHC$\underline{H}_2$), 3.05 (2H, br t, piperidine), 3.80 (2H, br d, piperidine), 4.05 (1H, ddt, piperidine), 4.21 (2H, m, C$\underline{H}_2$CH$_3$), 5.32 (1H, m, CONHC$\underline{H}$CH$_2$), 6.54 (1H, t, pyrimidine), 6.91 (2H, d, C$_6$H$_4$), 7.71 (2H, d, C$_6$H$_4$), 8.28 (2H, d, pyrimidine)

Example 12

(3S)-]4-{4-(Pyrimidin-2-ylamino)piperidin-1-yl}benzoylamino]pent-4-ynic acid

Tetrahydrofuran (1.2 ml) and 0.4 ml of methanol were added to 15 mg of the compound prepared in Example 11 to prepare a solution. A 1 N aqueous sodium hydroxide solution (0.4 ml) was added to the solution. The mixture was stirred at 40° C. for 30 min, and then concentrated under the reduced pressure. The residue was purified by preparative thin-layer chromatography on silica gel (development system: methylene chloride-ethanol-water-concentrated aqueous ammonia=8:8:1:1), and then by Sephadex LH-20 (development system: methanol-concentrated aqueous ammonia=9:1) to prepare 13 mg of the title compound.

Physicochemical Properties of Compound Prepared in Example 12

(1) Color and form: Colorless solid
(2) Molecular formula: C$_{21}$H$_{23}$N$_5$O$_3$
(3) Mass spectrum (TSPMS): m/z 394 (M+H)$^+$
(4) Specific rotation: $[\alpha]_D^{25}$ +9.00° (c 0.65, MeOH-conc. NH$_4$OH (9:1))
(5) $^1$H NMR spectrum (400 MHz, CD$_3$OD) δ (ppm): 1.64 (2H, br q, piperidine), 2.08 (2H, br d, piperidine), 2.59 (1H, d, C≡CH), 2.67 (2H, dd, CONHCHC$\underline{H}_2$), 2.99 (2H, br t, piperidine), 3.89 (2H, br d, piperidine), 3.98 (1H, m, piperidine), 5.15 (1H, dt, CONHC$\underline{H}$CH$_2$), 6.59 (1H, t, pyrimidine), 6.98 (2H, br d, C$_6$H$_4$), 7.72 (2H, br d, C$_6$H$_4$), 8.26 (2H, d, pyrimidine)

Example 13 t-Butyl (2S)-(benzyloxycarbonyl)amino-3-[4-{4-(pyrimidin-2-ylamino)piperidin-1-yl}benzoylamino]-propionate Dimethylformamide (1.0 ml) and 1.0 ml of tetrahydrofuran were added to 64 mg of intermediate 5 to prepare a solution. t-Butyl (2S)-N-benzyloxycarbonyl-2,3-diaminopropionate hydrochloride (92 mg) was added to the solution. Further, 43 mg of 1-hydroxybenzotriazole, 71 µl of N-methylmorpholine, and 62 mg of 1-ethyl-3-(3-dimethylaminopropyl)carbodiimide hydrochloride were added thereto. The mixture was then stirred at room temperature for 14 hr. The reaction solution was then concentrated under the reduced pressure. The residue was subjected to azeotropic distillation five times with toluene, and then purified by column chromatography on silica gel (development system: methylene chloride-methanol=30:1) to prepare 123 mg of the title compound.

Physicochemical Properties of Compound Prepared in Example 13

(1) Color and form: Colorless oil
(2) Molecular formula: C$_{31}$H$_{38}$N$_6$O$_5$
(3) Mass spectrum (TSPMS): m/z 575 (M+H)$^+$
(4) Specific rotation: $[\alpha]_D^{23}$ −13° (c 0.71, MeOH)

(5) $^1$H NMR spectrum (400 MHz, CDCl$_3$) δ (ppm): 1.45 (9H, s, t-Bu), 1.60 (2H, br q, piperidine), 2.16 (2H, dd, piperidine), 3.03 (2H, ddd, piperidine), 3.80 (4H, m, piperidine and CONHC$\underline{H}_2$CH), 4.04 (1H, dtt, piperidine), 4.44 (1H, q, CONHCH$_2$C$\underline{H}$), 5.11 (2H, s, C$\underline{H}_2$C$_6$H$_5$), 6.54 (1H, t, pyrimidine), 6.88 (2H, d, C$_6$H$_4$), 7.30 (5H, m, CH$_2$C$_6$$\underline{H}_5$), 7.66 (2H, d, C$_6$H$_4$), 8.28 (2H, d, pyrimidine)

Example 14

(2S)-(Benzyloxycarbonyl)amino-3-]4-{4-(pyrimidin-2-ylamino)piperidin-1-yl}benzoylamino]-propionic acid Methylene chloride (0.5 ml) was added to 120 mg of the compound prepared in Example 13 to prepare a solution. Trifluoroacetic acid (0.5 ml) was added at 0° C. to the solution. The mixture was stirred at room temperature for 2 hr before the reaction solution was concentrated under the reduced pressure. The residue was purified by column chromatography on silica gel (development system: chloroform-methanol-acetic acid=50:10:1), and then by Sephadex LH-20 (development system: methanol-concentrated aqueous ammonia=9:1) to prepare 80 mg of the title compound.
Physicochemical Properties of Compound Prepared in Example 14
(1) Color and form: Colorless solid
(2) Molecular formula: C$_{27}$H$_{30}$N$_6$O$_5$
(3) Mass spectrum (TSPMS): m/z 519 (M+H)$^+$
(4) Specific rotation: $[\alpha]_D^{24}$ −16° (c 0.13, MeOH-conc. NH$_4$OH (10:1))
(5) $^1$H NMR spectrum (400 MHz, DMSO-d$_6$) δ (ppm): 1.54 (2H, br q, piperidine), 1.91 (2H, m, piperidine), 2.93 (2H, br t, piperidine), 3.57 (2H, t, CONHC$\underline{H}_2$CH), 3.86 (2H, br d, piperidine), 3.95 (1H, m, piperidine), 4.21 (1H, q, CONHCH$_2$C$\underline{H}$), 5.02 (2H, s, C$\underline{H}_2$C$_6$H$_5$), 6.59 (1H, t, pyrimidine), 6.96 (2H, d, C$_6$H$_4$), 7.33 (5H, m, CH$_2$C$_6$$\underline{H}_5$), 7.68 (2H, d, C$_6$H$_4$), 8.29 (2H, d, pyrimidine)

Example 15

(2S)-Amino-3-[4-{4-(1,4,5,6-tetrahydropyrimidin-2-ylamino)piperidin-1-yl}benzoyl-amino]propionic acid Acetic acid (5 ml) and 0.5 ml of concentrated hydrochloric acid were added to 10 mg of the compound prepared in Example 14 to prepare a solution, and 5.0 mg of 10% palladium-carbon was added to the solution. The mixture was then vigorously shaken under a hydrogen pressure of 3 atm at room temperature for two hr. The insolubles were collected by filtration, and then washed twice with water and twice with methanol. The filtrate was combined with the washings, followed by concentration under the reduced pressure. The residue was subjected to azeotropic distillation twice with toluene to prepare 10 mg of tetrahydrochloride of the title compound.
Physicochemical Properties of Compound Prepared in Example 15
(1) Color and form: Pale yellow solid
(2) Molecular formula: C$_{19}$H$_{28}$N$_6$O$_3$
(3) Mass spectrum (TSPMS): m/z 389 (M+H)$^+$
(4) $^1$H NMR spectrum (400 MHz, CD$_3$OD) (as tetrahydrochloride) δ (ppm): 1.91 (2H, m, tetrahydropyrimidine), 2.11 (2H, m, piperidine), 2.27 (2H, m, piperidine), 3.33 (4H, m, tetrahydropyrimidine), 3.76 (6H, m, piperidine and CONHC$\underline{H}_2$CH), 3.90 (1H, m, piperidine), 4.17 (1H, m, CONHCH$_2$C$\underline{H}$), 7.80 (2H, m, C$_6$H$_4$), 7.97 (2H, m, C$_6$H$_4$)

Example 16

(2S)-(Benzyloxycarbonyl)amino-3-[4-{4-(1,4,5,6-tetrahydropyrimidin-2-ylamino)piperidin-1-yl}-benzoylamino]propionic acid Acetone (0.5 ml) and 0.5 ml of water were added to 15 mg of the compound prepared in Example 15 to prepare a solution. Potassium carbonate (25 mg) was added to the solution. Further, benzyloxycarbonyl chloride (8.0 ml) was added thereto at room temperature. The mixture was stirred for 2 hr, and then concentrated under the reduced pressure. The residue was purified by column chromatography on silica gel (development system: n-butanol-acetic acid-water=8:1:1), and then by Sephadex G-10 (development system: 0.05 N hydrochloric acid) to prepare 6.7 mg of trihydrochloride of the title compound.
Physicochemical Properties of Compound Prepared in Example 16
(1) Color and form: Colorless solid
(2) Molecular formula: C$_{27}$H$_{34}$N$_6$O$_5$
(3) Mass spectrum (TSPMS): m/z 523 (M+H)$^+$
(4) Specific rotation: $[\alpha]_D^{25}$ −8.6° (c 0.29, MeOH) (as trihydrochloride)
(5) $^1$H NMR spectrum (400 MHz, CD$_3$OD) (as trihydrochloride) δ (ppm): 1.98 (2H, quintet, tetrahydropyrimidine), 2.15 (2H, m, piperidine), 2.34 (2H, br d, piperidine), 3.40 (4H, t, tetrahydropyrimidine), 3.79 (7H, m, piperidine and CONHC$\underline{H}_2$CH), 4.51 (1H, dd, CONHCH$_2$C$\underline{H}$), 5.08 (2H, dd, C$\underline{H}_2$C$_6$H$_5$), 7.29 (5H, m, CH$_2$C$_6$$\underline{H}_5$), 7.85 (2H, d, C$_6$H$_4$), 7.96 (2H, d, C$_6$H$_4$)

Example 17

(2S)-Butane-1-sulfonylamino-3-[4-{4-(1,4,5,6-tetrahydropyrimidin-2-ylamino)piperidin-1-yl}-benzoylamino]propionic acid Acetone (0.5 ml) and 0.5 ml of water were added to 12 mg of the compound prepared in Example 15 to prepare a solution. Potassium carbonate (14 mg) was added to the solution. Further, 3.0 ml of n-butanesulfonyl chloride was added thereto at room temperature. In addition, the mixture was stirred for 6 hr, during which time 6 mg of potassium carbonate and 6.0 μl of n-butanesulfonyl chloride were added every two hr. The mixture was then concentrated under the reduced pressure. The residue was purified by column chromatography on silica gel (development system: n-butanol-acetic acid-water=8:1:1), and then by Sephadex G-10 (development system: 0.05 N hydrochloric acid) to prepare 11 mg of di-n-butanesulfonate of the title compound.
Physicochemical Properties of Compound Prepared in Example 17
(1) Color and form: Colorless solid
(2) Molecular formula: C$_{23}$H$_{36}$N$_6$O$_5$S
(3) Mass spectrum (TSPMS): m/z 509 (M+H)$^+$
(4) $^1$H NMR spectrum (400 MHz, D$_2$O)(as di-n-butanesulfonate) δ (ppm): 0.63 (3H, t, NHSO$_2$CH$_2$CH$_2$CH$_2$CH$_3$), 0.79 (6H, t, n-BuSO$_3$H), 1.15 (2H, ddt, piperidine), 1.30 (4H, sextet, n-BuSO3H), 1.55 (6H, m, NHSO$_2$CH$_2$CH$_2$CH$_2$CH$_3$ and n-BuSO$_3$H), 1.85 (4H, m, tetrahydropyrimidine and NHSO$_2$CH$_2$CH$_2$CH$_2$CH$_3$), 2.20 (2H, br d, piperidine), 2.78 (4H, m, n-BuSO$_3$H), 3.02 (2H, t, NHSO$_2$CH$_2$CH$_2$CH$_2$CH$_3$), 3.23 (4H, t, tetrahydropyrimidine), 3.50 (3H, m, piperidine and CONHCH$_2$CH), 3.74 (4H, m, CONHCH$_2$CH and piperidine), 4.22 (1H, dd, CONHCH$_2$CH), 7.54 (2H, d, C$_6$H$_4$), 7.82 (2H, d, C$_6$H$_4$)

Example 18 t-Butyl (2S)-benzenesulfonylamino-3-[N-(cyclopropylmethyl)-N-[4-{4-(pyrimidin-2-ylamino-piperidin-1-yl}benzoyl]amino]propionate 50% methanol/methylene chloride (12 ml) was added to 116 mg of t-butyl (2S)-benzenesulfonyl-2,3-diaminopropionate to prepare a solution, and 31 mg of cyclopropanecarboxaldehyde was added to the solution. A minor amount of acetic acid was added thereto. The reaction solution was adjusted to pH 3 to 4. Sodium boron cyanohydride (48 mg) was then added thereto, and a reaction was allowed to proceed at room temperature for 2 hr. The reaction solution was concentrated under the reduced pressure. A saturated aqueous sodium hydrogencarbonate solution (10 ml) was added to the residue, followed by extraction twice each with 10 ml of chloroform. The chloroform layers were combined, and concentrated under the reduced pressure. The residue was purified by column chromatography on silica gel (development system: chloroform-methanol-concentrated aqueous ammonia=1000:30:1) to prepare 74 mg of t-butyl (2S)-N-benzenesulfonyl-3-N-cyclopropylmethyl-2,3-diaminopropionate.
Physicochemical Properties of t-butyl (2S)-N-benzenesulfonyl-3-N-cyclopropylmethyl-2,3-diaminopropionate (1) Color and form: Colorless oil
(2) Molecular formula: C$_{17}$H$_{26}$N$_2$O$_4$S
(3) Mass spectrum (TSPMS): m/z 355 (M+H)$^+$
(4) Specific rotation: [α]$_D^{25}$ +22° (c 1.0, CHCl$_3$)
(5) $^1$H NMR spectrum (400 MHz, CDCl$_3$) δ (ppm): 0.09 (2H, m, cyclopropyl), 0.45 (2H, m, cyclopropyl), 0.87 (1H, m, cyclopropyl), 2.41 (2H, m, C$_3$H$_5$CH$_2$), 2.86 (1H, dd, C$_3$H$_5$CH$_2$ NHCH$_2$), 2.93 (1H, dd, C$_3$H$_5$CH$_2$ NHCH$_2$), 3.91 (1H, dd, PhSO$_2$NHCH), 7.50 (2H, m, SO$_2$C$_6$H$_5$), 7.57 (1H, m, SO$_2$C$_6$H$_5$), 7.86 (2H, m, SO$_2$C$_6$H$_5$)

Dimethylformamide (0.5 ml) and 0.5 ml of methylene chloride were added to 17 mg of intermediate 5 to prepare a solution, and 20 mg of t-butyl (2S)-N-benzenesulfonyl-3-N-cyclopropylmethyl-2,3-diaminopropionate was added to the solution. Further, 9.0 mg of 1-hydroxybenzotriazole, 12 ml of N-methylmorpholine, and 13 mg of 1-ethyl-3-(3-dimethylaminopropyl)carbodiimide hydrochloride were added thereto. The mixture was stirred at room temperature for 4 days. The reaction solution was concentrated under the reduced pressure. The residue was subjected to azeotropic distillation five times with toluene, and then purified by preparative thin-layer chromatography on silica gel (development system: chloroform-methanol=10:1) to prepare 16 mg of the title compound.

Physicochemical Properties of Compound Prepared in Example 18

(1) Color and form: Colorless oil
(2) Molecular formula: C$_{33}$H$_{42}$N$_6$O$_5$S
(3) Specific rotation: [α]$_D^{25}$ +24° (c 0.80, MeOH)
(4) $^1$H NMR spectrum (400 MHz, CDCl$_3$) δ (ppm): 0.11 (2H, br d, CH$_2$C$_3$H$_5$), 0.53 (2H, br d, CH$_2$C$_3$H$_5$), 0.87 (1H, m, CH$_2$C$_3$H$_5$), 1.28 (9H, s, t-Bu), 1.63 (2H, br q, piperidine), 2.17 (2H, br d, piperidine), 3.01 (2H, br t, piperidine), 3.22 (1H, dd, CH$_2$C$_3$H$_5$), 3.36 (1H, br dd, CH$_2$C$_3$H$_5$), 3.74 (2H, br d, piperidine), 3.81 (1H, dd, CONHCH$_2$CH), 4.02 (2H, m, piperidine and CONHCH$_2$CH), 4.25 (1H, m, CONHCH$_2$CH), 6.54 (1H, t, pyrimidine), 6.91 (2H, d, C$_6$H$_4$), 7.37 (2H, d, C$_6$H$_4$), 7.47 (2H, m, C$_6$H$_5$), 7.54 (1H, br t, C$_6$H$_5$), 7.85 (2H, d, C$_6$H$_5$), 8.29 (2H, d, pyrimidine)

Example 19

(2S)-Benzenesulfonylamino-3-[N-(cyclopropylmethyl)-N-[4-[4-(pyrimidin-2-ylamino)-piperidin-1-yl}benzoyl]amino]propionic acid Methylene chloride (0.50 ml) was added to 31 mg of the compound prepared in Example 18 to prepare a solution, and 0.50 ml of trifluoroacetic acid was added at 0° C. to the solution. The temperature of the mixture was raised to room temperature, followed by stirring for 5 hr. The reaction solution was then concentrated under the reduced pressure. The residue was purified by preparative thin-layer chromatography on silica gel (development system: chloroform-methanol=5:1) to prepare 19 mg of the title compound.
Physicochemical Properties of Compound Prepared in Example 19

(1) Color and form: Colorless solid
(2) Molecular formula: C$_{29}$H$_{34}$N$_6$O$_5$S
(3) Mass spectrum (TSPMS): m/z 579 (M+H)$^-$
(4) Specific rotation: [α]$_D^{23}$ +29° (c 0.94, MeOH)
(5) $^1$H NMR spectrum (400 MHz, CD$_3$OD) δ (ppm): 0.08 (2H, m, CH$_2$C$_3$H$_5$), 0.49 (2H, m, CH$_2$C$_{3H5}$), 0.92 (1H, m, CH$_2$C$_3$H$_5$), 1.67 (2H, br q, piperidine), 2.09 (2H, br d, piperidine), 2.95 (2H, t, piperidine), 3.30 (2H, m, CH$_2$C$_3$H$_5$), 3.82 (3H, br d, piperidine and CONHCH$_2$CH), 3.96 (2H, m, piperidine and CONHCH$_2$CH), 4.21 (1H, m, CONHCH$_2$CH), 6.59 (1H, t, pyrimidine), 7.01 (2H, d, C$_6$H$_4$), 7.35 (2H, d, C$_6$H$_4$), 7.51 (2H, t, C$_6$H$_5$), 7.57 (1H, t, C$_6$H$_5$), 7.85 (2H, m, C$_6$H$_5$), 8.26 (2H, d, pyrimidine)

Example 20

(2S)-Benzenesulfonylamino-3-[N-(cyclopropylmethyl)-N-[4-{4-(1,4,5,6-tetrahydro-pyrimidin-2-ylamino)piperidin-1-yl}benzoyl]amino] propionic acid Acetic acid (5.0 ml) and 0.50 ml of concentrated hydrochloric acid were added to 23 mg of the compound prepared in Example 19 to prepare a solution, and 11 mg of 10% palladium-carbon was added to the solution. The mixture was vigorously shaken under a hydrogen pressure of 3 atm at room temperature for 1.5 hr. The insolubles were collected by filtration, and then washed twice with water and twice with methanol. The filtrate was combined with the washings, followed by concentration under the reduced pressure. The residue was subjected to azeotropic distillation twice with toluene, and purified by column chromatography on silica gel (development system: methylene chloride-ethanol-water-concentrated aqueous ammonia=15:10:1:1) and then by Sephadex LH-20 (development system: methanol) to prepare 5.3 mg of the title compound.

Physicochemical Properties of Compound Prepared in Example 20

(1) Color and form: Colorless solid
(2) Molecular formula: $C_{29}H_{38}N_6O_5S$
(3) Mass spectrum (FABMS): m/z 583 (M+H)$^+$
(4) Specific rotation: $[\alpha]_D^{23}$ +38° (c 0.27, MeOH)
(5) $^1$H NMR spectrum (400 MHz, CD$_3$OD) δ (ppm): 0.03 (2H, m, CH$_2$C$_3$H$_5$), 0.48 (2H, m, CH$_2$C$_3$H$_5$), 0.91 (1H, m, CH$_2$C$_3$H$_5$), 1.58 (2H, br q, piperidine), 1.95 (4H, m, piperidine and tetrahydropyrimidine), 2.89 (2H, br t, piperidine), 3.30 (1H, m, CH$_2$C$_3$H$_5$), 3.36 (4H, t, tetrahydropyrimidine), 3.48 (1H, tt, CH$_2$C$_3$H$_5$), 3.77 (3H, m, piperidine and CONHCH$_2$CH), 3.87 (2H, m, piperidine and CONHCH$_2$CH), 4.02 (1H, m, CONHCH$_2$CH), 6.99 (2H, d, C$_6$H$_4$), 7.38 (2H, m, C$_6$H$_4$), 7.50 (2H, m, C$_6$H$_5$), 7.57 (1H, br t, C$_6$H$_5$), 7.85 (2H, m, C$_6$H$_5$)

Intermediate 20: 4-[4-{(t-Butoxycarbonyl)amino}-piperidin-1-yl]benzoic acid 1,4-Dioxane (2.0 ml) and 1.0 ml of water were added to 154 mg of intermediate 3 to prepare a solution. A 1 N aqueous sodium hydroxide solution (1.0 ml) and 170 mg of di-t-butyl dicarbonate were added at room temperature to the solution. The mixture was stirred for 30 min. The reaction solution was then concentrated under the reduced pressure to prepare ethyl 4-(4-t-butoxycarbonylamino-piperidin-1-yl)benzoate. Subsequently, 9.0 ml of tetrahydrofuran and 3.0 ml of methanol were added to this compound to prepare a solution. A 1 N aqueous sodium hydroxide solution (6.0 ml) was added to the solution. The mixture was stirred at 50° C. for 4.5 hr, and then adjusted to pH 6 by the addition of 1 N hydrochloric acid. Water (100 ml) was added thereto, followed by extraction three times with 150 ml of ethyl acetate. The combined organic layer was dried over anhydrous magnesium sulfate, and then concentrated under the reduced pressure to prepare 168 mg of the title compound.

Physicochemical Properties of Compound as Intermediate 20

(1) Color and form: Colorless solid
(2) Molecular formula: $C_{17}H_{24}N_2O_4$
(3) Mass spectrum (EIMS): m/z 320
(4) $^1$H NMR spectrum (400 MHz, CD$_3$OD) δ (ppm): 1.44 (9H, s, t-Bu), 1.51 (2H, m, piperidine), 1.93 (2H, br d, piperidine), 2.95 (2H, dt, piperidine), 3.55 (1H, m, piperidine), 3.88 (2H, br d, piperidine), 6.94 (2H, d, C$_6$H$_4$), 7.85 (2H, d, C$_6$H$_4$)

Intermediate 21: t-Butyl (2S)-benzenesulfonylamino-3-[4-[4-{(t-butoxycarbonyl)amino}piperidin-1-yl]benzoyl-amino]propionate Dimethylformamide (7.0 ml) was added to 81 mg of intermediate 20 to prepare a solution, and 77 mg of t-butyl (2S)-N-benzenesulfonyl-2,3-diaminopropionate hydrochloride was added to the solution. Further, 56 mg of 1-hydroxybenzotriazole, 0.15 ml of N-methylmorpholine, and 98 mg of 1-ethyl-3-(3-dimethylaminopropyl)carbodiimide hydrochloride were added thereto. The mixture was stirred at room temperature for 22 hr. A saturated aqueous sodium hydrogencarbonate solution (100 ml) was added to stop the reaction, followed by extraction twice with 150 ml of methylene chloride. The combined organic layer was dried over anhydrous magnesium sulfate, and then concentrated under the reduced pressure. The residue was purified by column chromatography on silica gel (development system: hexane-ethyl acetate=1:2) to prepare 111 mg of the title compound.

Physicochemical Properties of Compound as Intermediate 21

(1) Color and form: Colorless solid
(2) Molecular formula: $C_{30}H_{42}N_4O_7S$
(3) Mass spectrum (TSPMS): m/z 603 (M+H)$^+$
(4) $^1$H NMR spectrum (400 MHz, CDCl$_3$) δ (ppm): 1.28 (9H, s, t-Bu), 1.45 (9H, s, t-Bu), 1.48 (2H, br d, piperidine), 2.05 (2H, br d, piperidine), 2.95 (2H, br t, piperidine), 3.55 (1H, ddd, CONHCH$_2$CH), 3.68 (1H, m, piperidine), 3.77 (2H, br d, piperidine), 3.89 (2H, m, CONHCH$_2$CH), 6.89 (2H, d, C$_6$H$_4$), 7.50 (2H, m, C$_6$H$_5$), 7.57 (1H, m, C$_6$H$_5$), 7.69 (2H, d, C$_6$H$_4$), 7.84 (2H, m, C$_6$H$_5$)

Intermediate 22: t-Butyl 3-{4-(4-aminopiperidin-1-yl)benzoylamino}-(2S)-(benzenesulfonylamino)propionate Saturated hydrochloric acid-methanol (1.0 ml) was added to 10 mg of intermediate 21 to prepare a solution. The solution was stirred at room temperature for 4 hr before the reaction solution was poured into a mixed solution composed of 5.0 ml of methanol and 5.0 ml of concentrated aqueous ammonia, followed by concentration under the reduced pressure. The residue was purified by preparative thin-layer chromatography on silica gel (development system: chloroform-methanol-concentrated aqueous ammonia=30:10:1) to prepare 7.0 mg of the title compound.

Physicochemical Properties of Intermediate 22

(1) Color and form: Colorless solid
(2) Molecular formula: $C_{25}H_{34}N_4O_5S$
(3) Mass spectrum (TSPMS): m/z 502 (M+H)$^+$
(4) $^1$H NMR spectrum (400 MHz, CD$_3$OD) δ (ppm): 1.22 (9H, s, t-Bu), 1.47 (2H, dq, piperidine), 1.93 (2H, br d, piperidine), 2.87 (3H, m, piperidine), 3.49 (1H, dd, CONHCH$_2$CH), 3.64 (1H, dd, CONHCH$_2$CH), 3.88 (2H, br d, piperidine), 4.11 (1H, dd, CONHCH$_2$CH), 6.95 (2H, br d, C$_6$H$_4$CO), 7.47 (2H, br t, C$_6$H$_5$), 7.54 (1H, br t, C$_6$H$_5$), 7.65 (2H, br d, C$_6$H$_4$CO), 7.83 (2H, m, C$_6$H$_5$)

Example 21 t-Butyl (2S)-benzenesulfonylamino-3-{4-(4-guanidinopiperidin-1-yl)benzoylamino}propionate Dioxane (0.1 ml) and 0.1 ml of water were added to 18.8 mg of intermediate 22 to prepare a suspension. Diisopropylethylamine (0.03 ml) and 22 mg of 1 H-pyrazole-1-carboxyamidine hydrochloride were added to the suspension. The mixture was stirred at room temperature for 31 hr. The reaction solution was then concentrated under the reduced pressure. The residue was purified by preparative thin-layer chromatography on silica gel (development system: chloroform-methanol-concentrated aqueous ammonia=30:10:1) to prepare 17.1 mg of the title compound.

Physicochemical Properties of Compound Prepared in Example 21

(1) Color and form: Colorless solid
(2) Molecular formula: $C_{26}H_{36}N_6O_5S$ (3) Mass spectrum (FABMS): m/z 544 (M+H)+
(4) Specific rotation: $[\alpha]_D^{25}$ +24° (c 0.85, MeOH)
(5) $^1$H NMR spectrum (400 MHz, CD$_3$OD) δ (ppm): 1.23 (9H, s, t-Bu), 1.62 (2H, dq, piperidine), 2.04 (2H, br d, piperidine), 2.99 (2H, ddd, piperidine), 3.48 (1H, dd, CONHC$\underline{H}_2$CH), 3.63 (2H, m, CONHC$\underline{H}_2$CH and piperidine), 3.88 (2H, br d, piperidine), 4.12 (1H, dd, CONHCH$_2$C$\underline{H}$), 6.98 (2H, br d, C$_6$H$_4$CO), 7.47 (2H, br t, C$_6$H$_5$), 7.54 (1H, br t, C$_6$H$_5$), 7.68 (2H, d, C$_6$H$_4$CO), 7.83 (2H, m, C$_6$H$_5$)

Example 22

(2S)-Benzenesulfonylamino-3-{4-(4-guanidinopiperidin-1-yl)benzoylamino}propionic acid Methylene chloride (0.5 ml) was added to 17.0 mg of the compound prepared in Example 21 to prepare a solution, and 0.5 ml of trifluoroacetic acid was added to the solution. The mixture was stirred at room temperature for 3 hr. The reaction solution was then concentrated under the reduced pressure. The residue was purified by column chromatography on silica gel (development system: methylene chloride-ethanol-concentrated aqueous ammonia-water= 8:8:1:1), and then by Sephadex LH-20 (development system: methanol-concentrated aqueous ammonia=10:1) to prepare 10.2 mg of the title compound.

Physicochemical Properties of Compound Prepared in Example 22

(1) Color and form: Colorless solid
(2) Molecular formula: C$_{22}$H$_{28}$N$_6$O$_5$S
(3) Mass spectrum (TSPMS): m/z 488 (M+H)+
(4) Specific rotation: $[\alpha]_D^{23}$ +126° (c 0.05, DMSO)
(5) $^1$H NMR spectrum (400 MHz, CD$_3$OD) δ (ppm): 1.61 (2H, br q, piperidine), 2.01 (2H, br d, piperidine), 2.96 (2H, t, piperidine), 3.60 (3H, m, CONHC$\underline{H}_2$CH and piperidine), 3.74 (1H, dd, CONHCH$_2$C$\underline{H}$), 3.85 (2H, br d, piperidine), 6.96 (2H, br d, C$_6$H$_4$CO), 7.47 (2H, br t, C$_6$H$_5$), 7.54 (1H, br t, C$_6$H$_5$), 7.70 (2H, br d, C$_6$H$_4$CO), 7.85 (2H, dd, C$_6$H$_5$)

Example 23 t-Butyl 3-[4-{4-(1H-benzimidazol-2-ylamino)piperidin-1-yl}benzoylamino]-(2S)-{(benzyloxy-carbonyl)amino}propionate Dimethylformamide (1.3 ml) was added to 42 mg of intermediate 19 to prepare a solution. t-Butyl (2S)-N-benzyloxycarbonyl-2,3-diaminopropionate hydrochloride (53.7 mg) was added to the solution. Further, 25.4 mg of 1-hydroxybenzotriazole, 41 μl of N-methylmorpholine, and 36 mg of 1-ethyl-3-(3-dimethylaminopropyl)carbodiimide hydrochloride were added thereto. The mixture was stirred at room temperature for 19 hr. A saturated aqueous sodium hydrogencarbonate solution (50 ml) was added to stop the reaction, followed by extraction three times with 50 ml of methylene chloride. The combined organic layer was dried over anhydrous sodium sulfate, and concentrated under the reduced pressure. The residue was purified by preparative thin-layer chromatography on silica gel (development system: methylene chloride-methanol=7:1) to prepare 58.8 mg of the title compound.

Physicochemical Properties of Compound Prepared in Example 23

(1) Color and form: Colorless solid
(2) Molecular formula: C$_{34}$H$_{40}$N$_6$O$_5$
(3) Mass spectrum (TSPMS): m/z 613 (M+H)+
(4) Specific rotation: $[\alpha]_D^{23}$ −11° (c 1.0, MeOH)
(5) $^1$H NMR spectrum (400 MHz, CD$_3$OD) δ (ppm): 1.42 (9H, s, t-Bu), 1.67 (2H, br q, piperidine), 2.15 (2H, m, piperidine), 3.06 (2H, br t, piperidine), 3.72 (2H, d, CONHC$\underline{H}_2$CH), 3.85 (3H, m, piperidine), 4.36 (1H, t, CONHCH$_2$C$\underline{H}$), 5.08 (2H, dd, C$\underline{H}_2$C$_6$H$_5$), 6.99 (2H, d, C$_6$H$_4$CO), 7.02 (2H, m, benzimidazole), 7.23 (2H, m, benzimidazole), 7.31 (5H, m, CH$_2$C$_6\underline{H}_5$), 7.70 (2H, d, C$_6$H$_4$CO)

Example 24

3-[4-{4-(1H-Benzimidazol-2-ylamino)piperidin-1-yl}benzoylamino]-(2S)-{(benzyloxy-carbonyl)amino}propionic acid Methylene chloride (0.5 ml) was added to 37.4 mg of the compound prepared in Example 23 to prepare a solution. Trifluoroacetic acid (0.5 ml) was added to the solution. The mixture was stirred at room temperature for 1.5 hr. The reaction solution was concentrated under the reduced pressure. The residue was purified by column chromatography on silica gel (development system: methylene chloride-ethanol-concentrated aqueous ammonia-water=8:8:1:1) and then by Sephadex LH-20 (development system: methanol-concentrated aqueous ammonia=10:1) to prepare 7.0 mg of the title compound.

Physicochemical Properties of Compound Prepared in Example 24

(1) Color and form: Colorless solid
(2) Molecular formula: C$_{30}$H$_{32}$N$_6$O$_5$
(3) Mass spectrum (FABMS): m/z 557 (M+H)+
(4) Specific rotation: $[\alpha]_D^{23}$ −9.5° (c 0.35, MeOH-conc. NH$_4$OH (10:1))
(5) $^1$H NMR spectrum (400 MHz, DMSO-d$_6$) δ (ppm): 1.54 (2H, br q, piperidine), 2.01 (2H, br d, piperidine), 2.96 (2H, br t, piperidine), 3.56 (2H, m, CONHC$\underline{H}_2$CH), 3.83 (3H, m, piperidine and CONHCH$_2$C$\underline{H}$), 4.18 (1H, m, piperidine), 5.02 (2H, s, C$\underline{H}_2$C$_6$H$_5$), 6.97 (2H, d, C$_6$H$_4$CO), 7.11 (4H, m, benzimidazole and CH$_2$C$_6\underline{H}_5$), 7.32 (5H, m, benzimidazole and CH$_2$C$_6\underline{H}_5$), 7.38 (2H, d, C$_6$H$_4$CO)

Example 25 t-Butyl (2S)-(benzyloxycarbonyl)amino-3-[4-[4-{(1-t-butoxycarbonyl-1H-benzimidazol-2-yl)amino}-piperidin-1-yl]benzoylamino]propionate Methylene chloride (1.0 ml) was added to 50 mg of the compound prepared in Example 23 to prepare a solution. Triethylamine (34 μl) and 47 μl of di-t-butyl dicarbonate were added at room temperature to the solution. The mixture was stirred for one hr. A saturated aqueous sodium hydrogencarbonate solution (30 ml) was added to the reaction solution, followed by extraction three times with 30 ml of methylene chloride. The combined organic layer was then dried over anhydrous sodium sulfate, and concentrated under the reduced pressure. The residue was purified by preparative thin-layer chromatography on silica gel (development system: methylene chloride-methanol=7:1) to prepare 60 mg of the title compound.

Physicochemical Properties of Compound Prepared in Example 25
(1) Color and form: Colorless oil
(2) Molecular formula: $C_{39}H_{48}N_6O_7$
(3) Mass spectrum (FABMS): m/z 713 (M+H)$^+$
(4) $^1$H NMR spectrum (400 MHz, CDCl$_3$) δ (ppm): 1.46 (9H, s, t-Bu), 1.70 (9H, s, t-Bu), 1.96 (2H, br s, piperidine), 2.27 (2H, br dd, piperidine), 3.12 (2H, br t, piperidine), 3.80 (4H, m, CONHC$\underline{H}_2$CH and piperidine), 4.19 (1H, m, piperidine), 4.44 (1H, dd, CONHCH$_2$C$\underline{H}$), 5.11 (2H, s, C$\underline{H}_2$C$_6$H$_4$), 6.89 (2H, d, C$_6$H$_4$CO), 7.03 (1H, dt, benzimidazole), 7.19 (1H, dt, benzimidazole), 7.33 (5H, m, CH$_2$C$_6$H$_5$), 7.39 (1H, d, benzimidazole), 7.59 (1H, d, benzimidazole), 7.67 (2H, d, C$_6$H$_4$CO)

Example 26 t-Butyl (2S)-amino-3-[4-[4-{(1-t-butoxycarbonyl-1H-benzimidazol-2-yl)amino}piperidin-1-yl]benzoylamino]propionate Tetrahydrofuran (17.5 ml), 5.0 ml of water, and 2.5 ml of acetic acid were added to 50 mg of the compound prepared in Example 25 to prepare a solution. 10% palladium-carbon (50 mg) was added to the solution. The mixture was vigorously stirred under a hydrogen pressure of one atm at room temperature for 14 hr. The insolubles were then collected by filtration, and washed twice with ethanol. The filtrate was combined with the washings, followed by neutralization with a 1 N aqueous sodium hydroxide solution and concentration at 30° C. under the reduced pressure to remove tetrahydrofuran and ethanol. Salt was added to the aqueous solution to prepare a saturated solution which was then extracted three times with 50 ml of methylene chloride. The combined organic layer was dried over anhydrous sodium sulfate, and concentrated under the reduced pressure. The residue was purified by preparative thin-layer chromatography on silica gel (development system: methylene chloride-methanol=7:1) to prepare 26.1 mg of the title compound.

Physicochemical Properties of Compound Prepared in Example 26
(1) Color and form: Colorless oil
(2) Molecular formula: $C_{31}H_{42}N_6O_5$
(3) Mass spectrum (TSPMS): m/z 579 (M+H)$^+$
(4) Specific rotation: $[\alpha]_D^{23}$ +14° (c 0.97, MeOH)
(5) $^1$H NMR spectrum (400 MHz, CDCl$_3$) δ (ppm): 1.47 (9H, s, t-Bu), 1.70 (9H, s, t-Bu), 1.72 (2H, br dq, piperidine), 2.28 (2H, br dd, piperidine), 3.12 (2H, ddd, piperidine), 3.47 (1H, m, CONHC$\underline{H}_2$CH), 3.61 (1H, dd, CONHC$\underline{H}_2$CH), 3.81 (3H, m, piperidine and CONHCH$_2$C$\underline{H}$), 4.20 (1H, m, piperidine), 6.92 (2H, d, C$_6$H$_4$CO), 7.04 (1H, ddd, benzimidazole), 7.20 (1H, dt, benzimidazole), 7.39 (1H, d, benzimidazole), 7.60 (1H, d, benzimidazole), 7.70 (2H, d, C$_6$H$_4$CO)

Example 27 t-Butyl (2S)-(butane-1-sulfonylamino)-3-[4-[4-{(1-t-butoxycarbonyl-1H-benzimidazol-2-yl)amino}piperidin-1-yl]benzoylamino]propionate Dimethylformamide (0.5 ml) was added to 10.5 mg of the compound prepared in Example 26 to prepare a solution. Diisopropylethylamine (6.5 μl) and 2.4 μl of n-butanesulfonyl chloride were added at room temperature to the solution. The mixture was stirred for 1.5 hr. Piperazine (5 mg) was added thereto, followed by stirring for 5 min. A saturated aqueous sodium hydrogencarbonate solution (30 ml) was added to the reaction solution, followed by extraction three times with 30 ml of ethyl acetate. The combined organic layer was dried over anhydrous sodium sulfate, and concentrated under the reduced pressure. The residue was purified by preparative thin-layer chromatography on silica gel (development system: hexane-ethyl acetate=1:2) to prepare 10.5 mg of the title compound.

Physicochemical Properties of Compound Prepared in Example 27
(1) Color and form: Colorless oil
(2) Molecular formula: $C_{35}H_{50}N_6O_7S$
(3) Mass spectrum (TSPMS): m/z 699 (M+H)$^+$
(4) Specific rotation: $[\alpha]_D^{23}$ −1.5° (c 0.65, MeOH)
(5) $^1$H NMR spectrum (400 MHz, CDCl$_3$) δ (ppm): 0.92 (3H, t, CH$_2$CH$_2$CH$_2$C$\underline{H}_3$) 1.42 (2H, sextet, CH$_2$CH$_2$C$\underline{H}_2$CH$_3$), 1.50 (9H, s, t-Bu), 1.70 (9H, s, t-Bu), 1.70 (2H, m, piperidine), 1.78 (2H, sextet, CH$_2$C$\underline{H}_2$CH$_2$CH$_3$), 2.28 (2H, br dd, piperidine), 3.03 (2H, ddd, C$\underline{H}_2$CH$_2$CH$_2$CH$_3$), 3.13 (2H, ddd, piperidine), 3.68 (1H, ddd, CONHC$\underline{H}_2$CH), 3.79 (2H, br d, piperidine), 3.90 (1H, ddd, CONHC$\underline{H}_2$CH), 4.19 (1H, dt, CONHCH$_2$C$\underline{H}$), 4.21 (1H, m, piperidine), 6.92 (2H, d, C$_6$H$_4$CO), 7.13 (1H, dt, benzimidazole), 7.20 (1H, dt, benzimidazole), 7.39 (1H, d, benzimidazole), 7.59 (1H, d, benzimidazole), 7.70 (2H, d, C$_6$H$_4$CO)

Example 28

(2S)-Butane-1-sulfonylamino-3-[4-{4-(1H-benzimidazol-2-ylamino)piperidin-1-yl}benzoylamino]-propionic acid Methylene chloride (0.5 ml) was added to 15.2 mg of the compound prepared in Example 27 to prepare a solution. Anisole (5 μl) and 0.5 ml of trifluoroacetic acid were added to the solution. The mixture was stirred at room temperature for one hr. The reaction solution was concentrated under the reduced pressure. The residue was purified by preparative thin-layer chromatography on silica gel (development system: chloroform-methanol-concentrated aqueous ammonia=30:10:1) and then by Sephadex LH-20 (development system: methanol-concentrated aqueous ammonia=10:1) to prepare 7.5 mg of the title compound.

Physicochemical Properties of Compound Prepared in Example 28
(1) Color and form: Colorless solid
(2) Molecular formula: $C_{26}H_{34}N_6O_5S$
(3) Mass spectrum (TSPMS): m/z 543 (M+H)$^+$
(4) Specific rotation: $[\alpha]_D^{23}$ 5.9° (c 0.38, MeOH-conc. NH$_4$OH (10:1))
(5) $^1$H NMR spectrum (400 MHz, CD$_3$OD) δ (ppm): 0.89 (3H, t, CH$_2$CH$_2$CH$_2$C$\underline{H}_3$) 1.39 (2H, sextet, CH$_2$CH$_2$C$\underline{H}_2$CH$_3$), 1.75 (4H, m, piperidine and CH$_2$C$\underline{H}_2$CH$_2$CH$_3$), 2.12 (2H, br d, piperidine), 3.02 (4H, m, C$\underline{H}_2$CH$_2$CH$_2$CH$_3$ and piperidine), 3.63 (1H, dd, CONHC$\underline{H}_2$CH), 3.75 (2H, m, piperidine and CONHC$\underline{H}_2$CH), 3.88 (2H, br d, piperidine), 4.04 (1H, dd, CONHCH$_2$C$\underline{H}$), 6.98 (2H, d, C$_6$H$_4$CO), 7.23 (2H, dd, benzimidazole), 7.36 (2H, dd, benzimidazole), 7.75 (2H, d, C$_6$H$_4$CO)

Example 29

(2S)-Amino-3-[4-{4-(1H-benzimidazol-2-ylamino)piperidin-1-yl}benzoylamino]propionic acid Methylene chloride (1.0 ml) was added to 21 mg of the compound prepared in Example 26 to prepare a solution.

Trifluoroacetic acid (0.1 ml) was added to the solution. The mixture was stirred at room temperature for 24 hr. The reaction solution was concentrated under the reduced pressure. The residue was purified by preparative thin-layer chromatography on silica gel (development system: methylene chloride-ethanol-concentrated aqueous ammonia-water=8:8:1:1) and then by Sephadex LH-20 (development system: methanol-concentrated aqueous ammonia=10:1) to prepare 8.7 mg of the title compound.

Physicochemical Properties of Compound Prepared in Example 29
(1) Color and form: Colorless solid
(2) Molecular formula: $C_{22}H_{26}N_6O_3$
(3) Mass spectrum (TSPMS): m/z 423 (M+H)$^+$
(4) Specific rotation: $[\alpha]_D^{23}$ 2.8° (c 0.44, MeOH-conc. NH$_4$OH (1:1))
(5) $^1$H NMR spectrum (400 MHz, CD$_3$OD) δ (ppm): 1.71 (2H, br dq, piperidine), 2.17 (2H, br d, piperidine), 3.06 (2H, br ddd, piperidine), 3.82 (4H, m, CONHC$\underline{H}_2$C$\underline{H}$, and piperidine), 3.95 (2H, br d, piperidine), 7.02 (2H, d, C$_6$H$_4$CO), 7.13 (2H, dd, benzimidazole), 7.29 (2H, dd, benzimidazole), 7.77 (2H, d, C$_6$H$_4$CO)

Example 30 t-Butyl 3-[4-[4-{(1-t-butoxycarbonyl-1H-benzimidazol-2-yl)amino}piperidin-1-yl]benzoylaminol-(2S)-{(2,4,6-trimethylbenzenesulfonyl)amino}propionate Dimethylformamide (0.5 ml) was added to 20.2 mg of the compound prepared in Example 26 to prepare a solution. Diisopropylethylamine (10.3 µl) and 6.3 mg of 2,4,6-trimethylbenzenesulfonyl chloride were added at room temperature to the solution. The mixture was stirred for 1.5 hr. Then, 5 mg of piperazine was added, and the mixture was stirred for additional 5 min. A saturated aqueous sodium hydrogencarbonate solution (30 ml) was added to the reaction solution, followed by extraction three times with 30 ml of ethyl acetate. The combined organic layer was dried over anhydrous sodium sulfate, and concentrated under the reduced pressure. The residue was purified by preparative thin-layer chromatography on silica gel (development system: hexane-ethyl acetate=1:2) to prepare 10.0 mg of the title compound.

Physicochemical Properties of Compound Prepared in Example 30
(1) Color and form: Colorless oil
(2) Molecular formula: $C_{40}H_{52}N_6O_7S$
(3) Mass spectrum (TSPMS): m/z 761 (M+H)$^+$
(4) Specific rotation: $[\alpha]_D^3$ +20° (c 0.50, MeOH)
(5) $^1$H NMR spectrum (400 MHz, CDCl$_3$) δ (ppm): 1.30 (9H, s, t-Bu), 1.70 (9H, s, t-Bu), 1.72 (2H, m, piperidine), 2.27 (3H, s, C$_6$H$_2$M$\underline{e}$), 2.28 (2H, m, piperidine), 2.65, (6H, s, C$_6$H$_2$M$\underline{e}$), 3.14 (2H, ddd, piperidine), 3.58 (1H, ddd, CONHC$\underline{H}_2$CH), 3.83 (4H, m, piperidine and CONHCH$_2$C$\underline{H}$), 4.21 (1H, m, piperidine), 6.92 (2H, d, C$_6$H$_4$CO), 6.93 (2H, s, C$_6$H$_2$Me), 7.04 (1H, ddd, benzimidazole), 7.20 (1H, dt, benzimidazole), 7.40 (1H, d, benzimidazole), 7.60 (1H, d, benzimidazole), 7.70 (2H, d, C$_6$H$_4$CO)

Example 31

3-[4-{4-(1H-Benzimidazol-2-ylamino)piperidin-1-yl}benzoylamino]-(2S)-{(2,4,6-trimethylbenzenesulfonyl)amino}propionic acid Methylene chloride (0.5 ml) was added to 10 mg of the compound prepared in Example 30 to prepare a solution.

Anisole (3 µl) and 0.5 ml of trifluoroacetic acid were added at 0° C. to the solution. The mixture was stirred at room temperature for four hr. The reaction solution was concentrated under the reduced pressure. The residue was purified by preparative thin-layer chromatography on silica gel (development system: chloroform-methanol-concentrated aqueous ammonia=30:10:1) and then by Sephadex LH-20 (development system: methanol-concentrated aqueous ammonia=10:1) to prepare 5.0 mg of the title compound.

Physicochemical Properties of Compound Prepared in Example 31
(1) Color and form: Colorless solid
(2) Molecular formula: $C_{31}H_{36}N_6O_5S$
(3) Mass spectrum (TSPMS): m/z 605 (M+H)$^+$
(4) Specific rotation: $[\alpha]_D^{27}$ 55° (c 0.25, MeOH-conc. NH$_4$OH (1:1))
(5) $^1$H NMR spectrum (400 MHz, CD$_3$OD) δ (ppm): 1.70 (2H, br q, piperidine), 2.15 (2H, br d, piperidine), 2.22 (3H, s, C$_6$H$_2$M$\underline{e}$), 2.63 (6H, S, C$_6$H$_2$M$\underline{e}$), 3.05 (2H, br t, piperidine), 3.62 (3H, m, CONHC$\underline{H}_2$C$\underline{H}$), 3.81 (1H, m, piperidine), 3.92 (2H, br d, piperidine), 6.92 (2H, s, C$_6$$\underline{H}_2$Me) 6.99 (2H, d, C$_6$H$_4$CO), 7.10 (2H, dd, benzimidazole), 7.27 (2H, dd, benzimidazole), 7.69 (2H, d, C$_6$H$_4$CO)

Example 32 t-Butyl 3-[4-[4-{(1-t-butozycarbonyl-1H-benzimidazol-2-yl)amino}piperidin-1-yl]benzoylaminol-(2S)-{(4-fluorobenzenesulfonyl)amino}propionate Dimethylformamide (0.5 ml) was added to 26.1 mg of the compound prepared in Example 26 to prepare a solution. Diisopropylethylamine (16 µl) and 8.8 mg of 4-fluorobenzenesulfonyl chloride were added at room temperature to the solution. The mixture was stirred for 2.5 hr, and 5 mg of piperazine was then added thereto, followed by stirring for additional 5 min. A saturated aqueous sodium hydrogencarbonate solution (30 ml) was added to the reaction solution, followed by extraction three times with 30 ml of ethyl acetate. The combined organic layer was dried over anhydrous sodium sulfate, and concentrated under the reduced pressure. The residue was purified by preparative thin-layer chromatography on silica gel (development system: hexane-ethyl acetate=1:2) to prepare 23.0 mg of the title compound.

Physicochemical Properties of Compound Prepared in Example 32
(1) Color and form: Colorless oil
(2) Molecular formula: $C_{37}H_{45}N_6O_7FS$
(3) Mass spectrum (TSPMS): m/z 737 (M+H)$^+$
(4) Specific rotation: $[\alpha]_D^{26}$ +17° (c 1.2, MeOH)
(5) $^1$H NMR spectrum (400 MHz, CDCl$_3$) δ (ppm): 1.32 (9H, s, t-Bu), 1.70 (9H, s, t-Bu), 1.72 (2H, m, piperidine), 2.28 (2H, br dd, piperidine), 3.14 (2H, ddd, piperidine), 3.58 (1H, ddd, CONHC$\underline{H}_2$CH), 3.80 (2H, br dt, piperidine), 3.90 (2H, m, CONHCH$_2$C$\underline{H}$), 4.21 (1H, m, piperidine), 6.92 (2H, d, C$_6$H$_4$CO), 7.03 (1H, dt, benzimidazole), 7.15 (2H, t, C$_6$H$_4$F), 7.20 (1H, dt, benzimidazole), 7.39 (1H, d, benzimidazole), 7.59 (1H, d, benzimidazole), 7.69 (2H, d, C$_6$H$_4$CO), 7.87 (2H, dd, C$_6$H$_4$F)

Example 33

3-[4-{4-(1H-Benzimidazol-2-ylamino)piperidin-1-yl}benzoylamino]-(2S)-{(4-fluoro-benzenesulfonyl)amino}propionic acid Methylene chloride (0.5 ml) was added to 23.0 mg of the compound prepared in Example 32 to prepare a solution.

Anisole (7 μl) and 0.5 ml of trifluoroacetic acid were added at 0° C. to the solution. The mixture was stirred at room temperature for 4 hr. The reaction solution was concentrated under the reduced pressure. The residue was purified by preparative thin-layer chromatography on silica gel (development system: chloroform-methanol-concentrated aqueous ammonia=30:10:1) and then by Sephadex LH-20 (development system: methanol-concentrated aqueous ammonia=10:1) to prepare 10.0 mg of the title compound.

Physicochemical Properties of Compound Prepared in Example 33

(1) Color and form: Colorless solid
(2) Molecular formula: $C_{28}H_{29}N_6O_5FS$
(3) Mass spectrum (FABMS): m/z 581 (M+H)$^+$
(4) Specific rotation: $[\alpha]_D^{27}$ 36° (c 0.50, MeOH-conc. NH$_4$OH (1:1))
(5) $^1$H NMR spectrum (400 MHz, CD$_3$OD) δ (ppm): 1.72 (2H, br q, piperidine), 2.15 (2H, br d, piperidine), 3.04 (2H, br t, piperidine), 3.57 (1H, dd, CONHC$\underline{H}_2$CH), 3.64 (1H, dd, CONHC$\underline{H}_2$CH), 3.78 (1H, dd, CONHCH$_2$C$\underline{H}$), 3.80 (1H, m, piperidine), 3.92 (2H, br d, piperidine), 6.99 (2H, d, C$_6$H$_4$CO), 7.17 (4H, m, benzimidazole and C$_6$H$_4$F), 7.29 (2H, dd, benzimidazole), 7.70 (2H, d, C$_6$H$_4$CO), 7.89 (2H, dd, C$_6$H$_4$F)

Example 34 t-Butyl 3-[4-[4-{(1-t-butoxycarbonyl-1H-benzimidazol-2-yl)amino}piperidin-1-yl]benzoylamino]-(2S)-{(4-nitrobenzenesulfonyl)amino}propionate Dimethylformamide (1.0 ml) was added to 45.0 mg of the compound prepared in Example 26 to prepare a solution. Diisopropylethylamine (30 μl) and 17.2 mg of 4-nitrobenzenesulfonyl chloride were added at room temperature to the solution. The mixture was stirred for 2.5 hr. Piperazine (5 mg) was then added thereto, followed by stirring for additional 5 min. A saturated aqueous sodium hydrogencarbonate solution (50 ml) was added to the reaction solution, and the mixture was extracted three times with 50 ml of ethyl acetate. The combined organic layer was dried over anhydrous sodium sulfate, and then concentrated under the reduced pressure. The residue was purified by preparative thin-layer chromatography on silica gel (development system: hexane-ethyl acetate=1:1) to prepare 54.2 mg of the title compound.

Physicochemical Properties of Compound Prepared in Example 34

(1) Color and form: Yellow oil
(2) Molecular formula: $C_{37}H_{45}N_7O_9S$
(3) Mass spectrum (TSPMS): m/z 764 (M+H)$^+$
(4) Specific rotation: $[\alpha]_D^{28}$ −5.2° (c 1.1, MeOH)
(5) $^1$H NMR spectrum (400 MHz, CDCl$_3$) δ (ppm): 1.36 (9H, s, t-Bu), 1.70 (9H, s, t-Bu), 1.73 (2H, m, piperidine), 2.29 (2H, br dd, piperidine), 3.14 (2H, ddd, piperidine), 3.66 (1H, ddd, CONHC$\underline{H}_2$CH), 3.80 (3H, m, piperidine and CONHC$\underline{H}_2$CH), 4.08 (1H, m, CONHCH$_2$C$\underline{H}$), 4.22 (1H, m, piperidine), 6.87 (2H, d, C$_6$H$_4$CO), 7.04 (1H, dt, benzimidazole), 7.20 (1H, dt, benzimidazole), 7.40 (1H, d, benzimidazole), 7.59 (3H, m, benzimidazole and C$_6$H$_4$CO), 8.01 (2H, m, C$_6$H$_4$NO$_2$), 8.21 (2H, br d, C$_6$H$_4$NO$_2$)

Example 35

3-[4-{4-(1H-Benzimidazol-2-ylamino)piperidin-1-yl}benzoylamino]-(2S)-{(4-nitro-benzenesulfonyl)amino}propionic acid Methylene chloride (1.0 ml) was added to 58.0 mg of the compound prepared in Example 34 to prepare a solution. Anisole (17 μl) and 1.0 ml of trifluoroacetic acid were added at 0° C. to the solution. The mixture was stirred at room temperature for 4 hr. The reaction solution was concentrated under the reduced pressure. The residue was purified by preparative thin-layer chromatography on silica gel (development system: chloroform-methanol-concentrated aqueous ammonia=30:10:1) to prepare 15.1 mg of the title compound.

Physicochemical Properties of Compound Prepared in Example 35

(1) Color and form: Yellow solid
(2) Molecular formula: $C_{28}H_{29}N_7O_7S$
(3) Mass spectrum (TSPMS): m/z 609 (M+H)$^+$
(4) Specific rotation: $[\alpha]_D^{28}$ 24° (c 0.20, MeOH-conc. NH$_4$OH (10:1))
(5) $^1$H NMR spectrum (400 MHz, CD$_3$OD) δ (ppm): 1.68 (2H, br q, piperidine), 2.18 (2H, br d, piperidine), 3.07 (2H, br t, piperidine), 3.58 (2H, m, CONHC$\underline{H}_2$CH), 3.91 (4H, m, CONHCH$_2$C$\underline{H}$ and piperidine), 6.91 (2H, d, C$_6$H$_4$CO), 6.96 (2H, dd, benzimidazole), 7.20 (2H, dd, benzimidazole), 7.55 (2H, d, C$_6$H$_4$CO), 8.00 (2H, dt, C$_6$H$_4$NO$_2$), 8.14 (2H, dt, C$_6$H$_4$NO$_2$)

Example 36

(2S)-(4-Aminobenzenesulfonyl)amino-3-[4-{4-(1H-benzimidazol-2-ylamino)piperidin-1-yl}benzoylamino]-propionic acid Ethanol (5.0 ml) was added to 15.0 mg of the compound prepared in Example 35 to prepare a solution, and 15 mg of 10% palladium-carbon was added to the solution. The mixture was vigorously stirred under a hydrogen pressure of one atm at room temperature for 3 hr. The insolubles were collected by filtration, and then washed twice with methanol. The filtrate was combined with the washings, followed by concentration under the reduced pressure. The residue was purified by preparative thin-layer chromatography on silica gel (development system: methylene chloride-methanol= 7:1) and then by Sephadex LH-20 (development system: methanol-concentrated aqueous ammonia=10:1) to prepare 2.5 mg of the title compound.

Physicochemical Properties of Compound Prepared in Example 36

(1) Color and form: Colorless solid
(2) Molecular formula: $C_{28}H_{31}N_7O_5S$
(3) Mass spectrum (TSPMS): m/z 578 (M+H)$^+$
(4) Specific rotation: $[\alpha]_D^{23}$ +101° (c 0.14, MeOH)
(5) $^1$H NMR spectrum (400 MHz, CD$_3$OD) δ (ppm): 1.66 (2H, dq, piperidine), 2.16 (2H, br d, piperidine), 3.06 (2H, ddd, piperidine), 3.52 (1H, dd, CONHC$\underline{H}_2$CH), 3.63 (1H, dd, CONHC$\underline{H}_2$CH), 3.69 (1H, dd, CONHCH$_2$C$\underline{H}$), 3.85 (1H, ddd, piperidine), 3.91 (2H, br d, piperidine), 6.62 (2H, br d, C$_6$H$_4$NH$_2$), 6.96 (2H, dd, benzimidazole), 7.01 (2H, d, C$_6$H$_4$CO), 7.19 (2H, dd, benzimidazole), 7.53 (2H, br d, C$_6$H$_4$NH$_2$), 7.73 (2H, d, C$_6$H$_4$CO)

Intermediate 23: 1-(Ethoxycarbonyl)-4-{(1H-imidazo[4.5-b]pyridin-2-yl amino}piperidine Ethyl 4-amino-1-piperidine-carboxylate (3.36 g) was added to 1.50 g of 2-chloroimidazo[4,5-b]pyridine (F. Jung et al., *J. Med. Chem.*, 34(3), 1110, 1991). The mixture was stirred at 170° C. for 7 hr, and then cooled to room temperature. The reaction solution was then poured into a mixed solution of 300 ml of methylene chloride and 300 ml of a saturated aqueous sodium carbonate solution with stirring. The organic layer was separated, and the aqueous layer was extracted twice with 200 ml of methylene chloride. The combined organic layer was dried over anhydrous sodium sulfate, and then concentrated under the reduced pressure. The residue was purified by column chromatography on silica gel (development system: methylene chloride-methanol=15:1) to prepare 1.12 g of the title compound.

Physicochemical Properties of Intermediate 23

(1) Color and form: Colorless amorphous
(2) Molecular formula: $C_{14}H_{19}N_5O_2$
(3) Mass spectrum (TSPMS): m/z 290 (M+H)$^+$
(4) $^1$H NMR spectrum (400 MHz, CDCl$_3$) δ (ppm): 1.25 (3H, t, CO$_2$Et), 1.54 (2H, m, piperidine), 2.17 (2H, m, piperidine), 2.96 (2H, br t, piperidine), 4.09 (3H, m, piperidine), 4.12 (2H, q, CO$_2$Et), 6.96 (1H, br dd, C$_6$H$_3$N), 7.46 (1H, m, C$_6$H$_3$N), 7.99 (1H, m, C$_6$H$_3$N)

Intermediate 24: 4-{(1H-Imidazo]4,5-b]pyridin-2-yl)amino}piperidine

47% hydrobromic acid (9.0 ml) was added to 500 mg of intermediate 23 to prepare a solution. The solution was heated under reflux for 5 hr and was then cooled to room temperature. The reaction solution was then poured into aqueous ammonia with stirring under cooling at 0° C. The mixed solution was concentrated under reduced pressure. The residue was purified by Amberlyst 15 (development system: methanol-concentrated aqueous ammonia-water= 4:3:1) to prepare 226 mg of the title compound.

Physicochemical Properties of Intermediate 24

(1) Color and form: Colorless solid
(2) Molecular formula: $C_{11}H_{15}N_5$
(3) Mass spectrum (TSPMS): m/z 218
(4) $^1$H NMR spectrum (400 MHz, CD$_3$OD) δ (ppm): 1.50 (2H, dq, piperidine), 2.07 (2H, br d, piperidine), 2.74 (2H, dt, piperidine), 3.10 (2H, dt, piperidine), 3.80 (1H, tt, piperidine), 6.96 (1H, dd, C$_6$H$_3$N), 7.46 (1H, dd, C$_6$H$_3$N), 7.92 (1H, dd, C$_6$H$_3$N)

Intermediate 25: Ethyl 4-[4-{(1H-imidazo[4,5-b]pyridin-2-yl)amino}piperidin-1-yl]benzoate Dimethyl sulfoxide (1.0 ml) was added to 188 mg of intermediate 24 to prepare a solution, and 152 μl of ethyl 4-fluorobenzoate was added to the solution. The mixture was stirred at 130° C. for 18 hr, and then cooled to room temperature. A saturated aqueous sodium carbonate solution (100 ml) was added thereto, followed by extraction three times with 100 ml of methylene chloride. The combined organic layer was dried over anhydrous sodium sulfate, and then concentrated under the reduced pressure. The residue was purified by column chromatography on silica gel (development system: methylene chloride-methanol=20:1) to prepare 147 mg of the title compound.

Physicochemical Properties of Intermediate 25

(1) Color and form: Yellow solid
(2) Molecular formula: $C_{20}H_{23}N_5O_2$
(3) Mass spectrum (TSPMS): m/z 366 (M+H)$^+$
(4) $^1$H NMR spectrum (400 MHz, DMSO-d$_6$) δ (ppm): 1.28 (3H, t, CO$_2$Et), 1.54 (2H, br q, piperidine), 2.20 (2H, br d, piperidine), 3.01 (2H, m, piperidine), 3.90 (3H, m, piperidine), 4.23 (2H, q, CO$_2$Et), 6.90 (1H, m, C$_6$H$_3$N), 7.00 (2H, d, C$_6$H$_4$CO), 7.36 (1H, m, C$_6$H$_3$N), 7.77 (2H, d, C$_6$H$_4$CO), 7.92 (1H, m, C$_6$H$_3$N)

Example 37 t-Butyl (2S)-benzenesulfonylamino-3-[4-[4-{(1H-imidazo[4,5-b]pyridin-2-yl)amino}piperidin-1-yl]-benzoylamino]propionate Tetrahydrofuran (4.5 ml) and 1.5 ml of methanol were added to 100 mg of intermediate 25 to prepare a solution, and 1.5 ml of a 1 N aqueous sodium hydroxide solution was added to the solution. The mixture was stirred at 40° C. for 7 hr, and then concentrated under the reduced pressure. The residue was purified by column chromatography on silica gel (development system: chloroform-methanol-concentrated aqueous ammonia=30:10:1) to prepare 92 mg of a crude compound. Subsequently, 3.0 ml of dimethylformamide was added to the crude compound to prepare a suspension. t-Butyl (2S)-N-benzenesulfonyl-2,3-diaminopropionate hydrochloride (111 mg) was added to the suspension. Further, 56 mg of 1-hydroxybenzotriazole, 90 μl of N-methylmorpholine, and 79 mg 1-ethyl-3-(3-dimethylaminopropyl)carbodiimide hydrochloride were added thereto, followed by stirring at room temperature for 20 hr. A saturated aqueous sodium hydrogencarbonate solution (60 ml) and 30 ml of a saturated aqueous potassium carbonate solution were added to the reaction solution, followed by extraction three times with 60 ml of methylene chloride. The combined organic layer was dried over anhydrous sodium sulfate, and then concentrated under the reduced pressure. The residue was purified by column chromatography on silica gel (development system: methylene chloride-methanol=10:1) to prepare 83.2 mg of the title compound.

Physicochemical Properties of Compound Prepared in Example 37

(1) Color and form: Colorless solid
(2) Molecular formula: $C_{31}H_{37}N_7O_5S$
(3) Mass spectrum (TSPMS): m/z 620 (M+H)$^+$
(4) Specific rotation: $[\alpha]_D^{24}$ +29° (c 0.85, MeOH)
(5) $^1$H NMR spectrum (400 MHz, DMSO-d$_6$) δ (ppm): 1.12 (9H, s, t-Bu), 1.56 (2H, br q, piperidine), 2.01 (2H, br d, piperidine), 2.95 (2H, m, piperidine), 3.31 (1H, m, CONHC$\underline{H}_2$CH), 3.44 (1H, m, CONHC$\underline{H}_2$CH), 3.87 (3H, m, piperidine), 4.20 (1H, br t, CONHCH$_2$C$\underline{H}$), 6.88 (1H, m, C$_6$H$_3$N), 6.96 (2H, d, C$_6$H$_4$CO), 7.36 (1H, m, C$_6$H$_3$N), 7.51 (2H, t, C$_6$H$_5$), 7.57 (1H, t, C$_6$H$_5$), 7.64 (2H, d, C$_6$H$_4$CO), 7.76 (2H, br d, C$_6$H$_5$), 8.17 (1H, t, C$_6$H$_3$N)

Example 38

(2S)-Benzenesulfonylamino-3-[4-[4-{(1H-imidazo[4,5-b]pyridin-2-yl)amino}piperidin-1-yl]benzoyl-amino]propionic acid Methylene chloride (0.5 ml) was added to 42.0 mg of the compound prepared in Example 37 to prepare a solution. Trifluoroacetic acid (0.5 ml) was added to the solution. The mixture was stirred at room temperature for 7 hr. The reaction solution was concentrated under the reduced pressure. The residue was purified by preparative thin-layer chromatography on silica gel (development system: methylene chloride-ethanol-concentrated aqueous ammonia-water=8:8:1:1), and then purified by Sephadex LH-20 (development system: methanol-concentrated aqueous ammonia=10:1) to prepare 38.0 mg of the title compound.

Physicochemical Properties of Compound Prepared in Example 38

(1) Color and form: Colorless solid
(2) Molecular formula: $C_{29}H_{29}N_7O_5S$
(3) Mass spectrum (FABMS): m/z 564 (M+H)$^+$
(4) Specific rotation: $[\alpha]_D^{23}$ +53° (c 0.35, MeOH-conc. NH$_4$OH (10:1))
(5) $^1$H NMR spectrum (400 MHz, DMSO-d$_6$) δ (ppm): 1.57 (2H, br q, piperidine), 2.01 (2H, br d, piperidine), 2.96 (2H, t, piperidine), 3.33 (1H, m, CONHC$\underline{H}_2$CH), 3.45 (1H, m, CONHC$\underline{H}_2$CH), 3.89 (3H, m, piperidine), 3.96 (1H, t, CONHCH$_2$C$\underline{H}$), 6.85 (1H, br t, C$_6$H$_3$N), 6.96 (2H, d, C$_6$H$_4$CO), 7.38 (1H, dd, C$_6$H$_3$N), 7.46 (2H, m, C$_6$H$_5$), 7.54 (1H, br t, C$_6$H$_5$), 7.62 (2H, d, C$_6$H$_4$CO), 7.75 (2H, m, C$_6$H$_5$), 8.18 (1H, br t, C$_6$H$_3$N)

Intermediate 26: Ethyl 4-[4-[3-{2-(t-butoxycarbonylamino)ethyl}thioureido]piperidin-1-yl]-benzoate Tetrahydrofuran (0.5 ml) was added to 30.0 mg of intermediate 3 to prepare a solution. A solution (0.5 ml) of 29 mg of N-t-butoxycarbonyl-2-isothiocyanatoethylamine in tetrahydrofuran was added to the solution. The mixture was stirred at room temperature for 19 hr. The reaction solution was concentrated under the reduced pressure. The residue was purified by preparative thin-layer chromatography on silica gel (development system: methylene chloride-methanol=7:1) to prepare 50.1 mg of the title compound.

Physicochemical Properties of Intermediate 26

(1) Color and form: Colorless solid
(2) Molecular formula: $C_{22}H_{34}N_4O_4S$
(3) Mass spectrum (TSPMS): m/z 451 (M+H)$^+$
(4) $^1$H NMR spectrum (400 MHz, CDCl$_3$) δ (ppm): 1.37 (3H, t, CO$_2$Et), 1.42 (9H, s, t-Bu), 1.62 (2H, m, piperidine), 2.15 (2H, m, piperidine), 3.03 (2H, br t, piperidine), 3.31 (2H, m, CH$_2$CH$_2$), 3.55 (2H, m, CH$_2$CH$_2$), 3.85 (2H, br d, piperidine), 4.33 (2H, q, CO$_2$Et), 4.98 (1H, m, piperidine), 6.97 (2H, d, C$_6$H$_4$CO), 7.92 (2H, d, C$_6$H$_4$CO)

Intermediate 27: Ethyl 4-{4-(4,5-dihydro-1H-imidazol-2-ylamino)piperidin-1-yl}benzoate Ethanol (0.5 ml) and 0.5 ml of ethyl bromide were added to 14.2 mg of intermediate 26 to prepare a solution. The solution was stirred at 60° C. for 13 hr, and then cooled to room temperature. The reaction solution was then concentrated under the reduced pressure. The residue was purified by preparative thin-layer chromatography on silica gel (development system: methylene chloride-methanol=7:1) to prepare a crude compound. Subsequently, 0.5 ml of water and 1.0 ml of trifluoroacetic acid were added to the crude compound to prepare a solution. The solution was stirred at room temperature for 3 hr. The reaction solution was concentrated under the reduced pressure. Ethanol (1.0 ml) was added to the residue to prepare a solution. This solution was added dropwise to a solution (1.0 ml) of 18.0 mg of sodium ethoxide in ethanol over a period of 3 hr. The mixture was further stirred at room temperature for 16 hr. The reaction solution was concentrated under the reduced pressure. The residue was purified by preparative thin-layer chromatography on silica gel (development system: methylene chloride-methanol=7:1) to prepare 6.1 mg of the title compound.

Physicochemical Properties of Intermediate 27

(1) Color and form: Colorless oil
(2) Molecular formula: $C_{17}H_{24}N_4O_2$
(3) Mass spectrum (TSPMS): m/z 317 (M+H)$^+$
(4) $^1$H NMR spectrum (400 MHz, CDCl$_3$) δ (ppm): 1.37 (3H, t, CO$_2$Et), 1.76 (2H, br q, piperidine), 2.02 (2H, br d, piperidine), 2.95 (2H, ddd, piperidine), 3.53 (1H, m, piperidine), 3.70 (4H, s, CH$_2$CH$_2$), 3.76 (2H, br d, piperidine), 4.32 (2H, q, CO$_2$Et), 6.81 (2H, d, C$_6$H$_4$CO), 7.89 (2H, d, C$_6$H$_4$CO)

Intermediate 28: Ethyl 4-[4-[{4,5-dihydro-1-(4-methoxybenzyl)-1H-imidazol-2-yl}amino]piperidin-1-yl]-benzoate Dimethylformamide (1.5 ml) was added to 43.9 mg of intermediate 27 to prepare a solution. Potassium carbonate (58 mg) and 23 µl of 4-methoxybenzyl chloride were added to the solution. The mixture was stirred at room temperature for 16 hr. A saturated aqueous potassium carbonate solution (60 ml) was then added thereto, followed by extraction three times with 60 ml of methylene chloride. The combined organic layer was dried over anhydrous sodium sulfate, and then concentrated under the reduced pressure. The residue was subjected to azeotropic distillation twice with toluene. The residue was purified by preparative thin-layer chromatography on silica gel (development system: chloroform-methanol-concentrated aqueous ammonia=30:10:1) to prepare 15.0 mg of the title compound.

Physicochemical Properties of Intermediate 28

(1) Color and form: Colorless oil
(2) Molecular formula: $C_{25}H_{32}N_4O_3$
(3) Mass spectrum (TSPMS): m/z 437 (M+H)$^+$
(4) $^1$H NMR spectrum (400 MHz, CD$_3$OD) δ (ppm): 1.35 (3H, t, CO$_2$Et), 1.74 (2H, dq, piperidine), 2.06 (2H, br d, piperidine), 2.96 (2H, br t, piperidine), 3.62 (5H, m, piperidine and CH$_2$CH$_2$), 3.79 (3H, s, CH$_2$C$_6$H$_4$O$\underline{Me}$), 4.02 (2H, br d, piperidine), 4.30 (2H, q, CO$_2$Et), 4.47 (2H, s, C$\underline{H}_2$C$_6$H$_4$OMe), 6.94 (2H, d, C$_6$H$_4$CO), 6.99 (2H, d, CH$_2$C$_6$$\underline{H}_4$OMe), 7.21 (2H, d, CH$_2$C$_6$$\underline{H}_4$OMe), 7.87 (2H, d, C$_6$H$_4$CO)

Example 39 t-Butyl (2S)-benzenesulfonylamino-3-[4-[4-[{4,5-dihydro-1-(4-methoxybenzyl)-1H-imidazol-2-yl}-amino]piperidin-1-yl]benzoylamino]propionate Tetrahydrofuran (1.5 ml) and 0.5 ml of methanol were added to 18.0 mg of intermediate 28 to prepare a solution. A 1 N aqueous sodium hydroxide solution (0.5 ml) was added to the solution. The mixture was stirred at 40° C. for 5 hr, and then concentrated under the reduced pressure. Water (2 ml) was added to the residue. Further, the mixture was adjusted to pH 4 by the addition of 1 N hydrochloric acid with stirring. The resultant precipitate was collected by filtration through a glass filter, washed twice with water, and then dried to prepare 14.2 mg of a crude compound. Subsequently, dimethylformamide (0.5 ml) was added to this compound to prepare a suspension. t-Butyl (2S)-N-benzenesulfonyl-2,3-diaminopropionate hydrochloride (14.0 mg) was added to the suspension. Further, 7.0 mg of 1-hydroxybenzotriazole, 20 µl of N-methylmorpholine, and 10.0 mg of 1-ethyl-3-(3-dimethylaminopropyl)carbodiimide hydrochloride were added thereto, followed by stirring at room temperature for 12 hr. The reaction solution was concentrated under the reduced pressure. The residue was subjected to azeotropic distillation twice with toluene. The residue was purified by preparative thin-layer chromatography on silica gel (development system: chloroform-methanol-concentrated aqueous ammonia=30:10:1) to prepare 20.8 mg of the title compound.

Physicochemical Properties of Compound Prepared in Example 39

(1) Color and form: Colorless solid
(2) Molecular formula: $C_{36}H_{46}N_6O_6S$
(3) Mass spectrum (FABMS): m/z 691 (M+H)$^+$
(4) Specific rotation: $[\alpha]_D^{24}$ +22° (c 1.0, MeOH)
(5) $^1$H NMR spectrum (400 MHz, CDCl$_3$) δ (ppm): 1.23 (9H, s, t-Bu), 1.84 (2H, m, piperidine), 1.98 (2H, m, piperidine), 2.68 (2H, m, piperidine), 3.26 (2H, br t, CH$_2$CH$_2$), 3.52 (4H, m, CH$_2$CH$_2$ and piperidine), 3.64 (1H, m, CONHC$\underline{H}$CH), 3.72 (4H, m, CONHC$\underline{H}_2$CH and CH$_2$C$_6$H$_4$OMe), 3.94 (1H, m, piperidine), 4.08 (1H, dd, CONHCH$_2$C$\underline{H}$), 4.54 (2H, dd, C$\underline{H}_2$C$_6$H$_4$OMe), 6.50 (2H, br d, C$_6$H$_4$CO), 6.76 (2H, d, CH$_2$C$_6\underline{H}_4$OMe), 7.06 (2H, d, CH$_2$C$_6\underline{H}_4$OMe), 7.30 (2H, br t, C$_6$H$_5$), 7.39 (1H, br t, C$_6$H$_5$), 7.67 (2H, br d, C$_6$H$_4$CO), 7.77 (2H, d, C$_6$H$_5$)

Example 40

(2S)-Benzenesulfonylamino-3-[4-{4-(4.5-dihydro-1H-imidazol-2-ylamino)piperidin-1-yl}benzoylamino]propionic acid Methylene chloride (0.5 ml) was added to 20.0 mg of the compound prepared in Example 39 to prepare a solution. Trifluoroacetic acid (0.5 ml) was added to the solution, and the mixture was stirred at 40° C. for 20 hr. The reaction solution was then concentrated under the reduced pressure. The residue was purified by preparative thin-layer chromatography on silica gel (development system: methylene chloride-ethanol-concentrated aqueous ammonia-water=8:8:1:1), and then purified by Sephadex LH-20 (development system: methanol-concentrated aqueous ammonia=10:1) to prepare 12.1 mg of the title compound.

Physicochemical Properties of Compound Prepared in Example 40

(1) Color and form: Colorless solid
(2) Molecular formula: $C_{24}H_{30}N_6O_5S$
(3) Mass spectrum (TSPMS): m/z 515 (M+H)$^+$
(4) Specific rotation: $[\alpha]_D^{23}$ +31° (c 0.16, DMSO)
(5) $^1$H NMR spectrum (400 MHz, DMSO-d$_6$) δ (ppm): 1.42 (2H, br q, piperidine), 1.85 (2H, m, piperidine), 2.72 (2H, m, piperidine), 3.08 (1H, br t, CONHC$\underline{H}_2$CH), 3.35 (2H, m, CONHC$\underline{H}_2$CH and piperidine), 3.56 (4H, s, CH$_2$CH$_2$), 3.64 (3H, m, piperidine and CONHCH$_2$C$\underline{H}$), 6.89 (2H, d, C$_6$H$_4$CO), 7.54 (2H, br t, C$_6$H$_5$), 7.60 (3H, m, C$_6$H$_5$ and C$_6$H$_4$CO), 7.81 (2H, br d, C$_6$H$_5$)

Intermediate 29: Ethyl 4-{4-(4,5,6,7-tetrahydro-1H-[1,3]diazepin-2-ylamino)piperidin-1-yl}benzoate Tetrahydrofuran (2.0 ml) was added to 100 mg of intermediate 3 to prepare a solution. A solution (0.5 ml) of 111 mg of N-t-butoxycarbonyl-4-isothiocyanatobutylamine in tetrahydrofuran was added to the solution. The mixture was stirred at room temperature for 18 hr. The reaction solution was concentrated under the reduced pressure. The residue was purified by preparative thin-layer chromatography on silica gel (development system: methylene chloride-methanol=7:1) to prepare 230.3 mg of a crude compound. Subsequently, 4.0 ml of ethanol and 4.0 ml of ethyl bromide were added to the crude compound to prepare a solution. The solution was stirred at 60° C. for 24 hr. The reaction solution was cooled to room temperature, and then concentrated under the reduced pressure. The residue was purified by preparative thin-layer chromatography on silica gel (development system: methylene chloride-methanol=7:1) to prepare 161.1 mg of a crude compound. Water (1.0 ml) and 1.0 ml of trifluoroacetic acid were then added to 138.2 mg of the crude compound to prepare a solution. The solution was stirred at room temperature for 3 hr. The reaction solution was concentrated under the reduced pressure. Ethanol (5.0 ml) was added to the residue to prepare a solution. This solution was added dropwise at room temperature to a solution (5.0 ml) of 149 mg of sodium ethoxide in ethanol over a period of 2 hr, followed by stirring for additional 13 hr. The reaction solution was concentrated under the reduced pressure. The residue was purified by preparative thin-layer chromatography on silica gel (development system: methylene chloride-methanol=7:1) to prepare 71.8 mg of the title compound.

Physicochemical Properties of Intermediate 29

(1) Color and form: Colorless oil
(2) Molecular formula: $C_{17}H_{24}N_4O_2$
(3) Mass spectrum (TSPMS): m/z 317 (M+H)$^+$
(4) $^1$H NMR spectrum (400 MHz, CD$_3$OD) δ (ppm): 1.26 (3H, t, CO$_2$Et), 1.51 (2H, dq, piperidine), 1.61 (4H, tt, CH$_2$C$\underline{H}_2$C$\underline{H}_2$CH$_2$), 1.91 (2H, br d, piperidine), 2.90 (2H, ddd, piperidine), 3.18 (4H, m, C$\underline{H}_2$CH$_2$CH$_2$C$\underline{H}_2$), 3.54 (1H, tt, piperidine), 3.83 (2H, br d, piperidine), 4.20 (2H, q, CO$_2$Et), 6.87 (2H, br d, C$_6$H$_4$CO), 7.76 (2H, br d, C$_6$H$_4$CO)

Example 41 t-Butyl (2S)-benzenesulfonylamino-3-[4-{4-(4,5,6,7-tetrahydro-1H-[1,3]diazepin-2-ylamino)-piperidin-1-yl}benzoylamino]propionate Tetrahydrofuran (0.6 ml) and 0.2 ml of methanol were added to 6.9 mg of intermediate 29 to prepare a solution. A 1 N aqueous sodium hydroxide solution (0.2 ml) was added to the solution. The mixture was stirred at 40° C. for 2.5 hr, and then concentrated under the reduced pressure. The residue was purified by preparative thin-layer chromatography on silica gel (development system: chloroform-methanol-concentrated aqueous ammonia=30:10:1) to prepare 4.5 mg of a crude compound. Dimethylformamide (0.5 ml) was then added to the crude compound to prepare a solution. t-Butyl (2S)-N-benzenesulfonyl-2,3-diaminopropionate hydrochloride (6.7 mg) was added to the solution. Further, 3.2 mg of 1-hydroxybenzotriazole, 11 μl of N-methylmorpholine, and 4.6 mg of 1-ethyl-3-(3-dimethylaminopropyl)carbodiimide hydrochloride were added thereto, followed by stirring at room temperature for 12 hr. The reaction solution was concentrated under the reduced pressure. The residue was subjected to azeotropic distillation twice with toluene, and was purified by preparative thin-layer chromatography on silica gel (development system: methylene chloride-methanol=7:1) to prepare 2.0 mg of the title compound.

Physicochemical Properties of Compound Prepared in Example 41

(1) Color and form: Colorless oil
(2) Molecular formula: $C_{30}H_{42}N_6O_6S$
(3) Mass spectrum (TSPMS): m/z 599 (M+H)$^+$
(4) $^1$H NMR spectrum (400 MHz, CDCl$_3$) δ (ppm): 1.26 (9H, s, t-Bu), 1.55 (2H, m, piperidine), 1.61 (4H, m, CH$_2$CH$_2$CH$_2$CH$_2$), 1.94 (2H, br d, piperidine), 2.85 (2H, br t, piperidine), 3.22 (4H, m, CH$_2$CH$_2$CH$_2$CH$_2$), 3.52 (2H, m, piperidine), 3.70 (1H, m, CONHCH$_2$CH), 3.78 (1H, m, CONHCH$_2$CH), 3.88 (1H, m, piperidine), 4.09 (1H, dd, CONHCH$_2$CH), 6.59 (2H, d, C$_6$H$_4$CO), 7.41 (2H, br t, C$_6$H$_5$), 7.49 (1H, br t, C$_6$H$_5$), 7.66 (2H, d, C$_6$H$_4$CO), 7.85 (2H, br d, C$_6$H$_5$)

Example 42

(2S)-Benzenesulfonylamino-3-[4-{4-(4,5,6,7-tetrahydro-1H-[1,3]diazepin-2-ylamino)piperidin-1-yl}-benzoylamino]propionic acid Methylene chloride (0.5 ml) was added to 2.0 mg of the compound prepared in Example 41 to prepare a solution. Trifluoroacetic acid (0.5 ml) was added to the solution. The mixture was stirred at room temperature for 2 hr. The reaction solution was concentrated under the reduced pressure. The residue was purified by preparative thin-layer chromatography on silica gel (development system: chloroform-methanol-concentrated aqueous ammonia=30:10:1) to prepare 1.7 mg of the title compound.

Physicochemical Properties of Compound Prepared in Example 42

(1) Color and form: Colorless amorphous
(2) Molecular formula: C$_{26}$H$_{34}$N$_6$O$_5$S
(3) Mass spectrum (FABMS): m/z 543 (M+H)$^+$
(4) Specific rotation: $[\alpha]_D^{25}$ +53° (c 0.24, (MeOH-conc. NH$_4$OH (10:1))
(5) $^1$H NMR spectrum (400 MHz, CD$_3$OD) δ (ppm): 1.61 (2H, br q, piperidine), 1.70 (4H, m, CH$_2$CH$_2$CH$_2$CH$_2$), 1.98 (2H, br d, piperidine), 2.94 (2H, ddd, piperidine), 3.28 (4H, m, CH$_2$CH$_2$CH$_2$CH$_2$), 3.60 (3H, m, CONHCH$_2$CH and piperidine), 3.73 (1H, dd, CONHCH$_2$CH), 3.86 (2H, br d, piperidine), 6.96 (2H, d, C$_6$H$_4$CO), 7.48 (2H, br t, C$_6$H$_5$), 7.54 (1H, br t, C$_6$H$_5$), 7.71 (2H, d, C$_6$H$_4$CO), 7.86 (2H, br d, C$_6$H$_5$)

Intermediate 30: Ethyl 4-[4-[{N-methyl-N-(pyrimidin-2-yl)}amino]piperidin-1-yl]benzoate Anhydrous dimethylformamide (3.6 ml) was added to 179 mg of intermediate 4 to prepare a solution. Methyl iodide (156 mg) was added to the solution. 60% sodium hydride in oil (43.9 mg) was added thereto, and a reaction was allowed to proceed at 45° C. for 11 hr. The reaction solution was extracted with 200 ml of ethyl acetate. The extract was washed once with distilled water, once with a saturated aqueous sodium hydrogencarbonate solution, and once with saturated saline in that order, and then dried over anhydrous sodium sulfate, concentrated under the reduced pressure, and dried to prepare 186 mg of the title compound.

Physicochemical Properties of Intermediate 30

(1) Color and form: Colorless solid
(2) Molecular formula: C$_{19}$H$_{24}$N$_4$O$_2$
(3) Mass spectrum (TSPMS): m/z 341 (M+H)$^+$
(4) $^1$H NMR spectrum (400 MHz, CDCl$_3$) δ (ppm): 1.37 (3H, t, Et), 1.80 (2H, br d, piperidine), 1.90 (2H, dq, piperidine), 3.01 (3H, s, Me), 3.04 (2H, br dt, piperidine), 3.99 (2H, br d, piperidine), 4.33 (2H, q, Et), 4.90 (1H, dddd, piperidine), 6.48 (1H, t, pyrimidine), 6.90 (2H, d, C$_6$H$_4$), 7.93 (2H, d, C$_6$H$_4$), 8.32 (2H, d, pyrimidine)

Intermediate 31: 4-[4-[{N-Methyl-N-(pyrimidin-2-yl)}-amino]piperidin-1-yl]benzoic acid Tetrahydrofuran (18 ml) and 6.0 ml of methanol were added to 209 mg of intermediate 30 to prepare a solution. A 1 N aqueous sodium hydroxide solution (6.0 ml) was added to the solution, and a reaction was allowed to proceed at 45° C. for 10 hr. The reaction solution was concentrated under the reduced pressure. Distilled water (19 ml) was added to the residue to prepare a solution. The solution was neutralized with 5 N hydrochloric acid to precipitate a carboxylic acid which was then allowed to stand at 0° C. for 16 hr. The precipitate was then collected by filtration, washed with 4 ml of distilled water, and then dried over phosphorus pentoxide at 50° C. to prepare 68.0 mg of the title compound. On the other hand, the filtrate was combined with the washings, followed by concentration under the reduced pressure. The residue was purified by column chromatography on silica gel (12 g, chloroform-methanol-concentrated aqueous ammonia=30:10:1) to prepare 102 mg of the title compound.

Physicochemical Properties of Intermediate 31

(1) Color and form: Colorless acicular crystal
(2) Melting point: 257° C.
(3) Molecular formula: C$_{17}$H$_{20}$N$_4$O$_2$
(4) Mass spectrum (TSPMS): m/z 313 (M+H)$^+$
(5) $^1$H NMR spectrum (400 MHz, 67% CD$_3$OD/CDCl$_3$) δ (ppm): 1.80 (2H, br d, piperidine), 1.94 (2H, dq, piperidine), 3.01 (3H, s, Me), 3.03 (2H, br t, piperidine), 4.06 (2H, br d, piperidine), 4.86 (1H, dddd, piperidine), 6.57 (1H, t, pyrimidine), 6.96 (2H, d, C$_6$H$_4$), 7.91 (2H, d, C$_6$H$_4$), 8.32 (2H, d, pyrimidine)

Example 43 t-Butyl (2S)-benzenesulfonylamino-3-[4-[4-[{N-methyl-N-(pyrimidin-2-yl)}amino]piperidin-1-yl]-benzoylamino]propionate Anhydrous dimethylformamide (4.1 ml) and 4.1 ml of methylene chloride were added to 162 mg of intermediate 31 and 344 mg of benzotriazole-1-yloxytris(dimethylamino) phosphonium hexafluorophosphate to prepare a solution. Diisopropylethylamine (0.14 ml) was added to the solution. A reaction was allowed to proceed at room temperature for 2 hr. Thus, an active ester was prepared. On the other hand, methylene chloride (4.1 ml) was added to 187 mg of t-butyl (2S)-N-benzenesulfonyl-2,3-diaminopropionate to prepare a solution which was then added to the active ester solution. Further, diisopropylethylamine (68 μl) was added thereto, and a reaction was allowed to proceed at room temperature for 16 hr. The reaction solution was concentrated under the reduced pressure. The residue was extracted with 30 ml of ethyl acetate. The extract was washed once with a saturated aqueous sodium hydrogencarbonate solution and once with saturated saline in that order, and then dried over anhydrous sodium sulfate, followed by concentration under the reduced pressure. The residue was purified by column chromatography on silica gel (22 g, 2.5% methanol/methylene chloride) to prepare 303 mg of the title compound.

Physicochemical Properties of Compound Prepared in Example 43

(1) Color and form: Colorless syrup
(2) Molecular formula: C$_{30}$H$_{38}$N$_6$O$_5$S
(3) Mass spectrum (TSPMS): m/z 595 (M+H)$^+$
(4) Specific rotation: $[\alpha]_D^{25}$ +55° (c 2.0, CH$_2$Cl$_2$)
(5) $^1$H NMR spectrum (400 MHz, CDCl$_3$) δ (ppm): 1.29 (9H, s, t-Bu), 1.80 (2H, br d, piperidine), 1.92 (2H, dq, piperidine), 3.02 (3H, s, Me), 3.02 (2H, br t, piperidine), 3.58 (1H, ddd, CONHCH$_2$CH), 3.85–4.00 (4H, m, CONHCH$_2$CH, CONHCH$_2$CH and piperidine), 4.89 (1H, dddd, piperidine), 6.48 (1H, t, pyrimidine), 6.92 (2H, d, C$_6$H$_4$), 7.49 (2H, br t, C$_6$H$_5$), 7.57 (1H, br t, C$_6$H$_5$), 7.71 (2H, d, C$_6$H$_4$), 7.86 (2H, m, C$_6$H$_5$), 8.32 (2H, d, pyrimidine)

Example 44

(2S)-Benzenesulfonylamino-3-[4-[4-[{N-methyl-N-(pyrimidin-2-yl)}amino]piperidin-1-yl]benzoylamino]propionic acid Methylene chloride (4.0 ml) was added to 292 mg of the compound prepared in Example 43 to prepare a solution. Anisole (0.20 ml) was added to the solution, and the mixture was cooled to 0° C. Trifluoroacetic acid (4.0 ml) was added thereto at 0° C., and a reaction was then allowed to proceed at room temperature for 16 hr. The reaction solution was concentrated under the reduced pressure. The residue was subjected to azeotropic distillation twice with toluene, and then dried. The solid thus obtained was washed twice each with 10 ml of diisopropyl ether by decantation. The residue was purified by column chromatography on silica gel (22 g, chloroform-methanol-concentrated aqueous ammonia= 90:20:1) to prepare 262 mg of the title compound.

Physicochemical Properties of Compound Prepared in Example 44
(1) Color and form: Colorless solid
(2) Molecular formula: C$_{26}$H$_{30}$N$_6$O$_5$S
(3) Mass spectrum (TSPMS): m/z 539 (M+H)$^+$
(4) Specific rotation: [α]$_D^{25}$ +78° (c 0.5, 50% MeOH/CHCl$_3$)
(5) $^1$H NMR spectrum (400 MHz, CD$_3$OD) δ (ppm): 1.77 (2H, br d, piperidine), 1.95 (2H, dq, piperidine), 2.96 (2H, br t, piperidine), 3.00 (3H, s, Me), 3.55 (1H, dd, CONHCH$_2$CH), 3.66 (1H, dd, CONHCH$_2$CH), 3.81 (1H, dd, CONHCH$_2$CH), 4.03 (2H, br d, piperidine), 6.57 (1H, t, pyrimidine), 7.00 (2H, d, C$_6$H$_4$), 7.45 (2H, m, C$_6$H$_5$), 7.52 (1H, m, C$_6$H$_5$), 7.69 (2H, d, C$_6$H$_4$), 7.85 (2H, m, C$_6$H,), 8.32 (2H, d, pyrimidine)

Example 45

(2S)-Benzenesulfonylamino-3-[4-[4-[{N-methyl-N-(1,4,5,6-tetrahydropyrimidin-2-yl)}amino]-piperidin-1-yl]benzoylamino]propionic acid Acetic acid (4.0 ml) and 0.36 ml of concentrated hydrochloric acid were added to 36.5 mg of the compound prepared in Example 44 to prepare a solution. 10% palladium-carbon (36 mg) was added to the solution. The mixture was vigorously shaken under a hydrogen pressure of 2.5 atm at room temperature for 2 hr. The catalyst was collected by filtration, and then washed twice each with 2.0 ml of acetic acid. The filtrate was combined with the washings, followed by concentration under the reduced pressure. The residue was subjected to azeotropic distillation twice with toluene, and was purified by preparative thin-layer chromatography on silica gel (development system: methylene chloride-ethanol-water-concentrated aqueous ammonia=15:10:1:1) and then by column chromatography on Sephadex LH-20 (30 ml, methanol) to prepare 29.0 mg of the title compound.

Physicochemical Properties of Compound Prepared in Example 45
(1) Color and form: Colorless solid
(2) Molecular formula: C$_{26}$H$_{34}$N$_6$O$_5$S
(3) Mass spectrum (FABMS): m/z 543 (M+H)$^+$
(4) Specific rotation: [α]$_D^{25}$ +83° (c 1.0, MeOH)
(5) $^1$H NMR spectrum (400 MHz, CD$_3$OD) δ (ppm): 1.74 (2H, br d, piperidine), 1.86 (2H, dq, piperidine), 1.93 (2H, quintet, tetrahydropyrimidine), 2.78 (3H, s, Me), 2.86 (2H, br t, piperidine), 3.38 (4H, t, tetrahydropyrimidine), 3.57 (1H, dd, CONHCH$_2$CH), 3.65 (1H, dd, CONHCH$_2$CH), 3.73 (1H, dd, CONHCH$_2$CH), 3.92 (2H, br d, piperidine), 6.92 (2H, d, C$_6$H$_4$), 7.47 (2H, m, C$_6$H$_5$), 7.53 (1H, m, C$_6$H$_5$), 7.70 (2H, d, C$_6$H$_4$), 7.86 (2H, m, C$_6$H$_5$)

Intermediate 32: 4-{4-(Pyrimidin-2-ylamino)piperidin-1-yl}benzyl alcohol

Anhydrous methylene chloride (5.6 ml) was added to 200 mg of intermediate 4 to prepare a solution. A 1 M toluene solution (1.5 ml) of diisobutylaluminum hydride was added dropwise to the solution under cooling at −78° C. over a period of 10 min. A reaction was then allowed to proceed at −78° C. for 3 hr. Methanol (0.50 ml) was then added thereto, and the temperature was raised to room temperature. Methylene chloride (30 ml) was added to the reaction solution, followed by extraction. A saturated aqueous Rochelle salt solution (30 ml) was added thereto, followed by vigorous stirring at room temperature for 30 min. The methylene chloride layer was separated, washed twice with saturated saline, and then dried over anhydrous sodium sulfate, followed by concentration under the reduced pressure to prepare 170 mg of the title compound.

Physicochemical Properties of Intermediate 32
(1) Color and form: Colorless solid
(2) Molecular formula: C$_{16}$H$_{20}$N$_4$O$_1$
(3) Mass spectrum (TSPMS): m/z 28.5 (M+H)$^+$
(4) $^1$H NMR spectrum (400 MHz, CDCl$_3$) δ (ppm): 1.61 (2H, dq, piperidine), 2.14 (2H, br d, piperidine), 2.92 (2H, br t, piperidine), 3.65 (2H, br d, piperidine), 3.97 (1H, m, piperidine), 4.60 (2H, br s, ArCH$_2$OH), 6.53 (1H, t, pyrimidine), 6.94 (2H, d, C$_6$H$_4$), 7.27 (2H, d, C$_6$H$_4$), 8.27 (2H, d, pyrimidine)

Intermediate 33: 4-{4-(Pyrimidin-2-ylamino)piperidin-1-yl}benzaldehyde

Methylene chloride (16 ml) was added to 156 mg of intermediate 32 to prepare a solution. Active manganese dioxide (312 mg) was added to the solution. The mixture was vigorously stirred at room temperature for 16 hr. The insolubles were collected by filtration, and washed twice each with 5.0 ml of 50% methanollmethylene chloride. The filtrate was combined with the washings, followed by concentration under the reduced pressure. Methylene chloride (4.0 ml) was added to the residue to prepare a solution which was then exposed to ultrasonics for about 30 sec. The solution was then filtered, and the filtrate was concentrated under the reduced pressure to prepare 144 mg of the title compound.

Physicochemical Properties of Intermediate 33
(1) Color and form: Colorless solid
(2) Molecular formula: C$_{16}$H$_{18}$N$_4$O$_1$
(3) Mass spectrum (TSPMS): m/z 283 (M+H)$^+$
(4) $^1$H NMR spectrum (400 MHz, CDCl$_3$) δ (ppm): 1.59 (2H, br q, piperidine), 2.19 (2H, br d, piperidine), 3.15 (2H, br t, piperidine), 3.93 (2H, br d, piperidine), 4.10 (1H, m, piperidine), 6.55 (1H, t, pyrimidine), 6.94 (2H, d, C$_6$H$_4$), 7.75 (2H, d, C$_6$H$_4$), 8.28 (2H, d, pyrimidine), 9.77 (1H, s, CHO)

Example 46 t-Butyl (2S)-benzenesulfonylamino-3-[4-{4-(pyrimidin-2-ylamino)piperidin-1-yl}benzylamino]-propionate Methanol (11 ml) and 7.4 ml of methylene chloride were added to 144 mg of intermediate 33 and 230 mg of t-butyl (2S)-N-benzenesulfonyl-2,3-diaminopropionate to prepare a solution. Acetic acid (0.30 ml) was added to the solution. Sodium boron cyanohydride (161 mg) was added thereto, and a reaction was allowed to proceed at room temperature for one hr. The reaction solution was concentrated under the reduced pressure. The residue was extracted with 28 ml of chloroform, followed by washing once with a saturated aqueous sodium hydrogencarbonate solution. The chloroform layer was dried over anhydrous sodium sulfate, and then concentrated under the reduced pressure. The residue was purified by column chromatography on silica gel (40 g, chloroform-methanol-concentrated aqueous ammonia=1000:33:1) to prepare 289 mg of the title compound.

Physicochemical Properties of Compound Prepared in Example 46
(1) Color and form: Colorless syrup
(2) Molecular formula: $C_{29}H_{38}N_6O_4S$
(3) Mass spectrum (TSPMS): m/z 567 $(M+H)^+$
(4) Specific rotation: $[\alpha]_D^{25}$ +14° (c 1.0, $CHCl_3$)
(5) $^1$H NMR spectrum (400 MHz, $CDCl_3$) δ (ppm): 1.25 (9H, s, t-Bu), 1.66 (2H, dq, piperidine), 2.16 (2H, br d, piperidine), 2.85 (1H, dd, $CH_2NHC\underline{H}_2CH$), 2.91 (1H, dd, $CH_2NHC\underline{H}_2CH$), 2.92 (2H, dt, piperidine), 3.60 (1H, d, $ArC\underline{H}_2$), 3.63 (2H, br d, piperidine), 3.73 (1H, d, $ArC\underline{H}_2$), 3.96 (1H, dd, $CH_2NHCH_2C\underline{H}$), 3.98 (1H, m, piperidine), 6.53 (1H, t, pyrimidine), 6.90 (2H, d, $C_6H_4$), 7.16 (2H, d,

Example 47

(2S)-Benzenesulfonylamino-3-[4-{4-(pyrimidin-2-ylamino)piperidin-1-yl}benzylamino]-propionic acid Methylene chloride (4.0 ml) was added to 289 mg of the compound prepared in Example 46 to prepare a solution. Anisole (0.2 ml) was added to the solution. Trifluoroacetic acid (4.0 ml) was added thereto under cooling at 0° C., and a reaction was allowed to proceed at room temperature for 10 hr. The reaction solution was concentrated under the reduced pressure. The residue was subjected to azeotropic distillation twice with toluene, followed by drying. The solid thus obtained was washed twice each with 10 ml of diisopropyl ether by decantation, and then dried to prepare 402 mg of the title compound as a crude compound. A part (23.3 mg) of the crude compound was purified by preparative thin-layer chromatography on silica gel (development system: chloroform-methanol-concentrated aqueous ammonia=90:20:1) to prepare 13.1 mg of the title compound.

Physicochemical Properties of Compound Prepared in Example 47
(1) Color and form: Colorless solid
(2) Molecular formula: $C_{25}H_{30}N_6O_4S$
(3) Mass spectrum (FABMS): m/z 511 $(M+H)^+$
(4) Specific rotation: $[\alpha]_D^{25}$ +56° (c 0.7, 10% conc. $NH_4OH/MeOH$)
(5) $^1$H NMR spectrum (400 MHz, 10% conc. $ND_4OD/CD_3OD$) δ (ppm): 1.72 (2H, dq, piperidine), 2.13 (2H, br d, piperidine), 2.79 (1H, dd, $CH_2NHC\underline{H}_2CH$), 2.89 (2H, br t, piperidine), 2.91 (1H, dd, $CH_2NHC\underline{H}_2CH$), 3.61 (1H, d, $ArC\underline{H}_2$), 3.66 (2H, br d, piperidine), 3.72 (1H, dd, $CH_2NHCH_2CH$), 3.73 (1H, d, $ArC\underline{H}_2$), 3.92 (1H, dddd, piperidine), 6.62 (1H, t, pyrimidine), 6.99 (2H, d, $C_6H_4$), 7.23 (2H, d, $C_6H_4$), 7.53 (2H, br t, $C_6H_5$), 7.60 (1H, br t, $C_6H_5$), 7.88 (2H, m, $C_6H_5$), 8.27 (2H, d, pyrimidine)

Example 48

(2S)-Benzenesulfonylamino-3-[4-{4-(1,4,5,6-tetrahydropyrimidin-2-ylamino)piperidin-1-yl}benzyl-amino]propionic acid Acetic acid (20 ml) and 1.8 ml of concentrated hydrochloric acid were added to 200 mg of the crude compound before the purification prepared in Example 47 to prepare a solution. 10% palladium-carbon (180 mg) was added to the solution. The mixture was vigorously shaken under a hydrogen pressure of 3.0 atm at room temperature for 2 hr. The catalyst was collected by filtration, and then washed twice each with 8.0 ml of acetic acid. The filtrate was combined with the washings, followed by concentration under the reduced pressure. The residue was subjected to azeotropic distillation twice with toluene, and was purified by column chromatography on silica gel (10 g, methylene chloride-ethanol-water-concentrated aqueous ammonia=12:10:1:1) to prepare 108 mg of the title compound as a crude compound. A part (24.5 mg) of the crude compound was purified by column chromatography on Sephadex LH-20 (30 ml, methanol) to prepare 21.4 mg of the title compound.

Physicochemical Properties of Compound Prepared in Example 48
(1) Color and form: Colorless solid
(2) Molecular formula: $C_{25}H_{34}N_6O_4S$
(3) Mass spectrum (TSPMS): m/z 515 $(M+H)^+$
(4) Specific rotation: $[\alpha]_D^{25}$ +57° (c 1.0, MeOH)
(5) $^1$H NMR spectrum (400 MHz, $CD_3OD$) δ (ppm): 1.61 (2H, m, piperidine), 1.94 (2H, quintet, tetrahydropyrimidine), 1.97 (2H, br d, piperidine), 2.83 (2H, br t, piperidine), 2.92 (1H, dd, $CH_2NHC\underline{H}_2CH$), 2.97 (1H, dd, $CH_2NHC\underline{H}_2CH$), 3.34 (4H, t, tetrahydropyrimidine), 3.45 (1H, dddd, piperidine), 3.64 (2H, br d, piperidine), 3.66 (1H, dd, $CH_2NHCH_2C\underline{H}$), 3.76 (1H, d, $ArC\underline{H}_2$), 3.83 (1H, d, $ArC\underline{H}_2$), 6.95 (2H, d, $C_6H_4$), 7.25 (2H, d, $C_6H_4$), 7.52 (2H, m, $C_6H_5$), 7.59 (1H, m, $C_6H_5$), 7.88 (2H, m, $C_6H_5$)

Example 49

(2S)-Benzenesulfonylamino-3-[N-benzyl-N-[4-{4-(1,4,5,6-tetrahydropyrimidin-2-ylamino)piperidin-1-yl}benzyl]amino]propionic acid Methanol (2.1 ml) and 2.1 ml of methylene chloride were added to 41.7 mg of the crude compound before the purification by column chromatography on Sephadex prepared in Example 48 to prepare a solution. Benzaldehyde (17.2 mg) and 0.03 ml of acetic acid were added to the solution. Sodium boron cyanohydride (10.2 mg) was added thereto, and a reaction was allowed to proceed at room temperature for 16 hr. The reaction solution was purified, without any post-treatment, by preparative thin-layer chromatography on silica gel (development system: methylene chloride-ethanol-water-concentrated aqueous ammonia=8:8:1:1) and then purified by column chromatography on Sephadex LH-20 (30 ml, 90% methanol/methylene chloride) to prepare 34.6 mg of the title compound.

Physicochemical Properties of Compound Prepared in Example 49
(1) Color and form: Colorless syrup
(2) Molecular formula: $C_{32}H_{40}N_6O_4S$
(3) Mass spectrum (FABMS): m/z 605 $(M+H)^+$
(4) Specific rotation: $[\alpha]_D^{25}$ +12° (c 1.0, 80% MeOH/$CH_2Cl_2$)
(5) $^1$H NMR spectrum (400 MHz, 90% $CD_3OD/CDCl_3$) δ (ppm): 1.63 (2H, m, piperidine), 1.92 (2H, quintet, tetrahydropyrimidine), 1.96 (2H, br d, piperidine), 2.71 (1H, dd, $CH_2N(CH_2Ph)C\underline{H}_2CH$), 2.74–2.84 (3H, m, piperidine and $CH_2N(CH_2Ph)C\underline{H}_2CH$), 3.32 (4H, t, tetrahydropyrimidine), 3.36–3.66 (7H, m, 3H of piperidine and 4H of $ArCH_2$), 3.77 (1H, dd, $CH_2N$ (CH₂Ph)CH₂CH), 6.91 (2H, d, C₆H₄), 7.22 (2H, d, C₆H₄), 7.24–7.32 (5H, m, NCH₂Ph), 7.45 (2H, m, C₆H₅), 7.53 (1H, m, C₆H,), 7.79 (2H, m, C₆H₅)

Intermediate 34: Methyl 3-fluoro-4-(4-hydroxypiperidin-1-yl)benzoate

Dimethyl sulfoxide (100 ml) was added to 24.5 g of 4-hydroxypiperidine to prepare a solution. Methyl 3,4-difluorobenzoate (33.2 g) was added to the solution. The mixture was stirred at 120° C. for 8 hr. The reaction solution was then cooled to room temperature, and poured into 1,000 ml of water, followed by extraction twice with 750 ml of ethyl acetate. The combined organic layer was washed twice with 500 ml of saturated saline, dried over anhydrous magnesium sulfate, and then concentrated under the reduced pressure to prepare 42.3 g of the title compound.
Physicochemical Properties of Intermediate 34
(1) Color and form: Pale yellow solid
(2) Molecular formula: $C_{13}H_{16}NO_3F$
(3) Mass spectrum (TSPMS): m/z 254 $(M+H)^+$
(4) $^1H$ NMR spectrum (400 MHz, CDCl₃) δ (ppm): 1.74 (2H, ddt, piperidine), 2.04 (2H, m, piperidine), 2.96 (2H, ddd, piperidine), 3.50 (2H, m, piperidine), 3.89 (4H, m, CO₂Me and piperidine), 6.91 (1H, t, C₆H₃CO), 7.64 (1H, dd, C₆H₃CO), 7.72 (1H, dd, C₆H₃CO)

Intermediate 35: Methyl 4-(4-azidopiperidin-1-yl)-3-fluorobenzoate

Methylene chloride (700 ml) was added to 24.8 g of intermediate 34 to prepare a solution. Triethylamine (70.0 ml) was added to the solution. Methanesulfonyl chloride (11.5 ml) was added slowly dropwise thereto at room temperature. The mixture was stirred at that temperature for one hr. Water (1,000 ml) was added to stop the reaction, followed by extraction twice with 1,000 ml of chloroform. The combined organic layer was dried over anhydrous magnesium sulfate, and then concentrated under reduced pressure. Water (500 ml) was added to the residue, and the mixture was extracted twice with 1,000 ml of a mixed organic solvent (ethyl acetate-hexane-methylene chloride=1:1:1). The combined organic layer was dried over anhydrous magnesium sulfate, and then concentrated under the reduced pressure to prepare 30.0 g of methyl 3-fluoro-4-{4-(methanesulfonyloxy)piperidin-1-yl}benzoate. Dimethylformamide was added to 10.0 g of the methyl 3-fluoro-4-{4-(methanesulfonyloxy)piperidin-1-yl}benzoate to prepare a solution. Sodium azide (3.9 g) was added to the solution. The mixture was stirred at 80° C. for 5 hr. The reaction solution was then cooled to room temperature, and poured into 1,000 ml of water, followed by extraction twice with 500 ml of ethyl acetate. The combined organic layer was washed twice with 500 ml of saturated saline, dried over anhydrous magnesium sulfate, and then concentrated under the reduced pressure. Water (1,000 ml) was added to the residue, and the mixture was extracted twice with 500 ml of hexane. The combined organic layer was dried over anhydrous magnesium sulfate, and then concentrated under the reduced pressure to prepare 7.7 g of the title compound.
Physicochemical Properties of Intermediate 35
(1) Color and form: Brown syrup
(2) Molecular formula: $C_{13}H_{15}N_4O_2F$
(3) Mass spectrum (TSPMS): m/z 279 $(M+H)^+$
(4) $^1H$ NMR spectrum (400 MHz, CDCl₃) δ (ppm): 1.82 (2H, ddt, piperidine), 2.05 (2H, m, piperidine), 2.99 (2H, ddd, piperidine), 3.47 (2H, m, piperidine), 3.62 (1H, tt, piperidine), 3.88 (3H, S, CO₂Me), 6.92 (1H, t, C₆H₃CO), 7.66 (1H, dd, C₆H₃CO), 7.74 (1H, dd, C₆H₃CO)

Intermediate 36: Methyl 4-(4-aminopiperidin-1-yl)-3-fluorobenzoate

Dioxane (190 ml), 27 ml of acetic acid, and 54 ml of water were added to 7.5 g of intermediate 35 to prepare a solution. 10% palladium-carbon (750 mg) was added to the solution. The mixture was vigorously stirred under a hydrogen pressure of one atm at room temperature for 4 hr. The insolubles were collected by filtration, and then washed twice with methanol. The filtrate was combined with the washings, followed by concentration under the reduced pressure. The residue was subjected to azeotropic distillation twice with toluene. Water (500 ml) and 500 ml of 1 N hydrochloric acid were added thereto to prepare a solution which was then washed twice with 500 ml of ethyl acetate. The aqueous layer was cooled to 0° C., and then was adjusted to pH 14 by the addition of concentrated aqueous ammonia. Further, salt was added thereto at room temperature to prepare a saturated solution which was then extracted three times with one liter of methylene chloride. The combined organic layer was dried over anhydrous sodium sulfate, and then concentrated under the reduced pressure to prepare 5.78 g of the title compound.
Physicochemical Properties of Intermediate 36
(1) Color and form: Pale yellow solid
(2) Molecular formula: $C_{13}H_{17}N_2O_2F$
(3) Mass spectrum (TSPMS): m/z 253 $(M+H)^+$
(4) $^1H$ NMR spectrum (400 MHz, CDCl₃) δ (ppm): 1.54 (2H, dq, piperidine), 1.94 (2H, br d, piperidine), 2.85 (3H, m, piperidine), 3.58 (2H, dt, piperidine), 3.88 (3H, s, CO₂Me), 6.92 (1H, t, C₆H₃CO), 7.65 (1H, dd, C₆H₃CO), 7.73 (1H, dd, C₆H₃CO)

Intermediate 37: Methyl 3-fluoro-4-{4-(pyrimidin-2-ylamino)piperidin-1-yl}benzoate Dimethyl sulfoxide (230 ml) was added to 5.78 g of intermediate 36 to prepare a solution. 2-Bromopyrimidine (3.64 g) was added to the solution. Further, 23 ml of diisopropylethylamine was added thereto. The mixture was heated to 122° C., and stirred for 12 hr. The reaction solution was cooled to room temperature. Saturated saline (1 liter) and 1 liter of water were then added thereto, followed by extraction three times with 500 ml of ethyl acetate. The combined organic layer was washed twice with 500 ml of saturated saline, dried over anhydrous sodium sulfate, and concentrated under the reduced pressure to prepare 6.74 g of the title compound.
Physicochemical Properties of Intermediate 37
(1) Color and form: Pale yellow solid
(2) Molecular formula: $C_{17}H_{19}N_4O_2F$
(3) Mass spectrum (TSPMS): m/z 331 $(M+H)^+$
(4) $^1H$ NMR spectrum (400 MHz, CDCl₃) δ (ppm): 1.71 (2H, dq, piperidine), 2.20 (2H, br d, piperidine), 2.99 (2H, ddd, piperidine), 3.59 (2H, dt, piperidine), 3.89 (3H, s, CO₂Me), 4.03 (1H, dddd, piperidine), 6.55 (1H, t, pyrimidine), 6.94 (1H, t, C₆H₃CO), 7.67 (1H, dd, C₆H₃CO), 7.75 (1H, ddd, C₆H₃CO), 8.29 (2H, d, pyrimidine)

Intermediate 38: 3-Fluoro-4-{4-(pyrimidin-2-ylamino)piperidin-1-yl}benzoic acid

Tetrahydrofuran (300 ml) and 100 ml of methanol were added to 6.6 g of intermediate 37 to prepare a solution. A 1

N aqueous sodium hydroxide solution (100 ml) was added to the solution. The mixture was stirred at 40° C. for 6 hr, and then concentrated under the reduced pressure. Water (1 liter) was added to the residue to prepare a solution which was then washed with 1 liter of ethyl acetate. The aqueous layer was adjusted to pH 6 by the addition of 1 N hydrochloric acid. The precipitated solid was collected by filtration through a glass filter, and then washed twice with water to prepare 4.96 g of the title compound.

Physicochemical Properties of Intermediate 38
  (1) Color and form: Colorless solid
  (2) Molecular formula: $C_{16}H_{17}N_4O_2F$
  (3) Mass spectrum (TSPMS): m/z 317 $(M+H)^+$
  (4) $^1H$ NMR spectrum (400 MHz, DMSO-$d_6$) δ (ppm): 1.63 (2H, br q, piperidine), 1.96 (2H, br d, piperidine), 2.88 (2H, br t, piperidine), 3.53 (2H, br d, piperidine), 3.89 (1H, m, piperidine), 6.54 (1H, t, pyrimidine), 7.08 (1H, t, $C_6H_3CO$), 7.54 (1H, dd, $C_6H_3CO$), 7.66 (1H, dd, $C_6H_3CO$), 8.26 (2H, d, pyrimidine)

Example 50 t-Butyl (2S)-benzenesulfonylamino-3-[3-fluoro-4-{4-(pyrimidin-2-ylamino)piperidin-1-yl}benzoylamino]propionate Dimethylformamide (30 ml) was added to 1.0 g of intermediate 38 to prepare a suspension. t-Butyl (2S)-N-benzenesulfonyl-2,3-diaminopropionate hydrochloride (1.17 g) was added to the suspension. Further, 1-hydroxybenzotriazole (512 mg), 1.04 ml of N-methylmorpholine, and 727 mg of 1-ethyl-3-(3-dimethylaminopropyl)carbodiimide hydrochloride were added thereto. The mixture was stirred at room temperature for 13 hr. A saturated aqueous sodium hydrogencarbonate solution (300 ml) and 100 ml of a saturated aqueous potassium carbonate solution were added to the reaction solution, followed by extraction three times with 200 ml of methylene chloride. The combined organic layer was washed with a mixed solution composed of 250 ml of saturated saline and 250 ml of water, dried over anhydrous sodium sulfate, and then concentrated under the reduced pressure. The residue was purified by column chromatography on silica gel (development system: methylene chloride-methanol=25:1) to prepare 1.77 g of the title compound.

Physicochemical Properties of Compound Prepared in Example 50
  (1) Color and form: Colorless solid
  (2) Molecular formula: $C_{29}H_{35}N_6O_5FS$
  (3) Mass spectrum (TSPMS): m/z 599 $(M+H)^+$
  (4) Specific rotation: $[\alpha]_D^{25}$ +26° (c 0.52, MeOH)
  (5) $^1H$ NMR spectrum (400 MHz, $CDCl_3$) δ (ppm): 1.23 (9H, s, t-Bu), 1.74 (2H, br q, piperidine), 2.12 (2H, br d, piperidine), 2.94 (2H, br t, piperidine), 3.49 (1H, dd, CONH$CH_2$CH), 3.59 (2H, br d, piperidine), 3.66 (1H, dd, CONH$CH_2$CH), 3.95 (1H, m, piperidine), 4.12 (1H, br t, CONHCH$_2$C$\underline{H}$), 6.59 (1H, t, pyrimidine), 7.08 (1H, t, $C_6H_3CO$), 7.47 (3H, m, $C_6H_3CO$ and $C_6H_5$), 7.54 (2H, m, $C_6H_3CO$ and $C_6H_5$), 7.83 (2H, d, $C_6H_5$), 8.27 (2H, d, pyrimidine)

Example 51

(2S)-Benzenesulfonylamino-3-[3-fluoro-4-{4-(pyrimidin-2-ylamino)piperidin-1-yl}benzoylamino]-propionic acid Methylene chloride (10 ml) was added to 600 mg of the compound prepared in Example 50 to prepare a solution. Trifluoroacetic acid (10 ml) was added to the solution. The mixture was stirred at room temperature for 4 hr. The reaction solution was concentrated under the reduced pressure to prepare 542 mg of tritrifluoroacetate of the title compound.

Physicochemical Properties of Compound Prepared in Example 51
  (1) Color and form: Colorless solid
  (2) Molecular formula: $C_{25}H_{27}N_6O_5FS$
  (3) Mass spectrum (TSPMS): m/z 543 $(M+H)^+$
  (4) Specific rotation: $[\alpha]_D^{23}$ +17° (c 0.53, MeOH-DMF (1:1)) (as tritrifluoroacetate)
  (5) $^1H$ NMR spectrum (400 MHz, $CD_3OD$) (as tritrifluoroacetate) δ (ppm): 1.81 (2H, dq, piperidine), 2.14 (2H, br d, piperidine), 2.95 (2H, dt, piperidine), 3.48 (1H, dd, CONH$CH_2$CH), 3.61 (2H, br d, piperidine), 3.72 (1H, dd, CONH$CH_2$CH), 4.03 (1H, tt, piperidine), 4.19 (1H, dd, CONHCH$_2$C$\underline{H}$), 6.80 (1H, t, pyrimidine), 7.08 (1H, t, $C_6H_3CO$), 7.46 (4H, m, $C_6H_3CO$ and $C_6H_5$), 7.53 (1H, dd, $C_6H_3CO$), 7.82 (2H, m, $C_6H_5$), 8.43 (2H, d, pyrimidine)

Example 52

(2S)-Benzenesulfonylamino-3-[3-fluoro-4-{4-(1,4,5,6-tetrahydropyrimidin-2-ylamino)piperidin-1-yl}-benzoylamino]propionic acid Dioxane (10 ml) and 1.0 ml of water were added to 542 mg of the tritrifluoroacetate of the compound prepared in Example 51 to prepare a solution. 10% palladium-carbon (120 mg) was added to the solution. The mixture was vigorously stirred under a hydrogen pressure of one atm at room temperature for 24 hr. The insolubles were collected by filtration, and then washed with a mixed solvent composed of 100 ml of dioxane and 10 ml of water. The filtrate was combined with the washings, followed by concentration under the reduced pressure. The residue was subjected to azeotropic distillation twice with toluene. A mixed solvent (ethanol-water-concentrated aqueous ammonia=8:1:1) (10 ml) was added thereto to prepare a solution which was allowed to stand at 5° C. for 22 hr. The resultant precipitate was collected by filtration, washed twice with 5 ml of water, and then dried to prepare 451 mg of the title compound.

Physicochemical Properties of Compound Prepared in Example 52
  (1) Color and form: Colorless solid
  (2) Molecular formula: $C_{25}H_{31}N_6O_5FS$
  (3) Mass spectrum (TSPMS): m/z 547 $(M+H)^+$
  (4) Specific rotation: $[\alpha]_D^{26}$ +79° (c 0.56, DMSO)
  (5) $^1H$ NMR spectrum (400 MHz, $CD_3OD$) δ (ppm): 1.68 (2H, br q, piperidine), 1.96 (2H, quintet, tetrahydropyrimidine), 2.02 (2H, br d, piperidine), 2.87 (2H, br t, piperidine), 3.37 (4H, t, tetrahydropyrimidine), 3.48 (1H, m, piperidine), 3.52 (2H, br d, piperidine), 3.57 (1H, dd, CONH$CH_2$CH), 3.65 (1H, dd, CONH$CH_2$CH), 3.73 (1H, dd, CONHCH$_2$C$\underline{H}$), 7.04 (1H, t, $C_6H_3CO$), 7.53 (5H, m, $C_6H_3CO$ and $C_6H_5$), 7.86 (2H, br d, $C_6H_5$)

Intermediate 39: 3-Fluoro-4-{4-(4,5-dihydro-1H-imidazol-2-ylamino)piperidin-1-yl}benzoic acid Tetrahydrofuran (2.0 ml) was added to 100 mg of intermediate 36 to prepare a solution. N-t-Butoxycarbonyl-2-isothiocyanatoethylamine (109 mg) was added to the solution. The mixture was stirred at room temperature for 23 hr.

The reaction solution was concentrated under the reduced pressure. The residue was purified by preparative thin-layer chromatography on silica gel (development system: methylene chloride-methanol=7:1) to prepare a crude compound. Ethanol (4.0 ml) and 4.0 ml of ethyl bromide were then added to the crude compound to prepare a solution which was then stirred at 60° C. for 9 hr. The reaction solution was then cooled to room temperature, and concentrated under the reduced pressure. The residue was purified by preparative thin-layer chromatography on silica gel (development system: methylene chloride-methanol=7:1) to prepare a crude compound. Water (1.0 ml) and 1.0 ml of trifluoroacetic acid were then added to the crude compound to prepare a solution. The solution was stirred at room temperature for 19 hr. The reaction solution was concentrated under the reduced pressure. Ethanol (8.0 ml) was added to the residue to prepare a solution. This solution was added dropwise at room temperature to a solution (8.0 ml) of 195 mg of sodium ethoxide in ethanol over a period of one hr, followed by stirring for additional 22 hr. The reaction solution was concentrated under the reduced pressure. The residue was purified by preparative thin-layer chromatography on silica gel (development system: chloroform-methanol-concentrated aqueous ammonia=30:10:1) to prepare 84.8 mg of a crude compound. Tetrahydrofuran (3.0 ml) and 1.0 ml of methanol were added to 53.6 mg of the crude compound to prepare a solution. A 1 N aqueous sodium hydroxide solution (1.0 ml) was added to the solution. The mixture was stirred at 40° C. for 3 hr, and then concentrated under the reduced pressure. Water (30 ml) was added to the residue. Further, 1 N hydrochloric acid was added to adjust pH to 5, followed by concentration under the reduced pressure. The residue was purified by Sephadex LH-20 (development system: methanol) to prepare 49.0 mg of the title compound.

Physicochemical Properties of Intermediate 39

(1) Color and form: Colorless oil
(2) Molecular formula: $C_{15}H_{19}N_4O_2F$
(3) Mass spectrum (TSPMS): m/z 307 (M+H)$^+$
(4) $^1$H NMR spectrum (400 MHz, CD$_3$OD) δ (ppm): 1.74 (2H, br dq, piperidine), 2.06 (2H, br d, piperidine), 2.92 (2H, br t, piperidine), 3.51 (1H, m, piperidine), 3.61 (2H, br d, piperidine), 3.73 (4H, s, CH$_2$CH$_2$), 7.07 (1H, t, C$_6$H$_3$CO), 7.62 (1H, d, C$_6$H$_3$CO), 7.75 (1H, d, C$_6$H$_3$CO)

Example 53 t-Butyl (2S)-benzenesulfonylamino-3-[3-fluoro-4-{4-(4,5-dihydro-1H-imidazol-2-ylamino)-piperidin-1-yl}benzoylamino]propionate Dimethylformamide (1.0 ml) was added to 100 mg of intermediate 39 to prepare a solution. t-Butyl (2S)-N-benzenesulfonyl-2,3-diaminopropionate hydrochloride (108 mg) was added to the solution. Further, 1-hydroxybenzotriazole (66.1 mg), 108 μl of N-methylmorpholine, and 93.7 mg of 1-ethyl-3-(3-dimethylaminopropyl)carbodiimide hydrochloride were added thereto. The mixture was stirred at room temperature for 12 hr. The reaction solution was concentrated under the reduced pressure. The residue was purified by column chromatography on silica gel (development system: chloroform-methanol-concentrated aqueous ammonia= 30:10:1) to prepare 8.2 mg of the title compound.

Physicochemical Properties of Compound Prepared in Example 53

(1) Color and form: Colorless solid
(2) Molecular formula: $C_{28}H_{37}N_6O_5FS$
(3) Mass spectrum (TSPMS): m/z 589 (M+H)$^+$
(4) Specific rotation: $[\alpha]_D^{20}$ +20° (c 0.41, MeOH)
(5) $^1$H NMR spectrum (400 MHz, CD$_3$OD) δ (ppm): 1.23 (9H, s, t-Bu), 1.72 (2H, m, piperidine), 2.06 (2H, br d, piperidine), 2.89 (2H, br t, piperidine), 3.47 (1H, dd, CONHCH$_2$CH), 3.49 (1H, m, piperidine), 3.57 (2H, br d, piperidine), 3.66 (1H, dd, CONHCH$_2$CH), 3.73 (4H, s, CH$_2$CH$_2$), 4.12 (1H, dd, CONHCH$_2$CH), 7.06 (1H, t, C$_6$H$_3$CO), 7.48 (2H, m, C$_6$H$_5$), 7.54 (2H, m, C$_6$11 and C$_6$H$_3$CO), 7.67 (1H, ddt, C$_6$H$_3$CO), 7.83 (2H, br d, C$_6$H$_5$)

Example 54

(2S)-Benzenesulfonylamino-3-[3-fluoro-4-{4-(4,5-dihydro-1H-imidazol-2-ylamino)piperidin-1-yl}-benzoylamino]propionic acid Methylene chloride (0.5 ml) was added to 17.0 mg of the compound prepared in Example 53 to prepare a solution. Trifluoroacetic acid (0.5 ml) was added to the solution. The mixture was stirred at 40° C. for 3 hr. The reaction solution was concentrated under the reduced pressure. The residue was purified by preparative thin-layer chromatography on silica gel (development system: methylene chloride-ethanol-concentrated aqueous ammonia-water=8:8:1:1) and then purified by Sephadex LH-20 (development system: methanol) to prepare 7.4 mg of the title compound.

Physicochemical Properties of Compound Prepared in Example 54

(1) Color and form: Colorless solid
(2) Molecular formula: $C_{24}H_{29}N_6O_5FS$
(3) Mass spectrum (TSPMS): m/z 533 (M+H)$^+$
(4) Specific rotation: $[\alpha]_D^{23}$ +37° (c 0.060, MeOH)
(5) $^1$H NMR spectrum (400 MHz, CD$_3$OD) δ (ppm): 1.74 (2H, dd, piperidine), 2.06 (2H, br d, piperidine), 2.89 (2H, br t, piperidine), 3.47 (1H, m, piperidine), 3.49 (1H, dd, CONHCH2CH), 3.57 (2H, br d, piperidine), 3.70 (1H, dd, CONHCH$_2$CH), 3.73 (4H, s, CH$_2$CH$_2$), 4.07 (1H, dd, CONHCH$_2$CH), 7.05 (1H, t, C$_6$H$_3$CO), 7.49 (5H, m, C$_6$H$_5$ and C$_6$H$_3$CO), 7.83 (2H, br d, C$_6$H$_5$)

Intermediate 40: Methyl 2,3-difluoro-4-(4-hydroxypiperidin-1-yl)benzoate

Anhydrous methanol (50 ml) and 5.0 ml of concentrated sulfuric acid were added to 5.00 g of 2,3,4-trifluorobenzoic acid. The mixture was heated under reflux for 5 hr. The reaction solution was added dropwise to 1.0 liter of a saturated aqueous sodium hydrogencarbonate solution, followed by extraction with 1.0 liter of diethyl ether. The extract was dried over anhydrous sodium sulfate, and then concentrated under the reduced pressure to prepare crude methyl 2,3,4-trifluorobenzoate as a colorless oil. 4-Hydroxypiperidine (2.87 g) and 10 ml of dimethyl sulfoxide were added thereto. The mixture was heated at 110° C. for 2 hr. The reaction solution was then cooled to room temperature, and 1.0 liter of ethyl acetate was added thereto. The mixture was extracted, followed by washing with 1.0 liter of a 2% aqueous sodium hydrogencarbonate solution. The aqueous layer was reextracted with 200 ml of ethyl acetate. The ethyl acetate layers were combined, washed with saturated saline, and dried over anhydrous sodium sulfate, followed by concentration under the reduced pressure. The residue was purified by column chromatography on silica gel (750 g, 60% ethyl acetate/hexane) to prepare 4.73 g of the title compound. Further, at that time, 1.26 g of a compound, wherein hydroxypiperidine had been introduced into the 2-position of benzoic acid, was obtained as a by-product.

Physicochemical Properties of Intermediate 40
(1) Color and form: Colorless solid
(2) Molecular formula: $C_{13}H_{15}NO_3F_2$
(3) Mass spectrum (EIMS): m/z 271 (M)$^+$
(4) $^1$H NMR spectrum (400 MHz, CDCl$_3$) δ (ppm): 1.73 (2H, m, piperidine), 2.04 (2H, m, piperidine), 3.03 (2H, ddd, piperidine), 3.54 (2H, m, piperidine), 3.90 (3H, s, Me), 3.91 (1H, m, piperidine), 6.68 (1H, ddd, Ar), 7.61 (1H, ddd, Ar)

Intermediate 41: Methyl 2,3-difluoro-4-{4 (methanesulfonyloxy)piperidin-1-yl}benzoate Methylene chloride (94 ml) was added to 4.70 g of intermediate 40 to prepare a solution. Methanesulfonyl chloride (1.5 ml) was added to the solution. Triethylamine (2.9 ml) and 106 mg of 4-dimethylaminopyridine were added thereto under cooling at 0° C. A reaction was allowed to proceed at room temperature for 2 hr. 1,3-Diaminopropane (257 mg) was added, and 150 ml of methylene chloride was further added to the reaction mixture, followed by washing once with a 5% aqueous potassium hydrogensulfate solution, once with a saturated aqueous sodium hydrogencarbonate solution, and once with saturated saline in that order. The organic layer was dried over anhydrous sodium sulfate, and then concentrated under the reduced pressure to prepare 5.95 g of the title compound.

Physicochemical properties of intermediate 41
(1) Color and form: Colorless acicular crystal
(2) Melting point: 160–161° C
(3) Molecular formula: $C_{14}H_{17}NO_5F_2S$
(4) Mass spectrum (APCIMS): m/z 350 (M+H)$^+$
(5) $^1$H NMR spectrum (400 MHz, CDCl$_3$) δ (ppm): 2.07 (2H, m, piperidine), 2.17 (2H, m, piperidine), 3.07 (3H, s, SO$_2$Me), 3.18 (2H, ddd, piperidine), 3.46 (2H, ddd, piperidine), 3.91 (3H, s, CO$_2$Me), 4.95 (1H, m, piperidine), 6.68 (1H, ddd, Ar), 7.63 (1H, ddd, Ar)

Intermediate 42: Methyl 4-(4-azidopiperidin-1-yl)-2,3-difluorobenzoate

Anhydrous dimethylformamide (118 ml) was added to 5.92 g of intermediate 41 and 2.20 g of sodium azide. The mixture was heated at 90° C for 8 hr. Ethyl acetate (2.0 liters) was added to the reaction solution to perform extraction, followed by washing with 2.0 liters of distilled water. The aqueous layer was reextracted with 500 ml of ethyl acetate. The ethyl acetate layers were combined, washed with a saturated aqueous sodium hydrogencarbonate solution and saturated saline in that order, dried over anhydrous sodium sulfate, and then concentrated under the reduced pressure. The residue was purified by column chromatography on silica gel (300 g, 30% ethyl acetate/hexane) to prepare 4.88 g of the title compound.

Physicochemical Properties of Intermediate 42
(1) Color and form: Colorless oil
(2) Molecular formula: $C_{13}H_4N_4O_2F_2$
(3) Mass spectrum (APCIMS): m/z 297 (M+H)$^+$
(4) $^1$H NMR spectrum (400 MHz, CDCl$_3$) δ (ppm): 1.82 (2H, m, piperidine), 2.05 (2H, m, piperidine), 3.05 (2H, ddd, piperidine), 3.50 (2H, m, piperidine), 3.64 (1H, m, piperidine), 3.91 (3H, s, Me), 6.67 (1H, ddd, Ar), 7.62 (1H, ddd, Ar)

Intermediate 43: Methyl 4-(4-aminopiperidin-1-yl)-2,3-difluorobenzoate 1,4-Dioxane (140 ml), 40 ml of distilled water, and 20 ml of acetic acid were added to 4.86 g of intermediate 42 to prepare a solution. 10% palladium-carbon (1.20 g) was added to the solution. The mixture was vigorously stirred under a hydrogen atmosphere at room temperature for 16 hr. The catalyst was collected by filtration, and then washed twice with an organic solvent having the same composition as the solvent for the reaction. The filtrate was combined with the washings, and concentrated under the reduced pressure. The residue was then subjected to azeotropic distillation twice each with 50 ml of toluene. The residue was purified by column chromatography on silica gel (250 g, chloroform-methanol-concentrated aqueous ammonia= 100:10:1→100:15:1) to prepare 2.10 g of the title compound.

Physicochemical Properties of Intermediate 43
(1) Color and form: Colorless platy crystal
(2) Melting point: 70–71° C.
(3) Molecular formula: $C_{13}H_{16}N_2O_2F_2$
(4) Mass spectrum (ESIMS): m/z 271 (M+H)$^+$
(5) $^1$H NMR spectrum (400 MHz, CDCl$_3$) δ (ppm): 1.52 (2H, m, piperidine), 1.93 (2H, m, piperidine), 2.83–2.93 (3H, m, piperidine), 3.62 (2H, br d, piperidine), 3.90 (3H, s, Me), 6.66 (1H, ddd, Ar), 7.60 (1H, ddd, Ar)

Intermediate 44: Methyl 2,3-difluoro-4-{4-(pyrimidin-2-ylamino)piperidin-1-yl}benzoate Dimethyl sulfoxide (24 ml) was added to 600 mg of intermediate 43 to prepare a solution. Diisopropylethylamine (2.0 ml) and 529 mg of pyrimidine dibromide were added to the solution. A reaction was allowed to proceed at 120° C. for 12 hr. Ethyl acetate (500 ml) was added to the reaction solution to perform extraction, followed by washing with 500 ml of distilled water. The aqueous layer was reextracted with 125 ml of ethyl acetate. The ethyl acetate layers were combined, washed with a saturated aqueous sodium hydrogencarbonate solution and saturated saline in that order, dried over anhydrous sodium sulfate, and then concentrated under the reduced pressure. The residue was purified by column chromatography on silica gel (65 g, 8.5% acetone/chloroform) to prepare 638 mg of the title compound.

Physicochemical Properties of Intermediate 44
(1) Color and form: Colorless solid
(2) Molecular formula: $C_{17}H_{18}N_4O_2F_2$
(3) Mass spectrum (ESIMS): m/z 349 (M+H)$^+$
(4) $^1$H NMR spectrum (400 MHz, CDCl$_3$) δ (ppm): 1.69 (2H, m, piperidine), 2.20 (2H, m, piperidine), 3.03 (2H, br t, piperidine), 3.63 (2H, br d, piperidine), 3.91 (3H, S, Me), 4.04 (1H, m, piperidine), 6.55 (1H, t, pyrimidine), 6.69 (1H, ddd, Ar), 7.62 (1H, ddd, Ar), 8.29 (2H, d, pyrimidine)

Intermediate 45: 2,3-Difluoro-4-{4-(pyrimidin-2-ylamino)piperidin-1-yl}benzoic acid Tetrahydrofuran (42 ml) and 14 ml of methanol were added to 638 mg of intermediate 44 to prepare a solution. A 1 N aqueous sodium hydroxide solution (14 ml) was added to the solution. A reaction was allowed to proceed at 45° C. for 2 hr. The reaction solution was concentrated under the reduced pressure. Distilled water (28 ml) was added to the residue to prepare a solution. The solution was neutralized by the addition of 2.1 ml of 5 N hydrochloric acid and then 2.8 ml of 1 N hydrochloric acid. The mixture containing a solid precipitated therein was allowed to stand at 0° C. for 48 hr. The solid was then collected by filtration, washed three times with distilled water, and heat-dried over phosphorus pentoxide at 60° C. for one hr. Thus, 402 mg of the title compound was prepared.

Physicochemical Properties of Intermediate 45

(1) Color and form: Colorless solid
(2) Molecular formula: $C_{16}H_{16}N_4O_2F_2$
(3) Mass spectrum (ESIMS): m/z 335 (M+H)$^+$
(4) $^1$H NMR spectrum (400 MHz, DMSO-d$_6$) δ (ppm): 1.63 (2H, m, piperidine), 1.97 (2H, br d, piperidine), 2.97 (2H, br t, piperidine), 3.59 (2H, br d, piperidine), 3.92 (1H, m, piperidine), 6.56 (1H, t, pyrimidine), 6.90 (1H, br t, Ar), 7.58 (1H, br t, Ar), 8.28 (2H, d, pyrimidine)

Example 55 t-Butyl (2S)-benzenesulfonylamino-3-[2,3-difluoro-4-{4-(pyrimidin-2-ylamino)piperidin-1-yl}-benzoylamino]propionate Anhydrous dimethylformamide (6.8 ml) and 6.8 ml of methylene chloride were added to 130 mg of intermediate 45 to prepare a solution. Benzotriazole-1-yloxytris(dimethylamino)phosphonium hexafluorophosphate (258 mg) and 0.10 ml of diisopropylethylamine were added in that order to the solution. A reaction was allowed to proceed at room temperature for 2 hr to prepare an active ester. Separately, 6.8 ml of methylene chloride was added to 140 mg of t-butyl (2S)-N-benzenesulfonyl-2,3-diaminopropionate to prepare a solution. Diisopropylethylamine (51 μl) was added to the solution. The active ester solution prepared above was added thereto under cooling at −10° C. A reaction was allowed to proceed at room temperature for 30 min. The reaction solution was concentrated under the reduced pressure. The residue was extracted with 50 ml of ethyl acetate. The extract was washed once with a saturated aqueous sodium hydrogencarbonate solution and once with saturated saline in that order, dried over anhydrous sodium sulfate, and then concentrated under the reduced pressure. The residue was purified by column chromatography on silica gel (27 g, chloroform-methanol-concentrated aqueous ammonia=400:20:1) to prepare 239 mg of the title compound.

Physicochemical Properties of Compound Prepared in Example 55

(1) Color and form: Colorless syrup
(2) Molecular formula: $C_{29}H_{34}N_6O_5F_2S$
(3) Mass spectrum (ESIMS): m/z 617 (M+H)$^+$
(4) Specific rotation: $[\alpha]_D^{25}$ +39° (c 1.0, CHCl$_3$)
(5) $^1$H NMR spectrum (400 MHz, CDCl$_3$) δ (ppm): 1.29 (9H, s, t-Bu), 1.70 (2H, br q, piperidine), 2.19 (2H, br s, piperidine), 3.01 (2H, br t, piperidine), 3.59 (2H, br d, piperidine), 3.67–3.86 (2H, m, CONHC$\underline{H}_2$CH), 3.97–4.07 (2H, m, CONHCH$_2$C$\underline{H}$ and piperidine), 6.54 (1H, t, pyrimidine), 6.74 (1H, br t, C$_6$H$_2$F$_2$), 7.46 (2H, br t, C$_6$H$_5$), 7.53 (1H, br t, C$_6$H$_5$), 7.68 (1H, br t, C$_6$H$_2$F$_2$), 7.85 (2H, m, C$_6$H$_5$), 8.30 (2H, d, pyrimidine)

Example 56

(2S)-Benzenesulfonylamino-3-[2,3-difluoro-4-{4-(pyrimidin-2-ylamino)piperidin-1-yl}benzoylamino]-propionic acid Methylene chloride (3.0 ml) was added to 226 mg of the compound prepared in Example 55 to prepare a solution. Anisole (0.15 ml) was added to the solution. Trifluoroacetic acid (3.0 ml) was added thereto under cooling at 0° C. A reaction was allowed to proceed at 0° C. for 12 hr. The reaction solution was concentrated under the reduced pressure. The residue was subjected to azeotropic distillation twice each with 8.0 ml of toluene, and then dried. The solid thus obtained was washed twice each with 8.0 ml of diisopropyl ether by decantation, and then dried. The dried solid was then purified by column chromatography on silica gel (27 g, chloroform-methanol-concentrated aqueous ammonia=90:20:1) to prepare 177 mg of the title compound.

Physicochemical Properties of Compound Prepared in Example 56

(1) Color and form: Colorless solid
(2) Molecular formula: $C_{25}H_{26}N_6O_5F_2S$
(3) Mass spectrum (APCIMS): m/z 561 (M+H)$^+$
(4) Specific rotation: $[\alpha]_D^{25}$ +69° (c 0.5, 10% conc. NH$_4$OH/MeOH)
(5) $^1$H NMR spectrum (400 MHz, 10% conc. ND$_4$OD/CD$_3$OD) δ (ppm): 1.75 (2H, dq, piperidine), 2.13 (2H, br d, piperidine), 3.01 (2H, br t, piperidine), 3.56 (1H, dd, CONHC$\underline{H}_2$CH), 3.63 (2H, br d, piperidine), 3.72 (1H, dd, CONHC$\underline{H}_2$CH), 3.78 (2H, dd, CONHCH$_2$C$\underline{H}$), 3.96 (1H, dddd, piperidine), 6.63 (1H, t, pyrimidine), 6.92 (1H, br t, C$_6$H$_2$F$_2$), 7.45–7.56 (4H, m, 3H of C$_6$H$_5$ and 1H of C$_6$H$_2$F$_2$), 7.85 (2H, m, C$_6$H$_5$), 8.29 (2H, d, pyrimidine)

Example 57

(2S)-Benzenesulfonylamino-3-[2,3-difluoro-4-{4-(1,4,5,6-tetrahydropyrimidin-2-ylamino)piperidin-1yl}benzoylamino]propionic acid 1,4-Dioxane (7.0 ml), 4.0 ml of acetic acid, and 4.0 ml of 0.5 N hydrochloric acid were added to 100 mg of the compound prepared in Example 56 to prepare a solution. 10% palladium-carbon (25 mg) was added to the solution. The mixture was vigorously stirred under a hydrogen atmosphere at room temperature for 16 hr. The catalyst was collected by filtration, and then washed twice with a mixed solvent (1,4-dioxane-acetic acid-water=7:2:2). The filtrate was combined with the washings, and then concentrated under the reduced pressure. The residue was subjected to azeotropic distillation twice each with 4.0 ml of toluene, and was purified by column chromatography on silica gel (12 g, methylene chloride-ethanol-water-concentrated aqueous ammonia=8:8:1:1) and then purified by column chromatography on Sephadex LH-20 (120 ml, methylene chloride-ethanol-water-concentrated aqueous ammonia=6:8:1:1) to prepare 87.2 mg of the title compound.

Physicochemical Properties of Compound Prepared in Example 57

(1) Color and form: Colorless solid
(2) Molecular formula: $C_{25}H_{30}N_6O_5F_2S$
(3) Mass spectrum (ESIMS): m/z 565 (M+H)$^+$
(4) Specific rotation: $[\alpha]_D^{25}$ +92° (c 0.6, DMSO)
(5) $^1$H NMR spectrum (400 MHz, DMSO-d$_6$) δ (ppm): 1.54 (2H, m, piperidine), 1.81 (2H, quintet, tetrahydropyrimidine), 1.87 (2H, br d, piperidine), 2.73 (2H, br t, piperidine), 3.08 (1H, br t, CONHC$\underline{H}_2$CH), 3.21 (4H, br t, tetrahydropyrimidine), 3.43 (22H, m, piperidine), 3.80 (1H, m, CONHC$\underline{H}_2$CH), 6.87 (1H, br t, C$_6$H$_2$F$_2$), 7.51 (1H, br t, C$_6$H$_2$F$_2$), 7.56 (2H, m, C$_6$H$_5$), 7.63 (1H, m, C$_6$H$_5$), 7.84 (2H, m, C$_6$H$_5$)

Intermediate 46: Methyl 3-chloro-4-(4-hydroxypiperidin-1-yl)benzoate

Dimethyl sulfoxide (10 ml) was added to 2.6 g of 4-hydroxypiperidine to prepare a solution. Methyl 3-chloro-4-fluorobenzoate (6.2 g) was added to the solution. The mixture was stirred at 120° C. for 2 hr. The reaction solution was then cooled to room temperature, and poured into 2,000 ml of water, followed by extraction twice with 1,000 ml of ethyl acetate. The combined organic layer was dried over anhydrous magnesium sulfate, and then concentrated under the reduced pressure to prepare 5.8 g of the title compound.

Physicochemical Properties of Intermediate 46
(1) Color and form: Colorless solid
(2) Molecular formula: C$_{13}$H$_{16}$NO$_3$Cl
(3) Mass spectrum (TSPMS): m/z 270 (M+H)$^+$
(4) $^1$H NMR spectrum (400 MHz, CDCl$_3$) δ (ppm): 1.74 (2H, ddt, piperidine), 2.04 (2H, m, piperidine), 2.89 (2H, ddd, piperidine), 3.40 (2H, m, piperidine), 3.88 (1H, m, piperidine), 3.89 (3H, s, CO$_2$Me), 7.02 (1H, d, C$_6$H$_3$CO), 7.85 (1H, dd, C$_6$H$_3$CO), 8.01 (1H, d, C$_6$H$_3$CO)

Intermediate 47: Methyl 3-chloro-4-{4-(methanesulfonyl-oxy)piperidin-1-yl}benzoate Methylene chloride (200 ml) was added to 5.8 g of intermediate 46 to prepare a solution. Triethylamine (15 ml) was added to the solution. Methanesulfonyl chloride (2.5 ml) was added slowly dropwise thereto at room temperature. The mixture was stirred at that temperature for 20 min. Water (1,000 ml) was added to stop the reaction, followed by extraction twice with 500 ml of chloroform. The combined organic layer was dried over anhydrous magnesium sulfate, and then concentrated under the reduced pressure. Water (500 ml) was added to the residue, and the solution was extracted with 1,000 ml of a mixed organic solvent (ethyl acetate-hexane=1:2). The organic layer was dried over anhydrous magnesium sulfate, and then concentrated under the reduced pressure to prepare 5.8 g of the title compound.

Physicochemical Properties of Intermediate 47
(1) Color and form: Colorless, transparent syrup
(2) Molecular formula: C$_{14}$H$_{18}$NO$_5$ClS
(3) Mass spectrum (TSPMS): m/z 348 (M+H)$^+$
(4) $^1$H NMR spectrum (400 MHz, CDCl$_3$) δ (ppm): 2.10 (2H, ddt, piperidine), 2.20 (2H, dq, piperidine), 3.05 (2H, ddd, piperidine), 3.07 (3H, s, SO$_3$Me), 3.34 (2H, ddd, piperidine), 3.90 (3H, s, CO$_2$Me), 4.94 (1H, tt, piperidine), 7.03 (1H, d, C$_6$H$_3$CO), 7.88 (1H, dd, C$_6$H$_3$CO), 8.03 (1H, d, C$_6$H$_3$CO)

Intermediate 48: Methyl 4-(4-azidopiperidin-1-yl)-3-chlorobenzoate

Dimethylformamide was added to 5.8 g of intermediate 47 to prepare a solution. Sodium azide (2.5 g) was added to the solution. The mixture was stirred at 120° C. for 4 hr. The reaction solution was then cooled to room temperature, and poured into 1,500 ml of water, followed by extraction three times with 500 ml of ethyl acetate. The combined organic layer was washed twice with 500 ml of saturated saline, dried over anhydrous magnesium sulfate, and then concentrated under the reduced pressure. The residue was purified by column chromatography on silica gel (development system: hexane-ethyl acetate=1:1) to prepare 4.1 g of the title compound.

Physicochemical Properties of Intermediate 48
(1) Color and form: Colorless solid
(2) Molecular formula: C$_{13}$H$_{15}$N$_4$O$_2$Cl
(3) Mass spectrum (TSPMS): m/z 295 (M+H)$^+$
(4) $^1$H NMR spectrum (400 MHz, CDCl$_3$) δ (ppm): 1.86 (2H, ddt, piperidine), 2.06 (2H, m, piperidine), 2.92 (2H, ddd, piperidine), 3.37 (2H, m, piperidine), 3.62 (1H, tt, piperidine), 3.89 (3H, s, CO$_2$Me), 7.02 (1H, d, C$_6$H$_3$CO), 7.86 (1H, dd, C$_6$H$_3$CO), 8.01 (1H, d, C$_6$H$_3$CO)

Intermediate 49: Methyl 4-(4-aminopiperidin-1-yl)-3-chlorobenzoate

Acetic acid (200 ml) and 20 ml of concentrated hydrochloric acid were added to 4.0 g of intermediate 48 to prepare a solution. 10% palladium-carbon (1.0 g) was added to the solution. The mixture was vigorously stirred under a hydrogen pressure of one atm at room temperature for 6 hr. The insolubles were collected by filtration, and then washed with acetic acid. The filtrate was combined with the washings, and then concentrated under the reduced pressure. The residue was purified by column chromatography on silica gel (development system: methylene chloride-methanol-concentrated aqueous ammonia=90:10:1) to prepare 595 mg of the title compound.

Physicochemical Properties of Intermediate 49
(1) Color and form: Colorless solid
(2) Molecular formula: C$_{13}$H$_{17}$N$_2$O$_2$Cl
(3) Mass spectrum (TSPMS): m/z 269 (M+H)$^+$
(4) $^1$H NMR spectrum (400 MHz, CD$_3$OD) δ (ppm): 1.84 (2H, dq, piperidine), 2.12 (2H, m, piperidine), 2.86 (2H, dt, piperidine), 3.28 (1H, m, piperidine), 3.56 (2H, br d, piperidine), 3.88 (3H, S, CO$_2$Me), 7.19 (1H, d, C$_6$H$_3$CO), 7.90 (1H, dd, C$_6$H$_3$CO), 7.98 (1H, d, C$_6$H$_3$CO)

Intermediate 50: Methyl 3-chloro-4-{4-(pyrimidin-2-ylamino)piperidin-1-yl}benzoate Dimethyl sulfoxide (10 ml) was added to 255 mg of intermediate 49 to prepare a solution. 2-Bromopyrimidine (153 mg) was added to the solution. Further, 1.0 ml of diisopropylethylamine was added thereto. The mixture was heated to 120° C., and stirred for 11 hr. The reaction solution was then cooled to room temperature, and poured into 500 ml of water, followed by extraction twice with 500 ml of ethyl acetate. The combined organic layer was dried over anhydrous magnesium sulfate, and then concentrated under the reduced pressure. The residue was purified by column chromatography on silica gel (development system: methylene chloride-methanol-concentrated aqueous ammonia= 190:10:1) to prepare 169 mg of the title compound.

Physicochemical Properties of Intermediate 50
(1) Color and form: Colorless solid
(2) Molecular formula: C$_{17}$H$_{19}$N$_4$O$_2$Cl
(3) Mass spectrum (TSPMS): m/z 347 (M+H)$^+$
(4) $^1$H NMR spectrum (400 MHz, CDCl$_3$) δ (ppm): 1.75 (2H, dq, piperidine), 2.21 (2H, m, piperidine), 2.92 (2H, dt, piperidine), 3.50 (2H, br d, piperidine), 3.89

(3H, s, CO$_2$Me), 4.03 (1H, m, piperidine), 6.55 (1H, t, pyrimidine), 7.04 (1H, d, C$_6$H$_3$CO), 7.88 (1H, dd, C$_6$H$_3$CO), 8.03 (1H, d, C$_6$H$_3$CO), 8.29 (2H, d, pyrimidine)

Intermediate 51: 3-Chloro-4-{4-(pyrimidin-2-ylamino)piperidin-1-yl}benzoic acid

Tetrahydrofuran (6.0 ml) and 2.0 ml of methanol were added to 169 mg of intermediate 50 to prepare a solution. A 1 N aqueous sodium hydroxide solution (2.0 ml) was added to the solution. The mixture was stirred 60° C. for 7 hr. The reaction solution was then cooled to room temperature, adjusted to pH 4 by the addition of 1 N hydrochloric acid, and then poured into 1,000 ml of water. The resultant precipitate was collected by filtration through a glass filter, and then dried to prepare 109 mg of the title compound.

Physicochemical Properties of Intermediate 51

(1) Color and form: Colorless solid
(2) Molecular formula: C$_{16}$H$_{17}$N$_4$O$_2$Cl
(3) Mass spectrum (FABMS): m/z 333 (M+H)$^+$
(4) $^1$H NMR spectrum (400 MHz, DMSO-d$_6$) δ (ppm): 1.67 (2H, dq, piperidine), 1.97 (2H, m, piperidine), 2.81 (2H, br t, piperidine), 3.41 (2H, br d, piperidine), 3.89 (1H, br d, piperidine), 6.54 (1H, t, pyrimidine), 7.19 (1H, t, C$_6$H$_3$CO), 7.81 (1H, dd, C$_6$H$_3$CO), 7.85 (1H, d, C$_6$H$_3$CO), 8.26 (2H, d, pyrimidine)

Example 58 t-Butyl (2S)-benzenesulfonylamino-3-[3-chloro-4-{4-(pyrimidin-2-ylamino)piperidin-1-yl}benzoylamino]propionate Dimethylformamide (30 ml) was added to 107 mg of intermediate 51 to prepare a solution. t-Butyl (2S)-N-benzenesulfonyl-2,3-diaminopropionate hydrochloride (97 mg) was added to the solution. Further, 69 mg of 1-hydroxybenzotriazole, 180 μl of N-methylmorpholine, and 126 mg of 1-ethyl-3-(3-dimethylaminopropyl) carbodiimide hydrochloride were added thereto. The mixture was stirred at room temperature for one day. Saturated aqueous sodium hydrogencarbonate solution was added to stop the reaction, followed by extraction twice with 400 ml of ethyl acetate. The combined organic layer was washed with 500 ml of saturated saline, dried over anhydrous magnesium sulfate, and then concentrated under the reduced pressure. The residue was dissolved in 10 ml of methanol. The solution was added dropwise to 1,000 ml of water. The resultant precipitate was collected by filtration through a glass filter, and then dried to prepare 168 mg of the title compound.

Physicochemical Properties of Compound Prepared in Example 58

(1) Color and form: Colorless solid
(2) Molecular formula: C$_{29}$H$_{35}$N$_6$O$_5$ClS
(3) Mass spectrum (TSPMS): m/z 615 (M+H)$^+$
(4) Specific rotation: $[\alpha]_D^{25}$ +49° (c 1.0, CH$_2$Cl$_2$)
(5) $^1$H NMR spectrum (400 MHz, CDCl$_3$) δ (ppm): 1.29 (9H, s, t-Bu), 1.75 (2H, br q, piperidine), 2.21 (2H, br d, piperidine), 2.91 (2H, br t, piperidine), 3.47 (2H, br d, piperidine), 3.56 (1H, ddd, CONHC$\underline{H}_2$CH), 3.90 (2H, m, CONHCH$_2$C$\underline{H}$), 4.03 (1H, m, piperidine), 6.55 (1H, t, pyrimidine), 7.07 (1H, d, C$_6$H$_3$CO), 7.51 (2H, m, C$_6$H$_5$), 7.58 (1H, m, C$_6$H$_5$), 7.65 (1H, dd, C$_6$H$_3$CO), 7.84 (1H, dd, C$_6$H$_3$CO), 7.86 (2H, br d, C$_6$H$_5$), 8.29 (2H, d, pyrimidine)

Example 59

(2S)-Benzenesulfonylamino-3-[3-chloro-4-{4-(pyrimidin-2-ylamino)piperidin-1-yl}benzoylamino]-propionic acid Methylene chloride (10 ml) was added to 168 mg of the compound prepared in Example 58 to prepare a solution. Trifluoroacetic acid (10 ml) was added to the solution. The mixture was stirred at room temperature for 5 hr. The reaction solution was concentrated under the reduced pressure to prepare 180 mg of tritrifluoroacetate of the title compound.

Physicochemical Properties of Compound Prepared in Example 59

(1) Color and form: Pale yellow solid
(2) Molecular formula: C$_{25}$H$_{27}$N$_6$O$_5$ClS
(3) Mass spectrum (TSPMS): m/z 559 (M+H)$^+$
(4) Specific rotation: $[\alpha]_D^{25}$ +73° (c 0.53, MeOH) (as tritrifluoroacetate)
(5) $^1$H NMR spectrum (400 MHz, CD$_3$OD) (as tritrifluoroacetate) δ (ppm): 1.88 (2H, dq, piperidine), 2.16 (2H, br d, piperidine), 2.91 (2H, br t, piperidine), 3.47 (1H, dd, CONHC$\underline{H}_2$CH), 3.52 (2H, br d, piperidine), 3.72 (1H, dd, CONHC$\underline{H}_2$CH), 4.07 (1H, m, piperidine), 4.20 (1H, dd, CONHCH$_2$C$\underline{H}$), 6.88 (1H, t, pyrimidine), 7.19 (1H, d, C$_6$H$_3$CO), 7.46 (3H, m, C$_6$H$_5$), 7.67 (1H, dd, C$_6$H$_3$CO), 7.77 (1H, d, C$_6$H$_3$CO), 7.82 (2H, m, C$_6$H$_5$), 8.50 (2H, d, pyrimidine)

Example 60

(2S)-Benzenesulfonylamino-3-[3-chloro-4-{4-(1,4,5,6-tetrahydropyrimidin-2-ylamino)piperidin-1-yl}-benzoylamino]propionic acid Acetic acid (25 ml) and 2.5 ml of concentrated hydrochloric acid were added to 51 mg of the compound prepared in Example 59 to prepare a solution. 10% palladium-carbon (26 mg) was added to the solution. The mixture was vigorously shaken under a hydrogen pressure of 3 atm at room temperature for 5 hr. The insolubles were collected by filtration, and washed with acetic acid. The filtrate was combined with the washings, and then concentrated under the reduced pressure. The residue was purified by column chromatography on silica gel (development system: methylene chloride ethanol-water-concentrated aqueous ammonia=8:8:1:1) and then purified by chromatography on Sephadex LH-20 (development system: methanol) to prepare 15 mg of the title compound.

Physicochemical Properties of Compound Prepared in Example 60

(1) Color and form: Colorless solid
(2) Molecular formula: C$_{25}$H$_{31}$N$_6$O$_5$SCl
(3) Mass spectrum (TSPMS): m/z 563 (M+H)$^+$
(4) Specific rotation: $[\alpha]_D^{25}$ +64° (c 0.2, MeOH)
(5) $^1$H NMR spectrum (400 MHz, CD$_3$OD) δ (ppm): 1.73 (2H, m, piperidine), 1.97 (2H, quintet, tetrahydropyrimidine), 2.04 (2H, m, piperidine), 2.84 (2H, br t, piperidine), 3.37 (4H, br t, tetrahydropyrimidine), 3.43 (2H, br d, piperidine), 3.48 (1H, m, piperidine), 3.56 (1H, dd, CONHC$\underline{H}_2$CH), 3.66 (1H, dd, CONHC$\underline{H}_2$CH), 3.74 (1H, dd, CONHCH$_2$C$\underline{H}$), 7.15 (1H, d, C$_6$H$_3$CO), 7.47 (2H, m, C$_6$H$_5$), 7.53 (1H, m, C$_6$H$_5$), 7.72 (1H, dd, C$_6$H$_3$CO), 7.85 (3H, m, C$_6$H$_3$CO and C$_6$H$_5$)

Example 61 t-Butyl 2-(N-benzenesulfonyl-N-methyl)amino-3-[4-{4-(pyrimidin-2-ylamino)piperidin-1-yl}benzoylamino]propionate Anhydrous dimethylformamide (1.2 ml) was added to 60.0 mg of the compound prepared in Example 1 to prepare a solution. Methyl iodide (73.3 mg) and 94.4 mg of diazabicycloundecene were added in that order to the solution. A reaction was allowed to proceed at room temperature for 16 hr. The reaction solution was concentrated under the reduced pressure. The residue was extracted with 20 ml of ethyl acetate. The extract was washed once with distilled water and once with saturated saline in that order, dried over anhydrous sodium sulfate, and then concentrated under the reduced pressure. The residue was purified by preparative thin-layer chromatography on silica gel (development system: chloroform-methanol-concentrated aqueous ammonia=400:20:1) to prepare 53.1 mg of the title compound.

Physicochemical Properties of Compound Prepared in Example 61

(1) Color and form: Colorless solid
(2) Molecular formula: $C_{30}H_{38}N_6O_5S$
(3) Mass spectrum (FABMS): m/z 595 (M+H)$^+$
(4) $^1$H NMR spectrum (400 MHz, CDCl$_3$) δ (ppm): 1.30 (9H, s, t-Bu), 1.62 (2H, m, piperidine), 2.17 (2H, br d, piperidine), 2.89 (3H, s, NMe), 3.05 (2H, br t, piperidine), 3.77 (1H, dt, CONHC$\underline{H}_2$CH), 3.81 (2H, br d, piperidine), 3.88 (1H, dt, CONHC$\underline{H}_2$CH), 4.05 (1H, m, piperidine), 4.73 (1H, dd, CONHCH$_2$C$\underline{H}$), 6.54 (1H, t, pyrimidine), 6.92 (2H, d, C$_6$H$_4$), 7.50 (2H, m, C$_6$H$_5$), 7.57 (1H, m, C$_6$H$_5$), 7.75 (2H, d, C$_6$H$_4$), 7.87 (2H, m, C$_6$H$_5$), 8.28 (2H, d, pyrimidine)

Example 62

2-(N-Benzenesulfonyl-N-methyl)amino-3-[4-{4-(pyrimidin-2-ylamino)piperidin-1-yl}benzoylamino]-propionic acid Methylene chloride (0.70 ml) was added to 52.9 mg of the compound prepared in Example 61 to prepare a solution. Anisole (0.03 ml) was added to the solution. Trifluoroacetic acid (0.70 ml) was added thereto under cooling at 0° C. A reaction was allowed to proceed at 0° C. for 16 hr. The reaction solution was concentrated under the reduced pressure. The residue was subjected to azeotropic distillation twice with toluene, and then dried. The solid was washed twice with duisopropyl ether by decantation, and then dried. The residue was purified by preparative thin-layer chromatography on silica gel (development system: chloroform-methanol-concentrated aqueous ammonia=90:20:1) to prepare 44.1 mg of the title compound.

Physicochemical Properties of Compound Prepared in Example 62

(1) Color and form: Colorless solid
(2) Molecular formula: $C_{26}H_{30}N_6O_5S$
(3) Mass spectrum (ESIMS): m/z 539 (M+H)$^+$
(4) $^1$H NMR spectrum (400 MHz, CD$_3$OD) δ (ppm): 1.65 (2H, br dq, piperidine), 2.09 (2H, br d, piperidine), 2.90 (3H, s, NMe), 3.00 (2H, br t, piperidine), 3.72 (1H, dd, CONHC$\underline{H}_2$CH), 3.76 (1H, dd, CONHC$\underline{H}_2$CH), 3.89 (2H, br d, piperidine), 3.99 (1H, m, piperidine), 4.74 (1H, dd, CONHCH$_2$C$\underline{H}$), 6.59 (1H, t, pyrimidine), 6.98 (2H, d, C$_6$H$_4$), 7.38 (2H, br t, C$_6$H$_5$), 7.46 (1H, br t, C$_6$H$_5$), 7.67 (2H, d, C$_6$H$_4$), 7.85 (2H, m, C$_6$H$_5$), 8.26 (2H, d, pyrimidine)

Example 63

2-(N-Benzenesulfonyl-N-methyl)amino-3-[4-{4-(1,4,5,6-tetrahydropyrimidin-2-ylamino)piperidin-1-yl}-benzoylamino]propionic acid Acetic acid (4.0 ml) and 0.36 ml of concentrated hydrochloric acid were added to 38.5 mg of the compound prepared in Example 62 to prepare a solution. 10% palladium-carbon (36 mg) was added to the solution. The mixture was vigorously shaken under a hydrogen pressure of 3.0 atm at room temperature for 3 hr. The catalyst was collected by filtration, and then washed twice with acetic acid. The filtrate was combined with the washings, and then concentrated under the reduced pressure. The residue was subjected to azeotropic distillation twice with toluene. The residue was purified by preparative thin-layer chromatography on silica gel (development system: methylene chloride-ethanol-water-concentrated aqueous ammonia=15:10:1:1) and then purified by column chromatography on Sephadex LH-20 (30 ml, methylene chloride-methanol-concentrated aqueous ammonia=2:10:1) to prepare 14.1 mg of the title compound.

Physicochemical Properties of Compound Prepared in Example 63

(1) Color and form: Colorless solid
(2) Molecular formula: $C_{26}H_{34}N_6O_5S$
(3) Mass spectrum (FABMS): m/z 543 (M+H)$^+$
(4) $^1$H NMR spectrum (400 MHz, 77% CD$_3$OD/D$_2$O) δ (ppm): 1.60 (2H, br q, piperidine), 1.96 (2H, quintet, tetrahydropyrimidine), 2.02 (2H, br d, piperidine), 2.89 (3H, s, NMe), 2.98 (2H, br t, piperidine), 3.36 (4H, t, tetrahydropyrimidine), 3.55 (1H, m, piperidine), 3.71 (2H, m, CONHC$\underline{H}_2$CH), 3.81 (2H, br d, piperidine), 6.99 (2H, d, C$_6$H$_4$), 7.41 (2H, m, C$_6$H$_5$), 7.48 (1H, m, C$_6$H$_5$), 7.66 (2H, d, C$_6$H$_4$), 7.83 (2H, m, C$_6$H$_5$)

Intermediate 52: Methyl 3-fluoro-4-{4-(1,4,5,6-tetrahydropyrimidin-2-ylamino)piperidin-1-yl}benzoate Dioxane (50 ml) and 10 ml of water were added to 1.73 g of intermediate 37 to prepare a solution. Acetic acid (5.0 ml) and 350 mg of 10% palladium-carbon were added to the solution. The mixture was vigorously stirred under a hydrogen pressure of one atm at room temperature for 15 hr. The insolubles were collected by filtration, and then washed with methanol. The filtrate was combined with the washings, and then concentrated under the reduced pressure. The residue was subjected to azeotropic distillation twice with toluene to prepare 1.7 g of the title compound.

Physicochemical Properties of Intermediate 52

(1) Color and form: Colorless amorphous
(2) Molecular formula: $C_{17}H_{23}N_4O_2F$
(3) Mass spectrum (TSPMS): m/z 335 (M+H)$^+$
(4) $^1$H NMR spectrum (400 MHz, CD$_3$OD) δ (ppm): 1.69 (2H, dq, piperidine), 1.97 (2H, quintet, tetrahydropyrimidine), 2.04 (2H, br d, piperidine), 2.93 (2H, ddd, piperidine), 3.38 (4H, t, tetrahydropyrimidine), 3.50 (1H, tt, piperidine), 3.61 (2H, br d, piperidine), 3.87 (3H, s, CO$_2$Me), 7.07 (1H, t, C$_6$H$_3$CO), 7.62 (1H, dd, C$_6$H$_3$CO), 7.75 (1H, dd, C$_6$H$_3$CO)

Intermediate 53: Methyl 3-fluoro-4-[4-[{N-(1,4,5,6-tetrahydropyrimidin-2-yl)-N-(4-methoxybenzyl)}amino]-piperidin-1-yl]benzoate Dimethylformamide (8.0 ml) was added to 262 mg of intermediate 52 to prepare a solution. Potassium carbonate (540 mg) and 320 μl of 4-methoxybenzyl chloride were added to the solution. The mixture was stirred at room temperature for 18 hr. A saturated aqueous ammonium chloride solution (200 ml) was then added thereto, followed by extraction three times with 100 ml of methylene chloride. The combined organic layer was dried over anhydrous sodium sulfate, and then concentrated under the reduced pressure. The residue was subjected to azeotropic distillation twice with toluene, and purified by column chromatography on silica gel (development system: methylene chloride-methanol=15:1) to prepare 153 mg of the title compound.

Physicochemical Properties of Intermediate 53

(1) Color and form: Colorless amorphous
(2) Molecular formula: $C_{25}H_{31}N_4O_3F$
(3) Mass spectrum (TSPMS): m/z 455 (M+H)$^+$
(4) $^1$H NMR spectrum (400 MHz, CDCl$_3$) δ (ppm): 1.75 (2H, m, piperidine), 1.96 (2H, m, tetrahydropyrimidine), 2.07 (2H, m, piperidine), 3.03 (2H, br t, piperidine), 3.38 (4H, m, tetrahydropyrimidine), 3.49 (2H, m, piperidine), 3.79 (3H, s, CH$_2$C$_6$H$_4$OMe), 3.87 (3H, S, CO$_2$Me), 4.26 (1H, m, piperidine), 4.61 (2H, S, CH$_2$C$_6$H$_4$OMe), 6.84 (1H, t, C$_6$H$_3$CO), 6.89 (2H, d, CH$_2$C$_6$H$_4$OMe), 7.12 (2H, d, CH$_2$C$_6$H$_4$OMe), 7.58 (1H, br d, C$_6$H$_3$CO), 7.67 (1H, d, C$_6$H$_3$CO)

Example 64 t-Butyl (2S)-(benzyloxycarbonyl)amino-3-[3-fluoro-4-[4-[{N-(1,4,5,6-tetrahydropyrimidin-2-yl)-N-(4-methoxybenzyl)}amino]piperidin-1-yl] benzoylamino]-propionate Tetrahydrofuran (12 ml) and 4.0 ml of methanol were added to 176 mg of intermediate 53 to prepare a solution. A 1 N aqueous sodium hydroxide solution (4.0 ml) was added to the solution. The mixture was stirred at 40° C. for 16 hr. The reaction solution was then concentrated under the reduced pressure. Water (100 ml) was added to the residue. The solution was adjusted to pH 4 by the addition of 1 N hydrochloric acid. Salt was added to this mixed solution to prepare a saturated solution, followed by extraction three times with 100 ml of methylene chloride. The combined organic layer was dried over anhydrous sodium sulfate, and concentrated under the reduced pressure. The residue was purified by column chromatography on silica gel (development system: chloroform-methanol-concentrated aqueous ammonia=30:10:1) to prepare 170 mg of a crude compound. Dimethylformamide (2.0 ml) was then added to 100 mg of the crude compound to prepare a solution. t-Butyl (2S)-N-benzyloxycarbonyl-2,3-diaminopropionate hydrochloride (66.8 mg) was added to the solution. Further, 33.6 mg of 1-hydroxybenzotriazole, 50 μl of N-methylmorpholine, and 47.9 mg of 1-ethyl-3-(3-dimethylaminopropyl)carbodiimide hydrochloride were added thereto. The mixture was stirred at room temperature for 16 hr. A saturated aqueous potassium carbonate solution (20 ml) and 40 ml of saturated saline were added to stop the reaction, followed by extraction three times with 50 ml of methylene chloride. The combined organic layer was dried over anhydrous sodium sulfate, and then concentrated under the reduced pressure. The residue was purified by column chromatography on silica gel (development system: methylene chloride-methanol=7:1) to prepare 45.0 mg of the title compound.

Physicochemical Properties of Compound Prepared in Example 64

(1) Color and form: Colorless amorphous
(2) Molecular formula: $C_{39}H_{49}N_6O_6F$
(3) Mass spectrum (TSPMS): m/z 717 (M+H)$^+$
(4) $^1$H NMR spectrum (400 MHz, CD$_3$OD) δ (ppm): 1.42 (9H, s, t-Bu), 1.76 (2H, dq, piperidine), 1.99 (4H, m, tetrahydropyrimidine and piperidine), 2.87 (2H, br t, piperidine), 3.42 (4H, q, tetrahydropyrimidine), 3.51 (2H, br d, piperidine), 3.59 (1H, tt, piperidine), 3.71 (2H, d, CONHCH$_2$CH), 3.77 (3H, s, CH$_2$C$_6$H$_4$OMe), 4.36 (1H, t, CONHCH$_2$CH), 4.59 (2H, s, CH$_2$C$_6$H$_4$OMe), 5.08 (2H, dd, CH$_2$C$_6$H$_5$), 6.95 (2H, dt, CH$_2$C$_6$H$_4$OMe), 7.03 (1H, t, C$_6$H$_3$CO), 7.22 (2H, d, CH$_2$C$_6$H$_4$OMe), 7.29 (5H, m, C$_6$H$_5$), 7.49 (1H, dd, C$_6$H$_3$CO), 7.56 (1H, dd, C$_6$H$_3$CO)

Example 65 t-Butyl (2S)-amino-3-[3-fluoro-4-[4-[{N-(1,4,5,6-tetrahydropyrimidin-2-yl)-N-(4-methoxybenzyl)}-amino]piperidin-1-yl]benzoylamino]propionate Tetrahydrofuran (1.0 ml) was added to 40.0 mg of the compound prepared in Example 64 to prepare a solution. 10% palladium-carbon (8.0 mg) was added to the solution. The mixture was vigorously stirred under a hydrogen pressure of one atm at room temperature for 20 hr. The insolubles were collected by filtration, and then washed twice with methanol. The filtrate was combined with the washings, and then concentrated under the reduced pressure. The residue was purified by preparative thin-layer chromatography on silica gel (development system: methylene chloride-methanol=7:1) to prepare 25.3 mg of the title compound.

Physicochemical Properties of Compound Prepared in Example 65

(1) Color and form: Colorless oil
(2) Molecular formula: $C_{31}H_{43}N_6O_4F$
(3) Mass spectrum (TSPMS): m/z 583 (M+H)$^+$
(4) $^1$H NMR spectrum (400 MHz, CD$_3$OD) δ (ppm): 1.44 (9H, s, t-Bu), 1.77 (2H, br dq, piperidine), 1.98 (2H, m, piperidine), 2.00 (2H, quintet, tetrahydropyrimidine), 2.87 (2H, br t, piperidine), 3.42 (4H, q, tetrahydropyrimidine), 3.56 (6H, m, piperidine and CONHCH$_2$CH), 3.78 (3H, s, CH$_2$C$_6$H$_4$OMe), 4.59 (2H, s, CH$_2$C$_6$H$_4$OMe), 6.96 (2H, d, CH$_2$C$_6$H$_4$OMe), 7.05 (1H, t, C$_6$H$_3$CO), 7.22 (2H, d, CH$_2$C$_6$H$_4$OMe), 7.54 (1H, dd, C$_6$H$_3$CO), 7.60 (1H, dd, C$_6$H$_3$CO)

Example 66 t-Butyl 3-[3-fluoro-4-[4-[{N-(1,4,5,6-tetrahydropyrimidin-2-yl)-N-(4-methoxybenzyl)} amino]-piperidin-1-yl]benzoylamino]-(2S)-{(4-nitrobenzene-sulfonyl)amino}propionate Dimethylformamide (0.5 ml) was added to 12.8 mg of the compound prepared in Example 65 to prepare a solution. Diisopropylethylamine (8.0 μl) was added to the solution. Further, 4.9 mg of 4-nitrobenzenesulfonyl chloride was added thereto at room temperature. The mixture was stirred for 3 hr. Piperazine (5 mg) was then added thereto, followed by stirring for additional 5 min. A saturated aqueous sodium hydrogencarbonate solution (30 ml) was added to the reaction solution, followed by extraction three times with 30 ml of methylene chloride. The combined organic layer was dried over anhydrous sodium sulfate, and then concentrated under the reduced pressure. The residue was purified by preparative thin-layer chromatography on silica gel (development system: nethylene chloride-methanol-acetic acid=70:10:1) to prepare 8.3 mg of the title compound.
Physicochemical Properties of Compound Prepared in Example 66

(1) Color and form: Colorless solid
(2) Molecular formula: $C_{37}H_{46}N_7O_8FS$
(3) Mass spectrum (TSPMS): m/z 768 (M+H)$^+$
(4) $^1$H NMR spectrum (400 MHz, CD$_3$OD) (as 4-nitrobenzenesulfonate) δ (ppm): 1.36 (9H, s, t-Bu), 1.78 (2H, br q, piperidine), 1.98 (2H, m, piperidine), 2.01 (2H, quintet, tetrahydropyrimidine), 2.88 (2H, br t, piperidine), 3.42 (5H, m, tetrahydropyrimidine and CONHC$\underline{H}_2$CH), 3.52 (2H, br d, piperidine), 3.57 (1H, m, piperidine), 3.66 (1H, dd, CONHC$\underline{H}_2$CH), 3.78 (3H, s, CH$_2$C$_6$H$_4$O$\underline{Me}$), 4.23 (1H, dd, CONHCH$_2$C$\underline{H}$), 4.59 (2H, s, C$\underline{H}_2$C$_6$H$_4$OMe), 6.92 (1H, t, C$_6$H$_3$CO), 6.96 (2H, d, CH$_2$C$_6\underline{H}_4$OMe), 7.21 (2H, m, CH$_2$C$_6\underline{H}_4$OMe), 7.34 (2H, m, C$_6$H$_3$CO), 7.98 (2H, dt, HO$_3$SC$_6$H$_4$NO$_2$), 8.03 (2H, dt, C$_6\underline{H}_4$NO$_2$), 8.16 (2H, dt, C$_6\underline{H}_4$NO$_2$), 8.29 (2H, dt, HO$_3$SC$_6$H$_4$NO$_2$)

Example 67

3-[3-Fluoro-4-{4-(1,4,5,6-tetrahydropyrimidin-2-ylamino)piperidin-1-yl}benzoyl-amino]-(2S)-{(4-nitrobenzenesulfonyl)amino}propionic acid Trifluoroacetic acid (0.5 ml) was added to 2.7 mg of the compound prepared in Example 66. The mixture was stirred at 40° C. for 4.5 hr. The reaction solution was concentrated under the reduced pressure. The residue was subjected to azeotropic distillation twice with toluene. The residue was purified by preparative thin-layer chromatography on silica gel (development system: chloroform-methanol-concentrated aqueous ammonia=30:10:1) and then by Sephadex LH-20 (development system: methanol) to prepare 2.2 mg of the title compound.
Physicochemical Properties of Compound Prepared in Example 67

(1) Color and form: Colorless solid
(2) Molecular formula: $C_{25}H_{30}N_7O_7FS$
(3) Mass spectrum (TSPMS): m/z 592 (M+H)$^+$
(4) $^1$H NMR spectrum (400 MHz, CD$_3$OD) δ (ppm): 1.71 (2H, br dq, piperidine), 1.97 (2H, quintet, tetrahydropyrimidine), 2.04 (2H, br d, piperidine), 2.92 (2H, br t, piperidine), 3.38 (4H, t, tetrahydropyrimidine), 3.53 (4H, m, piperidine and CONHC$\underline{H}_2$CH), 3.63 (1H, dd, CONHC$\underline{H}_2$CH), 3.97 (1H, dd, CONHCH$_2$C$\underline{H}$), 6.96 (1H, t, C$_6$H$_3$CO), 7.39 (2H, m, C$_6$H$_3$CO), 8.01 (2H, dt, C$_6\underline{H}_4$NO$_2$), 8.17 (2H, dt, C$_6\underline{H}_4$NO$_2$)

Example 68

(2S)-(4-Aminobenzenesulfonyl)amino-3-[3-fluoro-4-{4-(1,4,5,6-tetrahydropyrimidin-2-ylamino)-piperidin-1-yl}benzoylamino]propionic acid Dioxane (0.7 ml) and 0.2 ml of water were added to 6.9 mg of the compound prepared in Example 67 to prepare a solution. 10% palladium-carbon (7.0 mg) was added to the solution. The mixture was vigorously stirred under a hydrogen pressure of one atm at room temperature for 5 hr. The insolubles were collected by filtration, and then washed twice with methanol and twice with a mixed solvent composed of 7 ml of dioxane and 2 ml of water. The filtrate was combined with the washings, and then concentrated under the reduced pressure. To the residue was added 0.1 N hydrochloric acid. The mixture was purified by CHP-20 (development system: dioxane-water=4:1) to prepare 2.8 mg of tetrahydrochloride of the title compound.
Physicochemical Properties of Compound Prepared in Example 68

(1) Color and form: Colorless solid
(2) Molecular formula: $C_{25}H_{32}N_7O_5FS$
(3) Mass spectrum (TSPMS): m/z 562 (M+H)$^+$
(4) $^1$H NMR spectrum (400 MHz, CD$_3$OD) (as tetrahydrochloride) δ (ppm): 1.67 (2H, br q, piperidine), 1.96 (2H, quintet, tetrahydropyrimidine), 2.00 (2H, m, piperidine), 2.86 (2H, br t, piperidine), 3.37 (4H, t, tetrahydropyrimidine), 3.48 (5H, m, piperidine and CONHC$\underline{H}_2$CH), 3.64 (1H, dd, CONHC $\underline{H}_2$CH), 3.69 (1H, m, CONHCH$_2$C$\underline{H}$), 6.63 (2H, br d, C$_6\underline{H}_4$NH$_2$), 7.04 (1H, t, C$_6$H$_3$CO), 7.53 (3H, m, C$_6$H$_3$CO and C$_6\underline{H}_4$NH$_2$), 7.58 (1H, dd, C$_6$H$_3$CO)

Example 69 t-Butyl (2S)-(benzyloxycarbonyl)amino-3-[3-fluoro-4-{4-(pyrimidin-2-ylamino)piperidin-1-yl}benzoyl-amino]propionate Dimethylformamide (1.5 ml) was added to 43.1 mg of intermediate 38 to prepare a solution. t-Butyl (2S)-N-benzyloxycarbonyl-2,3-diaminopropionate hydrochloride (37.3 mg) was added to the solution. Further, 22.0 mg of 1-hydroxybenzotriazole, 45 μl of N-methylmorpholine, and 31.3 mg of 1-ethyl-3-(3-dimethylaminopropyl)carbodiimide hydrochloride were added thereto. The mixture was stirred at room temperature for 15 hr. A saturated aqueous potassium carbonate solution (20 ml) and 40 ml of saturated saline were added to stop the reaction, followed by extraction three times with 50 ml of ethyl acetate. The combined organic layer was dried over anhydrous sodium sulfate, and then concentrated under the reduced pressure. The residue was purified by column chromatography on silica gel (development system: methylene chloride-methanol=25:1) to prepare 74.9 mg of the title compound.
Physicochemical Properties of Compound Prepared in Example 69

(1) Color and form: Pale yellow solid
(2) Molecular formula: $C_{31}H_{37}N_6O_5F$
(3) Mass spectrum (TSPMS): m/z 593 (M+H)$^+$
(4) Specific rotation: $[\alpha]_D^{27}$ −12° (c 0.64, CHCl$_3$)
(5) $^1$H NMR spectrum (400 MHz, CD$_3$OD) δ (ppm): 1.43 (9H, s, t-Bu), 1.74 (2H, dq, piperidine), 2.11 (2H, br d, piperidine), 2.94 (2H, dt, piperidine), 3.58 (2H, br d, piperidine), 3.71 (2H, d, CONHC$\underline{H}_2$CH), 3.95 (1H, tt, piperidine), 4.37 (1H, t, CONHCH$_2$C$\underline{H}$), 5.08 (2H, dd, C$\underline{H}_2$C$_6$H$_5$), 6.59 (1H, t, pyrimidine), 7.07 (1H, t, C$_6$H$_3$CO), 7.30 (5H, m, CH$_2$C$_6\underline{H}_5$), 7.49 (1H, dd, C$_6$H$_3$CO), 7.55 (1H, dd, C$_6$H$_3$CO), 8.26 (2H, d, pyrimidine)

Example 70 t-Butyl (2S)-amino-3-[3-fluoro-4-{4-(pyrimidin-2-ylamino)piperidin-1-yl}benzoylamino]-propionate Tetrahydrofuran (10 ml) was added to 500 mg of the compound prepared in Example 69 to prepare a solution.

10% palladium-carbon (100 mg) was added to the solution. The mixture was vigorously stirred under a hydrogen pressure of one atm at room temperature for 12 hr. The insolubles were collected by filtration, and then washed twice with methanol. The filtrate was combined with the washings, and then concentrated under the reduced pressure. The residue was purified by column chromatography on silica gel (development system: methylene chloride-methanol=7:1) to prepare 334 mg of the title compound.

Physicochemical Properties of Compound Prepared in Example 70
  (1) Color and form: Colorless amorphous
  (2) Molecular formula: $C_{23}H_{31}N_6O_3F$
  (3) Mass spectrum (TSPMS): m/z 459 (M+H)$^+$
  (4) $^1$H NMR spectrum (400 MHz, CD$_3$OD) δ (ppm): 1.43 (9H, s, t-Bu), 1.74 (2H, dq, piperidine), 2.11 (2H, br d, piperidine), 2.93 (2H, ddd, piperidine), 3.60 (5H, m, piperidine and CONHC$\underline{H}_2$C$\underline{H}$), 3.95 (1H, tt, piperidine), 6.59 (1H, t, pyrimidine), 7.09 (1H, t, C$_6$H$_3$CO), 7.54 (1H, dd, C$_6$H$_3$CO), 7.60 (1H, dd, C$_6$H$_3$CO), 8.26 (2H, d, pyrimidine)

Example 71 t-Butyl 3-[3-fluoro-4-{4-(pyrimidin-2-ylamino)piperidin-1-yl}benzoylamino]-(2S)-{(4-methoxybenzenesulfonyl)amino}propionate Dimethylformamide (1.0 ml) was added to 31.0 mg of the compound prepared in Example 70 to prepare a solution. Diisopropylethylamine (25 µl) and 14.2 mg of 4-methoxybenzenesulfonyl chloride were added at room temperature to the solution. The mixture was stirred for 0.5 hr. Piperazine (5 mg) was then added thereto, followed by stirring for additional 5 min. A saturated aqueous sodium hydrogencarbonate solution (30 ml) was added to the reaction solution, followed by extraction three times with 30 ml of methylene chloride. The combined organic layer was dried over anhydrous sodium sulfate, and then concentrated under the reduced pressure. The residue was purified by preparative thin-layer chromatography on silica gel (development system:
methylene chloride-methanol=7:1) to prepare 39.0 mg of the title compound.

Physicochemical Properties of Compound Prepared in Example 71
  (1) Color and form: Colorless oil
  (2) Molecular formula: $C_{30}H_{37}N_6O_6FS$
  (3) Mass spectrum (TSPMS): m/z 629 (M+H)$^+$
  (4) Specific rotation: $[\alpha]_D^{26}$ +76° (c 0.45, CHCl$_3$)
  (5) $^1$H NMR spectrum (400 MHz, CDCl$_3$) δ (ppm): 1.31 (9H, s, t-Bu), 1.72 (2H, dq, piperidine), 2.19 (2H, br d, piperidine), 2.96 (2H, dt, piperidine), 3.55 (3H, m, piperidine and CONHC$\underline{H}_2$CH), 3.84 (3H, s, C$_6$H$_4$O$\underline{Me}$), 3.90 (2H, m, CONHC$\underline{H}_2$C$\underline{H}$), 4.02 (1H, tq, piperidine), 6.54 (1H, t, pyrimidine), 6.95 (2H, br d, C$_6$$\underline{H}_4$OMe), 7.25 (1H, t, C$_6$H$_3$CO), 7.50 (2H, m, C$_6$H$_3$CO), 7.78 (2H, br d, C$_6$$\underline{H}_4$OMe), 8.29 (2H, d, pyrimidine)

Example 72

3-[13-Fluoro-4-{4-(pyrimidin-2-ylamino)piperidin-1-yl}benzoylamino]-(2S)-}(4-methoxybenzenesulfonyl)amino}propionic acid Methylene chloride (1.0 ml) was added to 8.9 mg of the compound prepared in Example 71 to prepare a solution. The solution was cooled to −78° C. before 30 µl of a 1.0 M methylene chloride solution of boron tribromide was added to the solution. The temperature of the mixture was raised to 0° C. over a period of three hr, followed by cooling again to −78° C. A 1.0 M methylene chloride solution (30 µl) of boron tribromide was added thereto. The temperature was raised to room temperature over a period of three hr, followed by stirring at that temperature for additional 13 hr. Methanol was added to the reaction solution, followed by concentration under the reduced pressure. The residue was purified by preparative thin-layer chromatography on silica gel (development system: chloroform-methanol-concentrated aqueous ammonia=30:10:1) to prepare 4.6 mg of the title compound.

Physicochemical Properties of Compound Prepared in Example 72
  (1) Color and form: Colorless solid
  (2) Molecular formula: $C_{26}H_{29}N_6O_6FS$
  (3) Mass spectrum (TSPMS): m/z 573 (M+H)$^+$
  (4) Specific rotation: $[\alpha]_D^{20}$ +82° (c 0.23, MeOH)
  (5) $^1$H NMR spectrum (400 MHz, CD$_3$OD) δ (ppm): 1.75 (2H, dq, piperidine), 2.12 (2H, br d, piperidine), 2.94 (2H, dt, piperidine), 3.50 (1H, dd, CONHC$\underline{H}_2$CH), 3.59 (2H, br d, piperidine), 3.67 (1H, dd, CONHC$\underline{H}_2$CH), 3.79 (1H, dd, CONHCH$_2$C$\underline{H}$), 3.80 (3H, s, C$_6$H$_4$O$\underline{Me}$), 3.96 (1H, tt, piperidine), 6.59 (1H, t, pyrimidine), 6.93 (2H, br d, C$_6$$\underline{H}_4$OMe), 7.07 (1H, t, C$_6$H$_3$CO), 7.46 (1H, dd, C$_6$H$_3$CO), 7.53 (1H, dd, C$_6$H$_3$CO), 7.76 (2H, br d, C$_6$$\underline{H}_4$OMe), 8.27 (2H, d, pyrimidine)

Example 73

3-[3-Fluoro-4-{4-(1,4,5,6-tetrahydropyrimidin-2-ylamino)piperidin-1-yl}benzoyl-amino]-(2S)-{(4-methoxybenzenesulfonyl)amino}propionic acid Dioxane 1.0 ml and 0.1 ml of water were added to 30.0 mg of tritrifluoroacetate of the compound prepared in Example 72 to prepare a solution. 10% palladium-carbon (6.0 mg) was added to the solution. The mixture was vigorously stirred under a hydrogen pressure of one atm at room temperature for 12 hr. The insolubles were collected by filtration, and then washed with a mixed solvent composed of 20 ml of dioxane and 2 ml of water. The filtrate was combined with the washings, followed by concentration under the reduced pressure. Dimethyl sulfoxide (0.35 ml) was added to the residue to prepare a solution, and 3.5 ml of water was then added to the solution. The resultant precipitate was collected by filtration, washed twice with 0.5 ml of water, and then dried to prepare 24.7 mg of the title compound.

Physicochemical Properties of Compound Prepared in Example 73
  (1) Color and form: Colorless solid
  (2) Molecular formula: $C_{26}H_{33}N_6O_6FS$
  (3) Mass spectrum (TSPMS): m/z 577 (M+H)$^+$
  (4) Specific rotation: $[\alpha]_D^{23}$ +60° (c 0.085, DMSO)
  (5) $^1$H NMR spectrum (400 MHz, CD$_3$OD) δ (ppm): 1.69 (2H, br dq, piperidine), 1.96 (2H, quintet, tetrahydropyrimidine), 2.03 (2H, br d, piperidine), 2.90 (2H, br t, piperidine), 3.37 (4H, t, tetrahydropyrimidine), 3.51 (4H, m, CONHC$\underline{H}_2$CH and piperidine), 3.66 (1H, dd, CONHC$\underline{H}_2$CH), 3.79 (1H, m, CONHCH$_2$C$\underline{H}$), 3.80 (3H, s, C$_6$H$_4$O$\underline{Me}$), 6.92 (2H, br d, C$_6$$\underline{H}_4$OMe), 7.03 (1H, t, C$_6$H$_3$CO), 7.46 (1H, dd, C$_6$H$_3$CO), 7.53 (1H, dd, C$_6$H$_3$CO), 7.75 (2H, br d, C$_6$$\underline{H}_4$OMe)

Example 74

3-[3-Fluoro-4-{4-(pyrimidin-2-ylamino)-piperidin-1-yl}benzoylamino]-(2S)-{(4-hydroxybenzenesulfonyl)amino}propionic acid Dichloroethane (5.0 ml) was added to 66.8 mg of the compound prepared in Example 71 to prepare a solution. A 1.0 M methylene chloride solution (1.1 ml) of boron tribromide was added to the solution. The reaction solution as a suspension was stirred at 40° C. for 2.5 hr. A mixed solution composed of 1.0 ml of dioxane and 0.2 ml of water was added to the reaction solution. Further, 1.0 ml of triethylamine was added thereto, followed by concentration under the reduced pressure. The residue was purified by preparative thin-layer chromatography on silica gel (development system: chloroform-methanol-concentrated aqueous ammonia=30:10:1) and then purified by Sephadex LH-20 (development system: methanol) to prepare 20.0 mg of the title compound.

Physicochemical Properties of Compound Prepared in Example 74

(1) Color and form: Colorless solid
(2) Molecular formula: $C_{25}H_{27}N_6O_6FS$
(3) Mass spectrum (TSPMS): m/z 559 (M+H)$^+$
(4) Specific rotation: $[\alpha]_D^{26}$ +36° (c 0.46, MeOH)
(5) $^1$H NMR spectrum (400 MHz, CD$_3$OD) δ (ppm): 1.75 (2H, dq, piperidine), 2.12 (2H, br d, piperidine), 2.94 (2H, br t, piperidine), 3.49 (1H, dd, CONHC$\underline{H}_2$CH), 3.59 (2H, br d, piperidine), 3.69 (1H, dd, CONHCH$_2$CH), 3.86 (1H, dd, CONHCH$_2$C$\underline{H}$), 3.95 (1H, tt, piperidine), 6.60 (1H, t, pyrimidine), 6.78 (2H, br d, C$_6\underline{H}_4$OH), 7.08 (1H, t, C$_6$H$_3$CO), 7.48 (1H, dd, C$_6$H$_3$CO), 7.53 (1H, dd, C$_6$H$_3$CO), 7.66 (2H, br d, C$_6\underline{H}_4$OH), 8.27 (2H, d, pyrimidine)

Example 75

3-[3-Fluoro-4-{4-(1,4,5,6-tetrahydropyrimidin-2-ylamino)piperidin-1-yl}benzoyl-amino]-(2S)-{(4-hydroxybenzenesulfonyl)amino}propionic acid Dioxane (0.7 ml), 0.1 ml of acetic acid, and 0.2 ml of water were added to 36.3 mg of the compound prepared in Example 74 to prepare a solution. 10% palladium-carbon (7.0 mg) was added to the solution. The mixture was vigorously stirred under a hydrogen pressure of one atm at room temperature for 8 hr. The insolubles were collected by filtration, and then washed with a mixed solvent composed of 20 ml of dioxane, 2 ml of water, and 1 ml of acetic acid and with methanol. The filtrate was combined with the washings, and then concentrated under the reduced pressure. The residue was purified by column chromatography on silica gel (development system: methylene chloride-ethanol-concentrated aqueous ammonia-water=8:8:1:1) and then purified by Sephadex LH-20 (development system: methanol) to prepare 10.7 mg of the title compound.

Physicochemical Properties of Compound Prepared in Example 75

(1) Color and form: Colorless solid
(2) Molecular formula: $C_{25}H_{31}N_6O_6Fs$
(3) Mass spectrum (ESIMS): m/z 563 (M+H)$^+$
(4) Specific rotation: $[\alpha]_D^{26}$ +108° (c 0.54, MeOH-conc. NH$_4$OH (10:1))
(5) $^1$H NMR spectrum (400 MHz, CD$_3$OD) δ (ppm): 1.69 (2H, dq, piperidine), 1.97 (2H, quintet, tetrahydropyrimidine), 2.03 (2H, br d, piperidine), 2.89 (2H, br t, piperidine), 3.37 (4H, t, tetrahydropyrimidine), 3.51 (4H, m, CONHC$\underline{H}_2$CH and piperidine), 3.68 (1H, dd, CONC$\underline{H}_2$CH), 3.78 (1H, dd, CONHCH$_2$C$\underline{H}$), 6.80 (2H, br d, C$_6\underline{H}_4$OH), 7.05 (1H, t, C$_6$H$_3$CO), 7.51 (1H, dd, C$_6$H$_3$CO), 7.56 (1H, dd, C$_6$H$_3$CO), 7.67 (2H, br d, C$_6\underline{H}_4$OH)

Example 76 t-Butyl (2S)-(4-carboxybenzenesulfonyl)amino-3-[3-fluoro-4-{4-(pyrimidin-2-ylamino)piperidin-1-yl}benzoylamino]-propionate Pyridine (0.7 ml) was added to 30.0 mg of the compound prepared in Example 70 to prepare a solution. 4-Dimethylaminopyridine (1.6 mg) was added to the solution. Further, 15.9 mg of 4-(chlorosulfonyl)benzoic acid was added thereto at room temperature over a period of 3.5 hr. The reaction solution was stirred for one hr, and then concentrated under the reduced pressure. The residue was purified by preparative thin-layer chromatography on silica gel (development system: chloroform-methanol-concentrated aqueous ammonia=30:10:1) to prepare 22.4 mg of the title compound.

Physicochemical Properties of Compound Prepared in Example 76

(1) Color and form: Colorless solid
(2) Molecular formula: $C_{30}H_{35}N_6O_7FS$
(3) Mass spectrum (TSPMS): m/z 643 (M+H)$^+$
(4) Specific rotation: $[\alpha]_D^{23}$ +185° (c 0.33, MeOH)
(5) $^1$H NMR spectrum (400 MHz, CD$_3$OD) δ (ppm): 1.23 (9H, s, t-Bu), 1.74 (2H, dq, piperidine), 2.11 (2H, br d, piperidine), 2.94 (2H, br t, piperidine), 3.50 (1H, dd, CONHC$\underline{H}_2$CH), 3.59 (2H, br d, piperidine), 3.66 (1H, dd, CONHC$\underline{H}_2$CH), 3.95 (1H, tt, piperidine), 4.13 (1H, dd, CONHCH$_2$C$\underline{H}$), 6.59 (1H, t, pyrimidine), 7.08 (1H, t, C$_6$H$_3$CO), 7.48 (1H, dd, C$_6$H$_3$CO), 7.49 (1H, dd, C$_6$H$_3$CO), 7.83 (2H, d, C$_6\underline{H}_4$CO$_2$H), 8.03 (2H, d, C$_6\underline{H}_4$CO$_2$H), 8.26 (2H, d, pyrimidine)

Example 77

(2S)-(4-Carboxybenzenesulfonyl)amino-3-[3-fluoro-4-{4-(pyrimidin-2-ylamino)piperidin-1-yl}benzoyl-amino]propionic acid Methylene chloride (0.5 ml) and 0.5 ml of trifluoroacetic acid were added at room temperature to 26.0 mg of the compound prepared in Example 76. The mixture was stirred for 15 hr. The reaction solution was concentrated under the reduced pressure. The residue was subjected to azeotropic distillation twice with toluene to prepare 26 mg of tritrifluoroacetate of the title compound.

Physicochemical Properties of Compound Prepared in Example 77

(1) Color and form: Colorless solid
(2) Molecular formula: $C_{26}H_{27}N_6O_7FS$
(3) Mass spectrum (TSPMS): m/z 587 (M+H)$^+$
(4) Specific rotation: $[\alpha]_D^{23}$ −22° (c 0.21, dioxane) (as tritrifluoroacetate)
(5) $^1$H NMR spectrum (400 MHz, CD$_3$OD) (as tritrifluoroacetate) δ (ppm): 1.87 (2H, dq, piperidine), 2.15 (2H, m, piperidine), 2.97 (2H, br t, piperidine), 3.47 (1H, dd, CONHC$\underline{H}_2$CH), 3.63 (2H, br d, piperidine), 3.73 (1H, dd, CONHC$\underline{H}_2$CH), 4.13 (1H, tt, piperidine), 4.27 (1H, dd, CONHCH$_2$C$\underline{H}$), 6.96 (1H, t, pyrimidine), 7.20 (1H, t, C$_6$H$_3$CO), 7.40 (2H, m, $C_6H_3CO$), 7.87 (2H, dt, $C_6\underline{H}_4CO_2H$), 7.98 (2H, dt, $C_6\underline{H}_4CO_2H$), 8.58 (2H, m, pyrimidine)

Example 78

(2S)-(4-Carboxybenzenesulfonyl)amino-3-[3-fluoro-4-{4-(1.4.5.6-tetrahydropyrimidin-2-ylamino)-piperidin-1-yl}benzoylamino]propionic acid Dioxane (1.0 ml) and 0.1 ml of water were added to 25.0 mg of tritrifluoroacetate of the compound prepared in Example 77 to prepare a solution. 10% palladium-carbon (5.0 mg) was added to the solution. The mixture was vigorously stirred under a hydrogen pressure of one atm at room temperature for 9 hr. The insolubles were collected by filtration, and then washed with a mixed solution composed of 8 ml of ethanol, 1 ml of concentrated aqueous ammonia, and 1 ml of water. The filtrate was combined with the washings, and then concentrated under the reduced pressure. The residue was purified by preparative thin-layer chromatography on silica gel (development system: methylene chloride-ethanol-concentrated aqueous ammonia-water= 8:8:1:1) and then purified by Sephadex LH-20 (development system: ethanol-concentrated aqueous ammonia-water= 8:1:1) to prepare 15.1 mg of the title compound.

Physicochemical Properties of Compound Prepared in Example 78

(1) Color and form: Colorless solid
(2) Molecular formula: $C_{26}H_{31}N_6O_7FS$
(3) Mass spectrum (TSPMS): m/z 591 (M+H)$^+$
(4) Specific rotation: $[\alpha]_D^{26}$ +36° (c 0.76, MeOH-conc. $NH_4OH$ (10:1))
(5) $^1$H NMR spectrum (400 MHz, $CD_3OD$) δ (ppm): 1.71 (2H, br q, piperidine), 1.96 (4H, m, tetrahydropyrimidine and piperidine), 2.96 (2H, br t, piperidine), 3.37 (4H, t, tetrahydropyrimidine), 3.55 (5H, m, CONH C$\underline{H}_2$CH and piperidine), 3.84 (1H, dd, CONHCH$_2$C$\underline{H}$), 6.97 (1H, t, $C_6H_3CO$), 7.29 (1H, dd, $C_6H_3CO$), 7.45 (1H, dd, $C_6\underline{H}_3CO$), 7.76 (2H, d, $C_6\underline{H}_4CO_2H$), 7.88 (2H, d, $C_6\underline{H}_4CO_2H$)

Example 79 t-Butyl (2S)-acetamido-3-[3-fluoro-4-[4-[{N-(1,4,5,6-tetrahydropyrimidin-2-yl)-N-(4-methoxybenzyl)}amino]piperidin-1-yl]benzoylamino]propionate Dimethylformamide (1.0 ml) was added to 26.0 mg of acetate of the compound prepared in Example 65 to prepare a solution. Diisopropylethylamine (15.9 μl) was added to the solution. Further, 9.9 mg of 4-nitrobenzenesulfonyl chloride was added at room temperature thereto. The mixture was stirred for 3.5 hr. Piperazine (5 mg) was then added thereto, followed by stirring for additional 5 min. A saturated aqueous sodium hydrogencarbonate solution (30 ml) was added to the reaction solution. The mixture was extracted three times with 30 ml of methylene chloride. The combined organic layer was dried over anhydrous sodium sulfate, and then concentrated under the reduced pressure. The residue was purified by preparative thin-layer chromatography on silica gel (development system: chloroform-methanol-concentrated aqueous ammonia=30:10:1) to prepare 10.7 mg of 4-nitrobenzenesulfonate of the title compound.

Physicochemical Properties of Compound Prepared in Example 79

(1) Color and form: Colorless solid
(2) Molecular formula: $C_{33}H_{45}N_6O_5F$
(3) Mass spectrum (TSPMS): m/z 625 (M+H)$^+$
(4) $^1$H NMR spectrum (400 MHz, $CD_3OD$) δ (ppm): 1.43 (9H, s, t-Bu), 1.77 (2H, br q, piperidine), 1.97 (2H, m, piperidine), 1.98 (3H, s, Ac), 2.00 (2H, quintet, tetrahydropyrimidine), 2.86 (2H, br t, piperidine), 3.41 (4H, q, tetrahydropyrimidine), 3.51 (2H, br d, piperidine), 3.55 (1H, m, piperidine), 3.67 (1H, dd, CONHC$\underline{H}_2$CH), 3.72 (1H, dd, CONHC$\underline{H}_2$CH), 3.78 (3H, s, CH$_2$C$_6$H$_4$OMe), 4.54 (1H, dd, CONHCH$_2$C$\underline{H}$), 4.59 (2H, s, C$\underline{H}_2$C$_6$H$_4$OMe), 6.95 (2H, br d, CH$_2$C$_6$H$_4$OMe), 7.04 (1H, t, $C_6H_3CO$), 7.21 (2H, br d, CH$_2$C$_6$H$_4$OMe), 7.51 (1H, dd, $C_6H_3CO$), 7.57 (1H, dd, $C_6H_3CO$), 8.02 (2H, dt, $HO_3SC_6H_4NO_2$), 8.29 (2H, dt, $HO_3SC_6H_4NO_2$)

Example 80

(2S)-Acetamido-3-[3-fluoro-4-{4-(1,4,5,6-tetrahydropyrimidin-2-ylamino)piperidin-1-yl}benzoyl-amino]propionic acid Methylene chloride (1.0 ml) and 1.0 ml of trifluoroacetic acid were added to 10.7 mg of the compound prepared in Example 79. The mixture was stirred at 40° C. for 16 hr. The reaction solution was concentrated under the reduced pressure. The residue was subjected to azeotropic distillation twice with toluene. The residue was purified by preparative thin-layer chromatography on silica gel (development system: methylene chloride-ethanol-concentrated aqueous ammonia-water=8:8:1:1) and then purified by Sephadex LH-20 (development system: methanol) to prepare 3.3 mg of the title compound.

Physicochemical Properties of Compound Prepared in Example 80

(1) Color and form: Colorless solid
(2) Molecular formula: $C_{21}H_{29}N_6O_4F$
(3) Mass spectrum (FABMS): m/z 449 (M+H)$^+$
(4) Specific rotation: $[\alpha]_D^{25}$ +9.30 (c 0.17, MeOH)
(5) $^1$H NMR spectrum (400 MHz, $CD_3OD$) δ (ppm): 1.68 (2H, br q, piperidine), 1.96 (3H, s, Ac), 1.97 (2H, m, tetrahydropyrimidine), 2.02 (2H, br d, piperidine), 2.87 (2H, br t, piperidine), 3.37 (4H, t, tetrahydropyrimidine), 3.47 (1H, m, piperidine), 3.53 (2H, br d, piperidine), 3.66 (1H, dd, CONHC$\underline{H}_2$CH), 3.74 (1H, dd, CONHC$\underline{H}_2$CH), 4.47 (1H, dd, CONHCH$_2$C$\underline{H}$), 7.05 (1H, t, $C_6H_3CO$), 7.51 (1H, dd, $C_6H_3CO$), 7.56 (1H, dd, $C_6H_3CO$)

Example 81 t-Butyl (2S)-(benzyloxycarbonyl)amino-3-[2,3-difluoro-4-{4-(pyrimidin-2-ylamino)piperidin-1-yl}benzoylamino]propionate Anhydrous dimethylformamide (20 ml) and 20 ml of methylene chloride were added to 398 mg of intermediate 45 to prepare a solution. Benzotriazol-1-yloxytris (dimethylamino)phosphonium hexafluorophosphate (790 mg) and 0.31 ml of diisopropylethylamine were added in that order to the solution. A reaction was allowed to proceed at room temperature for 2 hr. Thus, an active ester was prepared. Separately, 20 ml of methylene chloride was added to 421 mg of t-butyl (2S)-N-benzyloxycarbonyl-2,3-diaminopropionate to prepare a solution. Diisopropylethylamine (0.16 ml) was added to the solution. The active ester solution was added thereto under cooling at −10° C. A reaction was allowed to proceed at room temperature for 2 hr. The reaction solution was concentrated under the reduced pressure. The residue was extracted with 50 ml of ethyl acetate. The extract was washed once with distilled water, once with a saturated aqueous sodium hydrogencarbonate solution, and once with saturated saline in that order, dried over anhydrous sodium sulfate, and then concentrated under the reduced pressure. The residue was purified by column chromatography on silica gel (90 g, 2%→3% methanol/methylene chloride) to prepare 713 mg of the title compound.

Physicochemical Properties of Compound Prepared in Example 81

(1) Color and form: Colorless solid
(2) Molecular formula: $C_{31}H_{36}N_6O_5F_2$
(3) Mass spectrum (FABMS): m/z 611 (M+H)$^+$
(4) Specific rotation: $[\alpha]_D^{25}$ +5° (c 0.9, CHCl$_3$)
(5) $^1$H NMR spectrum (400 MHz, CDCl) δ (ppm): 1.46 (9H, s, t-Bu), 1.69 (2H, m, piperidine), 2.20 (2H, br d, piperidine), 3.01 (2H, br t, piperidine), 3.59 (2H, br d, piperidine), 3.83 (1H, dd, CONHC$\underline{H}_2$CH), 3.90 (1H, ddd, CONHC$\underline{H}_2$CH), 4.03 (1H, m, piperidine), 4.45 (1H, br ddd, CONHCH$_2$C$\underline{H}$), 5.11 (2H, br s, CO$_2$C$\underline{H}_2$C$_6$H$_5$), 6.55 (1H, t, pyrimidine), 6.75 (1H, br t, C$_6$H$_2$F$_2$), 7.29–7.37 (5H, m, C$_6$H$_5$), 7.71 (1H, ddd, C$_6$H$_2$F$_2$), 8.29 (2H, d, pyrimidine)

Example 82 t-Butyl (2S)-amino-3-[2,3-difluoro-4-{4-(pyrimidin-2-ylamino)piperidin-1-yl}benzoylamino]-propionate Freshly distilled tetrahydrofuran (22 ml) was added to 216 mg of the compound prepared in Example 81 to prepare a solution. 10% palladium-carbon (110 mg) was added to the solution. The mixture was vigorously stirred in a hydrogen atmosphere at room temperature for 4 hr. The catalyst was collected by filtration, and then washed twice each with 10 ml of tetrahydrofuran. The filtrate was combined with the washings, and then concentrated under the reduced pressure. The residue was purified by column chromatography on silica gel (50 g, diethyl ether-methylene chloride-methanol= 2:7:1→0:9:1) to prepare 79.1 mg of the title compound. Further, at that time, 61.4 mg of the compound of Example 81 was recovered.

Physicochemical Properties of Compound Prepared in Example 82

(1) Color and form: Colorless syrup
(2) Molecular formula: $C_{23}H_{30}N_6O_3F_2$
(3) Mass spectrum (ESIMS): m/z 477 (M+H)$^+$
(4) Specific rotation: $[\alpha]_D^{25}$ +3° (c 1.2, CHCl$_3$)
(5) $^1$H NMR spectrum (400 MHz, CDCl$_3$) δ (ppm): 1.48 (9H, s, t-Bu), 1.70 (2H, br q, piperidine), 2.20 (2H, br d, piperidine), 3.01 (2H, br t, piperidine), 3.50 (1H, m, CONHC$\underline{H}_2$CH), 3.58 (1H, dd, CONHCH$_2$C$\underline{H}$), 3.58 (2H, br d, piperidine), 3.85 (1H, m, CONHC$\underline{H}_2$CH), 4.03 (1H, m, piperidine), 6.55 (1H, t, pyrimidine), 6.76 (1H, br t, C$_6$H$_2$F$_2$), 7.74 (1H, ddd, C$_6$H$_2$F$_2$), 8.28 (2H, d, pyrimidine)

Example 83 t-Butyl 3-[2,3-difluoro-4-{4-(pyrimidin-2-ylamino) piperidin-1-yl}benzoylamino]-(2S)-{(4-methoxy-benzenesulfonyl)amino}propionate Anhydrous dimethylformamide (2.5 ml) was added to 127 mg of the compound prepared in Example 82 to prepare a solution. Diisopropylethylamine (70 μl) and 54.9 mg of 4-methoxybenzenesulfonyl chloride were added in that order to the solution. A reaction was allowed to proceed at room temperature for 3 hr. The reaction solution was concentrated under the reduced pressure. The residue was extracted with 25 ml of ethyl acetate. The extract was washed once with 5% saline, once with a saturated aqueous sodium hydrogencarbonate solution, and once with saturated saline in that order, dried over anhydrous sodium sulfate, and then concentrated under the reduced pressure. The residue was purified by column chromatography on silica gel (13 g, chloroform-methanol-concentrated aqueous ammonia=900:30:1) to prepare 172 mg of the title compound.

Physicochemical Properties of Compound Prepared in Example 83

(1) Color and form: Colorless solid
(2) Molecular formula: $C_{30}H_{36}N_6O_6F_2S$
(3) Mass spectrum (APCIMS): m/z 647 (M+H)$^+$
(4) Specific rotation: $[\alpha]_D^{25}$ +55° (c 1.0, CHCl$_3$)
(5) $^1$H NMR spectrum (400 MHz, CDCl$_3$) δ (ppm): 1.31 (9H, s, t-Bu), 1.70 (2H, br q, piperidine), 2.19 (2H, br d, piperidine), 3.01 (2H, br t, piperidine), 3.59 (2H, br d, piperidine), 3.69 (1H, m, CONHC$\underline{H}_2$CH), 3.82 (1H, m, CONHC$\underline{H}_2$CH), 3.83 (3H, s, OMe), 4.00 (2H, m, CONHCH$_2$C$\underline{H}$ and piperidine), 6.55 (1H, t, pyrimidine), 6.74 (1H, br t, C$_6$H$_2$F$_2$), 6.91 (2H, d, C$_6$H$_4$), 7.68 (1H, br t, C$_6$H$_2$F$_2$), 7.78 (2H, d, C$_6$H$_4$), 8.30 (2H, d, pyrimidine)

Example 84

3-[2,3-Difluoro-4-{4-(pyrimidin-2-ylamino) piperidin-1-yl}benzoylaminol]-(2S)-{(4-hydroxybenzenesulfonyl)amino}propionic acid Anhydrous 1,2-dichloroethane (2.6 ml) was added to 52.8 mg of the compound prepared in Example 83 to prepare a solution. A 1 M methylene chloride solution (0.82 ml) of boron tribromide was added to the solution. A reaction was allowed to proceed at 40° C. for 2 hr. An 80% aqueous 1,4-dioxane solution was added to the reaction solution. The system was adjusted to pH 4 by the addition of solid sodium hydrogencarbonate, and then concentrated under the reduced pressure. The residue was purified by column chromatography on silica gel (5 g, chloroform-methanol-concentrated aqueous ammonia=90:30:2) and then purified by column chromatography on Sephadex LH-20 (30 ml, methanol-water-concentrated aqueous ammonia=8:1:1) to prepare 17.5 mg of the title compound.

Physicochemical Properties of Compound Prepared in Example 84

(1) Color and form: Colorless solid
(2) Molecular formula: $C_{25}H_{26}N_6O_6F_2S$
(3) Mass spectrum (APCIMS): m/z 577 (M+H)$^+$
(4) Specific rotation: $[\alpha]_D^{25}$ +97° (c 0.5, MeOH—H$_2$O-conc. NH$_4$OH (8:1:1))
(5) $^1$H NMR spectrum (400 MHz, 10% conc. ND$_4$OD/CD$_3$OD) δ (ppm): 1.74 (2H, dq, piperidine), 2.12 (2H, br d, piperidine), 3.00 (2H, br t, piperidine), 3.57 (1H, dd, CONHC$\underline{H}_2$CH), 3.62 (2H, br d, piperidine), 3.70 (2H, m, CONHC$\underline{H}_2$C$\underline{H}$), 3.95 (1H, dddd, piperidine), 6.63 (1H, t, pyrimidine), 6.72 (2H, d, C$_6$H$_4$), 6.90 (1H, br t, C$_6$H$_2$F$_2$), 7.51 (1H, br t, C$_6$H$_2$F$_2$), 7.61 (2H, d, C$_6$H$_4$), 8.28 (2H, d, pyrimidine)

Example 85

3-[2.3-Difluoro-4-{4-(1,4,5,6-tetrahydropyrimidin-2-ylamino)piperidin-1-yl}benzoyl-amino]-(2S)-{(4-hydroxybenzenesulfonyl)amino}propionic acid 1,4-Dioxane (7.0 ml), 4.0 ml of acetic acid, and 4.0 ml of 0.5 N hydrochloric acid were added to 80.0 mg of the compound prepared in Example 84 to prepare a solution. 10% palladium-carbon (40 mg) was added to the solution. The mixture was vigorously stirred in a hydrogen atmosphere at room temperature for 6 hr. The catalyst was collected by filtration, and then washed twice with a mixed solvent (1,4-dioxane-acetic acid-water=7:2:2). The filtrate was combined with the washings, and then concentrated under the reduced pressure. The residue was subjected to azeotropic distillation twice each with 4.0 ml of toluene, and purified by column chromatography on silica gel (14 g, methylene chloride-ethanol-water-concentrated aqueous ammonia=8:8:1:1) and then purified by column chromatography on Sephadex LH-20 (50 ml, methanol-water-concentrated aqueous ammonia=8:1:1) to prepare 51.3 mg of the title compound.

Physicochemical Properties of Compound Prepared in Example 85

(1) Color and form: Colorless solid
(2) Molecular formula: $C_{25}H_{30}N_6O_6F_2S$
(3) Mass spectrum (FABMS): m/z 581 (M+H)$^+$
(4) Specific rotation: $[\alpha]_D^{25}$ +103° (c 1.0, methanol-water-concentrated aqueous ammonia=8:1:1)
(5) $^1$H NMR spectrum (400 MHz, CD$_3$OD—D$_2$O-conc. ND$_4$OD (8:1:1)) δ (ppm): 1.64 (2H, m, piperidine), 1.94 (2H, quintet, tetrahydropyrimidine), 2.01 (2H, br d, piperidine), 2.91 (2H, br t, piperidine), 3.35 (4H, t, tetrahydropyrimidine), 3.47–3.69 (6H, m, 3H of piperidine, 3H of CONHCH$_2$CH), 6.59 (2H, d, C$_6$H$_4$), 6.84 (1H, br t, C$_6$H$_2$F$_2$), 7.49 (1H, br t, C$_6$H$_2$F$_2$), 7.50 (2H, d, C$_6$H$_4$)

Example 86 t-Butyl (2S)-(4-carboxybenzenesulfonyl)amino-3-[2,3-difluoro-4-{4-(pyrimidin-2-ylamino)-piperidin-1-yl}benzoylamino]propionate Pyridine (1.2 ml) was added to 78.9 mg of the compound prepared in Example 82 to prepare a solution. 4-Dimethylaminopyridine (2.8 mg) was added to the solution. Further, 36.5 mg of 4-(chlorosulfonyl)benzoic acid was added dropwise thereto at room temperature over a period of 5 hr. The mixture was stirred for one hr. Piperazine (10.0 mg) was then added thereto, and the mixture was stirred for additional 5 min, followed by concentration under the reduced pressure. The residue was purified by preparative thin-layer chromatography on silica gel (development system: chloroform-methanol-concentrated aqueous ammonia=30:10:1) to prepare 38.1 mg of the title compound.

Physicochemical Properties of Compound Prepared in Example 86

(1) Color and form: Colorless amorphous
(2) Molecular formula: $C_{30}H_{34}N_6O_7F_2S$
(3) Mass spectrum (FABMS): m/z 661 (M+H)$^+$
(4) Specific rotation: $[\alpha]_D^{25}$+28° (c 0.25, MeOH-conc. NH$_4$OH (10:1))
(5) $^1$H NMR spectrum (400 MHz, CD$_3$OD) δ (ppm): 1.26 (9H, s, t-Bu), 1.73 (2H, dq, piperidine), 2.11 (2H, br d, piperidine), 3.00 (2H, br t, piperidine), 3.50 (1H, dd, CONHCH$_2$CH), 3.63 (2H, br d, piperidine), 3.70 (1H, dd, CONHCH$_2$CH), 3.97 (1H, tt, piperidine), 4.14 (1H, dd, CONHCH$_2$CH), 6.59 (1H, t, pyrimidine), 6.88 (1H, ddd, C$_6$H$_2$CO), 7.41 (1H, ddd, C$_6$H$_2$CO), 7.82 (2H, d, C$_6$H$_4$CO$_2$H), 8.03 (2H, d, C$_6$H$_4$CO$_2$H), 8.26 (2H, d, pyrimidine)

Example 87

(2S)-(4-Carboxybenzenesulfonyl)amino-3-[2,3-difluoro-4-{4-(pyrimidin-2-ylamino)piperidin-1-yl}-benzoylamino]propionic acid Methylene chloride (0.5 ml) and 0.5 ml of trifluoroacetic acid were added at room temperature to 38.0 mg of the compound prepared in Example 86. The mixture was stirred for 4 hr. The reaction solution was concentrated under the reduced pressure, and then subjected to azeotropic distillation twice with toluene to prepare 40.0 mg of tritrifluoroacetate of the title compound.

Physicochemical Properties of Compound Prepared in Example 87

(1) Color and form: Colorless solid
(2) Molecular formula: $C_{26}H_{26}N_6O_7F_2S$
(3) Mass spectrum (ESIMS): m/z 605 (M+H)$^+$
(4) Specific rotation: $[\alpha]_D^{25}$ +10° (c 0.18, MeOH) (as tritrifluoroacetate)
(5) $^1$H NMR spectrum (400 MHz, CD$_3$OD) (as tritrifluoroacetate) δ (ppm): 1.84 (2H, dq, piperidine), 2.15 (2H, br d, piperidine), 3.03 (2H, br t, piperidine), 3.44 (1H, dd, CONHCH$_2$CH), 3.67 (2H, br d, piperidine), 3.79 (1H, dd, CONHCH$_2$CH), 4.11 (1H, tt, piperidine), 4.28 (1H, dd, CONHCH$_2$CH), 6.84 (1H, br t, C$_6$H$_2$CO), 6.91 (1H, t, pyrimidine), 7.37 (1H, ddd, C$_6$H$_2$CO), 7.88 (2H, br d, C$_6$H$_4$CO$_2$H), 7.99 (2H, br d, C$_6$H$_4$CO$_2$H), 8.53 (2H, m, pyrimidine)

Example 88

(2S)-(4-Carboxybenzenesulfonyl)amino-3-[2,3-difluoro-4-{4-(1,4,5,6tetrahydropyrimidin-2-ylamino)-piperidin-1-yl}benzoylamino propionic acid Dioxane (1.0 ml) and 0.1 ml of water were added to 40.0 mg of tritrifluoroacetate of the compound prepared in Example 87 to prepare a solution. 10% palladium-carbon (8.0 mg) was added to the solution. The mixture was vigorously stirred under a hydrogen pressure of one atm at room temperature for 6.5 hr. The insolubles were collected by filtration, and then washed with a mixed solution composed of 10 ml of methanol and 1 ml of concentrated aqueous ammonia. The filtrate was combined with the washings, and then concentrated under the reduced pressure. The residue was purified by preparative thin-layer chromatography on silica gel (development system: methylene chloride-ethanol-concentrated aqueous ammonia-water=8:8:1:1) and then purified by Sephadex LH-20 (development system: methanol) to prepare 14.5 mg of the title compound.

Physicochemical Properties of Compound Prepared in Example 88

(1) Color and form: Colorless solid
(2) Molecular formula: $C_{26}H_{30}N_6O_7F_2S$
(3) Mass spectrum (TSPMS): m/z 609 (M+H)$^+$
(4) Specific rotation: $[\alpha]_D^{25}$ +36° (c 0.73, MeOH-conc. NH$_4$OH (10:1))
(5) $^1$H NMR spectrum (400 MHz, CD$_3$OD) δ (ppm): 1.69 (2H, m, piperidine), 1.95 (2H, quintet, tetrahydropyrimidine), 1.99 (ZH, m, piperidine), 2.98 (2H, br t, piperidine), 3.36 (4H, t, tetrahydropyrimidine), 3.53 (1H, m, piperidine), 3.61 (4H, m, piperidine and CONHCH$_2$CH), 3.83 (1H, dd, CONHCH$_2$CH), 6.80 (1H, br t, C$_6$H$_2$CO), 7.32 (1H, br t, C$_6$H$_2$CO), 7.80 (2H, d, C$_6$H$_4$CO$_2$H), 7.93 (2H, d, C$_6$H$_4$CO$_2$H)

Intermediate 54: Ethyl 4-{4-(1H-benzimidazol-2-ylmethyl)piperazin-1-yl}benzoate

Acetone (10 ml) and 5.0 ml of dimethyl sulfoxide were added to 250 mg of ethyl 4-(piperazin-1-yl)benzoate to prepare a solution. 2-(Chloromethyl)benzimidazole (180 mg) was added to the solution. Further, 300 mg of potassium carbonate was added thereto. The mixture was stirred at room temperature for one day. The reaction solution was poured into 200 ml of water. The mixture was extracted four times with 100 ml of methylene chloride. The combined organic layer was dried over anhydrous magnesium sulfate, concentrated under the reduced pressure. The residue was purified by column chromatography on silica gel (development system: methylene chloride-methanol-concentrated aqueous ammonia=100:10:1) to prepare 274 mg of the title compound.

Physicochemical Properties of Intermediate 54

(1) Color and form: Colorless solid
(2) Molecular formula: $C_{21}H_{24}N_4O_2$
(3) Mass spectrum (FABMS): m/z 365 (M+H)$^+$
(4) $^1$H NMR spectrum (400 MHz, CDCl$_3$) δ (ppm): 1.37 (3H, t, CH$_2$C$\underline{H}_3$), 2.73 (4H, br t, piperazine), 3.37 (4H, br t, piperazine), 3.90 (2H, s, —CH$_2$—), 4.33 (2H, q, C$\underline{H}_2$CH$_3$), 6.87 (2H, d, C$_6$H$_4$), 7.45 (2H, m, benzimidazole), 7.75 (2H, m, benzimidazole), 7.94 (2H, d, C$_6$H$_4$)

Intermediate 55: 4-{4-(1H-Benzimidazol-2-ylmethyl)piperazin-1-yl}benzoic acid

Tetrahydrofuran (10 ml) and 2.5 ml of methanol were added to 101 mg of intermediate 54 to prepare a solution. A 1 N aqueous sodium hydroxide solution (10 ml) was added to the solution. The mixture was stirred at 50° C. for one day, and then concentrated under the reduced pressure. The residue was purified by column chromatography on silica gel (development system: methylene chloride-ethanol-water-concentrated aqueous ammonia=8:8:1:1) to prepare 36 mg of the title compound.

Physicochemical Properties of Intermediate 55

(1) Color and form: Colorless solid
(2) Molecular formula: $C_{19}H_{20}N_4O_2$
(3) Mass spectrum (TSPMS): m/z 337 (M+H)$^+$
(4) $^1$H NMR spectrum (400 MHz, CD$_3$OD) δ (ppm): 2.61 (4H, br t, piperazine), 3.29 (4H, br t, piperazine), 3.77 (2H, s, —CH$_2$—), 6.85 (2H, m, C$_6$H$_4$), 7.13 (2H, dd, benzimidazole), 7.44 (2H, dd, benzimidazole), 7.77 (2H, m, C$_6$H$_4$)

Example 89 t-Butyl (2S)-benzenesulfonylamino-3-[4-{4-(1H-benzimidazol-2-ylmethyl)piperazin-1-yl}benzoylamino]propionate Dimethylformamide (2.0 ml) was added to 30 mg of intermediate 55 to prepare a solution. t-Butyl (2S)-N-benzenesulfonyl-2,3-diaminopropionate hydrochloride (30 mg) was added to the solution. Further, 18 mg of 1-hydroxybenzotriazole, 60 μl of N-methylmorpholine, and 34 mg of 1-ethyl-3-(3-dimethylaminopropyl)carbodiimide hydrochloride were added thereto. The mixture was stirred at room temperature for 6.5 hr. A saturated aqueous sodium hydrogencarbonate solution was added to stop the reaction, followed by extraction twice with 100 ml of methylene chloride. The combined organic layer was dried over anhydrous magnesium sulfate, and then concentrated under the reduced pressure. The residue was purified by column chromatography on silica gel (development system: methylene chloride-methanol-concentrated aqueous ammonia= 90:10:1) to prepare 31 mg of the title compound.

Physicochemical Properties of Compound Prepared in Example 89

(1) Color and form: Colorless solid
(2) Molecular formula: $C_{32}H_{38}N_6O_5S$
(3) Mass spectrum (FABMS): m/z 619 (M+H)$^+$
(4) $^1$H NMR spectrum (400 MHz, CDCl$_3$) δ (ppm): 1.27 (9H, s, t-Bu), 2.73 (4H, br t, piperazine), 3.33 (4H, br t, piperazine), 3.56 (1H, m, CONHC$\underline{H}_2$CH), 3.90 (4H, m, CONHC$\underline{H}_2$C$\underline{H}$ and —CH$_2$—), 6.89 (2H, d, C$_6$H$_4$), 7.26 (2H, m, benzimidazole), 7.52 (5H, m, benzimidazole and C$_6$H$_5$), 7.72 (2H, m, C$_6$H$_4$), 7.85 (2H, m, C$_6$H$_5$)

Example 90

(2S)-Benzenesulfonylamino-3-[4-{4-(1H-benzimidazol-2-ylmethyl)piperazin-1-yl}benzoylamino]-propionic acid Methylene chloride (1.0 ml) was added to 10.0 mg of the compound prepared in Example 89 to prepare a solution. Trifluoroacetic acid (1.0 ml) was added to the solution. Further, 10 μl of anisole was added thereto. The mixture was stirred at room temperature for 5.5 hr. The reaction solution was concentrated under the reduced pressure. The residue was purified by preparative thin-layer chromatography on silica gel (development system: ethylene chloride-ethanol-concentrated aqueous ammonia-water=8:8:1:1) and then purified by Sephadex LH-20 (development system: methanol) to prepare 0.64 mg of the title compound.

Physicochemical Properties of Compound Prepared in Example 90

(1) Color and form: Colorless solid
(2) Molecular formula: $C_{28}H_{30}N_6O_5S$
(3) Mass spectrum (FABMS): m/z 563 (M+H)$^+$
(4) $^1$H NMR spectrum (400 MHz, CD$_3$OD) δ (ppm): 2.72 (4H, br t, piperazine), 3.37 (4H, br t, piperazine), 3.53 (1H, dd, CONHC$\underline{H}_2$CH), 3.65 (1H, dd, CONHC$\underline{H}_2$CH), 3.82 (1H, dd, CONHCH$_2$C$\underline{H}$), 3.88 (2H, s, —CH$_2$—), 6.96 (2H, d, C$_6$H$_4$), 7.23 (2H, dd, benzimidazole), 7.43 (2H, m, C$_6$H$_5$), 7.50 (1H, m, C$_6$H$_5$), 7.55 (2H, dd, benzimidazole), 7.68 (2H, d, C$_6$H$_4$), 7.83 (2H, m, C$_6$H$_5$)

Intermediate 56: Methyl 4-fluoro-3-methoxybenzoate

Dimethylformamide (6.0 ml) was added to 100 mg of 4-fluoro-3-hydroxybenzoic acid to prepare a solution. Potassium carbonate (195 mg) and 88 μl of methyl iodide were added at room temperature to the solution. The mixture was stirred for 17 hr. The reaction solution was poured into a mixed solution composed of 100 ml of a saturated aqueous ammonium chloride solution and 60 ml of ethyl acetate, followed by extraction three times with ethyl acetate. The combined organic layer was washed twice with 100 ml of water, dried over anhydrous sodium sulfate, and then concentrated under the reduced pressure. The residue was purified by preparative thin-layer chromatography on silica gel (development system: hexane-ethyl acetate=3:1) to prepare 96.7 mg of the title compound.

Physicochemical Properties of Intermediate 56

(1) Color and form: Colorless solid
(2) Molecular formula: $C_9H_9O_3F$
(3) Mass spectrum (EIMS): m/z 184
(4) $^1$H NMR spectrum (400 MHz, CDCl$_3$) δ (ppm): 3.92 (3H, s, CO$_2$Me), 3.94 (3H, s, C$_6$H$_3$OM$\underline{e}$), 7.12 (1H, dd, C$_6$H$_3$CO), 7.64 (2H, m, C$_6$H$_3$CO)

Intermediate 57: Methyl 4-(4-hydroxypiperidin-1-yl)-3-methoxybenzoate

Dimethyl sulfoxide (10 ml) was added to 903 mg of intermediate 56 to prepare a solution. 4-Hydroxypiperidine (744 mg) was added to the solution. The mixture was stirred at 90*C for 24 hr. The reaction solution was cooled to room temperature before a mixed solution composed of 150 ml of saturated saline and 150 ml of water were added to the reaction solution. The mixture was extracted three times with 100 ml of ethyl acetate. The combined organic layer was washed twice with a mixed solution composed of 50 ml of saturated saline and 50 ml of water, dried over anhydrous sodium sulfate, and then concentrated under the reduced pressure. The residue was purified by column chromatography on silica gel (development system: methylene chloride-methanol=20:1) to prepare 605 mg of the title compound.

Physicochemical Properties of Intermediate 57
(1) Color and form: Colorless solid
(2) Molecular formula: $C_{14}H_{19}NO_4$
(3) Mass spectrum (TSPMS): m/z 266 (M+H)$^+$
(4) $^1$H NMR spectrum (400 MHz, CDCl$_3$) δ (ppm): 1.76 (2H, ddt, piperidine), 2.04 (2H, br ddd, piperidine), 2.86 (2H, ddd, piperidine), 3.47 (2H, tt, piperidine), 3.87 (1H, m, piperidine), 3.88 (3H, s, CO$_2$Me), 3.92 (3H, s, C$_6$H$_3$OMe), 6.92 (1H, d, C$_6$H$_3$CO), 7.51 (1H, d, C$_6$H$_3$CO), 7.62 (1H, dd, C$_6$H$_3$CO)

Intermediate 58: Methyl 4-(4-azidopiperidin-1-yl)-3-methoxybenzoate

Methylene chloride (20 ml) was added to 550 mg of intermediate 57 to prepare a solution. Triethylamine (0.8 ml) was added to the solution. Methanesulfonyl chloride (225 μl) was added dropwise thereto at room temperature. The mixture was stirred at that temperature for 15 min. A saturated aqueous sodium hydrogencarbonate solution (200 ml) was added to stop the reaction, followed by extraction three times with 100 ml of ethyl acetate. The combined organic layer was dried over anhydrous sodium sulfate, and then concentrated under the reduced pressure to prepare 690 mg of methyl 4-{4-(methanesulfonyloxy)piperidin-1-yl}-3-methoxybenzoate. Dimethylformamide (20 ml) was then added to 690 mg of this compound to prepare a solution. Sodium azide (161 mg) was added to the solution. The mixture was stirred at 90° C. for 4.5 hr. The reaction solution was then cooled to room temperature, and poured into 300 ml of water, followed by extraction three times with 200 ml of ethyl acetate. The combined organic layer was washed twice with 300 ml of water, dried over anhydrous sodium sulfate, and then concentrated under the reduced pressure to prepare 590 mg of the title compound.

Physicochemical Properties of Intermediate 58
(1) Color and form: Pale yellow oil
(2) Molecular formula: $C_{14}H_{18}N_4O_3$
(3) Mass spectrum (APCIMS): m/z 291 (M+H)$^+$
(4) $^1$H NMR spectrum (400 MHz, CDCl$_3$) δ (ppm): 1.86 (2H, ddt, piperidine), 2.07 (2H, m, piperidine), 2.88 (2H, ddd, piperidine), 3.46 (2H, tt, piperidine), 3.57 (1H, tt, piperidine), 3.89 (3H, S, CO$_2$Me), 3.93 (3H, s, C$_6$H$_3$OMe), 6.91 (1H, d, C$_6$H$_3$CO), 7.52 (1H, d, C$_6$H$_3$CO), 7.63 (1H, dd, C$_6$H$_3$CO)

Intermediate 59: Methyl 3-methoxy-4-{4-(pyrimidin-2-ylamino)piperidin-1-yl}benzoate Dioxane (21 ml) was added to 590 mg of intermediate 58 to prepare a solution. 10% palladium-carbon (60 mg) was added to the solution. The mixture was vigorously stirred under a hydrogen pressure of one atm at room temperature for 6 hr. The insolubles were collected by filtration, and then washed with dioxane. The filtrate was combined with the washings, followed by concentration under the reduced pressure to prepare a crude compound. Dimethyl sulfoxide (21 ml) was then added to the crude compound to prepare a solution. Diisopropylethylamine (2.1 ml) was added to the solution. Further, 346 mg of 2-bromopyrimidine was added thereto. The mixture was heated to 120° C., stirred for 15 hr, and then cooled to room temperature. A mixed solution composed of 100 ml of saturated saline and 100 ml of water was then added thereto, followed by extraction three times with 100 ml of ethyl acetate. The combined organic layer was washed twice with 100 ml of water, dried over anhydrous sodium sulfate, and concentrated under the reduced pressure. The residue was purified by column chromatography on silica gel (development system: hexane-ethyl acetate=1:1) to prepare 452 mg of the title compound.

Physicochemical Properties of Intermediate 59
(1) Color and form: Pale yellow solid
(2) Molecular formula: $C_{18}H_{22}N_4O_3$
(3) Mass spectrum (ESIMS): m/z 343 (M+H)$^+$
(4) $^1$H NMR spectrum (400 MHz, CDCl$_3$) δ (ppm): 1.75 (2H, dq, piperidine), 2.20 (2H, br d, piperidine), 2.86 (2H, ddd, piperidine), 3.58 (2H, br d, piperidine), 3.89 (3H, s, CO$_2$Me), 3.93 (3H, s, C$_6$H$_3$OMe), 4.02 (1H, m, piperidine), 6.54 (1H, t, pyrimidine), 6.94 (1H, d, C$_6$H$_3$CO), 7.51 (1H, d, C$_6$H$_3$CO), 7.64 (1H, dd, C$_6$H$_3$CO), 8.29 (2H, d, pyrimidine)

Intermediate 60: 3-Methoxy-4-{4-(pyrimidin-2-ylamino)-piperidin-1-yl}benzoic acid Tetrahydrofuran (15 ml) and 5.0 ml of methanol were added to 400 mg of intermediate 59 to prepare a solution. A 1 N aqueous sodium hydroxide solution (5.0 ml) was added to the solution. The mixture was stirred at 40° C. for 5 hr, and then concentrated under the reduced pressure. Water (25 ml) was added to the residue. The solution was adjusted to pH 7 by the addition of 1 N hydrochloric acid. The resultant precipitate was collected by filtration, washed with water, and then dried to prepare 261 mg of the title compound.

Physicochemical Properties of Intermediate 60
(1) Color and form: Colorless solid
(2) Molecular formula: $C_{17}H_{20}N_4O_3$
(3) Mass spectrum (ESIMS): m/z 329 (M+H)$^+$
(4) $^1$H NMR spectrum (400 MHz, DMSO-d$_6$) δ (ppm): 1.64 (2H, dq, piperidine), 1.93 (2H, br d, piperidine), 2.70 (2H, br t, piperidine), 3.50 (2H, br d, piperidine), 3.83 (3H, s, C$_6$H$_3$OMe), 3.85 (1H, m, piperidine), 6.55 (1H, t, pyrimidine), 6.93 (1H, d, C$_6$H$_3$CO), 7.41 (1H, d, C$_6$H$_3$CO), 7.49 (1H, dd, C$_6$H$_3$CO), 8.27 (2H, d, pyrimidine)

Example 91 t-Butyl (2S)-benzenesulfonylamino-3-[3-methoxy-4-{4-(pyrimidin-2-ylamino)piperidin-1-yl}-benzoylamino]propionate Dimethylformamide (1.5 ml) was added to 50.0 mg of intermediate 60 to prepare a suspension. t-Butyl (2S)-N-benzenesulfonyl-2,3-diaminopropionate hydrochloride (53.9 mg) was added to the suspension. Further, 41 mg of 1-hydroxybenzotriazole, 50 μl of N-methylmorpholine, and 58.2 mg of 1-ethyl-3-(3-dimethylaminopropyl)carbodiimide hydrochloride were addd thereto. The mixture was stirred at room temperature for 12 hr. A mixed solution composed of 10 ml of a saturated aqueous potassium carbonate solution and 20 ml of saturated saline was added to stop the reaction, followed by extraction three times with 30 ml of ethyl acetate. The combined organic layer was washed twice with a mixed solution composed of 10 ml of saturated saline and 10 ml of water, dried over anhydrous sodium sulfate, and then concentrated under the reduced pressure. The residue was purified by preparative thin-layer chromatography on silica gel (development system: methylene chloride-methanol=7:1) to prepare 99.2 mg of the title compound.

Physicochemical Properties of Compound Prepared in Example 91
(1) Color and form: Colorless oil
(2) Molecular formula: $C_{30}H_{38}N_6O_6S$
(3) Mass spectrum (FABMS): m/z 611 (M+H)$^+$
(4) Specific rotation: $[\alpha]_D^{22}$ +22° (c 1.0, MeOH)
(5) $^1$H NMR spectrum (400 MHz, CDCl$_3$) δ (ppm): 1.29 (9H, s, t-Bu), 1.76 (2H, br dq, piperidine), 2.20 (2H, br d, piperidine), 2.85 (2H, br t, piperidine), 3.53 (3H, m, piperidine and CONHC$\underline{H}_2$CH), 3.93 (1H, m, CONHC$\underline{H}_2$C$\underline{H}$), 3.95 (3H, s, C$_6$H$_3$OM$\underline{e}$), 4.02 (1H, m, piperidine), 6.54 (1H, t, pyrimidine), 6.95 (1H, d, C$_6$H$_3$CO), 7.33 (1H, dd, C$_6$H$_3$CO), 7.41 (1H, d, C$_6$H$_3$CO), 7.50 (2H, br t, C$_6$$\underline{H}_5$), 7.58 (1H, br t, C$_6$$\underline{H}_5$), 7.86 (2H, br d, C$_6$$\underline{H}_5$), 8.29 (2H, d, pyrimidine)

Example 92

(2S)-Benzenesulfonylamino-3-[3-methoxy-4-{4-(pyrimidin-2-ylamino)piperidin-1-yl}benzoylamino]-propionic acid Methylene chloride (1.5 ml) was added to 99 mg of the compound prepared in Example 91 to prepare a solution. Trifluoroacetic acid (1.5 ml) was added to the solution. The mixture was stirred at room temperature for 16 hr. The reaction solution was concentrated under the reduced pressure to prepare 100 mg of tritrifluoroacetate of the title compound.

Physicochemical Properties of Compound Prepared in Example 92
(1) Color and form: Colorless oil
(2) Molecular formula: $C_{26}H_{30}N_6O_6S$
(3) Mass spectrum (FABMS): m/z 555 (M+H)$^+$
(4) Specific rotation: $[\alpha]_D^{25}$ +42° (c 0.21, MeOH) (as tritrifluoroacetate)
(5) $^1$H NMR spectrum (400 MHz, CD$_3$OD) (as tritrifluoroacetate) δ (ppm): 2.13 (2H, br dq, piperidine), 2.37 (2H, br dd, piperidine), 3.49 (1H, dd, CONHC$\underline{H}_2$CH), 3.57 (2H, br t, piperidine), 3.79 (1H, dd, CONHC$\underline{H}_2$CH), 3.81 (2H, br d, piperidine), 4.07 (3H, s, C$_6$H$_3$OM$\underline{e}$), 4.23 (1H, dd, CONHCH$_2$C$\underline{H}$), 4.32 (1H, tt, piperidine), 6.91 (1H, t, pyrimidine), 7.16 (1H, m, C$_6$H$_3$CO), 7.45 (2H, br t, C$_6$$\underline{H}_5$), 7.52 (2H, m, C$_6$H$_3$CO and C$_6$$\underline{H}_5$), 7.64 (1H, d, C$_6$H$_3$CO), 7.83 (2H, br d, C$_6$$\underline{H}_5$), 8.53 (2H, br d, pyrimidine)

Example 93

(2S)-Benzenesulfonylamino-3-[3-methoxy-4-{4-(1,4,5,6tetrahydropyrimidin-2-ylamino)piperidin-1-yl}-benzoylamino]propionic acid Dioxane (1.0 ml) and 0.1 ml of water were added to 31.4 mg of tritrifluoroacetate of the compound prepared in Example 92 to prepare a solution. 10% palladium-carbon (6.0 mg) was added to the solution. The mixture was vigorously stirred under a hydrogen pressure of one atm at room temperature for 5 hr. The insolubles were collected by filtration, and then washed with a mixed solution composed of 10 ml of dioxane and 1 ml of water. The filtrate was combined with the washings, and then concentrated under the reduced pressure. The residue was purified by preparative thin-layer chromatography on silica gel (development system: methylene chloride-ethanol-water-concentrated aqueous ammonia=8:8:1:1) and then purified by Sephadex LH-20 (development system: methanol) to prepare 16.6 mg of the title compound.

Physicochemical Properties of Compound Prepared in Example 93
(1) Color and form: Colorless solid
(2) Molecular formula: $C_{26}H_{34}N_6O_6S$
(3) Mass spectrum (ESIMS): m/z 559 (M+H)$^+$
(4) Specific rotation: $[\alpha]_D^{25}$ +76° (c 0.83, MeOH-conc. NH$_4$OH (10:1))
(5) $^1$H NMR spectrum (400 MHz, CD$_3$OD) δ (ppm): 1.68 (2H, br dq, piperidine), 1.96 (2H, quintet, tetrahydropyrimidine), 1.99 (2H, m, piperidine), 2.72 (2H, br t, piperidine), 3.37 (4H, t, tetrahydropyrimidine), 3.45 (3H, m, piperidine), 3.56 (1H, dd, CONHC$\underline{H}_2$CH), 3.68 (1H, dd, CONHC$\underline{H}_2$CH), 3.75 (1H, dd, CONHCH$_2$C$\underline{H}$), 3.91 (3H, s, C$_6$H$_3$OM$\underline{e}$), 6.95 (1H, d, C$_6$H$_3$CO), 7.39 (1H, dd, C$_6$H$_3$CO), 7.43 (1H, d, C$_6$H3CO), 7.48 (2H, dt, C$_6$$\underline{H}_5$), 7.55 (1H, br t, C$_6$$\underline{H}_5$), 7.87 (2H, m, C$_6$$\underline{H}_5$)

Example 94

(2S)-Benzenesulfonylamino-3-[3-hydroxy-4-{4-(pyrimidin-2-ylamino)piperidin-1-yl}benzoylamino]-propionic acid Dichloroethane (3.6 ml) was added to 23.7 mg of the compound prepared in Example 91 to prepare a solution. A 1.0 M methylene chloride solution (0.7 ml) of boron tribromide was added to the solution to prepare a suspension as a reaction solution which was then stirred at 40° C. for 7 hr. A mixed solution composed of 1.0 ml of dioxane and 0.1 ml of water was added to the reaction solution. Further, 1.0 ml of concentrated aqueous ammonia was added thereto, followed by concentration under the reduced pressure. Water (20 ml) was added to the residue. The solution was washed twice with 20 ml of methylene chloride, and then concentrated under the reduced pressure. The residue was purified by CHP-20 (development system: methanol-water=3:7) to prepare 8.4 mg of the title compound.

Physicochemical Properties of Compound Prepared in Example 94
(1) Color and form: Colorless solid
(2) Molecular formula: $C_{25}H_{28}N_6O_6S$
(3) Mass spectrum (APCIMS): m/z 541 (M+H)$^+$
(4) Specific rotation: $[\alpha]_D^{26}$ +22° (c 0.42, MeOH)
(5) $^1$H NMR spectrum (400 MHz, CD$_3$OD) δ (ppm): 1.79 (2H, dq, piperidine), 2.10 (2H, br d, piperidine), 2.81 (2H, br t, piperidine), 3.46 (2H, br d, piperidine), 3.54 (1H, dd, CONHC$\underline{H}_2$CH), 3.66 (1H, dd, CONHC$\underline{H}_2$CH), 3.77 (1H, dd, CONHCH$_2$C$\underline{H}$), 3.93 (1H, m, piperidine), 6.59 (1H, t, pyrimidine), 7.05 (1H, d, C$_6$H$_3$CO), 7.27 (2H, m, C$_6$$\underline{H}_3$CO), 7.45 (2H, br t, C$_6$$\underline{H}_5$), 7.52 (1H, br t, C$_6$$\underline{H}_5$), 7.85 (2H, br d, C$_6$$\underline{H}_5$), 8.27 (2H, d, pyrimidine)

Example 95

(2S)-Benzenesulfonylamino-3-[3-hydroxy-4-{4-(1,4,5,6tetrahydropyrimidin-2-ylamino)piperidin-1-yl}-benzoylamino]propionic acid Dioxane (0.7 ml), 0.1 ml of acetic acid, and 0.2 ml of water were added to 8.0 mg of the compound prepared in Example 94 to prepare a solution. 10% palladium-carbon (2.0 mg) was added to the solution. The mixture was vigorously stirred under a hydrogen pressure of one atm at room temperature for 5 hr. The insolubles were collected by filtration, and then washed with a mixed solution composed of 20 ml of dioxane and 2 ml of water and with methanol. The filtrate was combined with the washings, and then concentrated under the reduced pressure. The residue was purified by column chromatography on silica gel (development system: methylene chloride-ethanol-concentrated aqueous ammonia-water=8:8:1:1) and then purified by Sephadex LH-20 (development system: methanol-concentrated aqueous ammonia=10:1) to prepare 3.5 mg of the title compound.

Physicochemical Properties of Compound Prepared in Example 95

(1) Color and form: Colorless solid
(2) Molecular formula: $C_{25}H_{32}N_6O_6S$
(3) Mass spectrum (ESIMS): m/z 545 (M+H)$^+$
(4) Specific rotation: $[\alpha]_D^{23}$ +40° (c 0.18, MeOH)
(5) $^1$H NMR spectrum (400 MHz, CD$_3$OD) δ (ppm): 1.74 (2H, br dq, piperidine), 1.99 (4H, m, piperidine and tetrahydropyrimidine), 2.74 (2H, br t, piperidine), 3.37 (4H, t, tetrahydropyrimidine), 3.44 (3H, m, piperidine), 3.56 (1H, dd, CONHC$\underline{H}_2$CH), 3.64 (1H, dd, CONHC$\underline{H}_2$CH), 3.74 (1H, dd, CONHCH$_2$C$\underline{H}$), 6.98 (1H, d, C$_6$H$_3$CO), 7.27 (2H, m, C$_6$H$_3$CO), 7.47 (2H, br t, C$_6$$\underline{H}_5$), 7.54 (1H, br t, C$_6$$\underline{H}_5$), 7.86 (2H, br d, C$_6$H$_5$)

Example 96 t-Butyl (2S)-(benzyloxycarbonyl)amino-3-[3-methoxy-4-{4-(pyrimidin-2-ylamino)piperidin-1-yl}-benzoylamino]propionate Dimethylformamide (2.5 ml) was added to 80.0 mg of intermediate 60 to prepare a solution. t-Butyl (2S)-N-benzyloxycarbonyl-2,3-diaminopropionate (78.9 mg) was added to the solution. Further, 66.0 mg of 1-hydroxybenzotriazole, 81 μl of N-methylmorpholine, and 93.5 mg of 1-ethyl-3-(3-dimethylaminopropyl)carbodiimide hydrochloride were added thereto. The mixture was stirred at room temperature for 12 hr. A saturated aqueous potassium carbonate solution (20 ml) and 40 ml of saturated saline were added to stop the reaction, followed by extraction three times with 50 ml of ethyl acetate. The combined organic layer was washed twice with a mixed solution composed of 15 ml of saturated saline and 15 ml of water, dried over anhydrous sodium sulfate, and then concentrated under the reduced pressure. The residue was purified by column chromatography on silica gel (development system: methylene chloride-methanol=25:1) to prepare 145 mg of the title compound.

Physicochemical Properties of Compound Prepared in Example 96

(1) Color and form: Colorless oil
(2) Molecular formula: $C_{32}H_{40}N_6O_6$
(3) Mass spectrum (FABMS): m/z 605 (M+H)$^+$
(4) Specific rotation: $[\alpha]_D^{22}$ −17° (c 0.62, MeOH)
(5) $^1$H NMR spectrum (400 MHz, CDCl$_3$) δ (ppm): 1.47 (9H, s, t-Bu), 1.75 (2H, dq, piperidine), 2.20 (2H, br d, piperidine), 2.84 (2H, br t, piperidine), 3.53 (2H, br d, piperidine), 3.78 (1H, m, CONHC$\underline{H}_2$CH), 3.86 (1H, m, CONHC$\underline{H}_2$CH), 3.92 (3H, s, C$_6$H$_3$OM$\underline{e}$), 4.01 (1H, m, piperidine), 4.46 (1H, m, CONHCH$_2$C$\underline{H}$), 5.11 (2H, s, C$\underline{H}_2$C$_6$H$_5$), 6.53 (1H, t, pyrimidine), 6.91 (1H, d, C$_6$H$_3$CO), 7.23 (1H, br d, C$_6$H$_3$CO), 7.33 (5H, m, CH$_2$C$_6$$\underline{H}_5$), 7.39 (1H, br d, C$_6$H$_3$CO), 8.29 (2H, d, pyrimidine)

Example 97 t-Butyl (2S)-amino-3-[3-methoxy-4-{4-(pyrimidin-2-ylamino)piperidin-1-yl}benzoylaminol]-propionate Tetrahydrofuran (2.0 ml) was added to 120 mg of the compound prepared in Example 96 to prepare a solution. 10% palladium-carbon (24 mg) was added to the solution. The mixture was vigorously stirred under a hydrogen pressure of one atm at room temperature for 22 hr. The insolubles were collected by filtration, and then washed twice with methanol. The filtrate was combined with the washings, and then concentrated under the reduced pressure. The residue was purified by column chromatography on silica gel (development system: methylene chloride-methanol=7:1) to prepare 74.1 mg of the title compound.

Physicochemical Properties of Compound Prepared in Example 97

(1) Color and form: Colorless oil
(2) Molecular formula: $C_{24}H_{34}N_6O_4$
(3) Mass spectrum (FABMS): m/z 471 (M+H)$^+$
(4) Specific rotation: $[\alpha]_D^{26}$ +20°(c 1.1, MeOH)
(5) $^1$H NMR spectrum (400 MHz, CD$_3$OD) δ (ppm): 1.44 (9H, s, t-Bu), 1.74 (2H, dq, piperidine), 2.09 (2H, br d, piperidine), 2.79 (2H, br t, piperidine), 3.54 (2H, br d, piperidine), 3.62 (3H, m, CONHC$\underline{H}_2$C$\underline{H}$), 3.92 (4H, m, piperidine and C$_6$H$_3$OM$\underline{e}$), 6.59 (1H, t, pyrimidine), 7.03 (1H, d, C$_6$H$_3$CO), 7.43 (2H, m, C$_6$H$_3$CO), 8.26 (2H, d, pyrimidine)

Example 98 t-Butyl (2S)-(4-methoxybenzenesulfonyl)amino-3-[3-methoxy-4-{4-(pyrimidin-2-ylamino)piperidin-1-yl}benzoylamino]propionate Dimethylformamide (1.0 ml) was added to 47.0 mg of the compound prepared in Example 97 to prepare a solution. Diisopropylethylamine (35 μl) and 20.6 mg of 4-methoxybenzenesulfonyl chloride were added at room temperature to the solution. The mixture was stirred for 2 hr. Piperazine (5 mg) was then added thereto. The mixture was stirred for additional 5 min. A saturated aqueous sodium hydrogencarbonate solution (30 ml) was added to the reaction solution, followed by extraction three times with 30 ml of ethyl acetate. The combined organic layer was washed twice with a mixed solution composed of 20 ml of saturated saline and 20 ml of water, dried over anhydrous sodium sulfate, and then concentrated under the reduced pressure. The residue was purified by preparative thin-layer chromatography on silica gel (development system: methylene chloride-methanol=7:1) to prepare 62.6 mg of the title compound.

Physicochemical Properties of Compound Prepared in Example 98
(1) Color and form: Colorless solid
(2) Molecular formula: $C_{31}H_{40}N_6O_7S$
(3) Mass spectrum (APCIMS): m/z 641 (M+H)$^+$
(4) Specific rotation: $[\alpha]_D^{26}$ +30° (c 0.16, MeOH)
(5) $^1$H NMR spectrum (400 MHz, CDCl$_3$) δ (ppm): 1.32 (9H, s, I-Bu), 1.75 (2H, br dq, piperidine), 2.19 (2H, br d, piperidine), 2.84 (2H, br t, piperidine), 3.54 (3H, m, piperidine and CONHC$\underline{H}_2$CH), 3.84 (3H, S, C$_6$H$_4$O$\underline{Me}$), 3.87 (1H, dd, CONHC$\underline{H}_2$CH), 3.92 (1H, m, CONHCH$_2$C$\underline{H}$), 3.94 (3H, s, C$_6$H$_3$O$\underline{Me}$), 4.01 (1H, m, piperidine), 6.54 (1H, t, pyrimidine), 6.95 (3H, m, C$_6$$\underline{H}_4$OMe and C$_6$H$_3$CO), 7.32 (1H, dd, C$_6$H$_3$CO), 7.41 (1H, d, C$_6$H$_3$CO), 7.78 (2H, br d, C$_6$$\underline{H}_4$OMe), 8.29 (2H, d, pyrimidine)

Example 99

(2S)-(4-Hydroxybenzenesulfonyl)amino-3-[3-hydroxy-4-{4-(pyrimidin-2-ylamino)piperidin-1-yl}-benzoylamino]propionic acid Dichloroethane (5.0 ml) was added to 60.0 mg of the compound prepared in Example 98 to prepare a solution. A 1.0 M methylene chloride solution (0.94 ml) of boron tribromide was added to the solution. The suspension as a reaction solution was stirred at 400C for 25 hr. A mixed solution composed of 1.0 ml of dioxane and 0.1 ml of water was added to the reaction solution. Further, 1.0 ml of concentrated aqueous ammonia was added thereto, and the mixture was concentrated under the reduced pressure. The residue was purified by CHP-20 (development system: methanol-water=3:7) to prepare 28.2 mg of the title compound.

Physicochemical Properties of Compound Prepared in Example 99
(1) Color and form: Colorless solid
(2) Molecular formula: $C_{25}H_{28}N_6O_7S$
(3) Mass spectrum (ESIMS): m/z 557 (M+H)$^+$
(4) Specific rotation: $[\alpha]_D^{23}$ +65° (c 0.54, MeOH)
(5) $^1$H NMR spectrum (400 MHz, CD$_3$OD) δ (ppm): 1.79 (2H, dq, piperidine), 2.10 (2H, br d, piperidine), 2.81 (2H, br t, piperidine), 3.46 (2H, br d, piperidine), 3.53 (1H, dd, CONHC$\underline{H}_2$CH), 3.66 (2H, m, CONHC$\underline{H}_2$C$\underline{H}$), 3.93 (1H, tt, piperidine), 6.59 (1H, t, pyrimidine), 6.81 (2H, br d, C$_6$$\underline{H}_4$OH), 7.05 (1H, br d, C$_6$$\underline{H}_3$CO), 7.28 (2H, m, C$_6$H$_3$CO), 7.68 (2H, br d, C$_6$$\underline{H}_4$OH), 8.26 (2H, d, pyrimidine)

Example 100

(2S)-(4-Hydroxybenzenesulfonyl)amino-3-[3-hydroxy-4-{1,4,5,6tetrahydropyrimidin-2-ylamino)piperidin-1-yl}benzoylamino]propionic acid Dioxane (0.7 ml), 0.1 ml of acetic acid, and 0.2 ml of water were added to 27.5 mg of the compound prepared in Example 99 to prepare a solution. 10% palladium-carbon (6.0 mg) was added to the solution. The mixture was vigorously stirred under a hydrogen pressure of one atm at room temperature for 4 hr. The insolubles were collected by filtration, and then washed with methanol. The filtrate was combined with the washings, and then concentrated under the reduced pressure. The residue was purified by column chromatography on silica gel (development system: ethanol-concentrated aqueous ammonia-water=4:1:1) and then purified by CHP-20 (development system: methanol-water=1:1) to prepare 19.8 mg of the title compound.

Physicochemical Properties of Compound Prepared in Example 100
(1) Color and form: Pale yellow solid
(2) Molecular formula: $C_{25}H_{32}N_6O_7S$
(3) Mass spectrum (TSPMS): m/z 561 (M+H)$^+$
(4) Specific rotation: $[\alpha]_D^{23}$ +88° (c 1.0, MeOH-conc. NH$_4$OH (10:1))
(5) $^1$H NMR spectrum (400 MHz, CD$_3$OD) δ (ppm): 1.70 (2H, br q, piperidine), 1.97 (4H, m, piperidine and tetrahydropyrimidine), 2.71 (2H, br t, piperidine), 3.37 (4H, t, tetrahydropyrimidine), 3.42 (3H, m, piperidine), 3.60 (3H, m, CONHC$\underline{H}_2$C$\underline{H}$), 6.75 (2H, br d, C$_6$$\underline{H}_4$OH), 6.96 (1H, d, C$_6$$\underline{H}_3$CO), 7.27 (2H, m, C$_6$H$_3$CO), 7.63 (2H, d, C$_6$$\underline{H}_4$OH)

Example 10 t-Butyl (2S)-(4-carboxybenzenesulfonyl)amino-3-[3-methoxy-4-{4-(pyrimidin-2-ylamino)-piperidin-1-yl benzoylamino]propionate Pyridine (1.7 ml) was added to 82.0 mg of the compound prepared in Example 97 to prepare a solution. 4-Dimethylaminopyridine (4.3 mg) was added to the solution. Further, 4-(chlorosulfonyl)benzoic acid (38.3 mg) was added dropwise thereto at room temperature over a period of 7 hr. The mixture was stirred for 12 hr. Piperazine (10.0 mg) was then added thereto. The mixture was stirred for additional 5 min, and then concentrated under the reduced pressure. The residue was purified by preparative thin-layer chromatography on silica gel (development system: methylene chloride-methanol=7:1) to prepare 57.6 mg of the title compound.

Physicochemical Properties of Compound Prepared in Example 101
(1) Color and form: Colorless solid
(2) Molecular formula: $C_{31}H_{38}N_6O_8S$
(3) Mass spectrum (FABMS): m/z 655 (M+H)$^+$
(4) Specific rotation: $[\alpha]_D^{25}$ +23° (c 0.86, MeOH)
(5) $^1$H NMR spectrum (400 MHz, CD$_3$OD) δ (ppm): 1.23 (9H, s, t-Bu), 1.74 (2H, dq, piperidine), 2.09 (2H, br d, piperidine), 2.80 (2H, br t, piperidine), 3.53 (3H, m, piperidine and CONHC$\underline{H}_2$CH), 3.68 (1H, dd, CONHC$\underline{H}_2$CH), 3.91 (4H, m, C$_6$H$_3$O$\underline{Me}$ and piperidine), 4.15 (1H, dd, CONHCH$_2$C$\underline{H}$), 6.58 (1H, t, pyrimidine), 7.00 (1H, d, C$_6$$\underline{H}_3$CO), 7.34 (1H, dd, C$_6$H$_3$CO), 7.40 (1H, d, C$_6$H$_3$CO), 7.83 (2H, br d, C$_6$$\underline{H}_4$CO$_2$H), 8.03 (2H, br d, C$_6$$\underline{H}_4$CO$_2$H), 8.26 (2H, d, pyrimidine)

Example 102

(2S)-(4-Carboxybenzenesulfonyl)amino-3-[3-methoxy-4-{4-(pyrimidin-2-ylamino)piperidin-1-yl}-benzoylamino]propionic acid Methylene chloride (0.5 ml) and 0.5 ml of trifluoroacetic acid were added at room temperature to 32.0 mg of the compound prepared in Example 101. The mixture was stirred for 16 hr. The reaction solution was concentrated under the reduced pressure. The residue was subjected to azeotropic distillation twice with toluene, and purified by preparative thin-layer chromatography on silica gel (development system: methylene chloride-ethanol-concentrated aqueous ammonia-water=8:8:1:1) to prepare 27.0 mg of the title compound.

Physicochemical Properties of Compound Prepared in Example 102
(1) Color and form: Colorless solid
(2) Molecular formula: $C_{27}H_{30}N_6O_8S$
(3) Mass spectrum (TSPMS): m/z 599 (M+H)$^+$
(4) Specific rotation: $[\alpha]_D^{25}$ +70° (c 0.21, MeOH-conc. NH$_4$OH (10:1))
(5) $^1$H NMR spectrum (400 MHz, CD$_3$OD) δ (ppm): 1.76 (2H, dq, piperidine), 2.09 (2H, br d, piperidine), 2.81 (2H, br t, piperidine), 3.55 (3H, m, piperidine and CONHC$\underline{H}_2$CH), 3.68 (1H, dd, CONHC$\underline{H}_2$CH), 3.86 (1H, dd, CONHCH$_2$C$\underline{H}$), 3.93 (4H, m, piperidine and C$_6$H$_3$OMe), 6.59 (1H, t, pyrimidine), 7.01 (1H, d, C$_6$$\underline{H}_3$CO), 7.33 (1H, dd, C$_6$H$_3$CO), 7.42 (1H, d, C$_6$H$_3$CO), 7.87 (2H, br d, C$_6$$\underline{H}_4$CO$_2$H), 8.01 (1H, d, C$_6$$\underline{H}_4$CO$_2$H), 8.26 (2H, d, pyrimidine)

Example 103

(2S)-(4-Carboxybenzenesulfonyl)amino-3-[3-methoxy-4-{4-(1,4,5,6tetrahydropyrimidin-2-ylamino)-piperidin-1-yl}benzoylamino]propionic acid Dioxane (1.4 ml), 0.2 ml of acetic acid, and 0.4 ml of water were added to 27.0 mg of the compound prepared in Example 102 to prepare a solution. 10% palladium-carbon (6.0 mg) was added to the solution. The mixture was vigorously stirred under a hydrogen pressure of one atm at room temperature for 6 hr. The insolubles were collected by filtration, and then washed with a mixed solution composed of 10 ml of methanol and 1 ml of concentrated aqueous ammonia. The filtrate was combined with the washings, and then concentrated under the reduced pressure. The residue was purified by preparative thin-layer chromatography on silica gel (development system: methylene chloride-ethanol-concentrated aqueous ammonia-water=8:8:1:1) and then purified by CHP-20 (development system: methanol-water= 1:10) to prepare 8.5 mg of the title compound.

Physicochemical Properties of Compound Prepared in Example 103
(1) Color and form: Colorless solid
(2) Molecular formula: $C_{27}H_{34}N_6O_8S$
(3) Mass spectrum (TSPMS): m/z 603 (M+H)$^+$
(4) Specific rotation: $[\alpha]_D^{25}$ +49° (c 0.43, MeOH-conc. NH$_4$OH (10:1))
(5) $^1$H NMR spectrum (400 MHz, CD$_3$OD) δ (ppm): 1.71 (2H, m, piperidine), 1.96 (4H, m, piperidine and tetrahydropyrimidine), 2.85 (2H, m, piperidine), 3.37 (4H, t, tetrahydropyrimidine), 3.50 (3H, m, piperidine), 3.60 (2H, m, CONHC$\underline{H}_2$CH), 3.84 (1H, dd, CONHCH$_2$C$\underline{H}$), 3.89 (3H, S, C$_6$$\underline{H}_3$OMe), 6.91 (1H, d, C$_6$$\underline{H}_3$CO), 7.10 (1H, dd, C$_6$H$_3$CO), 7.39 (1H, d, C$_6$H$_3$CO), 7.77 (2H, br d, C$_6$$\underline{H}_4$CO$_2$H), 7.90 (2H, br d, C$_{64}$CO$_2$H)

Example 104 t-Butyl (2S)-amino-3-[4-{4-(pyrimidin-2-ylamino) piperidin-1-yl}benzoylamino]propionate Freshly distilled tetrahydrofuran (50 ml) was added to 670 mg of the compound prepared in Example 13 to prepare a solution. 10% palladium-carbon (335 mg) was added to the solution. The mixture was vigorously stirred in a hydrogen atmosphere at room temperature for 18 hr. The catalyst was collected by filtration, and then washed twice each with 20 ml of tetrahydrofuran. The filtrate was combined with the washings, and then concentrated under the reduced pressure. The residue was purified by column chromatography on silica gel (70 g, diethyl ether-methylene chloride-methanol= 2:7:1→0:9:1) to prepare 285 mg of the title compound.

Physicochemical Properties of Compound Prepared in Example 104
(1) Color and form: Colorless solid
(2) Molecular formula: $C_{23}H_{32}N_6O_3$
(3) Mass spectrum (ESIMS): m/z 441 (M+H)$^+$
(4) Specific rotation: $[\alpha]_D^{25}$ +6° (c 1.1, CHCl$_3$)
(5) $^1$H NMR spectrum (400 MHz, CDCl$_3$) δ (ppm): 1.48 (9H, s, t-Bu), 1.61 (2H, br q, piperidine), 2.17 (2H, br d, piperidine), 3.04 (2H, br t, piperidine), 3.45 (1H, ddd, CONHC$\underline{H}_2$CH), 3.59 (11H, dd, CONHCH$_2$C$\underline{H}$), 3.79 (22H, br d, piperidine), 3.81 (1H, ddd, CONHC$\underline{H}_2$CH), 4.05 (1H, m, piperidine), 6.54 (1H, t, pyrimidine), 6.91 (2H, d, C$_6$H$_4$), 7.69 (2H, d, C$_6$H$_4$), 8.28 (2H, d, pyrimidine)

Example 105

Methyl (2S)-benzenesulfonylamino-3-[4-{4-(pyrimidin-2-ylamino)piperidin-1-yl}benzoylamino]-propionate Anhydrous methanol (8.0 ml) was added to 80 mg of the compound prepared in Example 2 to prepare a solution. A 1 M diethyl ether solution (0.50 ml) of hydrogen chloride was added to the solution. A reaction was allowed to proceed at room temperature for 16 hr. The reaction solution was neutralized with 87 mg of triethylamine, and then concentrated under the reduced pressure. The residue was purified by column chromatography on silica gel (8 g, 5%→20% methanol/methylene chloride) to prepare 11.8 mg of the title compound.

Physicochemical Properties of Compound Prepared in Example 108
(1) Color and form: Colorless solid
(2) Molecular formula: $C_{26}H_{30}N_6O_5S$
(3) Mass spectrum (TSPMS): m/z 539 (M+H)$^+$
(4) Specific rotation: $[\alpha]_D^{25}$ +29° (c 1.0, DMSO)
(5) $^1$H NMR spectrum (400 MHz, DMSO-d$_6$) δ (ppm): 1.54 (2H, br dq, piperidine), 1.92 (2H, br d, piperidine), 2.92 (2H, br t, piperidine), 3.36 (3H, s, Me), 3.37 (1H, dd, CONHC$\underline{H}_2$CH), 3.46 (1H, dd, CONHC$\underline{H}_2$CH), 3.86 (2H, br d, piperidine), 3.94 (1H, m, piperidine), 4.08 (1H, dd, CONHCH$_2$C$\underline{H}$), 6.55 (1H, t, pyrimidine), 6.94 (2H, d, C$_6$H$_4$), 7.51 (2H, m, C$_6$H$_5$), 7.58 (1H, m, C$_6$H$_5$), 7.61 (2H, d, C$_6$H$_4$), 7.75 (2H, m, C$_6$D$_5$), 8.26 (2H, d, pyrimidine)

Pharmacological Test Example 1

$\alpha_v\beta_3$ Binding Assay

Integrin $\alpha_v\beta_3$ antagonistic activity was measured for the compounds according to the present invention in a vitronectin-vitronectin receptor binding assay system in accordance with the method of Kouns et al. (W. C. Kouns, D. Kirchhofer, P. Hadvary, A. Edenhofer, T. Weller, G. Pfenninger, H. R. Baumgartner, L. K. Jennings and B. Steiner, Blood, 80, 2539–2547 (1992)).

Specifically, a vitronectin receptor (protein content: 118 µg/ml) purified from the human placenta in accordance with the method of Pytela et al. (R. Pytela, M. D. Pierschbacher, S. Argraves, S. Suzuki, and E. Ruoslahti, Method in Enzymology, 144, 475–489 (1987)) was diluted 50 times with TBS (20 mM Tris-HCl, 150 mM NaCl, 1 mM $CaCl_2$, 1 mM $MgCl_2$, pH 7.4), and distributed and coated on wells (50 μl/well) of a plate (Maxisorp, Nunc, 96 well Immuno Plate). The plate was then allowed to stand at 4° C. for 1 day, washed twice with TBS (200 μl/well), and then subjected to blocking with TBS (150 μl/well) containing 1% bovine serum albumin (SIGMA) at 4° C. overnight. After washing twice with TBS (200 μl/well), 50 μl of vitronectin (CALBIOCHEM) adjusted to 0.2 μg/ml by the addition of TBS (TBS-Tween) containing 0.01% Tween-20 was mixed with 50 μl of each test compound adjusted to each concentration in wells, and a reaction was allowed to proceed at room temperature for 4 hr. After the completion of the reaction, the wells were washed five times with TBS-Tween. A solution prepared by diluting anti-vitronectin rabbit anti-serum (CHEMICON) 500 times with TBS-Tween was added as a primary antibody in an amount of 50 μl/well, and a reaction was allowed to proceed at room temperature for 1.5 hr. After washing five times with 200 μl/well of TBS-Tween, a peroxidase (POD)-labeled anti-rabbit IgG antibody solution (CAPPEL) diluted 500 times with TBS-Tween was added as a secondary antibody in an amount of 50 μl/well, and a reaction was allowed to proceed at room temperature for 1.5 hr. After washing five times with TBS-Tween (200 μl/well), ABTS (2,2'-azino-bis(3-ethylbenzthiazoline-6-sulfonic acid), SIGMA) was adjusted to 1 mg/ml by the addition of a ten-fold diluted POD-buffer (ZYMED), and added in an amount of 50 μl/well, and a reaction was allowed to proceed for 5 to 10 min. A 0.1 M citric acid buffer (pH 4.3) containing 0.05% $NaN_3$ was added in an amount of 50 μl/well to stop the reaction, followed by the measurement of the absorbance at 415 nm with a microplate reader (MTP 32, Corona Electric) (reference: 675 nm). The total binding was defined as the absorbance after a reaction using 50 μl of TBS-Tween instead of the test compound, and the non-specific binding (100% inhibition) was defined as the absorbance after a reaction using 50 μl of TBS-Tween containing $2\times10^{-3}$ M RGDS. The inhibition was calculated by the following equation:

$$\text{Inhibition}(\%) = 100 - \frac{(\text{absorbance in the presence of test compound}) - \text{non-specific binding}}{(\text{total binding} - \text{non-specific binding})} \times 100$$

$IC_{50}$ was determined from a primary regression line of the logarithm of each concentration of the test compound and the logarithm of (100−inhibition)/inhibition.

As a result, all the compounds of Examples 22, 28, 31, 33, 35, 36, 38, 42, 52, 54, 57, 60, 68, 73, 75, 78, 93 and 95 had significant integrin $\alpha_v\beta_3$ antagonistic activity, and had an $IC_{50}$ value of not more than 1.0 nM.

Pharmacological Test Example 2
GP IIb/IIIa Antagonistic Activity and Human Platelet Aggregation Inhibitory Activity GP IIb/IIIa antagonistic activity was measured for the compounds according to the present invention. The measurement of the GP IIb/IIIa antagonistic activity was carried out according to the method described in Pharmacological Test 2 in WO 94/21599. As a result, all the compounds of Examples 24, 28, 31, 33, 35, 36, 38, 40, 42, 45, 52, 54, 57, 60, 68, 73, 75, 78, 93, and 95 had significant GP IIb/IIIa antagonistic activity, and had an $IC_{50}$ value of not more than 1.0 nM.

Human platelet aggregation inhibitory activity was measured for the compounds according to the present invention. The measurement of the human platelet aggregation activity was carried out according to the method described in Pharmacological Test 1 in WO 94/21599. As a result, the compounds of Examples 22, 40, 42, 45, 54, and 60 very strongly inhibited human platelet aggregation, and had an $IC_5$. value of not more than 90 nM.

Pharmacological Test Example 3
Inhibitory Activity Against Adhesion of Human Vascular Smooth Muscle Cells to Vitronectin The adhesion of human vascular smooth muscle cells =+to immobilized human vitronectin was measured in accordance with the method of Liaw et al. (Liaw L, Almeida M, Hart C E, Schwartz S M, and Giachelli C M, Circulation Research, 74 (2), 214–224 (1994)).

A Dulbecco's phosphate buffer (Dulbecco's PBS(−), Nissui Pharmaceutical Co., Ltd.) solution of human plasma-derived vitronectin (CALBIOCHEM) adjusted to a concentration of 4 μg/ml was first added to wells (50 μl/well) of a microplate (Maxisorp, Nunc), and a reaction for immobilization was allowed to proceed at 4° C. overnight. After washing twice with 150 μl of Dulbecco's phosphate buffer, a Dulbecco's phosphate buffer containing 10 mg/ml of bovine serum albumin (SIGMA) was added, followed by blocking at 37° C. for one hr. The assay plate was washed twice with 150 μl of Dulbecco's phosphate buffer.

Separately, human vascular smooth muscle cells cultivated at 37° C. under 5% carbon dioxide in a medium for vascular smooth muscle cells (Clonetics) were separated using a Dulbecco's phosphate buffer containing trypsin-EDTA (GIBCO BRL), washed with Dulbecco's phosphate buffer, and then suspended in a Dulbecco's modified Eagle's basal medium (Nissui Pharmaceutical Co., Ltd.) containing 0.1% bovine serum albumin to a concentration of $5\times10^5$/ml.

Next, 50 μl of a Dulbecco's modified Eagle's basal medium containing 10 mg/ml of bovine serum albumin with a medicament added thereto was added to the wells of the human vitronectin-coated assay microplate, followed by pre-cultivation under 5% carbon dioxide at 37° C. for 10 min. Thereafter, 50 μl of the medium with human vascular smooth muscle cells suspended therein was added thereto, and the plate was thoroughly stirred. A reaction was allowed to proceed under 5% carbon dioxide at 37° C. for 90 min. The reaction solution containing non-adherent cells were then removed, followed by washing three times with Dulbecco's phosphate buffer. For the adhered cells, 100 μl of a Dulbecco's phosphate buffer containing 4% paraformaldehyde (Wako Pure Chemical Industries, Ltd.) was added, and immobilization was allowed to proceed at room temperature for 10 min. Next, 100 μl of a Dulbecco's phosphate buffer containing 0.5% Toluidine Blue (Croma) and 4% paraformaldehyde was added, and staining was allowed to proceed at room temperature for 5 min, followed by thorough washing with distilled water. The inside of the wells was then air-dried, and a 1% aqueous sodium dodecylsulfate solution was then added to perform cytolysis. The absorbance of the microplate thus obtained was measured at 595 nm. The total binding was defined as the absorbance of the well not containing the test compound, and the non-specific binding (100% inhibition) was defined as the absorbance of the well which does not contain vitronectin and has been subjected to blocking with bovine serum albumin. The inhibition was calculated by the following equation. $IC_{50}$ was determined from a primary regression line of the logarithm of each concentration of the test compound and the logarithm of (100−inhibition)/inhibition.

$$\text{Inhibition}(\%) = 100 - \frac{(\text{absorbance in the presence of test compound} - \text{non-specific binding})}{(\text{total binding} - \text{non-specific binding})} \times 100$$

As a result, all the compounds of Examples 35, 52, 57, 60, 75, and 93 had strong cell adhesion inhibitory activity and had an $IC_{50}$ value on the inhibitory activity against the adhesion of human vascular smooth muscle cells to vitronectin of not more than 70 nM.

Pharmacological Test Example 4
$\alpha_5\beta_1$ Binding Assay

Integrin $\alpha_5\beta_1$ antagonistic activity (lethality) was measured for the compounds according to the present invention in a fibronectin-fibronectin receptor binding assay system in accordance with the method of Kouns et al. (W. C. Kouns, D. Kirchhofer, P. Hadvary, A. Edenhofer, T. Weller, G. Pfenninger, H. R. Baumgartner, L. K. Jennings, and B. Steiner, Blood, 80, 2539–2547 (1992)).

Specifically, a fibronectin receptor (protein content: 52.1 μg/ml) purified from the human placenta by the method of Pytela et al. (R. Pytela, M. D. Pierschbacher, S. Argraves, S. Suzuki, and E. Ruoslahti, Method in Enzymology, 144, 475–489 (1987)) was diluted 25 times with TBS (20 mM Tris-HCl, 150 mM NaCl, 1 mM $CaCl_2$, 1 mM $MgCl_2$, pH 7.4), and distributed and coated on wells (50 μl/well) of a plate (Maxisorp, Nunc, 96 well Immuno Plate). The plate was then allowed to stand at 4° C. for one day, washed twice with TBS (200 μl/well), and then subjected to blocking with TBS (150 μl/well) containing 3% skim milk (DIFCO) at 4° C. overnight. After washing twice with TBS (200 μl/well) containing 0.05% Tween-20 and then washing twice with TBS (200 μl/well), purification was carried out according to the method of E. Engvall et al. (E. Engvall, E. Ruoslahti, and E. J. Miller, J. Exp. Med., 147, 1584–1595 (1978)), and 50 11 of fibronectin adjusted to 0.2 μg/ml by the addition of TBS (TBS-Tween) containing 0.01% Tween-20 was mixed with 50 μl of each test compound adjusted to each concentration in the wells, and a reaction was allowed to proceed at room temperature for 3 hr. After the completion of the reaction, the wells were washed five times with TBS-Tween. A solution prepared by diluting a peroxidase-labeled fibronectin antibody (CAPPEL) 500 times with TBS-Tween was added in an amount of 50 μl per well, and a reaction was allowed to proceed at room temperature for 1.5 hr. After washing five times with TBS-Tween (200 μl/well), ABTS (SIGMA) adjusted to 1 mg/ml by the addition of a ten-fold diluted POD-buffer (ZYMED) was added in an amount of 50 μl/well, and a reaction was allowed to proceed for 5 to 10 min. A 0.1 M citric acid buffer (pH 4.3) containing 0.05% $NaN_3$ was added in an amount of 50 μl/well to stop the reaction, followed by the measurement of the absorbance at 415 nm with a microplate reader (MTP 32, Corona Electric) (reference: 675 nm). The total binding was defined as the absorbance after a reaction using 50 μl of TBS-Tween instead of the test compound, and the non-specific binding (100% inhibition) was defined as the absorbance after a reaction using 50 μl of TBS-Tween containing $2\times10^{-3}$ M RGDS. The inhibition was calculated by the following equation:

$$\text{Inhibition}(\%) = 100 - \frac{(\text{absorbance in the presence of test compound} - \text{non-specific binding})}{(\text{total binding} - \text{non-specific binding})} \times 100$$

$IC_{50}$ was determined from a primary regression line of the logarithm of each concentration of the test compound and the logarithm of (100−inhibition)/inhibition.

The results were as follows.

| Example | $\alpha_5\beta_1$ Binding inhibitory activity, μM |
|---|---|
| 3 | 1.6 |
| 10 | 1.6 |
| 22 | 2.5 |
| 24 | 6.9 |
| 28 | 1.3 |
| 52 | 0.33 |
| 68 | 11.5 |

This demostrates that the compounds according to the present invention can function as medicaments having very low side effect.

Acute Toxicity Test

The compound of Example 52 was intravenously administered to three mice at a dose of 50 mg/kg. As a result, all the mice survived. The change in weight was the same as a group of mice to which only a solvent had been administered.

Structure of Compounds

The compounds of Examples 1 to 105 have the following respective structures.

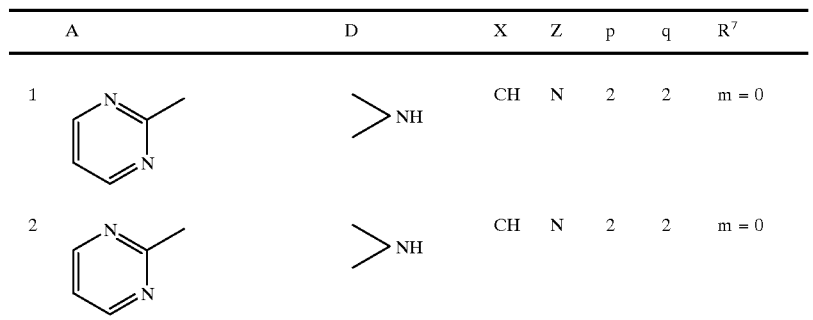

| | A | D | X | Z | p | q | $R^7$ |
|---|---|---|---|---|---|---|---|
| 1 | pyrimidinyl | >NH | CH | N | 2 | 2 | m = 0 |
| 2 | pyrimidinyl | >NH | CH | N | 2 | 2 | m = 0 |

-continued
| | | | | | | | |
|---|---|---|---|---|---|---|---|
| 3 | 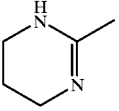 | 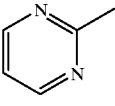NH | CH | N | 2 | 2 | m = 0 |
| 4 | 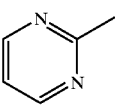 | >NH | CH | N | 2 | 1 | m = 0 |
| 5 | 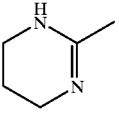 | >NH | CH | N | 2 | 1 | m = 0 |
| 6 | 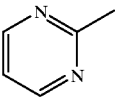 | >NH | CH | N | 2 | 1 | m = 0 |
| 7 | 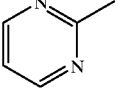 | >NH | CH | N | 2 | 1 | m = 0 |
| 8 | 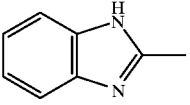 | >NH | CH | N | 2 | 1 | m = 0 |
| 9 | 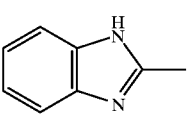 | >NH | CH | N | 2 | 2 | m = 0 |
| 10 | 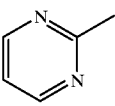 | >NH | CH | N | 2 | 2 | m = 0 |
| 11 | 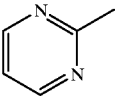 | >NH | CH | N | 2 | 2 | m = 0 |
| 12 | 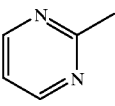 | >NH | CH | N | 2 | 2 | m = 0 |
| 13 | 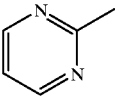 | >NH | CH | N | 2 | 2 | m = 0 |
| 14 |  | >NH | CH | N | 2 | 2 | m = 0 |

-continued

| | | | | | | | |
|---|---|---|---|---|---|---|---|
| 15 | [2-methyl-1,4,5,6-tetrahydropyrimidine] | >NH | CH | N | 2 | 2 | m = 0 |
| 16 | [2-methyl-1,4,5,6-tetrahydropyrimidine] | >NH | CH | N | 2 | 2 | m = 0 |
| 17 | [2-methyl-1,4,5,6-tetrahydropyrimidine] | >NH | CH | N | 2 | 2 | m = 0 |
| 18 | [2-methylpyrimidine] | >NH | CH | N | 2 | 2 | m = 0 |
| 19 | [2-methylpyrimidine] | >NH | CH | N | 2 | 2 | m = 0 |
| 20 | [2-methyl-1,4,5,6-tetrahydropyrimidine] | >NH | CH | N | 2 | 2 | m = 0 |
| 21 | [acetamidine] | >NH | CH | N | 2 | 2 | m = 0 |
| 22 | [acetamidine] | >NH | CH | N | 2 | 2 | m = 0 |
| 23 | [2-methylbenzimidazole] | >NH | CH | N | 2 | 2 | m = 0 |
| 24 | [2-methylbenzimidazole] | >NH | CH | N | 2 | 2 | m = 0 |
| 25 | [1-Boc-2-methylbenzimidazole] | >NH | CH | N | 2 | 2 | m = 0 |

-continued

| | | | | | | | |
|---|---|---|---|---|---|---|---|
| 26 | [Boc-2-methylbenzimidazole] | >NH | CH | N | 2 | 2 | m = 0 |
| 27 | [Boc-2-methylbenzimidazole] | >NH | CH | N | 2 | 2 | m = 0 |
| 28 | [2-methyl-1H-benzimidazole] | >NH | CH | N | 2 | 2 | m = 0 |
| 29 | [2-methyl-1H-benzimidazole] | >NH | CH | N | 2 | 2 | m = 0 |
| 30 | [Boc-2-methylbenzimidazole] | >NH | CH | N | 2 | 2 | m = 0 |
| 31 | [2-methyl-1H-benzimidazole] | >NH | CH | N | 2 | 2 | m = 0 |
| 32 | [Boc-2-methylbenzimidazole] | >NH | CH | N | 2 | 2 | m = 0 |
| 33 | [2-methyl-1H-benzimidazole] | >NH | CH | N | 2 | 2 | m = 0 |

-continued

| | | | | | | | |
|---|---|---|---|---|---|---|---|
| 34 | *(tert-butoxycarbonyl-2-methylbenzimidazole)* | >NH | CH | N | 2 | 2 | m = 0 |
| 35 | *(2-methylbenzimidazole)* | >NH | CH | N | 2 | 2 | m = 0 |
| 36 | *(2-methylbenzimidazole)* | >NH | CH | N | 2 | 2 | m = 0 |
| 37 | *(2-methylimidazo[4,5-b]pyridine)* | >NH | CH | N | 2 | 2 | m = 0 |
| 38 | *(2-methylimidazo[4,5-b]pyridine)* | >NH | CH | N | 2 | 2 | m = 0 |
| 39 | *(1-(4-methoxybenzyl)-2-methyl-4,5-dihydroimidazole)* | >NH | CH | N | 2 | 2 | m = 0 |
| 40 | *(2-methyl-4,5-dihydroimidazole)* | >NH | CH | N | 2 | 2 | m = 0 |
| 41 | *(2-methyl-4,5,6,7-tetrahydro-1,3-diazepine)* | >NH | CH | N | 2 | 2 | m = 0 |
| 42 | *(2-methyl-tetrahydrodiazepine)* | >NH | CH | N | 2 | 2 | m = 0 |
| 43 | *(2-methylpyrimidine)* | >N—Me | CH | N | 2 | 2 | m = 0 |

-continued
| | | | | | | | |
|---|---|---|---|---|---|---|---|
| 44 | 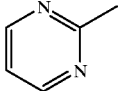 | 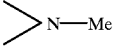 | CH | N | 2 | 2 | m = 0 |
| 45 | 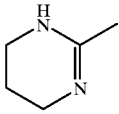 | 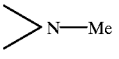 | CH | N | 2 | 2 | m = 0 |
| 46 | 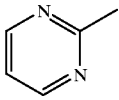 |  | CH | N | 2 | 2 | m = 0 |
| 47 | 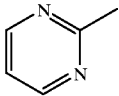 |  | CH | N | 2 | 2 | m = 0 |
| 48 | 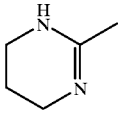 |  | CH | N | 2 | 2 | m = 0 |
| 49 | 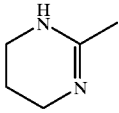 |  | CH | N | 2 | 2 | m = 0 |
| 50 | 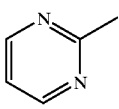 |  | CH | N | 2 | 2 | m = 0 |
| 51 | 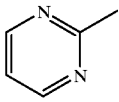 |  | CH | N | 2 | 2 | m = 0 |
| 52 | 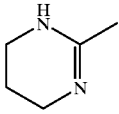 |  | CH | N | 2 | 2 | m = 0 |
| 53 | 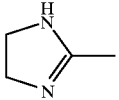 |  | CH | N | 2 | 2 | m = 0 |
| 54 | 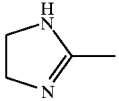 |  | CH | N | 2 | 2 | m = 0 |
| 55 | 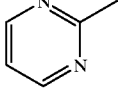 |  | CH | N | 2 | 2 | m = 0 |

-continued

| | | | | | | | |
|---|---|---|---|---|---|---|---|
| 56 | pyrimidine-CH₃ | >NH | CH | N | 2 | 2 | m = 0 |
| 57 | tetrahydropyrimidine-CH₃ | >NH | CH | N | 2 | 2 | m = 0 |
| 58 | pyrimidine-CH₃ | >NH | CH | N | 2 | 2 | m = 0 |
| 59 | pyrimidine-CH₃ | >NH | CH | N | 2 | 2 | m = 0 |
| 60 | tetrahydropyrimidine-CH₃ | >NH | CH | N | 2 | 2 | m = 0 |
| 61 | pyrimidine-CH₃ | >NH | CH | N | 2 | 2 | m = 0 |
| 62 | pyrimidine-CH₃ | >NH | CH | N | 2 | 2 | m = 0 |
| 63 | tetrahydropyrimidine-CH₃ | >NH | CH | N | 2 | 2 | m = 0 |
| 64 | tetrahydropyrimidine-CH₃ | >N—Bn* | CH | N | 2 | 2 | m = 0 |
| 65 | tetrahydropyrimidine-CH₃ | >N—Bn* | CH | N | 2 | 2 | m = 0 |
| 66 | tetrahydropyrimidine-CH₃ | >N—Bn* | CH | N | 2 | 2 | m = 0 |
| 67 | tetrahydropyrimidine-CH₃ | >NH | CH | N | 2 | 2 | m = 0 |

-continued
| | | | | | | | |
|---|---|---|---|---|---|---|---|
| 68 | 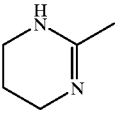 | 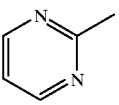 | CH | N | 2 | 2 | m = 0 |
| 69 | 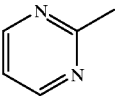 | >NH | CH | N | 2 | 2 | m = 0 |
| 70 | 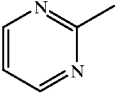 | >NH | CH | N | 2 | 2 | m = 0 |
| 71 | 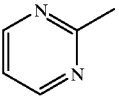 | >NH | CH | N | 2 | 2 | m = 0 |
| 72 | 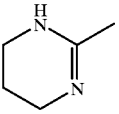 | >NH | CH | N | 2 | 2 | m = 0 |
| 73 | 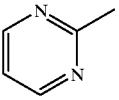 | >NH | CH | N | 2 | 2 | m = 0 |
| 74 | 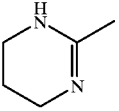 | >NH | CH | N | 2 | 2 | m = 0 |
| 75 | 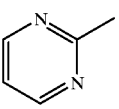 | >NH | CH | N | 2 | 2 | m = 0 |
| 76 | 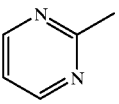 | >NH | CH | N | 2 | 2 | m = 0 |
| 77 | 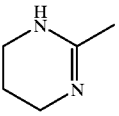 | >NH | CH | N | 2 | 2 | m = 0 |
| 78 | 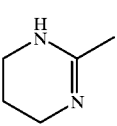 | >NH | CH | N | 2 | 2 | m = 0 |
| 79 | 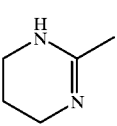 | >N—Bn* | CH | N | 2 | 2 | m = 0 |

-continued

| | | | | | | | |
|---|---|---|---|---|---|---|---|
| 80 | 2-methyl-1,4,5,6-tetrahydropyrimidine | >NH | CH | N | 2 | 2 | m = 0 |
| 81 | 2-methylpyrimidine | >NH | CH | N | 2 | 2 | m = 0 |
| 82 | 2-methylpyrimidine | >NH | CH | N | 2 | 2 | m = 0 |
| 83 | 2-methylpyrimidine | >NH | CH | N | 2 | 2 | m = 0 |
| 84 | 2-methylpyrimidine | >NH | CH | N | 2 | 2 | m = 0 |
| 85 | 2-methyl-1,4,5,6-tetrahydropyrimidine | >NH | CH | N | 2 | 2 | m = 0 |
| 86 | 2-methylpyrimidine | >NH | CH | N | 2 | 2 | m = 0 |
| 87 | 2-methylpyrimidine | >NH | CH | N | 2 | 2 | m = 0 |
| 88 | 2-methyl-1,4,5,6-tetrahydropyrimidine | >NH | CH | N | 2 | 2 | m = 0 |
| 89 | 2-methylbenzimidazole | >CH$_2$ | H | N | 2 | 2 | m = 0 |
| 90 | 2-methylbenzimidazole | >CH$_2$ | H | N | 2 | 2 | m = 0 |
| 91 | 2-methylpyrimidine | >NH | CH | N | 2 | 2 | m = 0 |

-continued
| | | | | | | | |
|---|---|---|---|---|---|---|---|
| 92 | 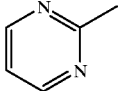 |  | CH | N | 2 | 2 | m = 0 |
| 93 | 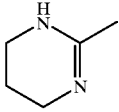 |  | CH | N | 2 | 2 | m = 0 |
| 94 | 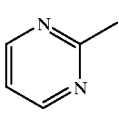 |  | CH | N | 2 | 2 | m = 0 |
| 95 | 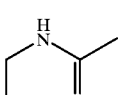 |  | CH | N | 2 | 2 | m = 0 |
| 96 | 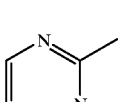 |  | CH | N | 2 | 2 | m = 0 |
| 97 | 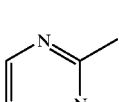 |  | CH | N | 2 | 2 | m = 0 |
| 98 | 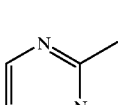 |  | CH | N | 2 | 2 | m = 0 |
| 99 | 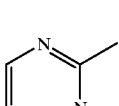 |  | CH | N | 2 | 2 | m = 0 |
| 100 | 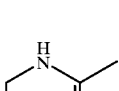 |  | CH | N | 2 | 2 | m = 0 |
| 101 | 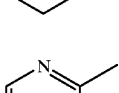 |  | CH | N | 2 | 2 | m = 0 |
| 102 | 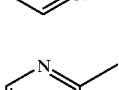 |  | CH | N | 2 | 2 | m = 0 |
| 103 | 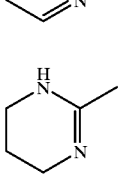 |  | CH | N | 2 | 2 | m = 0 |

-continued

| | | | | | | |
|---|---|---|---|---|---|---|
| 104 | 2-methylpyrimidine | >NH | CH | N | 2 2 | m = 0 |
| 105 | 2-methylpyrimidine | >NH | CH | N | 2 2 | m = 0 |

| | R$^8$ | Q | R$^9$ | R$^{10}$ | r | R$^{11}$ | R$^{12}$ |
|---|---|---|---|---|---|---|---|
| 1 | n = 0 | >C=O | H | H | 1 | —NHSO$_2$Ph | t-Bu |
| 2 | n = 0 | >C=O | H | H | 1 | —NHSO$_2$Ph | H |
| 3 | n = 0 | >C=O | H | H | 1 | —NHSO$_2$Ph | H |
| 4 | n = 0 | >C=O | H | H | 1 | —NHSO$_2$Ph | t-Bu |
| 5 | n = 0 | >C=O | H | H | 1 | —NHSO$_2$Ph | H |
| 6 | n = 0 | >C=O | H | H | 1 | —NHSO$_2$Ph | H |
| 7 | n = 0 | >C=O | H | H | 1 | —NHSO$_2$Ph | t-Bu |
| 8 | n = 0 | >C=O | H | H | 1 | —NHSO$_2$Ph | H |
| 9 | n = 0 | >C=O | H | H | 1 | —NHSO$_2$Ph | t-Bu |
| 10 | n = 0 | >C=O | H | H | 1 | —NHSO$_2$Ph | H |
| 11 | n = 0 | >C=O | H | —C≡CH | 1 | H | Et |
| 12 | n = 0 | >C=O | H | —C≡CH | 1 | H | H |
| 13 | n = 0 | >C=O | H | H | 1 | —NHCO$_2$CH$_2$Ph | t-Bu |
| 14 | n = 0 | >C=O | H | H | 1 | —NHCO$_2$CH$_2$Ph | H |
| 15 | n = 0 | >C=O | H | H | 1 | —NH$_2$ | H |
| 16 | n = 0 | >C=O | H | H | 1 | —NHCO$_2$CH$_2$Ph | H |

-continued

| | | | | | | | |
|---|---|---|---|---|---|---|---|
| 17 | n = 0 | 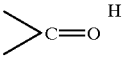 | H | H | 1 | —NHSO₂nBu | H |
| 18 | n = 0 | 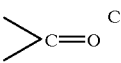 | Cyclopropylmethyl | H | 1 | —NHSO₂Ph | t-Bu |
| 19 | n = 0 | 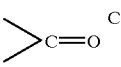 | Cyclopropylmethyl | H | 1 | —NHSO₂Ph | H |
| 20 | n = 0 | 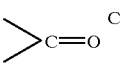 | Cyclopropylmethyl | H | 1 | —NHSO₂Ph | H |
| 21 | n = 0 | 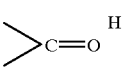 | H | H | 1 | —NHSO₂Ph | t-Bu |
| 22 | n = 0 | 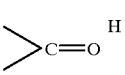 | H | H | 1 | —NHSO₂Ph | H |
| 23 | n = 0 | 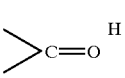 | H | H | 1 | —NHCO₂CH₂Ph | t-Bu |
| 24 | n = 0 | 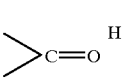 | H | H | 1 | —NHCO₂CH₂Ph | H |
| 25 | n = 0 | 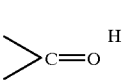 | H | H | 1 | —NHCO₂CH₂Ph | t-Bu |
| 26 | n = 0 | 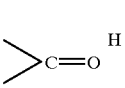 | H | H | 1 | —NH₂ | t-Bu |
| 27 | n = 0 | 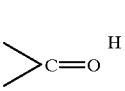 | H | H | 1 | —NHSO₂nBu | t-Bu |
| 28 | n = 0 |  | H | H | 1 | —NHSO₂nBu | H |
| 29 | n = 0 |  | H | H | 1 | —NH₂ | H |
| 30 | n = 0 |  | H | H | 1 | —NHSO₂Ph* (2,4,6-Me) | t-Bu |
| 31 | n = 0 |  | H | H | 1 | —NHSO₂Ph* (2,4,6-Me) | H |
| 32 | n = 0 |  | H | H | 1 | —NHSO₂Ph* (4-F) | t-Bu |
| 33 | n = 0 |  | H | H | 1 | —NHSO₂Ph* (4-F) | H |
| 34 | n = 0 | 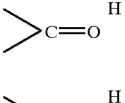 | H | H | 1 | —NHSO₂Ph* (4-NO₂) | t-Bu |
| 35 | n = 0 | 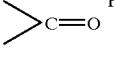 | H | H | 1 | —NHSO₂Ph* (4-NO₂) | H |

-continued

| 36 | n = 0 | >C=O H | H | 1 | —NHSO₂Ph* (4-NH₂) | H |
| 37 | n = 0 | >C=O H | H | 1 | —NHSO₂Ph | t-Bu |
| 38 | n = 0 | >C=O H | H | 1 | —NHSO₂Ph | H |
| 39 | n = 0 | >C=O H | H | 1 | —NHSO₂Ph | t-Bu |
| 40 | n = 0 | >C=O H | H | 1 | —NHSO₂Ph | H |
| 41 | n = 0 | >C=O H | H | 1 | —NHSO₂Ph | t-Bu |
| 42 | n = 0 | >C=O H | H | 1 | —NHSO₂Ph | H |
| 43 | n = 0 | >C=O H | H | 1 | —NHSO₂Ph | t-Bu |
| 44 | n = 0 | >C=O H | H | 1 | —NHSO₂Ph | H |
| 45 | n = 0 | >C=O H | H | 1 | —NHSO₂Ph | H |
| 46 | n = 0 | >CH₂ H | H | 1 | —NHSO₂Ph | t-Bu |
| 47 | n = 0 | >CH₂ H | H | 1 | —NHSO₂Ph | H |
| 48 | n = 0 | >CH₂ H | H | 1 | —NHSO₂Ph | H |
| 49 | n = 0 | >CH₂ Bn | H | 1 | —NHSO₂Ph | H |
| 50 | n = 1; 3-F | >C=O H | H | 1 | —NHSO₂Ph | t-Bu |
| 51 | n = 1; 3-F | >C=O H | H | 1 | —NHSO₂Ph | H |
| 52 | n = 1; 3-F | >C=O H | H | 1 | —NHSO₂Ph | H |
| 53 | n = 1; 3-F | >C=O H | H | 1 | —NHSO₂Ph | t-Bu |
| 54 | n = 1; 3-F | >C=O H | H | 1 | —NHSO₂Ph | H |

-continued

| | | | | | | | |
|---|---|---|---|---|---|---|---|
| 55 | n = 2; 2,3-F | >C=O H | H | 1 | —NHSO₂Ph | t-Bu | |
| 56 | n = 2; 2,3-F | >C=O H | H | 1 | —NHSO₂Ph | H | |
| 57 | n = 2; 2,3-F | >C=O H | H | 1 | —NHSO₂Ph | H | |
| 58 | n = 1; 3-Cl | >C=O H | H | 1 | —NHSO₂Ph | t-Bu | |
| 59 | n = 1; 3-Cl | >C=O H | H | 1 | —NHSO₂Ph | H | |
| 60 | n = 1; 3-Cl | >C=O H | H | 1 | —NHSO₂Ph | H | |
| 61 | n = 0 | >C=O H | H | 1 | —N(Me)(SO₂Ph) | t-Bu | |
| 62 | n = 0 | >C=O H | H | 1 | —N(Me)(SO₂Ph) | H | |
| 63 | n = 0 | >C=O H | H | 1 | —N(Me)(SO₂Ph) | H | |
| 64 | n = 1; 3-F | >C=O H | H | 1 | —NHCO₂CH₂Ph | t-Bu | |
| 65 | n = 1; 3-F | >C=O H | H | 1 | —NH₂ | t-Bu | |
| 66 | n = 1; 3-F | >C=O H | H | 1 | —NHSO₂Ph* (4-NO₂) | t-Bu | |
| 67 | n = 1; 3-F | >C=O H | H | 1 | —NHSO₂Ph* (4-NO₂) | H | |
| 68 | n = 1; 3-F | >C=O H | H | 1 | —NHSO₂Ph* (4-NH₂) | H | |
| 69 | n = 1; 3-F | >C=O H | H | 1 | —NHCO₂CH₂Ph | t-Bu | |
| 70 | n = 1; 3-F | >C=O H | H | 1 | —NH₂ | t-Bu | |
| 71 | n = 1; 3-F | >C=O H | H | 1 | —NHSO₂Ph* (4-MeO) | t-Bu | |
| 72 | n = 1; 3-F | >C=O H | H | 1 | —NHSO₂Ph* (4-MeO) | H | |
| 73 | n = 1; 3-F | >C=O H | H | 1 | —NHSO₂Ph* (4-MeO) | H | |

-continued

| | | | | | | | |
|---|---|---|---|---|---|---|---|
| 74 | n = 1; 3-F | >C=O H | H | 1 | —NHSO$_2$Ph* (4-OH) | H | |
| 75 | n = 1; 3-F | >C=O H | H | 1 | —NHSO$_2$Ph* (4-OH) | H | |
| 76 | n = 1; 3-F | >C=O H | H | 1 | —NHSO$_2$Ph* (4-COOH) | t-Bu | |
| 77 | n = 1; 3-F | >C=O H | H | 1 | —NHSO$_2$Ph* (4-COOH) | H | |
| 78 | n = 1; 3-F | >C=O H | H | 1 | —NHSO$_2$Ph* (4-COOH) | H | |
| 79 | n = 1; 3-F | >C=O H | H | 1 | —NHAc | t-Bu | |
| 80 | n = 1; 3-F | >C=O H | H | 1 | —NHAc | H | |
| 81 | n = 2; 2,3-F | >C=O H | H | 1 | —NHCO$_2$CH$_2$Ph | t-Bu | |
| 82 | n = 2; 2,3-F | >C=O H | H | 1 | —NH$_2$ | t-Bu | |
| 83 | n = 2; 2,3-F | >C=O H | H | 1 | —NHSO$_2$Ph* (4-MeO) | t-Bu | |
| 84 | n = 2; 2,3-F | >C=O H | H | 1 | —NHSO$_2$Ph* (4-OH) | H | |
| 85 | n = 2; 2,3-F | >C=O H | H | 1 | —NHSO$_2$Ph* (4-OH) | H | |
| 86 | n = 2; 2,3-F | >C=O H | H | 1 | —NHSO$_2$Ph* (4-COOH) | t-Bu | |
| 87 | n = 2; 2,3-F | >C=O H | H | 1 | —NHSO$_2$Ph* (4-COOH) | H | |
| 88 | n = 2; 2,3-F | >C=O H | H | 1 | —NHSO$_2$Ph* (4-COOH) | H | |
| 89 | n = 0 | >C=O H | H | 1 | —NHSO$_2$Ph | t-Bu | |
| 90 | n = 0 | >C=O H | H | 1 | —NHSO$_2$Ph | H | |
| 91 | n = 1; 3-MeO | >C=O H | H | 1 | —NHSO$_2$Ph | t-Bu | |
| 92 | n = 1; 3-MeO | >C=O H | H | 1 | —NHSO$_2$Ph | H | |

| No | n | | | | | |
|---|---|---|---|---|---|---|
| 93 | n = 1; 3-MeO | >C=O | H | H | 1 | —NHSO$_2$Ph | H |
| 94 | n = 1; 3-OH | >C=O | H | H | 1 | —NHSO$_2$Ph | H |
| 95 | n = 1; 3-OH | >C=O | H | H | 1 | —NHSO$_2$Ph | H |
| 96 | n = 1; 3-MeO | >C=O | H | H | 1 | —NHCO$_2$CH$_2$Ph | t-Bu |
| 97 | n = 1; 3-MeO | >C=O | H | H | 1 | —NH$_2$ | t-Bu |
| 98 | n = 1; 3-MeO | >C=O | H | H | 1 | —NHSO$_2$Ph* (4-MeO) | t-Bu |
| 99 | n = 1; 3-OH | >C=O | H | H | 1 | —NHSO$_2$Ph* (4-OH) | H |
| 100 | n = 1; 3-OH | >C=O | H | H | 1 | —NHSO$_2$Ph* (4-OH) | H |
| 101 | n = 1; 3-MeO | >C=O | H | H | 1 | —NHSO$_2$Ph* (4-COOH) | t-Bu |
| 102 | n = 1; 3-MeO | >C=O | H | H | 1 | —NHSO$_2$Ph* (4-COOH) | H |
| 103 | n = 1; 3-MeO | >C=O | H | H | 1 | —NHSO$_2$Ph* (4-COOH) | H |
| 104 | n = 0 | >C=O | H | H | 1 | —NH$_2$ | t-Bu |
| 105 | n = 0 | >C=O | H | H | 1 | —NHSO$_2$Ph | Me |

Me: methyl, Et: ethyl, Bu: bytyl, Ac: acetyl, Meo: methoxy, Ph: phenyl, Ph*: substituted phenyl, Bn: benzyl, Bn*: 4-methoxybenzyl

What is claimed is:

1. A compound represented by formula (I) or a pharmaceutically acceptable salt or solvate thereof:

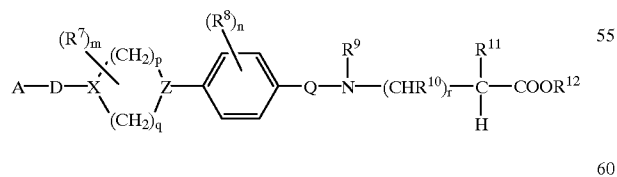

(I)

wherein

A represents a saturated or unsaturated five- to six-membered heterocyclic group represented by the following formula:

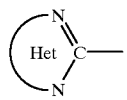

wherein two ring member atoms are nitrogen atoms and the remaining ring member atoms are carbon atoms, which heterocyclic group is optionally condensed with other saturated or unsaturated five- to seven-membered carbocyclic ring or heterocyclic ring to form a nine- or ten-membered bicyclic group wherein two or three member atoms are nitrogen atoms and the remaining member atoms are carbon atoms, which heterocyclic group and bicyclic group are optionally substituted by $C_{1-6}$ alkyl, $C_{3-6}$ cycloalkyl, $C_{4-6}$ cycloalkyl-alkyl, amino, $C_{1-6}$ alkoxy, $C_{1-6}$ alkoxycarbonyl, or aralkyl and the $C_{1-6}$ alkyl, $C_{3-6}$ cycloalkyl, $C_{4-6}$ cycloalkyl-alkyl, amino, $C_{1-6}$ alkoxy, $C_{1-6}$ alkoxycarbonyl, and aralkyl groups are optionally substituted by $C_{1-6}$ alkyl, $C_{3-6}$ cycloalkyl, $C_{4-6}$ cycloalkyl-alkyl, or $C_{1-6}$ alkoxy, or a group represented by formula

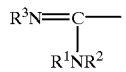

wherein
- $R^1$, $R^2$, and $R^3$ represent a hydrogen atom;
- D represents $>NR^4$ wherein $R^4$ represents a hydrogen atom or $C_{1-6}$ alkyl, $C_{3-6}$ cycloalkyl, or $C_{4-6}$ cycloalkyl-alkyl, which $C_{1-6}$ alkyl, $C_{3-6}$ cycloalkyl, and $C_{4-6}$ cycloalkyl-alkyl are optionally substituted by phenyl optionally substituted by $C_{1-6}$ alkoxy;
- X represents CH; Z represents N;
- $R^8$ represents $C_{1-6}$ alkoxy, a halogen atom, or hydroxyl, which $C_{1-6}$ alkoxy is optionally substituted by a halogen atom;
- Q represents $>C=O$ or $>CH_2$;
- $R^9$ represents a hydrogen atom, $C_{1-6}$ alkyl, $C_{3-6}$ cycloalkyl, $C_{4-6}$ cycloalkyl-alkyl, $C_{2-6}$ alkenyl, $C_{2-6}$ alkynyl, or aralkyl, which $C_{1-6}$ alkyl, $C_{3-6}$ cycloalkyl, $C_{4-6}$ cycloalkyl-alkyl, $C_{2-6}$ alkenyl, $C_{2-6}$ alkynyl, and aralkyl are optionally substituted by a halogen atom, $C_{1-6}$ alkoxy, amino, or hydroxyl;
- $R^{10}$ represents a hydrogen atom, $C_{1-6}$ alkyl, $C_{3-6}$ cycloalkyl, $C_{4-6}$ cycloalkyl-alkyl, $C_{2-6}$ alkenyl, $C_{2-6}$ alkynyl, aralkyl, or amino, which $C_{1-6}$ alkyl, $C_{3-6}$ cycloalkyl, $C_{4-6}$ cycloalkyl-alkyl, $C_{2-6}$ alkenyl, $C_{2-6}$ alkynyl, and aralkyl are optionally substituted by a halogen atom, $C_{1-6}$ alkoxy, amino, or hydroxyl and which amino is optionally substituted by $C_{1-6}$ alkyl, $C_{3-6}$ cycloalkyl, $C_{4-6}$ cycloalkyl-alkyl, $C_{1-6}$ alkoxycarbonyl, benzenesulfonyl in which the phenyl portion is optionally substituted by $C_{1-6}$ alkyl, $C_{3-6}$ cycloalkyl, $C_{4-6}$ cycloalkyl-alkyl, or benzyloxycarbonyl in which the phenyl portion is optionally substituted by $C_{1-6}$ alkyl, $C_{3-6}$ cycloalkyl, or $C_{4-6}$ cycloalkyl-alkyl;
- $R^{11}$ represents a hydrogen atom, $C_{1-6}$ alkyl, $C_{3-6}$ cycloalkyl, $C_{4-6}$ cycloalkyl-alkyl, $C_{2-6}$ alkenyl, $C_{2-6}$ alkynyl, aralkyl, or amino, which $C_{1-6}$ alkyl, $C_{3-6}$ cycloalkyl, $C_{4-6}$ cycloalkyl-alkyl, $C_{2-6}$ alkenyl, $C_{2-6}$ alkynyl, and aralkyl are optionally substituted by a halogen atom, $C_{1-6}$ alkoxy, amino, or hydroxyl and which amino is optionally substituted by carboxyl, sulfonyl, $C_{1-6}$ alkyl, $C_{3-6}$ cycloalkyl, $C_{4-6}$ cycloalkyl-alkyl, $C_{1-6}$ alkylcarbonyl, $C_{1-6}$ alkoxycarbonyl, $C_{1-6}$ alkylsulfonyl, $-C(=O)-O-(CH_2)_u-R^{14}$ wherein u is an integer of 0 to 4 and $R^{14}$ represents a saturated or unsaturated five- to seven-membered carbocyclic group, which carbocyclic group is optionally substituted by $C_{1-6}$ alkyl, $C_{3-6}$ cycloalkyl, $C_{4-6}$ cycloalkyl-alkyl, $C_{1-6}$ alkoxy, phenyl optionally condensed with the carbocyclic group, carboxyl, hydroxyl, nitro, amino, $C_{1-6}$ alkylamino, or a halogen atom, or $-S(=O)_2-(CH_2)_v-R^{14}$ wherein v is an integer of 0 to 4 and $R^{14}$ is as defined above;
- $R^{12}$ represents a hydrogen atom or $C_{1-6}$ alkyl, $C_{3-6}$ cycloalkyl, or $C_{4-6}$ cycloalkyl-alkyl;
- m is an integer of 0;
- n is an integer of 0 to 4;
- p is 2;
- q is 1 or 2; and
- r is 0 or 1.

2. The compound according to claim 1, wherein A represents a group of formula

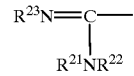

wherein
- $R^{21}$, $R^{22}$, and $R^{23}$ represent a hydrogen atom, or
- $R^{21}$ and $R^{23}$ may together form
  - group $-(CH_2)_3-$,
  - group $-CHR^{24}CH_2CH_2-$ wherein $R^{24}$ represents $C_{1-6}$ alkyl $C_{3-6}$ cycloalkyl, $C_{4-6}$ cycloalkyl-alkyl, or amino, which amino is optionally substituted by $C_{1-6}$ alkyl, $C_{3-6}$ cycloalkyl, $C_{4-6}$ cycloalkyl-alkyl, $C_{1-6}$ alkoxycarbonyl, aralkyl, or aralkyloxycarbonyl,
  - group $-CH_2CHR^{24}CH_2-$ wherein $R^{24}$ is as defined above,
  - group $-CH_2CH_2-$,
  - group $-CHR^{24}CH_2-$ wherein $R^{24}$ is as defined above,
  - group $-CR^{25}=CR^{26}-$ wherein $R^{25}$ and $R^{26}$, which may be the same or different, represent a hydrogen atom or $C_{1-6}$ alkyl, $C_{3-6}$ cycloalkyl, or $C_{4-6}$ cycloalkyl-alkyl, or $R^{25}$ and $R^{26}$ may together form $-CH=CH-CH=CH-$, $-CR^{24}=CH-CH=CH-$ wherein $R^{24}$ is as defined above, $-CH=CR^{24}-CH=CH-$ wherein $R^{24}$ is as defined above, $-N=CH-CH=CH-$, or $-CH=N-CH=CH-$, or
- $R^{21}$ and $R^{23}$ may together form $=CH-CH=CH-$, and $R^{22}$ may represent a single bond between $R^{21}$ and the nitrogen atom attached to $R^{21}$.

3. The compound according to claim 1, wherein D represents $>NH$.

4. The compound according to claim 1, wherein n represents an integer of 0 to 2.

5. The compound according to claim 2, wherein A represents a group of formula

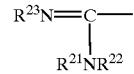

wherein
- $R^2$, $R^{22}$, and $R^{23}$ are as defined in claim 6;
- D represents $>NH$;
- X represents CH;
- Z represents N;
- Q represents $>C=O$ or $>CH_2$;
- $R^9$ represents a hydrogen atom, $C_{1-6}$ alkyl, $C_{3-6}$ cycloalkyl, $C_{4-6}$ cycloalkyl-alkyl, or aralkyl, which $C_{1-6}$ alkyl and aralkyl are optionally substituted by a halogen atom, $C_{1-6}$ alkoxy, amino, or hydroxyl;
- $R^{10}$ represents a hydrogen atom or $C_{2-6}$ alkynyl;
- $R^{11}$ represents a hydrogen atom or amino, which amino is optionally substituted by $C_{1-6}$ alkyl; $C_{3-6}$ cycloalkyl; $C_{4-6}$ cycloalkyl-alkyl; acetyl; $C_{1-6}$ alkoxycarbonyl; $C_{1-6}$ alkylsulfonyl; benzyloxycarbonyl in which the phenyl portion is optionally substituted by $C_{1-6}$ alkyl, $C_{3-6}$ cycloalkyl, $C_{4-6}$ cycloalkyl-alkyl, $C_{1-6}$ alkoxy, carboxyl, hydroxyl, nitro, amino, or a halogen atom; or benzenesulfonyl in which the phenyl portion is optionally substituted by $C_{1-6}$ alkyl, $C_{3-6}$ cycloalkyl, $C_{4-6}$ cycloalkyl-alkyl, $C_{1-6}$ alkoxy, carboxyl, hydroxyl, nitro, amino, or a halogen atom;

n represents an integer of 0 to 2;
p is 2;
q is 1 or 2; and
r is 1.

6. A compound selected from the group consisting of the following compounds, or a pharmaceutically acceptable salt or solvate thereof:

(1) t-butyl (2S)-benzenesulfonylamino-3-[4-{4-(pyrimidin-2-ylamino)piperidin-1-yl}benzoylamino]-propionate;
(2) (2S)-benzenesulfonylamino-3-[4-{4-(pyrimidin-2-ylamino)piperidin-1-yl}benzoylamino]propionic acid;
(3) (2S)-benzenesulfonylamino-3-[4-{4-(1,4,5,6-tetrahydropyrimidin-2-ylamino)piperidin-1-yl}benzoylamino]propionic acid;
(4) t-butyl (2S)-benzenesulfonylamino-3-[4-{(3S)-(pyrimidin-2-ylamino)pyrrolidin-1-yl}benzoylamino]-propionate;
(5) (2S)-benzenesulfonylamino-3-[4-{(3S)-(pyrimidin-2-ylamino)pyrrolidin-1-yl}benzoylamino]-propionic acid;
(6) (2S)-benzenesulfonylamino-3-[4-{(3S)-(1,4,5,6-tetrahydropyrimidin-2-ylamino)pyrrolidin-1-yl}-benzoylamino]propionic acid;
(7) t-butyl (2S)-benzenesulfonylamino-3-[4-{(3R)-(pyrimidin-2-ylamino)pyrrolidin-1-yl}benzoyiamino]-propionate;
(8) (2S)-benzenesulfonylamino-3-[4-{(3R)-(pyrimidin-2-ylamino)pyrrolidin-1-yl}benzoylamino]-propionic acid;
(9) t-butyl (2S)-benzenesulfonylamino-3-[4-{4-(1H-benzimidazol-2-ylamino)piperidin-1-yl}benzoylamino]-propionate;
(10) (2S)-benzenesulfonylamino-3-[4-{4-(1H-benzimidazol-2-ylamino)piperidin-1-yl}benzoylamino]-propionic acid;
(11) ethyl (3S)-[4-{4-(pyrimidin-2-ylamino)-piperidin-1-yl}benzoylamino]pent-4-ynate;
(12) (3S)-[4-{4-(pyrimidin-2-ylamino)piperidin-1-yl}benzoylamino]pent-4-ynic acid
(13) t-butyl (2S)-(benzyloxycarbonyl)amino-3-[4-{4-(pyrimidin-2-ylamino)piperidin-1-yl}benzoylamino]-propionate;
(14) (2S)-(benzyloxycarbonyl)amino-3-[4-{4-(pyrimidin-2-ylamino)piperidin-1-yl}benzoylamino]-propionic acid;
(15) (2S)-amino-3-[4-{4-(1,4,5,6-tetrahydro-pyrimidin-2-ylamino)piperidin-1-yl}benzoylamino]-propionic acid;
(16) (2S)-(benzyloxycarbonyl)amino-3-[4-{4-(1,4,5,6-tetrahydropyrimidin-2-ylamino)piperidin-1-yl}-benzoylamino]propionic acid;
(17) (2S)-butane-1-sulfonylamino-3-[4-{4-(1,4,5,6-tetrahydropyrimidin-2-ylamino)piperidin-1-yl}benzoylamino]propionic acid;
(18) t-butyl (2S)-benzenesulfonylamino-3-[N-(cyclopropylmethyl)-N-[4-{4-(pyrimidin-2-ylamino)-piperidin-1-yl}benzoyl]amino]propionate;
(19) (2S)-benzenesulfonylamino-3-[N-(cyclopropylmethyl)-N-[4-{4-(pyrimidin-2-ylamino)piperidin-1-yl}-benzoyl]amino]propionic acid;
(20) (2S)-benzenesulfonylamino-3-[N-(cyclopropylmethyl)-N-[4-{4-(1,4,5,6-tetrahydropyrimidin-2-ylamino)-piperidin-1-yl}benzoyl]amino]propionic acid;
(21) t-butyl (2S)-benzenesulfonylamino-3-{4-(4-guanidinopiperidin-1-yl)benzoylamino}propionate;
(22) (2S)-benzenesulfonylamino-3-{4-(4-guanidino-piperidin-1-yl)benzoylamino}propionic acid;
(23) t-butyl 3-[4-{4-(1H-benzimidazol-2-ylamino)-piperidin-1-yl}benzoylamino]-(2S)-{(benzyloxycarbonyl)-amino}propionate;
(24) 3-[4-{4-(1H-benzimidazol-2-ylamino)-piperidin-1-yl}benzoylamino]-(2S)-{(benzyloxycarbonyl)-amino}propionic acid;
(25) t-butyl (2S)-(benzyloxycarbonyl)amino-3-[4-[4-{(1-t-butoxycarbonyl-1H-benzimidazol-2-yl)amino}-piperidin-1-yl]benzoylamino]propionate;
(26) t-butyl (2S)-amino-3-[4-[4-{(1-t-butoxy-carbonyl-1H-benzimidazol-2-yl)amino}piperidin-1-yl]-benzoylamino]propionate;
(27) t-butyl (2S)-(butane-1-sulfonylamino)-3-[4-[4-{(1-t-butoxycarbonyl-1H-benzimidazol-2-yl)amino}-piperidin-1-yl]benzoylamino]propionate;
(28) (2S)-butane-1-sulfonylamino-3-[4-{4-(1H-benzimidazol-2-ylamino)piperidin-1-yl}benzoylamino]-propionic acid;
(29) (2S)-amino-3-[4-{4-(1H-benzimidazol-2-ylamino)piperidin-1-yl}benzoylamino]propionic acid;
(30) t-butyl 3-[4-[4-{(1-t-butoxycarbonyl-1H-benzimidazol-2-yl)amino}piperidin-1-yl]benzoylamino]-(2S)-{(2,4,6-trimethylbenzenesulfonyl)amino}propionate;
(31) 3-[4-{4-(1H-benzimidazol-2-ylamino)piperidin-1-yl}benzoylamino]-(2S)-{(2,4,6-trimethylbenzene-sulfonyl)amino}propionic acid;
(32) t-butyl 3-[4-[4-{(1-t-butoxycarbonyl-1H-benzimidazol-2-yl)amino}piperidin-1-yl]benzoylamino]-(2S)-{(4-fluorobenzenesulfonyl)amino}propionate;
(33) 3-[4-{4-(1H-benzimidazol-2-ylamino)piperidin-1-yl}benzoylamino]-(2S)-{(4-fluorobenzenesulfonyl)-amino}propionic acid;
(34) t-butyl 3-[4-[4-{(1-t-butoxycarbonyl-1H-benzimidazol-2-yl)amino}piperidin-1-yl]benzoylamino]-(2S)-{(4-nitrobenzenesulfonyl)amino}propionate;
(35) 3-[4-{4-(1H-benzimidazol-2-ylamino)piperidin-1-yl}benzoylamino]-(2S)-{(4-nitrobenzenesulfonyl)amino}-propionic acid;
(36) (2S)-(4-aminobenzenesulfonyl)amino-3-[4-{4-(1H-benzimidazol-2-ylamino)piperidin-1-yl}benzoylamino]-propionic acid;
(37) t-butyl (2S)-benzenesulfonylamino-3-[4-[4-{(1H-imidazo[4,5-b]pyridin-2-yl)amino}piperidin-1-yl]benzoylamino]propionate;
(38) (2S)-benzenesulfonylamino-3-[4-[4-{(1H-imidazo[4,5-b]pyridin-2-yl)amino}piperidin-1-yl]benzoyl-amino]propionic acid;
(39) t-butyl (2S)-benzenesulfonylamino-3-[4-[4-[{4,5-dihydro-1-(4-methoxybenzyl)-1H-imidazol-2-yl}-amino]piperidin-1-yl]benzoylamino]propionate;
(40) (2S)-benzenesulfonylamino-3-[4-{4-(4,5-dihydro-1H-imidazol-2-ylamino)piperidin-1-yl}benzoyl-amino]propionic acid;
(41) t-butyl (2S)-benzenesulfonylamino-3-[4-{4-(4,5,6,7-tetrahydro-1H-[1,3]diazepin-2-ylamino)-piperidin-1-yl}benzoylamino]propionate;
(42) (2S)-benzenesulfonylamino-3-[4-{(4-{4,5,6,7-tetrahydro-1H-[1,3]diazepin-2-ylamino)piperidin-1-yl}-benzoylamino]propionic acid;
(43) t-butyl (2S)-benzenesulfonylamino-3-[4-[4-[{N-methyl-N-(pyrimidin-2-yl)}amino]piperidin-1-yl]-benzoylamino]propionate;
(44) (2S)-benzenesulfonylamino-3-[4-[4-[{N-methyl-N-(pyrimidin-2-yl)}amino]piperidin-1-yl]benzoylamino]-propionic acid;
(45) (2S)-benzenesulfonylamino-3-[4-[4-[{N-methyl-N-(1,4,5,6-tetrahydropyrimidin-2-yl)}amino]piperidin-1-yl]benzoylamino]propionic acid

(46) t-butyl (2S)-benzenesulfonylamino-3-[4-{4-(pyrimidin-2-ylamino)piperidin-1-yl}benzylamino]propionate;
(47) (2S)-benzenesulfonylamino-3-[4-{4-(pyrimidin-2-ylamino)piperidin-1-yl}benzylamino]propionic acid;
(48) (2S)-benzenesulfonylamino-3-[4-{4-(1,4,5,6-tetrahydropyrimidin-2-ylamino)piperidin-1-yl}benzylamino]propionic acid;
(49) (2S)-benzenesulfonylamino-3-[N-benzyl-N-[4-{4-(1,4,5,6-tetrahydropyrimidin-2-ylamino)piperidin-1-yl}benzyl]amino]propionic acid;
(50) t-butyl (2S)-benzenesulfonylamino-3-[3-fluoro-4-{4-(pyrimidin-2-ylamino)piperidin-1-yl}benzoyl-amino]propionate;
(51) (2S)-benzenesulfonylamino-3-[3-fluoro-4-{4-(pyrimidin-2-ylamino)piperidin-1-yl}benzoylamino]propionic acid;
(52) (2S)-benzenesulfonylamino-3-[3-fluoro-4-{4-(1,4,5,6-tetrahydropyrimidin-2-ylamino)piperidin-1-yl}benzoylamino]propionic acid;
(53) t-butyl (2S)-benzenesulfonylamino-3-[3-fluoro-4-{4-(4,5-dihydro-1H-imidazol-2-ylamino)-piperidin-1-yl}benzoylamino]propionate;
(54) (2S)-benzenesulfonylamino-3-[3-fluoro-4-{4-(4,5-dihydro-1H-imidazol-2-ylamino)piperidin-1-yl}-benzoylamino]propionic acid;
(55) t-butyl (2S)-benzenesulfonylamino-3-[2,3-difluoro-4-{4-(pyrimidin-2-ylamino)piperidin-1-yl}-benzoylamino]propionate;
(56) (2S)-benzenesulfonylamino-3-[2,3-difluoro-4-{4-(pyrimidin-2-ylamino)piperidin-1-yl}benzoylamino]propionic acid;
(57) (2S)-benzenesulfonylamino-3-[2,3-difluoro-4-{4-(1,4,5,6-tetrahydropyrimidin-2-ylamino)piperidin-1-yl}benzoylamino]propionic acid;
(58) t-butyl (2S)-benzenesulfonylamino-3-[3-chloro-4-{4-(pyrimidin-2-ylamino)piperidin-1-yl}benzoyl-amino]propionate;
(59) (2S)-benzenesulfonylamino-3-[3-chloro-4-{4-(pyrimidin-2-ylamino)piperidin-1-yl}benzoylamino]propionic acid;
(60) (2S)-benzenesulfonylamino-3-[3-chloro-4-{4-(1,4,5,6-tetrahydropyrimidin-2-ylamino)piperidin-1-yl}-benzoylamino]propionic acid;
(61) t-butyl 2-(N-benzenesulfonyl-N-methyl)-amino-3-[4-{4-(pyrimidin-2-ylamino)piperidin-1-yl}-benzoylamino]propionate;
(62) 2-(N-benzenesulfonyl-N-methyl)amino-3-[4-{4-(pyrimidin-2-ylamino)piperidin-1-yl}benzoylamino]propionic acid;
(63) 2-(N-benzenesulfonyl-N-methyl)amino-3-[4-{4-(1,4,5,6-tetrahydropyrimidin-2-ylamino)piperidin-1-yl}-benzoylamino]propionic acid;
(64) t-butyl (2S)-(benzyloxycarbonyl)amino-3-[3-fluoro-4-[{N-(1,4,5,6-tetrahydropyrimidin-2-yl)-N-(4-methoxybenzyl)}amino]piperidin-1-yl]benzoylamino]propionate;
(65) t-butyl (2S)-amino-3-[3-fluoro-4-[{N-(1,4,5,6-tetrahydropyrimidin-2-yl)-N-(4-methoxybenzyl)}-amino]piperidin-1-yl]benzoylamino]propionate;
(66) t-butyl 3-[3-fluoro-4-[4-[{N-(1,4,5,6-tetrahydropyrimidin-2-yl)-N-(4-methoxybenzyl)}amino]-piperidin-1-yl]benzoylamino]-(2S)-{(4-nitrobenzenesulfonyl)amino}propionate;
(67) 3-[3-fluoro-4-{4-(1,4,5,6-tetrahydro-pyrimidin-2-ylamino)piperidin-1-yl}benzoylamino]-(2S)-{(4-nitrobenzenesulfonyl)amino}propionic acid;
(68) (2S)-(4-aminobenzenesulfonyl)amino-3-[3-fluoro-4-{4-(1,4,5,6-tetrahydropyrimidin-2-ylamino)-piperidin-1-yl}benzoylamino]propionic acid;
(69) t-butyl (2S)-(benzyloxycarbonyl)amino-3-[3-fluoro-4-{4-(pyrimidin-2-ylamino)piperidin-1-yl}benzoyl-amino]propionate;
(70) t-butyl (2S)-amino-3-[3-fluoro-4-{4-(pyrimidin-2-ylamino)piperidin-1-yl}benzoylamino]-propionate;
(71) t-butyl 3-[3-fluoro-4-(pyrimidin-2-ylamino)pipenidin-1-yl}benzoylamino]-(2S)-{(4-methoxybenzenesulfonyl)amino}propionate;
(72) 3-[3-fluoro-4-{4-(pyrimidin-2-ylamino)-piperidin-1-yl}benzoylamino]-(2S)-{(4-methoxybenzene-sulfonyl)amino}propionic acid;
(73) 3-[3-fluoro-4-{4-(1,4,5,6-tetrahydro-pyrimidin-2-ylamino)piperidin-1-yl}benzoylamino]-(2S)-{(4-methoxybenzenesulfonyl)amino}propionic acid;
(74) 3-[3-fluoro-4-{4-(pyrimidin-2-ylamino)-piperidin-1-yl}benzoylamino]-(2S)-{(4-hydroxybenzene-sulfonyl)amino}propionic acid;
(75) 3-[3-fluoro-4-{4-(1,4,5,6-tetrahydro-pyrimidin-2-ylamino)piperidin-1-yl}benzoylamino]-(2S)-{(4-hydroxybenzenesulfonyl)amino}propionic acid;
(76) t-butyl (2S)-(4-carboxybenzenesulfonyl)-amino-3-[3-fluoro-4-{4-(pyrimidin-2-ylamino)piperidin-1-yl}benzoylamino]propionate;
(77) (2S)-(4-carboxybenzenesulfonyl)amino-3-[3-fluoro-4-{4-(pyrimidin-2-ylamino)piperidin-1-yl}benzoyl-amino]propionic acid;
(78) (2S)-(4-carboxybenzenesulfonyl)amino-3-[3-fluoro-4-{4-(1,4,5,6-tetrahydropyrimidin-2-ylamino)-piperidin-1-yl)}benzoylamino]propionic acid;
(79) t-butyl (2S)-acetamido-3-[3-fluoro-4-[4-[{N-(1,4,5,6-tetrahydropyrimidin-2-yl)-N-(4-methoxy-benzyl)}amino]piperidin-1-yl]benzoylamino]propionate;
(80) (2S)-acetamido-3-[3-fluoro-4-{4-(1,4,5,6-tetrahydropyrimidin-2-ylamino)piperidin-1-yl}benzoyl-amino]propionic acid;
(81) t-butyl (2S)-(benzyloxycarbonyl)amino-3-[2,3-difluoro-4-{4-(pyrimidin-2-ylamino)piperidin-1-yl}-benzoylamino]propionate;
(82) t-butyl (2S)-amino-3-[2,3-difluoro-4-{4-(pyrimidin-2-ylamino)piperidin-1-yl}benzoylamino]-propionate;
(83) t-butyl 3-[2,3-difluoro-4-{4-(pyrimidin-2-ylamino)piperidin-1-yl}benzoylamino]-(2S)-{(4-methoxy-benzenesulfonyl)amino}propionate;
(84) 3-[2,3-difluoro-4-{4-(pyrimidin-2-ylamino)-piperidin-1-yl}benzoylamino]-(2S)-{(4-hydroxybenzene-sulfonyl)amino}propionic acid;
(85) 3-[2,3-difluoro-4-{4-(1,4,5,6-tetrahydro-pyrimidin-2-ylamino)piperidin-1-yl}benzoylamino]-(2S)-{(4-hydroxybenzenesulfonyl)amino}propionic acid;
(86) t-butyl (2S)-(4-carboxybenzenesulfonyl)-amino-3-[2,3-difluoro-4-{4-(pyrimidin-2-ylamino)-piperidin-1-yl}benzoylamino]propionate;
(87) (2S)-(4-carboxybenzenesulfonyl)amino-3-[2,3-difluoro-4-{4-(pyrimidin-2-ylamino)piperidin-1-yl}-benzoylamino]propionic acid;
(88) (2S)-(4-carboxybenzenesulfonyl)amino-3-[2,3-difluoro-4-{4-(1,4,5,6-tetrahydropyrimidin-2-ylamino)-piperidin-1-yl}benzoylamino]propionic acid;
(91) t-butyl (2S)-benzenesulfonylamino-3-[3-methoxy-4-{4-(pyrimidin-2-ylamino)piperidin-1-yl}-benzoylamino]propionate;
(92) (2S)-benzenesulfonylamino-3-[3-methoxy-4-{4-(pyrimidin-2-ylamino)piperidin-1-yl}benzoylamino]propionic acid;

(93) (2S)-benzenesulfonylamino-3-[3-methoxy-4-{4-(1,4,5,6-tetrahydropyrimidin-2-ylamino)piperidin-1-yl}benzoylamino]propionic acid;
(94) (2S)-benzenesulfonylamino-3-[3-hydroxy-4-{4-(pyrimidin-2-ylamino)piperidin-1-yl}benzoylamino]-propionic acid;
(95) (2S)-benzenesulfonylamino-3-[3-hydroxy-4-{4-(1,4,5,6-tetrahydropyrimidin-2-ylamino)piperidin-1-yl}-benzoylamino]propionic acid;
(96) t-butyl (2S)-(benzyloxycarbonyl)amino-3-[3-methoxy-4-{4-(pyrimidin-2-ylamino)piperidin-1-yl}-benzoylamino]propionate;
(97) t-butyl (2S)-amino-3-[3-methoxy-4-{4-(pyrimidin-2-ylamino)piperidin-1-yl}benzoylamino]-propionate;
(98) t-butyl (2S)-(4-methoxybenzenesulfonyl)-amino-3-[3-methoxy-4-(4-(pyrimidin-2-ylamino)piperidin-1-yl}benzoylamino]propionate;
(99) (2S)-(4-hydroxybenzenesulfonyl)amino-3-[3-hydroxy-4-{4-(pyrimidin-2-ylamino)piperidin-1-yl}-benzoylamino]propionic acid;
(100) (2S)-(4-hydroxybenzenesulfonyl)amino-3-[3-hydroxy-4-{4-(1,4,5,6-tetrahydropyrimidin-2-ylamino)-piperidin-1-yl}benzoylamino]propionic acid;
(101) t-butyl (2S)-(4-carboxybenzenesulfonyl)-amino-3-[3-methoxy-4-{4-(pyrimidin-2-ylamino)piperidin-1-yl}benzoylamino]propionate;
(102) (2S)-(4-carboxybenzenesulfonyl)amino-3-[3-methoxy-4-{4-(pyrimidin-2-ylamino)piperidin-1-yl}-benzoylamino]propionic acid;
(103) (2S)-(4-carboxybenzenesulfonyl)amino-3-[3-methoxy-4-{4-(1,4,5,6-tetrahydropyrimidin-2-ylamino)-piperidin-1-yl}benzoylamino]propionic acid;
(104) t-butyl (2S)-amino-3-[4-{4-(pyrimidin-2-ylamino)piperidin-1-yl}benzoylamino]propionate; and
(105) methyl (2S)-benzenesulfonylamino-3-[4-{4-(pyrimidin-2-ylamino)piperidin-1-yl}benzoylamino]-propionate.

7. A pharmaceutical composition comprising as active ingredient the compound according to any one of claim 1, 2, 3, 4, 5 or 6 or a pharmaceutically acceptable salt or solvate thereof together with a pharmaceutically acceptable carrier angiogenesis-related diseases such as diabetic retinopathy, diabetic vascular complication, or vascular grafting; cerebrovascular diseases such as cerebral infarction; cancers such as solid tumors or metastasis thereof; immunological diseases such as arthritis, particularly rheumatic arthritis; and osteopathy such as osteoporosis, hypercalcemia, periodontitis, hyperparathyroidism, periarticular sore, or Paget's diseases (DN & P, 10 (8),456 (1997)).

8. A method for treating an integrin $\alpha_v\beta_3$-mediated disease selected from the group consisting of cardiovascular diseases, angiogenesis-related diseases, cerebrovascular diseases, cancers and metastasis thereof, immunological diseases, and osteopathy, which method comprises the step of administering an effective amount of the compound according to any one of claim 1, 2, 3, 4, 5 or 6 or a pharmaceutically acceptable salt or solvate thereof, together with a pharmaceutically acceptable carrier, to mammals including humans.

9. A method for the treatment of platelet thrombosis or thromboembolism, the improvement of peripheral circulating blood stream, the inhibition of blood clotting during extracorporeal circulation, or the treatment of thrombotic thrombocytopenic purpura or hemolytic uremic syndrome, which method comprises the step of administering an effective amount of the compound according to any one of claim 1, 2, 3, 4, 5 or 6 or a pharmaceutically acceptable salt or solvate thereof, together with a pharmaceutically acceptable carrier, to mammals including humans.

10. A method for inhibiting platelet aggregation, which method comprising administering an effective amount of the compound according to any one of claim 1, 2, 3, 4, 5 or 6 or a pharmaceutically acceptable salt or solvate thereof, together with a pharmaceutically acceptable carrier, to mammals including humans.

* * * * *